United States Patent
Leban et al.

(10) Patent No.: US 9,580,438 B2
(45) Date of Patent: Feb. 28, 2017

(54) BIFLUORODIOXALANE-AMINO-BENZIMIDAZOLE KINASE INHIBITORS FOR THE TREATMENT OF CANCER, AUTOIMMUNEINFLAMMATION AND CNS DISORDERS

(71) Applicant: 4SC DISCOVERY GMBH, Planegg-Martinsried (DE)

(72) Inventors: Johann Leban, Vienna (AT); Mirko Zaja, Munich (DE)

(73) Assignee: 4SC DISCOVERY GMBH, Planegg-Martinsried (DE)

( * ) Notice: Subject to any disclaimer, the term of this patent is extended or adjusted under 35 U.S.C. 154(b) by 0 days.

(21) Appl. No.: 14/411,795

(22) PCT Filed: Jun. 27, 2013

(86) PCT No.: PCT/EP2013/063537
§ 371 (c)(1),
(2) Date: Dec. 29, 2014

(87) PCT Pub. No.: WO2014/001464
PCT Pub. Date: Jan. 3, 2014

(65) Prior Publication Data
US 2015/0158878 A1 Jun. 11, 2015

Related U.S. Application Data

(60) Provisional application No. 61/664,936, filed on Jun. 27, 2012.

(30) Foreign Application Priority Data

Jul. 2, 2012 (EP) .................................... 12174669

(51) Int. Cl.
C07D 491/056 (2006.01)
C07D 519/00 (2006.01)
A61K 31/4184 (2006.01)
A61K 31/4188 (2006.01)
C07D 491/02 (2006.01)

(52) U.S. Cl.
CPC ......... C07D 491/056 (2013.01); C07D 491/02 (2013.01); C07D 519/00 (2013.01)

(58) Field of Classification Search
CPC .............. C07D 295/023; C07D 265/30; C07D 295/027; C07D 213/74; C07D 491/056; C07D 519/00; C07C 213/02; A61K 31/4184; A61K 31/4188
USPC ..... 544/106, 405; 514/228.5, 394, 395, 463, 514/468; 548/302.1; 549/433, 448
See application file for complete search history.

(56) References Cited

U.S. PATENT DOCUMENTS 7,541,367 B2 6/2009 Chiu et al.
2009/0048249 A1 2/2009 Chiu et al.

FOREIGN PATENT DOCUMENTS

WO 2006130673 A1 12/2006

OTHER PUBLICATIONS

International Search Report for PCT/EP2013/063537 dated Sep. 18, 2013.
Kohl, B. et al., "(H+,K+)-ATPase Inhibiting 2-[(2-Pyridylmethyl) sulfinyl]benzimidazoles. 4.1 A novel series of dimethoxypyridyl-substituted inhibitors with enhanced selectivity. The selection of pantoprazole as a clinical candidate," J. Med. Chem., 1992, vol. 35, No. 1049-1057.
Bischof, J. et al., "2-Benzamido-N-(1H-benzo[d]imidazol-2-yl)thiazole-4-carboxamide derivatives as potent inhibitors of CK1," Amino Acids, 2012, vol. 43, pp. 1577-1591.

Primary Examiner — Alicia L Otton
Assistant Examiner — Sagar Patel
(74) Attorney, Agent, or Firm — Millen, White, Zelano, Branigan, P.C.

(57) ABSTRACT

The invention relates to a compound of the general formula (I) or a physiologically functional derivative, solvate or salt thereof,

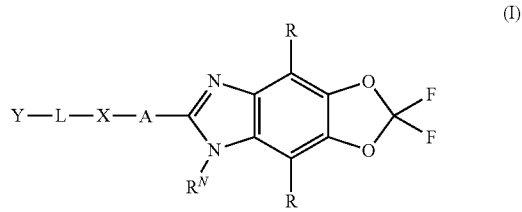

(I)

wherein
A, X, L, Y, R, and $R^N$ are as defined herein. The invention further relates to the use of the compounds of formula (I) as a medicament, a pharmaceutical composition comprising them, a method of treatment or prevention of a medical condition entailing the administration thereof, and the use thereof in the manufacture of a medicament for the treatment or prevention of a medical condition, particularly autoimmune inflammatory disorders, CNS disorders, sleeping disorders, or proliferative diseases including cancer. The invention further relates to a specific process for the preparation of said compounds.

26 Claims, 1 Drawing Sheet

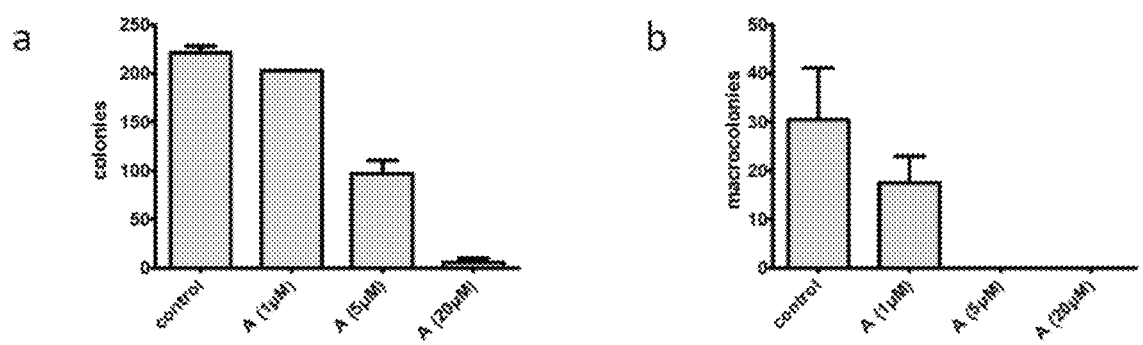

BIFLUORODIOXALANE-AMINO-BENZIMIDAZOLE KINASE INHIBITORS FOR THE TREATMENT OF CANCER, AUTOIMMUNEINFLAMMATION AND CNS DISORDERS

BACKGROUND OF THE INVENTION

Casein kinase 1 (CK1) is a family of highly related, constitutively active serine/threonine protein kinases (Christenson E, De Maggio A J and Hockstra M F. (1997). Recent Results Cancer Res. 143, 263-274; Gross S D and Anderson R A. (1998). Cell Signal 10, 699-711).

CK1 is ubiquitously expressed in eukaryotes. Mammalian family members comprise at least seven mammalian CK1 isoforms (α, β, γ1, γ2, γ3, δ and ε) and their various splice variants. (Fish K J, Cegielska A, Getman M E, Landes G M and Virshup D M. (1995). J. Biol. Chem. 270, 14875-14883; Graves P R, Haas D W, Hagedorn C H, De Paoli-Roach A A and Roach P J. (1993). J. Biol. Chem. 268, 6394-6401; Rowles J, Slaughter C, Moomaw C, Hsu J and Cobb M H. (1991). Proc. Natl. Acad. Sci. USA 88, 9548-9552; Zhai L, Graves P R, Robinson L C, Italiano M, Culbertson M R, Rowles J, Cobb M H, De Paoli-Roach A A and Roach P J. (1995). J. Biol. Chem. 270, 12717-12724).

These isoforms share a high degree of similarity within their protein kinase domains. For example CK1δ and CK1ε are 98% identical in this region (Fish K J, Cegielska A, Getman M E, Landes G M and Virshup D M. (1995). J. Biol. Chem. 270, 14875-14883; Graves P R, Haas D W, Hagedorn C H, De Paoli-Roach A A and Roach P J. (1993). J. Biol. Chem. 268, 6394-6401), but show considerable variation in the presence, length and primary structure of the C-terminal non-catalytic domain (Christenson E, De Maggio A J and Hockstra M F. (1997). Recent Results Cancer Res. 143, 263-274). These variable C-terminal domains are responsible for substrate specificity of the different isoforms (Cegielska A, Gietzen K F, Rivers A and Virshup D M. (1998). J. Biol. Chem. 273, 1357-1364; Graves P R and Roach P J. (1995). J. Bio. Chem. 270, 21689-21694) and are involved in the regulation of the interaction with other proteins, and/or subcellular structures.

Autophosphorylation, (Cegielska A, Gietzen K F, Rivers A and Virshup D M. (1998). J. Biol. Chem. 273, 1357-1364; and perhaps dimerization in the case of CK1δ Longenecker K L, Roach P J and Hurley T D. (1998). Acta Crystallogr. D. Biol. Crystallogr. 54, 473-475) are additional mechanisms that regulate CK1 activity, specificity, and sub-cellular localization. The list of known substrates of the CK1 family is still increasing, and so far includes cytoskeleton proteins such as spectrin, troponin, myosin and tau (Simkowski K W and Tao M. (1980) J. Biol. Chem. 255, 6456-6461; Singh T J, Akatsuka A, Blake K R and Huang K P. (1983). Arch. Biochem. Biophys. 220, 615-622; Singh T J, Grunke-Iqbal I and Iqbal K. (1995). J. Neurochem. 64, 1420-1423; and transcriptional components such as RNA polymerases I and II, SV40 T antigen and CREM Dahmus ME. (1981). J. Biol. Chem. 256, 11239-11243; de Groot R P, den Hertog J, Vandenhee de J R, Grois J and Sassone-Corsi P. (1993). EMBO J, 12, 3903-3911; Grässer F A, Scheidtmann K H, Tuazon P T, Traugh J A and Walter G. (1988). Virology 165, 13-22).

CK1 isoforms can influence the development of tumors in many ways. Their ability to modulate p53 and Mdm2 functions through site-directed phosphorylation, their function in centrosome and spindle regulation, the opposite roles of CK1 isoforms in Wnt signaling and their involvement in impeding apoptosis demonstrate the potential role of CK1 family members in proliferative diseases on multiple levels. Different isoforms seem to play an important role in the development and progression of certain tumor types. Therefore, the interest in targeting CK1 for drug development has increased within the last 5 years. The role of the casein kinase 1 (CK1) family in different signaling pathways is linked to cancer development (Uwe Knippschild et. al., Onkologie 2005; 28:508-514). Further information on specific disorders connected with the casein kinase 1 (CK1) family has been published in: Uwe Knippschild et al., Cellular Signalling 17 (2005) 675-689.

The Wnt and Hedgehog pathways are involved in the regulation of stem cell identity and the initiation and maintenance of many tumor types. Dysregulation of these pathways play an important role in cancer stem cell maintainence. Casein kinases 1ε and 1δ are mainly positive modulators of the Wnt and the Hh pathways. Thus, selective inhibition of Casein kinases 1ε and 1δ inhibit the proliferation and self renewal of cancer stem cells.

Multiple members of the casein kinase I family of serine/threonine protein kinases can have positive or negative effects on individual regulatory elements of the Wnt and Hedgehog pathway, which in summary leads to inhibition. These roles, including recent results on Casein kinase 1 (CK1) phosphorylation and activation of LRP6, CKI phosphorylation of Ci and mediation of Ci-Slimb/β-TrCP binding were revived ("CKI, There's more than one: casein kinase I family members in Wnt and Hedgehog signaling" Price M A, Genes & Dev. 2006. 20: 399-410). Both the Wnt and Hh signaling pathways are important in many developmental patterning events.

Alzheimer's disease is an age-related disorder characterized in part by the appearance of intracellular lesions composed of filamentous aggregates of the microtubule-associated protein tau. Abnormal tau phosphorylation accompanies tau aggregation and is considered to be an upstream pathological event in this disease. Enzymes implicated in tau hyperphosphorylation in Alzheimer's disease include members of the casein kinase 1 family. (Kannanayakal, T J et al. Nuerosci Lett. 2008; 432(2): 141-5.)

The circadian clock links our daily cycles of sleep and activity to the external environment. Deregulation of the clock is implicated in a number of human disorders, including depression, seasonal affective disorder and metabolic disorders. Casein kinase 1 epsilon (CK1ε) and casein kinase 1 delta (CK1δ) are Ser-Thr protein kinases, which are closely related to each other and serve as key clock regulators. This was demonstrated by mutations in CK1δ and CK1ε that dramatically alter the circadian period. Therefore, inhibitors of CK1 have utility in treating circadian disorders. (Walten, K. M. et al. JPET 330:430-439, 2009.)

Several publications describe casein kinase inhibitors: Wager Travis et. al. Abstracts of Papers, 238th ACS National Meeting, Washington, D.C., United States, Aug. 16-20, 2009; Oumata Nassima et al. Journal of Medicinal Chemistry Volume 51 Issue 17 Pages 5229-5242 Journal 2008; Mashhoon N. et al. J Biol Chem 200; 275(26): 20052-60; Pfeifer C. et al. J Med Chem. 2009 Dec. 10; 52(23):7618-30.

In addition several patent applications regarding CK1δ and/or ε inhibitors were published: US 2010/0179154 A1; US 2004/0110808 A1; US 2008/0027124 A1; US 2009/0099237 A1.

Several patents and patent applications described certain specific acyl-amino-benzimidazoles with pharmacological activity: EP 1 388 341 A1 and US 2004/0110808 A1; U.S. Pat. No. 7,132,438 B2; WO 2007/064932 A2; DE 27 54 930 A1; US 2003/0144286.

BRIEF SUMMARY OF THE INVENTION

In one aspect, the present invention provides compounds of Formula (I), and in further embodiments compounds of Formula (Ia), and their respective physiologically functional derivatives or salts, where the groups A, X, L, and Y are detailed further herein below.

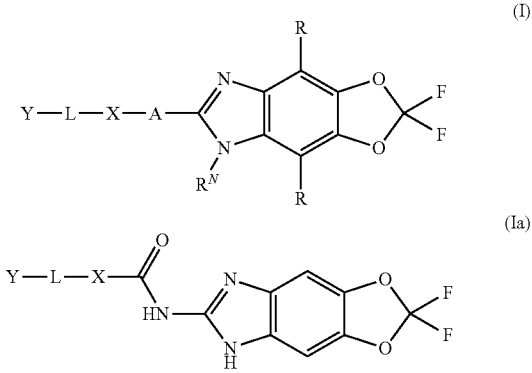

In another aspect, the present invention provides methods for preparation of compounds of Formulae (I) or (Ia), physiologically functional derivatives or salts thereof, as detailed further herein below.

In another aspect, the present invention provides methods for the treatment or prevention of certain medical conditions, the method comprising the administration of compounds of Formulae (I) or (Ia), physiologically functional derivatives or salts thereof, to a subject in need thereof, as detailed further herein below.

In another aspect, the present invention provides the use of compounds of Formulae (I) or (Ia), physiologically functional derivatives or salts thereof, in the manufacture of a medicament for the treatment or prevention of certain medical conditions, as detailed further herein below.

In another aspect, the present invention provides compounds of Formulae (I) or (Ia), physiologically functional derivatives or salts thereof, for use in the treatment or prevention of certain medical conditions, as detailed further herein below.

In another aspect, the present invention provides pharmaceutical compositions comprising compounds of Formulae (I) or (Ia), physiologically functional derivatives or salts thereof and one or more pharmaceutically acceptable excipients.

BRIEF DESCRIPTION OF THE FIGURES

FIG. 1 shows the inhibition of anchorage independent growth of colonies of the pancreatic cancer cell line PANC1 by the compound of Example 1 (columns marked as "A"), compared with DMSO as control. a) The compound of Example 1 reduces anchorage independent growth of PANC1 colonies. b) The compound of Example 1 is particularly potent in the inhibition of PANC1 macrocolonies, which represent a subpopulation the colonies of a).

DETAILED DESCRIPTION OF THE INVENTION

Described herein is a compound of the general formula (I) or a physiologically functional derivative, solvate or salt thereof,

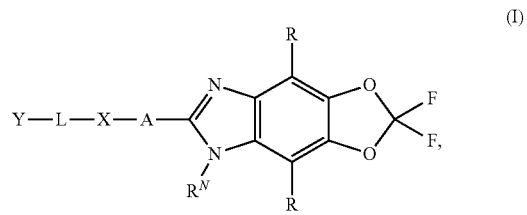

wherein

R is independently selected from the group comprising H, halogen, alkyl, haloalkyl, haloalkoxy, OH, alkoxy, aryl, heteroaryl, cycloalkyl, heterocyclyl, —S—R''', —SO—R''', nitro, —NH$_2$, —N(R''')$_2$, —NH(R'''), —NHCO(R'''), —CONH$_2$, —CONH(R'''), —CO(R'''), —COH, —COO (R'''), —COOH, —SO$_2$NH$_2$, —SO$_2$NH(R'''), —SO$_2$(R'''), —NH—SO$_2$(R'''), and —CNCOOR''', wherein in the cases where said group R is alkyl, haloalkyl, haloalkoxy, alkoxy, aryl, heteroaryl, cycloalkyl, or heterocyclyl, said group R may be substituted with one or more substituents R'' independently selected from the group comprising H, halogen, alkyl, haloalkyl, haloalkoxy, OH, alkoxy, aryl, heteroaryl, cycloalkyl, heterocyclyl, —S-alkyl, —S-haloalkyl, nitro, —NH$_2$, —N(alkyl)$_2$, —NH(alkyl), —NHCO(alkyl), —CONH$_2$, —CONH(alkyl), —CO(alkyl), —COH, —COO (alkyl), —COOH, —SO$_2$NH$_2$, —SO$_2$NH(alkyl), —SO$_2$ (alkyl), —NH—SO$_2$(alkyl), and —CN, and wherein R''' is independently selected from the group comprising H, alkyl, haloalkyl, aryl, heteroaryl, cycloalkyl and heterocyclyl;

$R^N$ is independently selected from the group comprising H, alkyl, haloalkyl, OH, aryl, heteroaryl, cycloalkyl, heterocyclyl, —SO—R''', —NH$_2$, —N(R''')$_2$, —NH(R'''), —NHCO (R'''), —CONH$_2$, —CONH(R'''), —CO(R'''), —COH, —COO(R'''), —COOH, —SO$_2$NH$_2$, —SO$_2$NH(R'''), —SO$_2$ (R'''), and —NH—SO$_2$(R'''), wherein in the cases where said group $R^N$ is alkyl, haloalkyl, aryl, heteroaryl, cycloalkyl, or heterocyclyl, said group $R^N$ may be substituted with one or more substituents R''' as defined above, and wherein R''' is as defined above;

A is independently selected from the group comprising a bond, alkyl optionally substituted with one or more substituents R'' as defined above, alkoxy optionally substituted with one or more substituents R'' as defined above, *—N (R''')CO—, *—CON(R''')—, *—N(R''')CON(R''')—, —S—, —SO—, *—N(R''')—, *—N(R''')CO—, *—CON (R''')—, —CO—, *—COO—, *—OOC—, *—SO$_2$N (R''')—, —SO$_2$, and *—N(R''')—SO$_2$—, wherein R''' is as defined above and wherein * specifies the point of attachment to X;

X is independently selected from the group comprising aryl, cycloalkyl, aralkyl, heterocyclyl and heteroaryl, wherein said group X may be substituted with one or more $R^X$ independently selected from the group comprising halogen, alkyl, haloalkyl, haloalkoxy, OH, alkoxy, aryl, heteroaryl, cycloalkyl, heterocyclyl, —S—(R'''), nitro, —NH$_2$, —N(R''')$_2$, —NH(R'''), —NHCO(R'''), —CONH$_2$, —CONH (R'''), —CO(R'''), —COH, —COO(R'''), —COOH, —SO$_2$NH$_2$, —SO$_2$NH(R'''), —SO$_2$(R'''), —NH—SO$_2$(R'''), cycloalkyl, and —CN, and wherein R''' is as defined above;
L is independently a bond or a linker group selected from the group comprising *—N(R$^N$)CO—, *—CON(R$^N$)—, *—N(R$^N$)—, *—C=N(R$^N$)—, *—N(R$^N$)-alkyl-, *-alkyl-N(R$^N$)—, *—N(R$^N$)CON(R$^N$)—, *—CO—, *—SO$_2$—, alkyl, *-alkyl-O-alkyl-, *—NCO—CH=CH—, *—CH=CH—CONH—, *—SO$_2$N(R$^N$)—, *—N(R$^N$)SO$_2$—, and heterocyclyl, wherein * specifies the point of attachment to X; and wherein R$^N$ is as defined above;
and wherein
Y is independently selected from the group comprising H, alkyl, aryl, aralkyl, cycloalkyl, heterocyclyl and heteroaryl, wherein said group Y may optionally be substituted with one or more R$^Y$ independently selected from the group comprising halogen, alkyl, haloalkyl, haloalkoxy, OH, alkoxy, aryl, heteroaryl, cycloalkyl, heterocyclyl, —S—(R'''), nitro, —NH$_2$, —N(R''')$_2$, —NH(R'''), —NHCO(R'''), —CONH$_2$, —CONH(R'''), —CO(R'''), —COH, —COO(R'''), —COOH, —SO$_2$NH$_2$, —SO$_2$NH(R'''), —SO$_2$(R'''), —NH—SO$_2$(R'''), cycloalkyl, and —CN, and wherein R''' is as defined above.

Embodiments of the present invention are enumerated in the following:

1. A compound of the general formula (I) or a physiologically functional derivative, solvate or salt thereof,

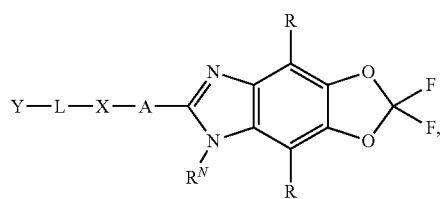

(I)

wherein
R is independently selected from the group comprising H, halogen, C$_{1-6}$-alkyl, C$_{1-6}$-haloalkyl, C$_{1-6}$-haloalkoxy, OH, C$_{1-6}$-alkoxy, —S—R''', —SO—R''', nitro, —N(R''')$_2$, —NH(R'''), —NHCO(R'''), —CONH$_2$, —CONH(R'''), —CO(R'''), —COH, —COO(R'''), —COOH, —SO$_2$NH$_2$, —SO$_2$NH(R'''), —SO$_2$(R'''), and —NH—SO$_2$(R'''),
wherein in the cases where said group R is C$_{1-6}$-alkyl, C$_{1-6}$-haloalkyl, C$_{1-6}$-haloalkoxy, or C$_{1-6}$-alkoxy, said group R may be substituted with one or more substituents R'' independently selected from the group comprising H, halogen, OH, nitro, —NH$_2$, —N(C$_{1-6}$-alkyl)$_2$, —NH(C$_{1-6}$-alkyl), —NHCO(C$_{1-6}$-alkyl), —CONH$_2$, —CONH(C$_{1-6}$-alkyl), —CO(C$_{1-6}$-alkyl), —COH, —COO(C$_{1-6}$-alkyl), —COOH, and —CN,
and wherein R''' is independently selected from the group comprising H, C$_{1-6}$-alkyl, C$_{1-6}$-haloalkyl, aryl, heteroaryl, cycloalkyl and heterocyclyl;
R$^N$ is independently selected from the group comprising H, alkyl, haloalkyl, OH, aryl, heteroaryl, cycloalkyl, heterocyclyl, —SO—R''', —NH$_2$, —N(R''')$_2$, —NH(R'''), —NHCO(R'''), —CONH$_2$, —CONH(R'''), —CO(R'''), —COH, —COO(R'''), —COOH, —SO$_2$NH$_2$, —SO$_2$NH(R'''), —SO$_2$(R'''), and —NH—SO$_2$(R'''), wherein R''' is as defined above,
wherein in the cases where said group R$^N$ is alkyl, haloalkyl, aryl, heteroaryl, cycloalkyl, or heterocyclyl, said group R$^N$ may be substituted with one or more substituents R''' as defined above;

A is independently selected from *—N(R$^a$)CO—, *—CON(R$^a$)—, *—SO$_2$N(R$^a$)—, and *—N(R$^a$)—SO$_2$—,
wherein R$^a$ is selected from H and C$_{1-4}$-alkyl,
and wherein * specifies the point of attachment to X; X is independently selected from the group comprising aryl, cycloalkyl, aralkyl, heterocyclyl and heteroaryl, wherein said group X may be substituted with one or more R$^X$ independently selected from the group comprising halogen, C$_{1-6}$-alkyl, C$_{1-6}$-haloalkyl, C$_{1-6}$-haloalkoxy, OH, C$_{1-6}$-alkoxy, aryl, heteroaryl, cycloalkyl, heterocyclyl, —S—C$_{1-6}$-alkyl, —S—C$_{1-6}$-haloalkyl, nitro, —NH$_2$, —N(C$_{1-6}$-alkyl)$_2$, —NH(C$_{1-6}$-alkyl), —NHCO(C$_{1-6}$-alkyl), —CONH$_2$, —CONH(C$_{1-6}$-alkyl), —CO(C$_{1-6}$-alkyl), —COH, —COO(C$_{1-6}$-alkyl), —COOH, —SO$_2$NH$_2$, —SO$_2$NH(C$_{1-6}$-alkyl), —SO$_2$(C$_{1-6}$-alkyl), —NH—SO$_2$(C$_{1-6}$-alkyl), C$_{3-6}$-cycloalkyl, and —CN;
L is independently a bond or a linker group selected from the group comprising *—NHCO—, *—CONH—, *—NH—, *—N(C$_{1-4}$-alkyl)-, *—C=N(C$_{1-4}$-alkyl)-, *—NH—C$_{1-4}$-alkyl-, *—C$_{1-4}$-alkyl-NH—, *—NHCONH—, *—CO—, *—SO$_2$—, C$_{1-4}$-alkyl, *—C$_{1-2}$-alkyl-O—C$_{1-2}$-alkyl-, *—NHCO—CH=CH—, *—CH=CH—CONH—, *—SO$_2$NH—, *—NHSO$_2$—, and pyridinyl, wherein * specifies the point of attachment to X; and
Y is independently selected from the group comprising H, alkyl, aryl, aralkyl, cycloalkyl, heterocyclyl and heteroaryl, wherein said group Y may optionally be substituted with one or more R$^Y$ independently selected from the group comprising halogen, C$_{1-6}$-alkyl, C$_{1-6}$-haloalkyl, C$_{1-6}$-haloalkoxy, OH, C$_{1-6}$-alkoxy, aryl, heteroaryl, cycloalkyl, heterocyclyl, —S—C$_{1-6}$-alkyl, —S—C$_{1-6}$-haloalkyl, nitro, —NH$_2$, —N(C$_{1-6}$-alkyl)$_2$, —NH(C$_{1-6}$-alkyl), —NHCO(C$_{1-6}$-alkyl), —CONH$_2$, —CONH(C$_{1-6}$-alkyl), —CO(C$_{1-6}$-alkyl), —COH, —COO(C$_{1-6}$-alkyl), —COOH, —SO$_2$NH$_2$, —SO$_2$NH(C$_{1-6}$-alkyl), —SO$_2$(C$_{1-6}$-alkyl), —NH—SO$_2$(C$_{1-6}$-alkyl), C$_{1-6}$-alkyl-heterocyclyl, cycloalkyl and —CN.

2. A compound according to the present invention, in particular according to above item 1, which is a compound of the general formula (Ia) or a physiologically functional derivative, solvate or salt thereof,

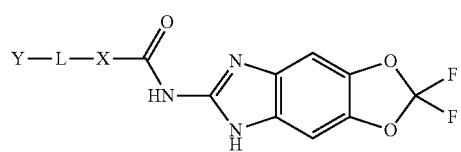

(Ia)

wherein
X is independently selected from the group comprising aryl, cycloalkyl, aralkyl, heterocyclyl and heteroaryl, wherein said group X may be substituted with one or more R$^X$ independently selected from the group comprising halogen, C$_{1-6}$-alkyl, C$_{1-6}$-haloalkyl, C$_{1-6}$-haloalkoxy, OH, C$_{1-6}$-alkoxy, aryl, heteroaryl, cycloalkyl, heterocyclyl, —S—C$_{1-6}$-alkyl, —S—C$_{1-6}$-haloalkyl, nitro, —NH$_2$, —N(C$_{1-6}$-alkyl)$_2$, —NH(C$_{1-6}$-alkyl), —NHCO(C$_{1-6}$-alkyl), —CONH$_2$, —CONH(C$_{1-6}$-alkyl), —CO(C$_{1-6}$-alkyl), —COH, —COO(C$_{1-6}$-alkyl), —COOH, —SO$_2$NH$_2$, —SO$_2$NH(C$_{1-6}$-alkyl), —SO$_2$(C$_{1-6}$-alkyl), —NH—SO$_2$(C$_{1-6}$-alkyl), C$_{3-6}$-cycloalkyl, and —CN;
L is independently a bond or a linker group selected from the group comprising *—NHCO—, *—CONH—, *—NH—, *—N(C$_{1-4}$-alkyl)-, *—C=N(C$_{1-4}$-alkyl)-, *—NH—C$_{1-4}$-alkyl-, *—C$_{1-4}$-alkyl-NH—, *—NHCONH—, *—CO—,

*—SO$_2$—, C$_{1-4}$-alkyl, *—C$_{1-2}$-alkyl-O—C$_{1-2}$-alkyl-, *—NHCO—CH=CH—, *—CH=CH—CONH—, *—SO$_2$NH—, *—NHSO$_2$—, and pyridinyl, wherein * specifies the point of attachment to X; and Y is independently selected from the group comprising H, alkyl, aryl, aralkyl, cycloalkyl, heterocyclyl and heteroaryl, wherein said group Y may optionally be substituted with one or more R$^Y$ independently selected from the group comprising halogen, C$_{1-6}$-alkyl, C$_{1-6}$-haloalkyl, C$_{1-6}$-haloalkoxy, OH, C$_{1-6}$-alkoxy, aryl, heteroaryl, cycloalkyl, heterocyclyl, —S—C$_{1-6}$-alkyl, —S—C$_{1-6}$-haloalkyl, nitro, —NH$_2$, —N(C$_{1-6}$-alkyl)$_2$, —NH(C$_{1-6}$-alkyl), —NHCO(C$_{1-6}$-alkyl), —CONH$_2$, —CONH(C$_{1-6}$-alkyl), —CO(C$_{1-6}$-alkyl), —COH, —COO(C$_{1-6}$-alkyl), —COOH, —SO$_2$NH$_2$, —SO$_2$NH(C$_{1-6}$-alkyl), —SO$_2$(C$_{1-6}$-alkyl), —NH—SO$_2$(C$_{1-6}$-alkyl), C$_{1-6}$-alkyl-heterocyclyl, cycloalkyl and —CN.

3. The compound according to the present invention, in particular according to above item 1 or 2 or a physiologically functional derivative, solvate or salt thereof, wherein X is independently selected from the group comprising aryl, cycloalkyl, heterocyclyl and heteroaryl, wherein said group X may be substituted with one or more R$^X$ independently selected from the group comprising F, Cl, Br, I, C$_{1-6}$-alkyl, C$_{1-6}$-haloalkyl, C$_{1-6}$-haloalkoxy, OH, C$_{1-6}$-alkoxy, nitro, —NH$_2$, —N(C$_{1-6}$-alkyl)$_2$, —NH(C$_{1-6}$-alkyl), —NHCO(C$_{1-6}$-alkyl), —CONH$_2$, —CONH(C$_{1-6}$-alkyl), —SO$_2$NH$_2$, —SO$_2$NH(C$_{1-6}$-alkyl), —SO$_2$(C$_{1-6}$-alkyl), C$_{3-6}$-cycloalkyl, —NH—SO$_2$(C$_{1-6}$-alkyl), —COO—C$_{1-6}$-alkyl, and —CN;

L is independently a bond or a linker group selected from the group comprising *—NHCO—, *—NH—, *—NHCH$_2$—, *—NHCONH—, *—NHCO—CH=CH—, *—NHSO$_2$—, *—SO$_2$—, and pyridinyl, wherein * specifies the point of attachment to X; and Y is independently selected from the group comprising H, aryl, cycloalkyl, heterocyclyl and heteroaryl, wherein said group Y may optionally be substituted with one or more R$^Y$ independently selected from the group comprising F, Cl, Br, C$_{1-6}$-alkyl, C$_{1-6}$-haloalkyl, C$_{1-6}$-haloalkoxy, C$_{1-6}$-alkoxy, C$_{1-6}$-alkyl-morpholinyl, and nitro.

4. The compound according to the present invention, in particular according to any of the above items 1 to 3 or a physiologically functional derivative, solvate or salt thereof, wherein X is independently selected from the group comprising aryl, aralkyl, cycloalkyl, heterocyclyl and heteroaryl, wherein said group X may be substituted with one or more R$^X$ independently selected from the group comprising F, Cl, Br, I, C$_{1-6}$-alkyl, C$_{1-6}$-haloalkyl, C$_{1-6}$-haloalkoxy, OH, C$_{1-6}$-alkoxy, nitro, —NH$_2$, —N(C$_{1-6}$-alkyl)$_2$, —NH(C$_{1-6}$-alkyl), —NHCO(C$_{1-6}$-alkyl), —CONH$_2$, —CONH(C$_{1-6}$-alkyl), —SO$_2$NH$_2$, —SO$_2$NH(C$_{1-6}$-alkyl), —SO$_2$(C$_{1-6}$-alkyl), C$_{3-6}$-cycloalkyl, —NH—SO$_2$(C$_{1-6}$-alkyl), —COO—C$_{1-6}$-alkyl, —COOH, and —CN;

L is independently a bond or a linker group selected from the group comprising *—NHCO—, *—NH—, *—NHCH$_2$—, *—NHCONH—, *—NHCO—CH=CH—, *—NHSO$_2$—, *—SO$_2$—, and pyridinyl, wherein * specifies the point of attachment to X; and Y is independently selected from the group comprising H, aryl, cycloalkyl, heterocyclyl and heteroaryl, wherein said group Y may optionally be substituted with one or more R$^Y$ independently selected from the group comprising F, Cl, Br, C$_{1-6}$-alkyl, C$_{1-6}$-haloalkyl, C$_{1-6}$-haloalkoxy, C$_{1-6}$-alkoxy, C$_{1-6}$-alkyl-morpholinyl, and nitro.

5. The compound according to the present invention, in particular according to any of the above items 1 to 4 or a physiologically functional derivative, solvate or salt thereof, wherein X is independently selected from the group comprising 1,2,3-thiadiazolyl, 1,2,4-thiadiazolyl, 1H-1,2,3-triazolyl, 1H-1,2,4-triazolyl, 1H-pyrazolyl, 1H-pyrrolyl, phenyl, benzo[b]thiophenyl, cyclohexyl, furyl, isoxazolyl, oxazolyl, imidazolyl, 1H-pyrazolyl, pyrazinyl, pyridyl, quinolinyl, 1-(naphthalen-2-yl)ethyl, thiazolyl and thiophenyl, wherein said group X may be substituted with one or more R$^X$ independently selected from the group comprising F, Cl, Br, methyl, tert-butyl, trifluoromethyl, trifluoromethoxy, difluoromethoxy, OH, acetyl, methylcarbamoyl, methoxy, nitro, —NH$_2$, —NEt$_2$, —NMe$_2$, —NHEt, —NHCOCH$_3$, —CONH$_2$, —SO$_2$NH$_2$, —SO$_2$Me, —NH—SO$_2$Me, and —CN;

L is independently a bond or a linker group selected from the group comprising comprising *—NHCO—, *—NH—, *—NHCH$_2$—, *—NHCONH—, *—NHCO—CH=CH—, *-pyridinyl-, —SO$_2$—, and *—NHSO$_2$—, wherein * specifies the point of attachment to X; and Y is independently selected from the group comprising H, phenyl, furyl, thiophenyl, pyridyl, pyrimidyl, 2,3-dihydrobenzo[b][1,4]dioxinyl, 2,3-dihydrobenzofuranyl, benzo[d][1,3]dioxolyl, thieno[3,2-d]pyrimidinyl, 2-oxo-2,3-dihydrobenzoimidazolyl, pyrrolidinyl, tetrazolyl, piperidinyl, pyrazolyl, 1,2,4-oxadiazolyl, 1,2,3-thiadiazolyl, pyrrolyl, imidazolyl, isoxazolyl, thiazolyl, and morpholinyl, wherein said group Y may be substituted with one or two R$^Y$ independently selected from the group comprising F, Cl, methyl, isopropyl, tert-butyl, trifluoromethyl, trifluoromethoxy, methoxy, methylcarbamoyl, cyclopropyl, 2-morpholinoethyl, and nitro.

6. The compound according to the present invention, in particular according to any of the above items 1 to 5 or a physiologically functional derivative, solvate or salt thereof, wherein X is independently selected from the group comprising 1,2,3-thiadiazolyl, 1,2,4-thiadiazolyl, 1H-1,2,3-triazolyl, 1H-1,2,4-triazolyl, 1H-pyrazolyl, 1H-pyrrolyl, phenyl, benzo[b]thiophenyl, cyclohexyl, furyl, isoxazolyl, oxazolyl, imidazolyl, 1H-pyrazolyl, pyrazinyl, pyridyl, quinolinyl, 1-(naphthalen-2-yl)ethyl, thiazolyl, benzyl and thiophenyl, wherein said group X may be substituted with one or more R$^X$ independently selected from the group comprising F, Cl, Br, methyl, tert-butyl, trifluoromethyl, trifluoromethoxy, difluoromethoxy, OH, acetyl, methylcarbamoyl, methoxy, nitro, —NH$_2$, —NEt$_2$, —NMe$_2$, —NHEt, —NHCOCH$_3$, —CONH$_2$, —SO$_2$NH$_2$, —SO$_2$Me, —NH—SO$_2$Me, —COOH, and —CN;

L is independently a bond or a linker group selected from the group comprising comprising *—NHCO—, *—NH—, *—NHCH$_2$—, *—NHCONH—, *—NHCO—CH=CH—, *-pyridinyl-, —SO$_2$—, and *—NHSO$_2$—, wherein * specifies the point of attachment to X; and Y is independently selected from the group comprising H, phenyl, furyl, thiophenyl, pyridyl, pyrimidyl, 2,3-dihydrobenzo[b][1,4]dioxinyl, 2,3-dihydrobenzofuranyl, benzo[d][1,3]dioxolyl, thieno[3,2-d]pyrimidinyl, 2-oxo-2,3-dihydrobenzoimidazolyl, pyrrolidinyl, tetrazolyl, piperidinyl, pyrazolyl, 1,2,4-oxadiazolyl, 1,2,3-thiadiazolyl, pyrrolyl, imidazolyl, isoxazolyl, thiazolyl, thiomorpholinyl, and morpholinyl, wherein said group Y may be substituted with one or two R$^Y$ independently selected from the group comprising F, Cl, methyl, isopropyl, tert-butyl, trifluoromethyl, trifluoromethoxy, methoxy, methylcarbamoyl, cyclopropyl, 2-morpholinoethyl, and nitro.

7. The compound according to the present invention, in particular according to any of the above items 1 to 6 or a physiologically functional derivative, solvate or salt thereof, wherein X is independently selected from the group comprising

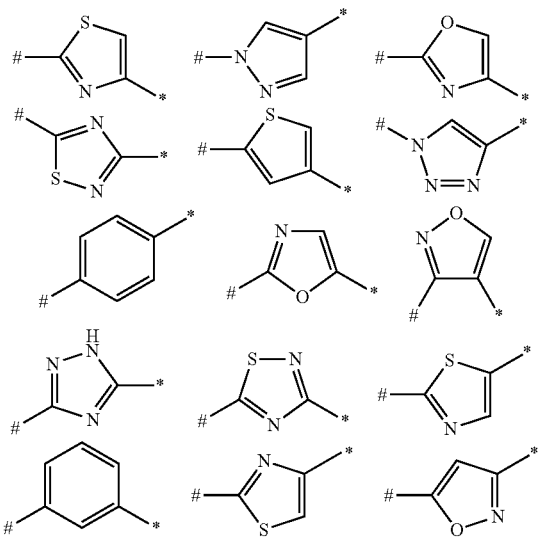

wherein * specifies the point of attachment to the central moiety, # specifies the point of attachment to L and wherein the group X may be substituted with one or more $R^X$;

L is independently a bond or a linker group selected from the group comprising *—NHCO—, *—NH—, *—NHCH$_2$—, *—NHCONH—, *—NHCO—CH=CH—, *-pyridinyl-, —SO$_2$—, and *—NHSO$_2$—, wherein * specifies the point of attachment to X;

Y is independently H or selected from the group comprising

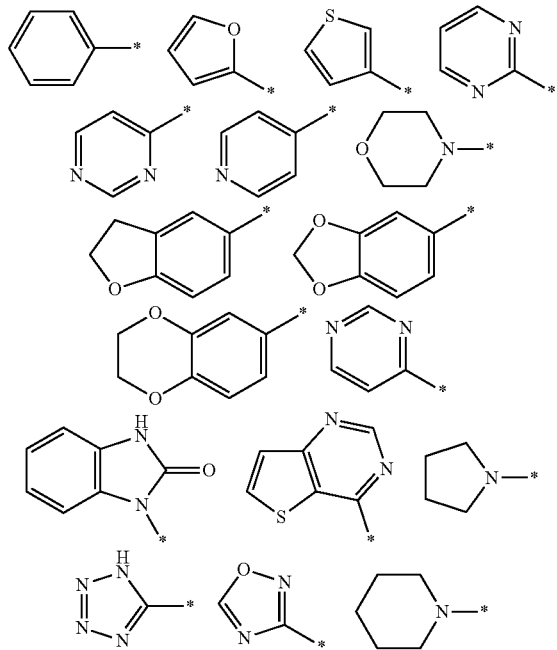

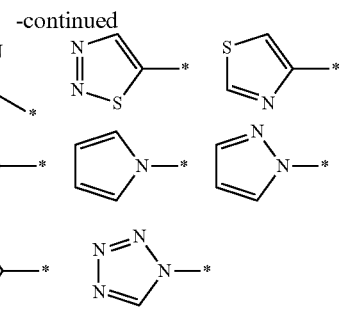

wherein * specifies the point of attachment to L and wherein the group Y may be substituted with one or more $R^Y$;

or wherein X is selected from the group comprising

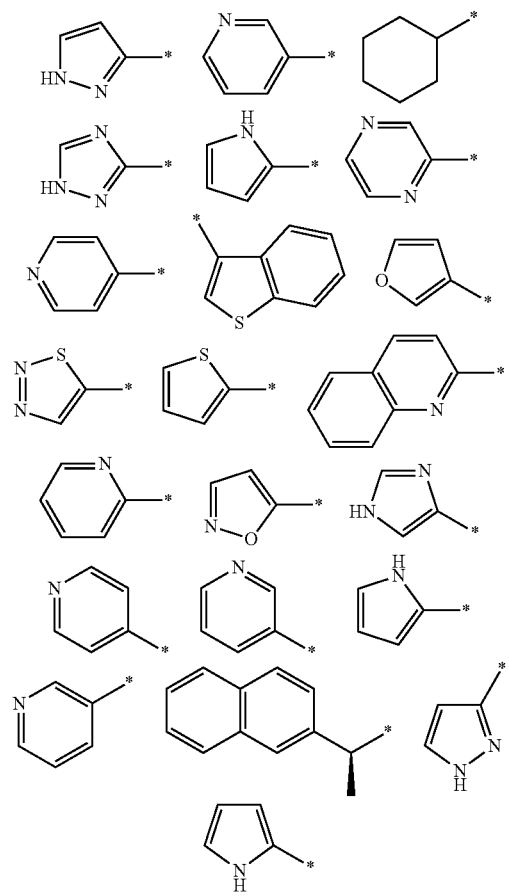

wherein * specifies the point of attachment to the central moiety, wherein L is a bond, Y is H, and wherein the group X may be substituted with one or more $R^X$;

wherein each $R^Y$ is independently selected from the group comprising F, Cl, methyl, isopropyl, tert-butyl, trifluoromethyl, trifluoromethoxy, methoxy, methylcarbamoyl, cyclopropyl, 2-morpholinoethyl, and nitro; and wherein each $R^X$ is independently selected from the group comprising F, Cl, Br, methyl, tert-butyl, trifluoromethyl, trifluoromethoxy, difluoromethoxy, OH, acetyl, methylcarbamoyl, methoxy, nitro, —NH$_2$, —NEt$_2$, —NMe$_2$, —NHEt, —NHCOCH$_3$, —CONH$_2$, —SO$_2$NH$_2$, —SO$_2$Me, —NH—SO$_2$Me, and —CN.

8. The compound according to the present invention, in particular according to any of the above items 1 to 7 or a physiologically functional derivative, solvate or salt thereof, wherein X is independently selected from the group comprising

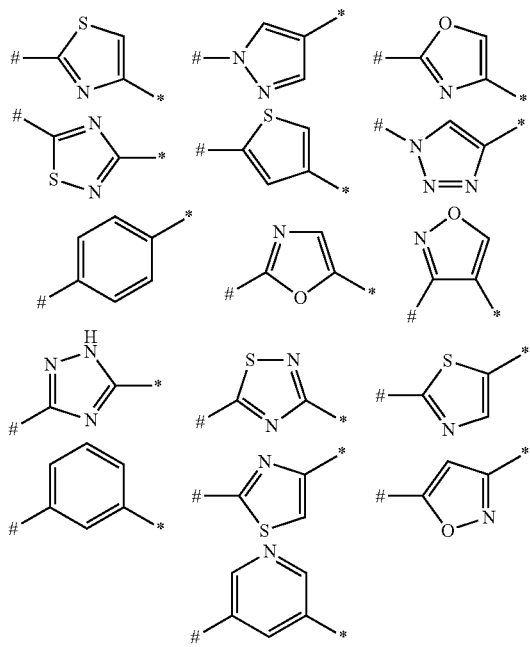

wherein * specifies the point of attachment to the central moiety, # specifies the point of attachment to L and wherein the group X may be substituted with one or more $R^X$;

L is independently a bond or a linker group selected from the group comprising *—NHCO—, *—NH—, *—NHCH$_2$—, *—NHCONH—, *—NHCO—CH═CH—, *-pyridinyl-, —SO$_2$—, and *—NHSO$_2$—, wherein * specifies the point of attachment to X;

Y is independently H or selected from the group comprising

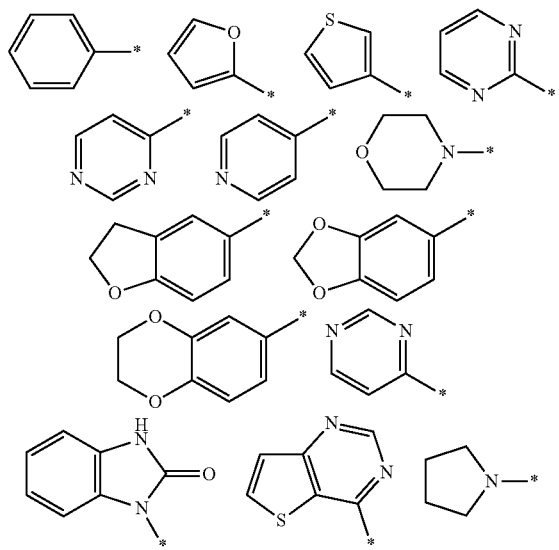

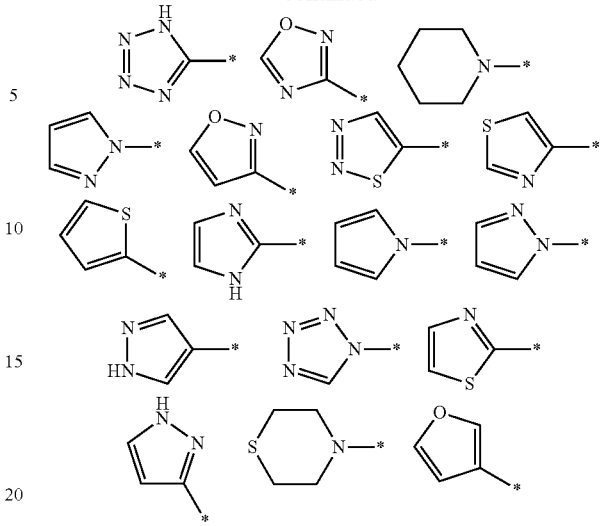

wherein * specifies the point of attachment to L and wherein the group Y may be substituted with one or more $R^Y$;

or wherein X is selected from the group comprising

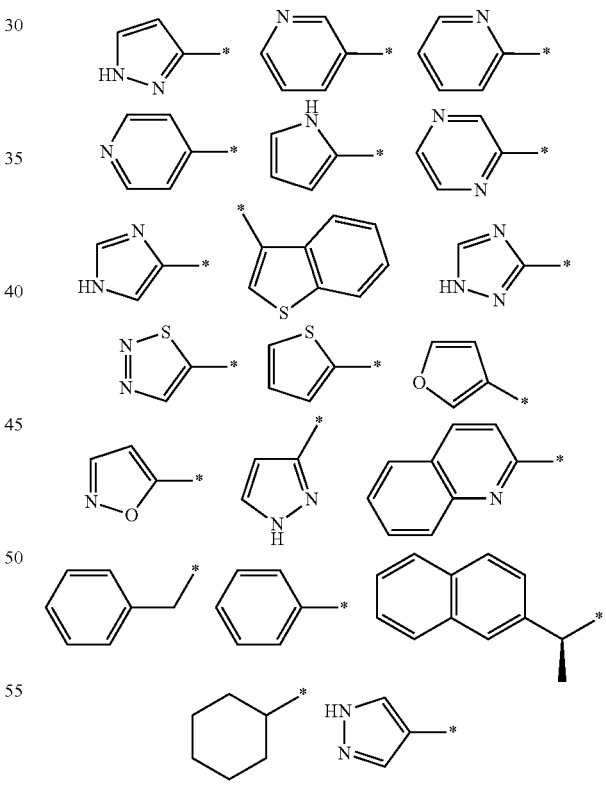

wherein * specifies the point of attachment to the central moiety, wherein L is a bond, Y is H, and wherein the group X may be substituted with one or more $R^X$;

wherein each $R^Y$ is independently selected from the group comprising F, Cl, methyl, isopropyl, tert-butyl, trifluoromethyl, trifluoromethoxy, methoxy, methylcarbamoyl, cyclopropyl, 2-morpholinoethyl, and nitro; and wherein each $R^X$ is independently selected from the group comprising F, Cl, Br, methyl, tert-butyl, trifluoromethyl, trifluoromethoxy, difluoromethoxy, OH, acetyl, methylcarbamoyl, methoxy, nitro, —NH$_2$, —NEt$_2$, —NMe$_2$, —NHEt, —NHCOCH$_3$, —CONH$_2$, —SO$_2$NH$_2$, —SO$_2$Me, —NH—SO$_2$Me, —COOH and —CN.

In certain embodiments of the present invention, Y is a phenyl group optionally substituted with one or more $R^Y$ as defined herein, more particularly a phenyl group substituted with one or more $R^Y$ as defined herein, wherein at least one of the substituents $R^Y$ is located in the meta of the phenyl group position, wherein the ortho positions of the phenyl group are H, and wherein said ortho and meta positions are in relation to the point of attachment to L, or in the case where L is a bond, the point of attachment to X, respectively.

In certain embodiments of the present invention, $R^X$ is in each occurrence independently selected from the group comprising alkyl, alkylsulfonyl, halogen, haloalkyl, hydroxy, amino, alkylamino, dialkylamino, benzylamino, nitro, alkoxy, haloalkoxy and cyano, more particularly selected from the group comprising methyl, methylsulfonyl, fluorine, chlorine, bromine, trifluoromethyl, hydroxyl, amino, dimethylamino, ethylamino, diethylamino, benzylamino, nitro, methoxy, trifluoromethoxy and cyano.

In certain embodiments of the present invention, L independently is a bond or selected from the group comprising *—NHCO—, *—NH SO$_2$—, *—SO$_2$—, *—CONH—, —NH—, —NHCONH—, and *—SO$_2$NH—, particularly *—NHCO—, *—NH, *—NHCONH—, and *—NHSO$_2$—, wherein * specifies the point of attachment to X. More particularly, L independently is *—NHCO, wherein * specifies the point of attachment to X.

In certain embodiments of the present invention, $R^Y$ is in each occurrence independently selected from the group comprising alkyl, halogen, haloalkyl, alkoxy, haloalkoxy and nitro, more particularly selected from the group comprising methyl, chlorine, fluorine, methoxy, trifluoromethoxy and nitro.

Particular compounds of the present invention are those having an IC$_{50}$ on cancer cell growth inhibition of 1 µM or lower, more particularly 100 nM or lower. Said IC$_{50}$ is particularly determined as described herein below in the exemplary section (under "9. Determination of proliferation inhibition on a panel of cancer cell lines; Proliferation Assay"), and particular cancer types in this context are the ones described therein.

Furthermore, particular compounds of the present invention are those having an IC$_{50}$ on CK1 delta and/or epsilon inhibition of 1 µM or lower, even more particularly 200 nM or lower. Said IC$_{50}$ is particularly determined as described herein below in the exemplary section (under "8. Determination of the inhibitory capacity; Kinase Assay"—Data shown in tables 1 and 2).

9. The compound according to the present invention, in particular according to any of the above items 1 to 8, wherein said compound is selected from one of the compounds 1 to 149 enumerated in the example section, or a physiologically functional derivative, solvate or salt thereof.

10. The compound according to the present invention, in particular according to any of the above items 1 to 9, wherein said compound is selected from one of the compounds 1 to 149 or 1B to 26B enumerated in the example section, or a physiologically functional derivative, solvate or salt thereof.

11. The compound according to the present invention, in particular according to any of the above items 1 to 10, wherein said compound is selected from one of the following compounds as enumerated in the example section: 1, 2, 3, 11, 17, 18, 19, 20, 21, 26, 29, 30, 31, 33, 37, 38, 41, 48, 49, 51, 52, 56, 57, 60, 62, 65, 66, 69, 70, 75, 76, 77, 78, 80, 81, 82, 83, 87, 88, 91, 92, 94, 100, 101, 102, 104, 105, 108, 111, 112, 113, 114, 116, 117, 118, 121, 122, 123, 124, 125, 126, 128, 130, 131, 132, 133, 134, 135, 136, 137, 138, 139, 140, 141, 142, 144, 147, 148, and 149,
or a physiologically functional derivative, solvate or salt thereof.

12. The compound according to the present invention, in particular according to any of the above items 1 to 11, wherein said compound is selected from one of the following compounds as enumerated in the example section: 1, 2, 3, 11, 17, 18, 19, 20, 21, 26, 29, 30, 31, 33, 37, 38, 41, 48, 49, 51, 52, 56, 57, 60, 62, 65, 66, 69, 70, 75, 76, 77, 78, 80, 81, 82, 83, 87, 88, 91, 92, 94, 100, 101, 102, 104, 105, 108, 111, 112, 113, 114, 116, 117, 118, 121, 122, 123, 124, 125, 126, 128, 130, 131, 132, 133, 134, 135, 136, 137, 138, 139, 140, 141, 142, 144, 147, 148, and 149, 1B, 2B, 3B, 4B, 5B, 6B, 7B, 8B, 9B, 10B, 11B, 12B, 13B, 14B, 15B, 16B, 17B, 22B, 23B, and 25B.
or a physiologically functional derivative, solvate or salt thereof.

13. The compound according to the present invention, in particular according to any of the above items 1 to 12 or a physiologically functional derivative, solvate or salt thereof for use as a medicament.

14. The compound according to the present invention, in particular according to any of the above items 1 to 12 or a physiologically functional derivative, solvate or salt thereof for use in the treatment or prevention of a medical condition selected from the group comprising autoimmuneinflammatory disorders, more particularly selected from the group comprising inflammatory Bowel disease, multiple sclerosis, rheumathoid arthritis, autoimmune uveitis, CNS disorders, particularly selected from the group comprising Alzheimer's disease, Parkinson's disease, Down's syndrome, sleeping disorders, particularly sleeping disorders in connection with the circadian clock mechanism, and proliferative diseases including cancer.

15. A pharmaceutical composition comprising a compound according to the present invention, in particular according to any of the above items 1 to 12 or a physiologically functional derivative, solvate or salt thereof and one or more pharmaceutically acceptable excipients.

Furthermore, the present invention relates to a method of treatment or prevention of the medical conditions specified herein, which comprises the administration of an effective amount of a compound according to the present invention, or a physiologically functional derivative, solvate or salt thereof to a subject in need thereof.

Furthermore, the present invention relates to the use of a compound according to the present invention, or a physiologically functional derivative, solvate or salt thereof in the treatment or prevention of the medical conditions specified herein.

16. A method of treatment or prevention of a medical condition selected from the group comprising autoimmune inflammatory disorders, CNS disorders, sleeping disorders, and proliferative diseases including cancer, which comprises the administration of an effective amount of a compound according to the present invention, in particular according to any of the above items 1 to 12, or a physiologically functional derivative, solvate or salt thereof to a subject in need thereof.

17. Use of a compound according to the present invention, in particular according to any of the above items 1 to 12, or a physiologically functional derivative thereof, solvate or salt in the manufacture of a medicament for the treatment or prevention of a medical condition selected from the group comprising autoimmune inflammatory disorders, CNS disorders, sleeping disorders, and proliferative diseases including cancer.

18. Process for the preparation of a compound according to the present invention, in particular according to any of the above items 1 to 12, wherein A is an —CONH— or —NHCO—, the process comprising the step of coupling a compound of below Formula IV with a compound of below formula II;

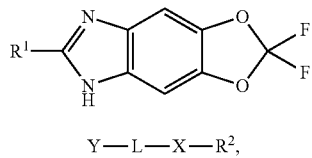

IV

Y—L—X—R²,

II wherein Y, L and X are as defined above, and
wherein either R¹ is NH₂ and R² is COOH or COOCl, or wherein R² is NH₂ and R¹ is COOH or COOCl, particularly R¹ is NH₂ and R² is COOH or COOCl.

The compounds of the present invention interact with Casein kinase delta and/or epsilon, suggesting their applicability in prevention and/or therapy of medical conditions wherein the function of Casein kinase delta and/or epsilon plays a role.

Particularly, the difluoromethylenedioxy group of the compounds according to the present invention unexpectedly shows two molecular interactions with the side chain residues of glutamyl 52 and tyrosin 56 of Casein kinase delta. Such additional binding interaction in addition to the hydrogen binding network of the benzimidazol heterocycle of the central moiety was not known from the prior art, and contributes to the favourable inhibitory activity of the compounds according to the present invention.

This unexpected finding shows, that an acyl aminobenzimidazol derivative containing a difloromethylendioxo residue on the benzole ring has specific interactions to kasein kinase delta.

The following definitions are meant to further define certain terms used in the context of the present invention. If a particular term used herein is not specifically defined, the term should not be considered to be indefinite. Rather, such terms are to be construed in accordance with their meaning as regularly understood by the skilled artisan in the field of art to which the invention is directed, particularly in the field of organic chemistry, pharmaceutical sciences and medicine.

As used herein, an alkyl group is to be understood to encompass alkanyl, alkenyl, alkynyl, wherein alkanyl means a completely saturated hydrocarbon chain, alkenyl means a hydrocarbon chain comprising at least one carbon-carbon double bond, alkynyl means a hydrocarbon chain comprising at least one carbon-carbon triple bond (including a hydrocarbon chain comprising one or more carbon-carbon double bonds and at least one carbon-carbon triple bond). In the context of the present invention, an alkanyl group, if not stated otherwise, particularly denotes a linear or branched $C_1$-$C_6$-alkanyl, particularly a linear or branched $C_1$-$C_5$-alkanyl; an alkenyl group, if not stated otherwise, particularly denotes a linear or branched $C_2$-$C_6$-alkenyl; and an alkynyl group, if not stated otherwise, particularly denotes a linear or branched $C_2$-$C_6$-alkynyl group. In particular embodiments the alkyl group is selected from the group comprising —CH₃, —C₂H₅, —CH=CH₂, —C≡CH, —C₃H₇, —CH(CH₃)₂, —CH₂—CH=CH₂, —C(CH₃)=CH₂, —CH=CH—CH₃, —C≡C—CH₃, —CH₂—C≡CH, —C₄H₉, —CH₂—CH(CH₃)₂, —CH(CH₃)—C₂H₅, —C(CH₃)₃, —C₅H₁₁, —C₆H₁₃, —C(R')₃, —C₂(R')₅, —CH₂—C(R')₃, —C₃(R')₇, —C₂H₄—C(R')₃, —C₂H₄—CH=CH₂, —CH=CH—C₂H₅, —CH=C(CH₃)₂, —CH₂—CH=CH—CH₃, —CH=CH—CH=CH₂, —C₂H₄—C≡CH, —C≡C—C₂H₅, —CH₂—C≡C—CH₃, —C≡C—CH=CH₂, —CH=CH—C≡CH, —C≡C—C≡CH, —C₂H₄—CH(CH₃)₂, —CH(CH₃)—C₃H₇, —CH₂—CH(CH₃)—C₂H₅, —CH(CH₃)—CH(CH₃)₂, —C(CH₃)₂—C₂H₅, —CH₂—C(CH₃)₃, —C₃H₆—CH=CH₂, —CH=CH—C₃H₇, —C₂H₄—CH=CH—CH₃, —CH₂—CH=C₂H₅, —CH₂—CH=CH—CH=CH₂, —CH=CH—CH=CH—CH₃, —CH=CH—CH₂—CH=CH₂, —C(CH₃)=CH—CH=CH₂, —CH=C(CH₃)—CH=CH₂, —CH=CH—C(CH₃)=CH₂, —CH₂—CH=C(CH₃)₂, C(CH₃)=C(CH₃)₂, —C₃H₆—C≡CH, —C≡C—C₃H₇, —C₂H₄—C≡C—CH₃, —CH₂—C≡C—C₂H₅, —CH₂—C≡C—CH=CH₂, —CH₂—CH=CH—C≡CH, —CH₂—C≡C—C≡CH, —C≡C—CH=CH—CH₃, —CH=CH—C≡C—CH₃, —C≡C—C≡C—CH₃, —C≡C—CH₂—CH=CH₂, —CH=CH—CH₂—C≡CH, —C≡C—CH₂—C≡CH, —C(CH₃)=CH—CH=CH₂, —CH=C(CH₃)—CH=CH₂, —CH=CH—C(CH₃)=CH₂, —C(CH₃)=CH—C≡CH, —CH=C(CH₃)—C≡CH, —C≡C—C(CH₃)=CH₂, —C₃H₆—CH(CH₃)₂, —C₂H₄—CH(CH₃)—C₂H₅, —CH(CH₃)—C₄H₉, —CH₂—CH(CH₃)—C₃H₇, —CH(CH₃)—CH₂—CH(CH₃)₂, —CH(CH₃)—CH(CH₃)—C₂H₅, —CH₂—CH(CH₃)—CH(CH₃)₂, —CH₂—C(CH₃)₂—C₂H₅, —C(CH₃)₂—C₃H₇, —C(CH₃)₂—CH(CH₃)₂, —C₂H₄—C(CH₃)₃, —CH(CH₃)—C(CH₃)₃, —C₄H₈—CH=CH₂, —CH=CH—C₄H₉, —C₃H₆—CH=CH—CH₃, —CH₂—CH=CH—C₃H₇, —C₂H₄—CH=CH—C₂H₅, —CH₂—C(CH₃)=C(CH₃)₂, —C₂H₄—CH=C(CH₃)₂, —C₄H₈—C≡CH, —C≡C—C₄H₉, —C₃H₆—C≡C—CH₃, —CH₂—C≡C—C₃H₇, and —C₂H₄—C≡C—C₂H₅. The alkyl, alkanyl, alkenyl, and alkynyl groups as defined above, including the groups enumerated as examples and particular embodiments thereof, are optionally substituted by one or more substituents R'.

As used herein, an aryl group denotes an aromatic mono- or polycyclic hydrocarbon ring system, which may optionally be fused to one or more cycloalkyl or heterocyclyl rings, and wherein the total number of ring atoms in the aryl group is six to fourteen, particularly six to ten. The point of attachment of of said aryl group to the central moiety may be located on the mono- or polycyclic hydrocarbon ring system or on the optionally fused cycloalkyl or heterocyclyl ring. Examples of the aryl group are phenyl, naphthyl, indenyl, azulenyl, fluorenyl, 1,2-dihydronaphthyl, 1,2,3,4-tetrahydronaphthyl, 2,3-dihydroindenyl, 1,5-dihydro-s-indacenyl, 1,6-dihydro-as-indacenyl, 1H-cyclopenta[a]naphthyl and 1H-cyclopenta[b]naphthyl, phenalenyl, phenanthrenyl, anthracenyl, 1,6-dihydropentalenyl, 1,6a-dihydropentalenyl, 1,2,3,4-tetrahydroanthracenyl, 1,2,3,4-tetrahydrophenanthrenyl, 2,3-dihydro-1H-cyclopenta[a]naphthalenyl, 2,3-dihydro-1H-cyclopenta[b]naphthalenyl, 2,3-dihydro-1H-phenalenyl, 2,3-dihydrobenzo[b]thiophenyl-1,1-dioxide, 1,2,3,4-tetrahydroisoquinolinyl, 1,2,3,4-tetrahydroquinolinyl, 2,3-dihydrobenzo[b][1,4]dioxinyl, 2,3-dihydrobenzo[b]thiophenyl, 2,3-dihydrobenzofuranyl, 2-oxo-2,3-dihydrobenzoimidazolyl, benzo[d][1,3]dioxolyl, chromanyl, indazolinyl and indolinyl. In particular embodiments, the aryl group is phenyl, 2,3-dihydrobenzo[b][1,4]dioxinyl, 2,3-dihydrobenzofuranyl, 2-oxo-2,3-dihydrobenzoimidazolyl or benzo[d][1,3]dioxolyl, more particularly phenyl. The aryl groups as defined above, including the groups enumerated as examples and particular embodiments thereof, are optionally substituted by one or more substituents R'.

As used herein, a heteroaryl group denotes an aromatic mono- or polycyclic hydrocarbon ring system wherein one or more carbon atoms are replaced by heteroatoms independently selected from the group comprising O, N and S, wherein the aromatic mono- or polycyclic hydrocarbon ring system may optionally be fused to one or more cycloalkyl or heterocyclyl rings, and wherein the total number of ring atoms in the heteroaryl group is five to fourteen, particularly five to ten, more particularly five or six. The point of attachment of of said heteroaryl group to the central moiety may be located on the mono- or polycyclic hydrocarbon ring system or on the optionally fused cycloalkyl or heterocyclyl ring. Examples of the heteroaryl group are thiadiazole, thiazol-2-yl, thiazol-4-yl, thiazol-5-yl, isothiazol-3-yl, isothiazol-4-yl, isothiazol-5-yl, oxazol-2-yl, oxazol-4-yl, oxazol-5-yl, isooxazol-3-yl, isooxazol-4-yl, isooxazol-5-yl, 1,2,4-oxadiazol-3-yl, 1,2,4-oxadiazol-5-yl, 1,2,5-oxadiazol-3-yl, benzooxazol-2-yl, benzooxazol-4-yl, benzooxazol-5-yl, benzoisooxazol-3-yl, benzoisooxazol-4-yl, benzoisooxazol-5-yl, 1,2,5-oxadiazol-4-yl, 1,3,4-oxadiazol-2-yl, 1,2,4-thiadiazol-3-yl, 1,2,4-thiadiazol-5-yl, 1,3,4-thiadiazol-2-yl, isothiazol-3-yl, isothiazol-4-yl, isothiazol-5-yl, benzoisothiazol-3-yl, benzoisothiazol-4-yl, benzoisothiazol-5-yl, 1,2,5-thiadiazol-3-yl, 1-imidazolyl, 2-imidazolyl, 1,2,5-thiadiazol-4-yl, 4-imidazolyl, benzoimidazol-4-yl, 1-pyrrolyl, 2-pyrrolyl, 3-pyrrolyl, 2-furanyl, 3-furanyl, 2-thienyl, 3-thienyl, 2-pyridyl, 3-pyridyl, 4-pyridyl, 2-pyranyl, 3-pyranyl, 4-pyranyl, 2-pyrimidinyl, 4-pyrimidinyl, 5-pyrimidinyl, pyrid-2-yl, pyrid-3-yl, pyrid-4-yl, pyrid-5-yl, pyrid-6-yl, 3-pyridazinyl, 4-pyridazinyl, 2-pyrazinyl, 1-pyrazolyl, 3-pyrazolyl, 4-pyrazolyl, 1,2,3-triazol-4-yl, 1,2,3-triazol-5-yl, 1,2,4-triazol-3-yl, 1,2,4-triazol-5-yl, 1H-tetrazol-2-yl, 1H-tetrazol-3-yl, tetrazolyl, acridyl, phenazinyl, carbazolyl, phenoxazinyl, indolizine, 2-indolyl, 3-indolyl, 4-indolyl, 5-indolyl, 6-indolyl, 7-indolyl, 1-isoindolyl, 3-isoindolyl, 4-isoindolyl, 5-isoindolyl, 6-isoindolyl, 7-isoindolyl, 2-indolinyl, 3-indolinyl, 4-indolinyl, 5-indolinyl, 6-indolinyl, 7-indolinyl, benzo[b]furanyl, benzofurazane, benzothiofurazane, benzotriazol-1-yl, benzotriazol-4-yl, benzotriazol-5-yl, benzotriazol-6-yl, benzotriazol-7-yl, benzotriazine, benzo[b]thiophenyl, benzimidazolyl, benzothiazolyl, quinazolinyl, quinoxazolinyl, cinnoline, quinolinyl, tetrahydroquinolinyl, isoquinolinyl, or tetrahydroisoquinolinyl, purine, phthalazine, pteridine, thiatetraazaindene, thiatriazaindene, isothiazolopyrazine, 6-pyrimidinyl, 2,4-dimethoxy-6-pyrimidinyl, benzimidazol-2-yl, 1H-benzimidazolyl, benzimidazol-4-yl, benz-imidazol-5-yl, benzimidazol-6-yl, benzimidazol-7-yl, tetrazole, tetrahydrothieno[3,4-d]imidazol-2-one, pyrazolo[5,1-c][1,2,4]triazine, isothiazolopyrimidine, pyrazolotriazine, pyrazolopyrimidine, imidazopyridazine, imidazopyrimidine, imidazopyridine, imidazolotriazine, triazolotriazine, triazolopyridine, triazolopyrazine, triazolopyrimidine, or triazolopyridazine. The heteroaryl groups as defined above, including the groups enumerated as examples and particular embodiments thereof, are optionally substituted by one or more substituents R'.

As used herein, a cycloalkyl group denotes a non-aromatic, mono- or polycyclic completely saturated or partially unsaturated hydrocarbon ring system. Said cycloalkyl is particularly mono- or bicyclic, more particularly monocyclic. Said cycloalkyl is particularly completely saturated. Said cycloalkyl particularly comprises 3 to 10 carbon atoms, more particularly 5 to 7 carbon atoms. Even more particularly, said cycloalkyl is selected from the group comprising cyclopropyl, cyclobutyl, cyclopentyl, cyclohexyl, cycloheptyl, 1-norbornyl, 2-norbornyl, 7-norbornyl, 1-adamantyl, and 2-adamantyl, yet even more particularly said cycloalkyl is cyclohexyl or cyclopropyl. The cycloalkyl groups as defined above, including the groups enumerated as examples and particular embodiments thereof, are optionally substituted by one or more substituents R'.

As used herein, a heterocyclyl group denotes a non-aromatic mono- or polycyclic completely saturated or partially unsaturated hydrocarbon ring system, wherein one or more of the carbon atoms are replaced by a heteroatom independently selected from N, O, or S. Said heterocyclyl is particularly mono- or bicyclic, more particularly monocyclic. Said heterocyclyl is particularly completely saturated. Said heterocyclyl particularly comprises a sum of 5 to 10 carbon and heteroatoms, more particularly a sum of 5 to 7 carbon and heteroatoms, even more particularly a sum of 6 carbon and heteroatoms. Even more particularly said heterocyclyl is selected from the group comprising morpholinyl, piperidinyl, dioxanyl, piperazinyl, thiomorpholinyl, piperidinyl, pyrrolidinyl, tetrahydrofuranyl, isoxazolidinyl, thiomorpholinyl, tetrahydrothiofuranyl and tetrahydropyranyl, more particularly selected from the group comprising morpholinyl, piperidinyl, dioxanyl, piperazinyl, thiomorpholinyl, piperidinyl, and pyrrolidinyl. The heterocyclyl groups as defined above, including the groups enumerated as examples and particular embodiments thereof, are optionally substituted by one or more substituents R'.

As used herein, a halo or halogen group denotes fluorine, chlorine, bromine or iodine; particularly chlorine or fluorine.

As used herein, a haloalkyl group denotes an alkyl group wherein one or more, particularly at least half, more particularly all of the hydrogen atoms on the hydrocarbon chain are replaced by halogen atoms. The haloalkyl group is particularly selected from the group comprising —C($R^{10}$)$_3$, —CH$_2$—C($R^{10}$)$_3$, —C($R^{10}$)$_2$—CH$_3$, —C($R^{10}$)$_2$—C($R^{10}$)$_3$, —C($R^{10}$)$_2$—CH($R^{10}$)$_2$, —CH$_2$—CH($R^{10}$)$_2$, —CH($R^{10}$)—C($R^{10}$)$_3$, —CH($R^{10}$)—CH$_3$, and —C$_2$H$_4$—C($R^{10}$)$_3$, more particularly —C($R^{10}$)$_3$, wherein $R^{10}$, $R^{10'}$ represents halogen, particularly F. More particularly, haloalkyl is —CF$_3$, —CHF$_2$, —CH$_2$CF$_3$, or CF$_2$Cl.

As used herein, an alkoxy group denotes an O-alkyl group, the alkyl group as defined above. The alkoxy group is particularly selected from the group comprising methoxy, ethoxy and propoxy, more particularly methoxy.

As used herein, alkylthio group denotes an —S-alkyl group, the alkyl group as defined above, particularly methylthio.

As used herein, a haloalkoxy group denotes an O-haloalkyl group, haloalkyl group being defined as defined above. The haloalkoxy group is particularly selected from the group comprising —OC($R^{10}$)$_3$, —OCR$^{10}$($R^{10'}$)$_2$, —OCH$_2$—C($R^{10}$)$_3$, and —OC$_2$H$_4$—C($R^{10}$)$_3$, wherein $R^{10}$, $R^{10'}$ represent F, Cl, Br or I, particularly F.

An alkylamino group is an NH-alkyl or N-dialkyl group, the alkyl group as defined above, particularly mono- or dimethylamino, mono- or diethylamino or isopropylamino, more particularly dimethylamino.

An arylalkyl or aralkyl group denotes a linear or branched C1-C6-alkyl as defined herein substituted with at least one aryl group as defined herein. Exemplary arylalkyl groups include styryl, benzyl, phenylethyl, 1-(naphthalen-2-yl) ethyl, particularly the arylalkyl group is styryl or 1-(naphthalen-2-yl)ethyl, wherein styryl is particularly optionally substituted at its phenyl part as defined above for the aryl group. In other particular embodiments, the arylalkyl group is benzyl, styryl or 1-(naphthalen-2-yl)ethyl.

R' is independently selected from the group comprising halogen, $C_{1-6}$-alkyl, $C_{1-6}$-haloalkyl, $C_{1-6}$-haloalkoxy, OH, $C_{1-6}$-alkoxy, aryl, heteroaryl, cycloalkyl, heterocyclyl, —S—$C_{1-6}$-alkyl, —S—$C_{1-6}$-haloalkyl, nitro, —$NH_2$, —N($C_{1-6}$-alkyl)$_2$, —NH($C_{1-6}$-alkyl), —NHCO($C_{1-6}$-alkyl), —$CONH_2$, —CONH($C_{1-6}$-alkyl), —CO($C_{1-6}$-alkyl), —COH, —COO($C_{1-6}$-alkyl), —COOH, —$SO_2NH_2$, —$SO_2$NH($C_{1-6}$-alkyl), —$SO_2$($C_{1-6}$-alkyl), and —CN, particularly selected from the group comprising F, Cl, $C_{1-3}$-alkyl, $C_{1-3}$-haloalkyl, $C_{1-3}$-haloalkoxy, OH, $C_{1-3}$-alkoxy, phenyl, pyridyl, pyrrolyl, thiophenyl, furanyl, cyclopentyl, cyclohexyl, piperidinyl, piperazinyl, tetrahydrofuranyl, morpholinyl, —S—$C_{1-3}$-alkyl, —S—$C_{1-3}$-haloalkyl, nitro, —$NH_2$, —N($C_{1-3}$-alkyl)$_2$, —NH($C_{1-3}$-alkyl), —NHCO ($C_{1-3}$-alkyl), —$CONH_2$, —CONH($C_{1-3}$-alkyl), —CO($C_{1-3}$-alkyl), —COH, —COO($C_{1-3}$-alkyl), —COOH, —$SO_2NH_2$, —$SO_2$NH($C_{1-3}$-alkyl), —$SO_2$($C_{1-3}$-alkyl), and —CN, more particularly selected from the group comprising F, Cl, methyl, ethyl, isopropyl, trifluoromethyl, trifluoromethoxy, OH, methoxy, methylsulfanyl, trifluoromethylsulfanyl, nitro, —$NH_2$, dimethylamino, diethylamino, diisopropylamino, methylamino, ethylamino, isopropylamino, —NHCO-methyl, —$CONH_2$, —CONH-methyl, —CONH-ethyl, —CO-methyl, —CO— ethyl, —COO-methyl, —COO-ethyl, —COOH, —$SO_2NH_2$, —$SO_2$NH-methyl, —$SO_2$-methyl, —$SO_2$NH-ethyl, —$SO_2$-ethyl, and —CN, even more particularly selected from the group comprising F, Cl, methyl, ethyl, isopropyl, trifluoromethyl, trifluoromethoxy, OH, methoxy, nitro, —$NH_2$, dimethylamino, diethylamino, methylamino, ethylamino, —$CONH_2$, —COO— methyl, —COO-ethyl, —COOH, and —CN, yet even more particularly selected from the group comprising F, Cl, methyl, trifluoromethyl, trifluoromethoxy, OH, methoxy, nitro, —$NH_2$, and —CN, most particularly selected from the group comprising F, Cl, methyl, trifluoromethyl, trifluoromethoxy, OH, and methoxy. Particularly, R' is not substituted by further groups.

Where chemically feasible from the viewpoint of molecule stability and/or chemical valence rules, a nitrogen heteroatom as defined herein, e.g. in the context of "heteroaryl" and "heterocycle", may include the N-oxide.

Where chemically feasible from the viewpoint of molecule stability under physiological conditions and/or chemical valence rules, the definition of a sulfur heteroatom as defined herein, e.g. in the context of "heteroaryl" and "heterocycle", may include the sulfur oxide and/or the sulfur dioxide, respectively.

As used herein the term "substituted with" or "substituted by" means that one or more hydrogen atoms connected to a carbon atom or heteroatom of a chemical group or entity are exchanged with a substituent group, respectively; e.g. substituted aryl comprises 4-hydroxyphenyl, wherein the H-atom in the 4-position of the phenyl group is exchanged with a hydroxyl group. Said hydrogen atom(s) to be replaced may be attached to a carbon atom or heteroatom, and may be expressedly shown in a specific formula, such as for example in an —NH— group, or may not expressedly be shown but intrinsically be present, such as for example in the typical "chain" notation which is commonly used to symbolize e.g. hydrocarbons. The skilled person will readily understand that particularly such substituents or substituent patterns are excluded, which lead to compounds which are not stable and/or not accessible via the synthesis methods known in the art.

As used herein, the term "central moiety" means the N-(2,2-difluoro-5H-[1,3]dioxolo[4',5':4,5]benzo[1,2-d]imidazol-6-yl) part of the molecule which is shown in the below graphic representation.

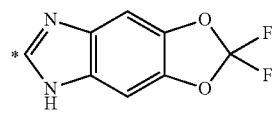 [SMILES: FC1(F)Oc2cc3nc[nH]c3cc2O1]

Unless specified otherwise, references to the compounds according to the present invention include the pharmaceutically acceptable derivatives, solvates or salts thereof as described herein, as well as to salts of said pharmaceutically acceptable derivatives, solvates of salts and pharmaceutically acceptable derivatives, and optionally solvates of salts of pharmaceutically acceptable derivatives.

As used herein, the term "pharmaceutically acceptable derivative" of a compound according to the present invention is for instance a prodrug of said compound, wherein at least one of the following groups are derivatized as specified in the following: A carboxylic acid group is derivatized into an ester, a hydroxyl group is derivatized into an ester, a carboxylic acid is derivatized into an amide, an amine is derivatized into an amide, a hydroxyl group is derivatized into a phosphate ester.

As used herein, the term "tautomer" used in reference to the compounds according to the present invention, in particular includes tautomers that typically form with respect to substituted benzimidazol groups. As an illustration two tautomeric forms of an exemplary substituted benzimidazol moiety, as is present in the compounds according to the present invention, are shown:

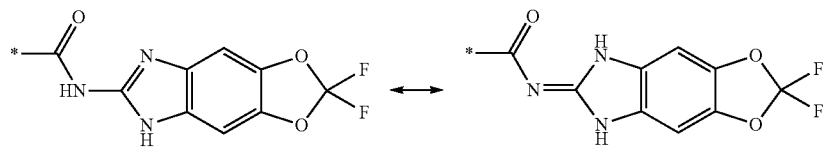 [SMILES: *C(=O)Nc1nc2cc3c(cc2[nH]1)OC(F)(F)O3 ; *C(=O)N=c1[nH]c2cc3c(cc2[nH]1)OC(F)(F)O3]

The compounds according to the present invention are to be understood to comprise all tautomeric forms thereof, even if not expressedly shown in the formulae described herein, including Formulae (I) and (Ia). Throughout this specification, whenever a chemical formula, generic or otherwise, discloses a compound having a 1H-benzimidazole moiety that is unsubstituted at the 1 position, as shown on the left-hand side of the above exemplary illustration, said chemical formula it is to be understood to implicitly also relate to compounds wherein the benzimidazole moiety is tautomerized to form the structure as shown on the right-hand side of the above exemplary illustration.

The compounds of Formulae (I) and (Ia) as defined herein are to be understood to encompass, where applicable, all stereoisomers of said compounds, unless specified otherwise. The term "stereoisomer" as used herein refers to a compound with at least one stereogenic centre, which may be R- or S-configured, as defined by the according IUPAC rules, and encompasses enantiomers and diastereomers as commonly understood by the skilled person. It has to be understood, that in compounds with more than one stereogenic centre, each of the individual stereogenic centres may independently from each other be R- or S-configured. The term "stereoisomer" as used herein also refers to salts of the compounds herein described with optically active acids or bases.

In the present invention, the salts of the compounds according to the present invention are particularly pharmaceutically acceptable salts of the compounds according to the present invention. Pharmaceutically acceptable salts are such salts which are usually considered by the skilled person to be suitable for medical applications, e.g. because they are not harmful to subjects which may be treated with said salts, or which give rise to side effects which are tolerable within the respective treatment. Usually, said pharmaceutically acceptable salts are such salts which are considered as acceptable by the regulatory authorities, such as the US Food and Drug Administration (FDA), the European Medicines Agency (EMA), or the Japanese Ministry of Health, Labor and Welfare Pharmaceuticals and Medical Devices Agency (PMDA). However, the present invention in principle also encompasses salts of the compounds according to the present invention which are as such not pharmaceutically acceptable, e.g. as intermediates in the production of the compounds according to the present invention or physiologically functional derivatives thereof, or as intermediates in the production pharmacologically acceptable salts of the compounds according to the present invention or physiologically functional derivatives thereof.

In each case, the skilled person can readily determine whether a certain compound according to the present invention or pharmaceutically acceptable derivative thereof can form a salt, i.e. whether said compound according to the present invention or pharmaceutically acceptable derivative thereof has a group which may carry a charge, such as e.g. an amino group, a carboxylic acid group, etc.

Exemplary salts of the compounds of the present invention are acid addition salts or salts with bases, particularly pharmacologically tolerable inorganic and organic acids and bases customarily used in pharmacy, which are either water insoluble or, particularly, water-soluble acid addition salts. Salts with bases may—depending on the substituents of the compounds of the present invention—also be suitable.

Pharmacologically intolerable salts, which can be obtained, for example, as process products during the preparation of the compounds according to the invention on an industrial scale, are also encompassed by the present invention and, if desired, may be converted into pharmacologically tolerable salts by processes known to the person skilled in the art.

According to expert's knowledge the compounds of the invention as well as their salts may contain, e.g. when isolated in crystalline form, varying amounts of solvents. Included within the scope of the invention are therefore solvates and in particular hydrates of the compounds of the present invention as well as solvates and in particular hydrates of the salts and/or physiologically functional derivatives of the compounds of the present invention. More particularly the invention encompasses hydrates of the compounds, salts and/or physiologically functional derivatives according to the present invention, comprising one, two or one half water molecule, with respect to their stoichiometry.

As used herein, the term "room temperature", "rt" or "r.t." relates to a temperature of about 25° C., unless specified otherwise.

As used herein, the term "stable" specifies a compound in which the chemical structure is not altered when the compound is stored at a temperature from about −80° C. to about +40° C., particularly from about −80° C. to +25° C. in the absence of light, moisture or other chemically reactive conditions for at least one week, particularly at least one month, more particularly at least six months, even more particularly, at least one year, and/or a compound which under IUPAC standard conditions and in the absence of light, moisture or other chemically reactive conditions maintains its structural integrity long enough to be useful for therapeutic or prophylactic administration to a patient, i.e. at least one week. Compounds which are not stable as described above are particularly not encompassed by the present invention. In particular, such compounds which at IUPAC standard conditions spontaneously decompose within a period of less then one day are regarded as not being stable compounds. The skilled person will readily recognize, based on his general knowledge in his field of expertise, which compounds and which substitution patterns result in stable compounds.

As used herein, the term "treatment" includes complete or partial healing of a disease, prevention of a disease, alleviation of a disease or stop of progression of a given disease.

As used herein, the term "medicament" includes the compounds of formula (I) as described herein, pharmacologically acceptable salts or physiologically functional derivatives thereof, which are to be administered to a subject in pure form, as well as compositions comprising at least one compound according to the present invention, a pharmacologically acceptable salt or physiologically functional derivative thereof, which is suitable for administration to a subject.

The compounds according to the present invention and their pharmacologically acceptable salts and physiologically functional derivatives can be administered to animals, particularly to mammals, and in particular to humans as therapeutics per se, as mixtures with one another or particularly in the form of pharmaceutical preparations or compositions which allow enteral (e.g. oral) or parenteral administration and which comprise as active constituent a therapeutically effective amount of at least one compound according to the present invention, or a salt or physiologically functional derivative thereof, in addition to e.g. one or more components selected from the group comprising customary adjuvants, pharmaceutically innocuous excipients, carriers, buffers, diluents, and/or other customary pharmaceutical auxiliaries.

The pharmaceutical compositions, medical uses and methods of treatment according to the present invention may comprise the more than one compound according to the present invention.

Pharmaceutical compositions comprising a compound according to the present invention, or a pharmaceutically acceptable salt or physiologically functional derivative may optionally comprise one or more further therapeutically active substances which are not compounds of formula (I) according to the present invention. As used herein, the term "therapeutically active substance" specifies a substance which upon administration can induce a medical effect in a subject. Said medical effect may include the medical effect described herein for the compounds of formula (I) of the present invention, but may also, in the case of therapeutically active substances which are to be co-administered with the compounds according to the present invention, include other medical substances, such as for example but not exclusively irinotecan, oxaliplatin, capecitabine, 5-fluorouracil, cetuximab (Erbitux), panitumumab (Vectibix), bevacizumab (Avastin), vincristine, vinblastine, vinorelbine, vindesine, taxol, amsacrine, etoposide, etoposide phosphate, Teniposide, actinomycin, anthracyclines, doxorubicin, valrubicin, valrubicin, idarubicin, epirubicin, bleomycin, plicamycin, mitomycin, mechlorethamine, cyclophosphamide, chlorambucil, ifosfamide and other kinase inhibitors.

The term "pharmaceutically acceptable" is well known to the skilled person and particularly means that the respective entity is not harmful to the subject to which the entity or the composition comprising the entity is administered, that said entity is stable and that said entity is chemically compatible (i.e. non-reactive) with other ingredients of the respective pharmaceutical composition.

Medicaments and pharmaceutical compositions according to the present invention, comprising at least one compound according to the present invention or a pharmacologically acceptable salt or a physiologically functional derivative thereof include those suitable for oral, rectal, bronchial, nasal, topical, buccal, sub-lingual, vaginal or parenteral (including transdermal, subcutaneous, intramuscular, intrapulmonary, intravascular, intracranial, intraperitoneal, intravenous, intraarterial, intracerebral, intraocular injection or infusion) administration, or those in a form suitable for administration by inhalation or insufflation, including powders and liquid aerosol administration, or by controlled release (e.g. sustained release, pH-controlled release, delayed, release, repeat action release, prolonged release, extended release) systems. Suitable examples of controlled release systems include semipermeable matrices of solid hydrophobic polymers containing the compound of the invention, which matrices may be in form of shaped articles, e.g. films or microcapsules or colloidal drug carriers e.g. polymeric nanoparticles, or controlled release solid dosage forms, e.g. core tablets or multi-layer tablets.

The production of medicaments or pharmaceutical compositions comprising the compounds according to the present invention and their application can be performed according to methods which are well-known to the medical practitioner.

Pharmaceutically acceptable carriers used in the preparation of a pharmaceutical composition or medicament comprising a compound according to the present invention, a pharmacologically acceptable salt or physiologically functional derivative thereof, can be either solid or liquid. Solid form pharmaceutical compositions comprising a compound according to the present invention, a pharmacologically acceptable salt or physiologically functional derivative thereof, include powders, tablets, pills, capsules, sachets, suppositories, and dispersible granules. A solid carrier may comprise one or more components, which may also act as diluents, flavouring agents, solubilizers, lubricants, suspending agents, binders, preservatives, tablet disintegrating agents, or an encapsulating material.

In powders, the carrier is a finely divided solid, which is in a mixture with the finely divided active component. In tablets, the active component is mixed with the carrier having the necessary binding capacity in suitable proportions and compacted in the shape and size desired. The tabletting mixture can be granulated, sieved and compressed or direct compressed. Suitable carriers are magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, sachets and lozenges are included. Tablets, powders, capsules, pills, sachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into conveniently sized moulds, allowed to cool, and thereby to solidify. Compositions suitable for vaginal administration may be presented as peccaries, tampons, creams, gels, pastes, foams or sprays containing in addition to the active ingredient such carriers as are known in the art to be appropriate. Liquid preparations include solutions, suspensions, and emulsions, for example, water or water-propylene glycol solutions. For example, parenteral injection liquid preparations can be formulated as solutions in aqueous polyethylene glycol solution.

The compounds according to the present invention may be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilizing and/or dispersing agents. Alternatively, the active ingredient may be in powder form, obtained by aseptic isolation of sterile solid or by lyophilization from solution, for re-constitution with a suitable vehicle, e.g. sterile, pyrogen-free water, before use.

Aqueous solutions suitable for oral administration can be prepared by dissolving the active component in water and adding for example suitable colorants, flavours, stabilizing and thickening agents, as desired. Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations, which are intended to be converted, shortly before administration, to liquid form preparations for oral administration. Such liquid forms include solutions, suspensions, and emulsions. These preparations may contain, in addition to the active component, for example colorants, flavours, stabilizers, buffers, artificial and natural sweeteners, dispersants, thickeners, solubilizing agents, and the like.

In an embodiment of the present invention the medicament is applied topically, e.g. in the form of transdermal therapeutic systems (e.g. patches) or topical formulations (e.g. liposomes, crèmes, ointment, lotion, gels, dispersion, suspension, spray, solution, foam, powder). This may be suitable to reduce possible side effects and, where appropriate, limit the necessary treatment to those areas affected.

Particularly the medicament may comprise carrier materials or excipients, including but not limited to a lipophilic phase (as for example Vaseline, paraffins, triglycerides, waxes, polyalkylsiloxanes), oils (olive oil, peanut oil, castor oil, triglyceride oil), emulsifier (as for example lecithin, phosphatidylglycerols, alkyl alcohols, sodium lauryl sulfate, polysorbates, Cholesterol, sorbitan fatty acid ester, polyoxyethylene fatty acid glycerol and -ester, poloxamers), preservatives (for instance benzalkonium chloride, chlorobutanol, parabene or thiomersal), flavouring agents, buffer substances (for example salts of acetic acid, citric acid, boric acid, phosphoric acid, tatric acid, trometamole or trolamine), solvents (for instance polyethyleneglycols, glycerol, ethanol, isopropanol or propyleneglycol) or solubilizers, agents for achieving a depot effect, salts for modifying the osmotic pressure, carrier materials for patches (for instance polypropylene, ethylene-vinylacetat-copolymer, polyacrylates, silicon) or antioxidants (for example ascorbate, tocopherol, butylhydroxyanisole, gallic acid esters or butylhydroxytoluol).

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatine and glycerine or sucrose and acacia; and mouthwashes comprising the active ingredient in a suitable liquid carrier.

Solutions or suspensions may be applied directly to the nasal cavity by conventional means, for example with a dropper, pipette or spray. The compositions may be provided in single or multi-dose form. In the latter case of a dropper or pipette, this may be achieved by the patient administering an appropriate, predetermined volume of the solution or suspension. In the case of a spray, this may be achieved for example by means of a metering atomizing spray pump.

Administration to the respiratory tract may also be achieved by means of an aerosol formulation in which the active ingredient is provided in a pressurized pack with a suitable propellant such as a chlorofluorocarbon (CFC), for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the medicament may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form, for example in capsules or cartridges of, e.g., gelatine, or blister packs from which the powder may be administered by means of an inhaler.

In compositions for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are particularly in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, sachet, or lozenge itself, or it can be the appropriate number of any of these in packaged form. Tablets or capsules for oral administration and liquids for intravenous administration and continuous infusion are particular compositions.

Further details on techniques for formulation and administration may be found in the 21$^{St}$ edition of Remington's Pharmaceutical Sciences (Maack Publishing Co. Easton, Pa.).

The compounds of the present invention may be used in combination with radiation therapy, or in combination with radiation therapy and other active compounds, already known for the treatment of the medical conditions disclosed herein, whereby a favourable additive or amplifying effect is noticed.

To prepare the pharmaceutical preparations, pharmaceutically inert inorganic or organic excipients can be used. To prepare pills, tablets, coated tablets and hard gelatine capsules, for example, lactose, cornstarch or derivatives thereof, talc, stearic acid or its salts, etc. can be used. Excipients for soft gelatine capsules and suppositories are, for example, fats, waxes, semi-solid and liquid polyols, natural or hardened oils etc. Suitable excipients for the production of solutions and syrups are, for example, water, sucrose, invert sugar, glucose, polyols etc. Suitable excipients for the production of injection solutions are, for example, water, alcohols, glycerol, polyols or vegetable oils.

The dose can vary within wide limits and is to be suited to the individual conditions in each individual case. For the above uses the appropriate dosage will vary depending on the mode of administration, the particular condition to be treated and the effect desired. In general, however, satisfactory results are achieved at dosage rates of about 1 to 100 mg/kg animal body weight particularly 1 to 50 mg/kg. Suitable dosage rates for larger mammals, for example humans, are of the order of from about 10 mg to 3 g/day, conveniently administered once, in divided doses 2 to 4 times a day, or in sustained release form.

The compounds of the present invention are suitable for the treatment of inflammatory disorders and hyperproliferative diseases, such as benign and malignant forms of neoplasia, including cancer.

Exemplary types of cancer in the context of the present invention are hepatocarcinoma, adrenocortical carcinoma, AIDS-related cancers including AIDS-related lymphoma, anal cancer, basal cell carcinoma, bile duct cancer, bone cancer, brain tumors including brain stem glioma, cerebellar astrocytoma, cerebral astrocytoma, malignant glioma, ependymoma, medulloblastoma, supratentorial primitive neuroectodermal tumors, visual pathway and hypothalamic glioma, breast cancer, bronchial adenomas/carcinoids, Burkitt's lymphoma, gastrointestinal, carcinoma of unknown primary site, central nervous system lymphoma, cervical cancer, chronic myeloproliferative disorders, colon cancer, colorectal cancer, cutaneous T-cell lymphoma, endometrial cancer, ependymoma, esophageal cancer, extracranial germ cell tumor, extragonadal germ cell tumor, ovarian germ cell tumor, eye cancer including intraocular melanoma and retinoblastoma, gallbladder cancer, gastrointestinal carcinoid tumor, gestational trophoblastic tumor, glioma, childhood brain stem glioma, head and neck cancer, hematologic cancer, adult and childhood (primary) hepatocellular cancer, hypopharyngeal cancer, islet cell or pancreatic cancer, renal cancer, laryngeal cancer, acute lymphoblastic leukemia, adult and childhood acute myeloid leukemia, chronic lymphocytic leukemia, chronic myelogenous leukemia, hairy cell leukemia, lip and oral cavity cancer, liver cancer, lung cancer, including non-small cell lung cancer and small cell lung cancer, Hodgkin's lymphoma, non-Hodgkin's lymphoma, primary central nervous system lymphoma, Waldenstrom's macroglobulinemia, merkel cell carcinoma, mesothelioma, metastatic squamous neck cancer with occult primary site, multiple endocrine neoplasia syndrome, multiple myeloma/plasma cell neoplasm, mycosis fungoides, myelodysplastic syndromes, myelodysplastic myeloproliferative diseases, multiple myeloma, chronic myeloproliferative disorders, nasal cavity and paranasal sinus cancer, nasopharyngeal cancer, neuroblastoma, oral cancer, oropharyngeal cancer, osteosarcoma/malignant fibrous histiocytoma of bone, ovarian cancer, ovarian epithelial cancer, ovarian low malignant potential tumor, pancreatic cancer, parathyroid cancer, penile cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter cancer, transitional cell cancer, rhabdomyosarcoma, salivary gland cancer, Ewing's sarcoma, Kaposi's sarcoma, soft tissue sarcoma, uterine sarcoma, sezary syndrome, skin cancer, including melanoma and non-melanoma skin cancer, small intestine cancer, squamous cell carcinoma, gastric cancer, supratentorial primitive neuroectodermal tumors, testicular cancer, thymoma, thymoma and thymic carcinoma, thyroid cancer, trophoblastic tumor, gestational, endometrial uterine cancer, uterine sarcoma, vaginal cancer, vulvar cancer, Waldenstrom's macroglobulinemia, Wilms' tumor.

In a more particular embodiment of the present invention, the compounds of the present invention may be used in the treatment of the following cancer types: Prostate, bladder, kidney (i.e. renal), muscle, ovary, skin, lung, pancreas, breast, cervix, colon, liver, connective tissue, placenta, bone, brain, uterus, salivary gland, or testes.

In particular embodiments of the present invention, in said cancer, the hedgehog signaling pathway is activated.

In particular embodiments of the present invention, in cells of said cancer, the hedgehog signaling pathway is activated.

In the present invention patients wherein in said cancer, or in cells of said cancer, the hedgehog signaling pathway is activated are in short referred to as "Hedgehog dependent patients", and patients wherein in said cancer, or in the cells of said cancer, the hedgehog signaling pathway is not activated are in short referred to as "Hedgehog independent patients". In the present invention, patients e.g. can be classified as Hedgehog dependent patients if the cancer said patient is suffering from is described in the known scientific literature as being associated with aberrant Hedgehog signaling pathway activity. In the present invention, patients can also be stratified into Wnt dependent patients and Wnt independent patients by a procedure comprising the steps of
1) providing a sample from said patient, wherein said sample comprises cancer cells from said patient,
2) optionally subjecting said sample to a work-up step,
3) adding a labeled antibody which specifically binds to at least one protein playing a role in the hedgehog signaling pathway,
or
adding a first antibody which specifically binds to at least one protein playing a role in the hedgehog signaling pathway, and subsequently adding a second antibody which specifically binds to said first antibody, and wherein said second antibody is a labeled antibody,
4) washing said sample after step 3,
5) determining whether said labeled antibody is detectable in said sample after step 4),
6) if in step 5) said marker moiety is detectable, classifying said patient as Hedgehog dependent patient, and if in step 5) said marker moiety is not detectable, classifying said patient as Hedgehog independent patient.

Antibodies used in the present invention are typically monoclonal antibodies.

The label in said labeled antibody can be selected from any label typically used as antibody label in the field of biochemistry, cellular biology, immunochemistry, etc., for a label selected from the group comprising a fluorescence label, a dye, a FRET label, a radioactive label. moiety, or an enzymatically active moiety. Said enzymatically active moiety can process a reaction which in turn results in the release of a detectable substance, e.g. a dye.

In the above method of stratifying patients into Hedgehog dependent patients and Hedgehog independent patients, the work-up step is e.g. in particular embodiments selected from the group comprising preservation, embedding, slicing and staining. Preservation can be performed by cryopreservation or fixation by e.g. formaldehyde or ethanol. Embedding the tumor material prepares it for slicing. Staining can be performed with direct or indirect methods. For further information and examples see DOI: 10.1354/vp. 42-4-405 J. A. Ramos-Vara, Technical Aspects of Immunohistochemistry, (2005) 42: 405 Vet Pathol.

In the context of the present invention, the expression "said labeled antibody is detectable" means that by the state of the art measurement methods used for detecting said label, no signal relating to said label is detectable, and/or said signal is not significant in relation to the background noise generated by said measurement method.

In the above method to stratify patients into Hedgehog dependent patients and Hedgehog independent patients, washing step 4 is to remove unbound and/or unspecifically bound antibodies from step 3. In particular embodiments, said washing step comprises washing with a buffer, e.g. a PBS buffer, and optionally a serum protein, e.g. BSA. Washing step 4 can be repeated as necessary to obtain a suitable signal/noise ratio, e.g. 2 or more, 3 or more, 4 or more times.

In certain embodiments of the above method to stratify patients into Hedgehog dependent cancer patients and Hedgehog independent cancer patients, background signal by unspecific binding of antibodies is excluded by an isotype control. This control can be utilized when working with monoclonal primary antibodies. A comparative sample treated as above is incubated with antibody diluent, supplemented with a non-immune immunoglobulin of the same isotype (for example, $IgG_1$, $IgG2_A$, $IgG2_B$, IgM) and concentration as the aforementioned antibody. The sample is then incubated with the labeled antibody and detection reagents. These steps will help ensure that what appears to be specific staining was not caused by non-specific interactions of immunoglobulin molecules with the sample. Examples and a further description of this method can be found in "Tissue Microarrays—Methods in Molecular Biology Volume 664, 2010, pp 113-126, Immunohistochemical Analysis of Tissue Microarrays; Ronald Simon, Martina Mirlacher, and Guido Sauter".

In the context of the present invention the G protein-coupled receptor Smoothened is interchangeably abbreviated as "Smoothened" and "Smo".

In the context of the present invention the expression "the activation of the hedgehog signaling pathway" in particular refers to the activation of expression of primary target genes of the Hedgehog signaling pathway, including GLI, HHIP, Ptch, more particularly of GLI expression via the hedgehog pathway. Typically, GLI expression is triggered via binding of hedgehog to the Smo/Ptch (Smoothened/Patched) complex and thereupon GLI expression via signalling by Smo.

In the context of the present invention said at least one protein playing a role in the hedgehog signaling pathway can e.g. be selected from the group comprising Patched, GLI, Smoothened, HHIP, Hedgehog and SUFU.

In the context of the present invention, the term "GLI" refers to members of the GLI protein family, such as GLI1, GLI2, GLI3 in particular embodiments and, unless specified otherwise particularly to GLI1.

In general, and unless specified otherwise, the proteins, genes and/or gene expression products as defined herein in certain embodiments also include variants of said proteins, genes and gene expression products, such as isoforms, homologs and mutants thereof, which share at least 95% sequence homology, more particularly at least 97% sequence homology, even more particularly at least 99% sequence homology with, the proteins, genes and/or gene expression products as defined herein, and in the case of proteins and/or gene expression products in certain embodiments have essentially the same enzymatic activity as, the proteins and/or gene expression products as defined herein, wherein however the enzymatic activity of said variants may differ (i.e. be higher or lower than) from the proteins, and/or gene expression products as defined herein by up to two orders of magnitude, particularly up to one order of magnitude, more particularly up to a factor of 2.

As used herein, the term "hedgehog signaling pathway" means a cellular signaling pathway comprising an interaction with a protein of the family known as hedgehog proteins, such as e.g. the proteins commonly known as "sonic hedgehog" (UniProtKB/Swiss-Prot: Q15465), "indian hedgehog" (UniProtKB/Swiss-Prot: Q14623) and "desert hedgehog" (UniProtKB/Swiss-Prot: O43323) (Ingham and McMahon, 2001).

As used herein, the term "sample" in principle comprises samples from natural sources, such as a sample obtainable from a mammal, and artificial samples, which are obtainable by admixing several ingredients, wherein said ingredients may or may not be derived from natural sources, and may e.g. comprise ingredients selected from the group comprising synthetic and/or natural proteins, peptides, oligo- or polynucleic acids, etc. In certain embodiments, samples are from natural sources, which include bodily fluids and/or tissue samples, such as bodily fluid and/or a tissue sample obtainable from mammals. Said samples from natural sources can be used in the present invention with or without further processing after being obtained from their source, e.g. a mammal. Such processing can for instance comprise separation, fractionation, dilution, dispersion, mechanical treatment such as sonification, or grinding, concentration, removal of certain components of said sample, or addition of compounds, such as salts, buffers, detergents, etc.

As used herein, the term "bodily fluid" or "body fluid" specifies a fluid or part of a fluid originating from the body of a patient, including fluids that are excreted or secreted from the body of the patient, including but not limited to blood, including peripheral blood, serum, plasma, urine, interstitial fluid, liquor, aqueous humour and vitreous humour, bile, breast milk, cerebrospinal fluid, endolymph, perilymph, ejaculate, gastric juice, mucus, peritoneal fluid, pleural fluid, saliva, sweat, tears and vaginal secretion, particularly peripheral blood, serum, plasma and urine. Said bodily fluid itself may or may not comprise diseased and/or non-diseased cells.

As used herein, the term "tissue sample" specifies a non-fluid material or solid originating from the body of a patient. Tissue samples include, but are not limited to samples of bone material, bone marrow, skin, hair follicle, mucosa, brain, cartilage, muscles, lung, kidney, stomach, intestines, bladder and liver. Said tissue sample itself may or may not comprise diseased cells, and may for instance be a sample taken from a diseased region of a patient's body, such as a biopsy of a tumor. In certain embodiments the tissue sample is selected from skin, hair follicle or oral mucosa.

In the embodiments of the present invention, the sample is obtained from the patient by any method and/or means commonly known to the skilled person in the field of medicine, e.g. in certain embodiments blood sample taking by venipuncture.

As used herein, the term "peripheral blood" specifies blood obtained from the circulation remote from the heart, i.e. the blood in the systemic circulation, as for example blood from acral areas.

As used herein, the term "whole blood" specifies unmodified blood comprising cells and fluid, as obtained from the donor of said blood, such as a patient.

As used herein, the term "small molecule" is to be understood as commonly used in the field of pharmacology and means a low molecular weight organic compound which is not a polymer, and which usually has a molecular weight of about 800 Daltons or lower, particularly, 700 Daltons or lower, more particularly 600 Daltons or lower, even more particularly 500 Daltons or lower. From a functional point of view, a small molecule has to molecular weight which allows the molecule to rapidly diffuse across cell membranes and/or reach the interior of a mammalian cell.

In particular embodiments of the present invention, in said cancer, the Wnt signaling pathway is activated.

In particular embodiments of the present invention, in cells of said cancer, the Wnt signaling pathway is activated.

Multiple cancer types are associated with aberrant Wnt signaling pathway activity. As reviewed by Anastas and Moon (Nature Reviews Cancer, 2013, January, p. 11-26) hematological and solid tumors including AML, ALL, Breast cancer, Adrenocortical cancer, Colorectal Cancer, Oesophageal carcinoma, Gastric Cancer, Glioblastoma, Lung Cancer, Prostate Cancer, Melanoma, HCC, Sarcoma, Ovarian carcinoma, Pancreatic Cancer exhibit an aberrant Wnt signaling pathway.

In the present invention patients wherein in said cancer, or in cells of said cancer, the Wnt signaling pathway is activated are in short referred to as "Wnt dependent patients", and patients wherein in said cancer, or in the cells of said cancer, the Wnt signaling pathway is not activated are in short referred to as "Wnt independent patients". In the present invention, patients e.g. can be classified as Wnt dependent patients if the cancer said patient is suffering from is described in the known scientific literature as being associated with aberrant Wnt signaling pathway activity, such as e.g. the cancer types described above by Anastas and Moon. In the present invention, patients can also be stratified into Wnt dependent patients and Wnt independent patients by by a procedure comprising the steps of
1) providing a sample from said patient, wherein said sample comprises cancer cells from said patient,
2) optionally subjecting said sample to a work-up step,
3) adding a labeled antibody which specifically binds to at least one protein playing a role in the Wnt signaling pathway,
   or
   adding a first antibody which specifically binds to at least one protein playing a role in the Wnt signaling pathway, and subsequently adding a second antibody which specifically binds to said first antibody, and wherein said second antibody is a labeled antibody,
4) washing said sample after step 3,
5) determining whether said labeled antibody is detectable in said sample after step 4),
6) if in step 5) said marker moiety is detectable, classifying said patient as Wnt dependent patient, and if in step 5) said marker moiety is not detectable, classifying said patient as Wnt independent patient.

Said patients can further be stratified into Wnt dependent patients and Wnt independent patients by determining by providing a sample comprising cancer cells of said patient, culturing said cancer cells in growth medium and comparing whether growth of said cancer cells can be inhibited by a known Wnt inhibitor, as compared to a control group of said cancer cells which is not treated said Wnt inhibitor.

The label in said labeled antibody can be selected from any label typically used as antibody label in the field of biochemistry, cellular biology, immunochemistry, etc., for a label selected from the group comprising a fluorescence label, a dye, a FRET label, a radioactive label. moiety, or an enzymatically active moiety. Said enzymatically active moiety can process a reaction which in turn results in the release of a detectable substance, e.g. a dye.

In the above method of stratifying patients into Wnt dependent patients and Wnt independent patients, the work-up step is e.g. in particular embodiments selected from the group comprising preservation, embedding, slicing and staining. Preservation can be performed by cryopreservation or fixation by e.g. formaldehyde or ethanol. Embedding the tumor material prepares it for slicing. Staining can be performed with direct or indirect methods. For further information and examples see DOI: 10.1354/vp. 42-4-405 J. A. Ramos-Vara, Technical Aspects of Immunohistochemistry, (2005) 42: 405 Vet Pathol.

In the above method to stratify patients into Wnt dependent patients and Wnt independent patients, washing step 4 is to remove unbound and/or unspecifically bound antibodies from step 3. In particular embodiments, said washing step comprises washing with a buffer, e.g. a PBS buffer, and optionally a serum protein, e.g. BSA. Washing step 4 can be repeated as necessary to obtain a suitable signal/noise ratio, e.g. 2 or more, 3 or more, 4 or more times.

In certain embodiments of the above method to stratify patients into Wnt dependent cancer patients and Wnt independent cancer patients, background signal by unspecific binding of antibodies is excluded by an isotype control. This control can be utilized when working with monoclonal primary antibodies. A comparative sample treated as above is incubated with antibody diluent, supplemented with a non-immune immunoglobulin of the same isotype (for example, $IgG_1$, $IgG2_A$, $IgG2_B$, IgM) and concentration as the aforementioned antibody. The sample is then incubated with the labeled antibody and detection reagents. These steps will help ensure that what appears to be specific staining was not caused by non-specific interactions of immunoglobulin molecules with the sample. Examples and a further description of this method can be found in "Tissue Microarrays—Methods in Molecular Biology Volume 664, 2010, pp 113-126, Immunohistochemical Analysis of Tissue Microarrays; Ronald Simon, Martina Mirlacher, and Guido Sauter".

In the context of the present invention the expression "the activation of the Wnt signaling pathway" in particular refers to the activation of expression of primary target genes of the Wnt signaling pathway, e.g. selected from the group comprising c-myc, Cyclin D, TCF1, LEF1, PPARdelta, c-jun, fra-1, MMP7, Axin2, ITF-2, CD44, BMP4, Survivin, VEGF, FGF18, FGF9, FGF20, Jagged, DKK1, LGR5, SOX2, SOX9, and OCT4.

In the context of the present invention said at least one protein playing a role in the Wnt signaling pathway can e.g. be selected from the group comprising Frizzled receptors (particularly FZD4, 5, 6, 7, ROR1, ROR2), Wnt ligands (particularly WNT1, 2, 3A, 5A, 7A), Wnt inhibitory factors (particularly WIF1), secreted frizzled-related proteins (particularly SFRP3, 4), nuclear β-Catenin, and TCF/LEF family members (particularly LEF1, TCF7L2).

As used herein, the term "Wnt signaling pathway" means a cellular signaling pathway comprising an interaction with a protein of the family known as Wnt proteins (UniProtKB/Swiss-Prot: e.g. P56704, O00755, Q9GZT5, O00744, Q93098, P41221, Q93097, O14905, O14904, Q9UBV4, O96014, Q9H1J7, P56706, Q9Y6F9, Q9H1J5, P56705, P56703, P09544, or P04628).

General Synthesis Procedure.

In the following description of the synthesis procedures for compounds of the present invention, which are exemplified for the amides of Formula (Ia), the residues X, L and Y, where present, have the meaning as defined above.

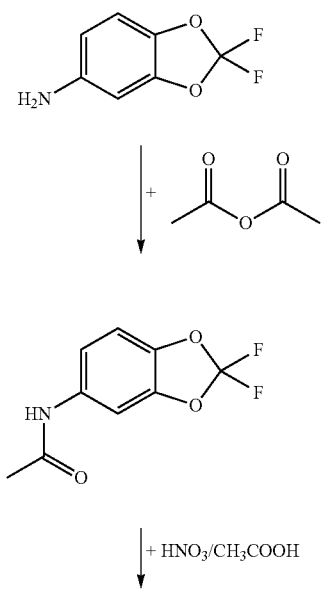

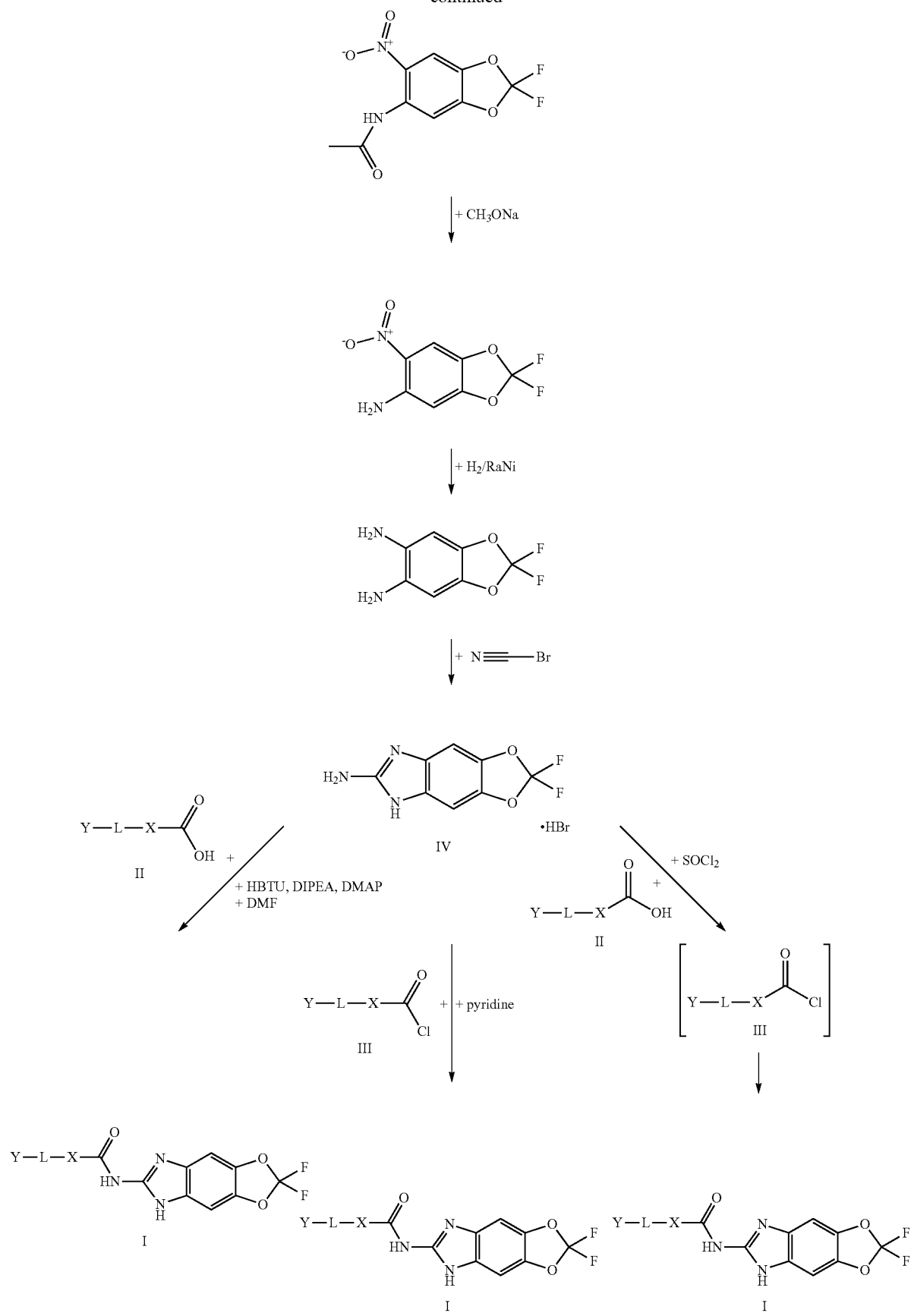

Examples

1. Synthesis of Precursors

1.1 Synthesis of N-(2,2-difluorobenzo[d][1,3]dioxol-5-yl)acetamide

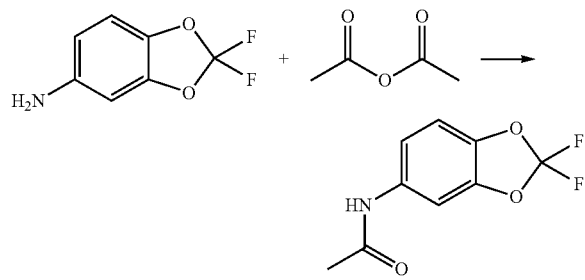

A solution of 5-Amino-2,2-difluoro-1,3-benzodioxole (26.0 g, 150.186 mmol) in dry toluene (410 ml) and acetic anhydride (16.2 ml, 1.15 eq.) was stirred at 100° C. for 2 h.

Subsequently, the solvent was removed under reduced pressure. The crude product was dissolved in 100 ml methanol to remove traces of acetic anhydride. The solvent was subsequently evaporated. The obtained crude product was recrystallized from toluene. The obtained product was filtered off and dried under high vacuo to obtain greyish-beige crystals (30.5 g, 92.5% yield, 98% purity).

$^1$H NMR (DMSO-$d_6$+CCl$_4$): 2.04 (3H, s, CH$_3$), 7.20-7.23 (1H, dd, CH-arom.), 7.30-7.33 (1H, s, CH-arom.), 7.74-7.75 (1H, d, CH-arom.), 10.12 (1H, s, NH).

1.2 Synthesis of N-(2,2-difluoro-6-nitrobenzo[d][1,3]dioxol-5-yl)acetamide

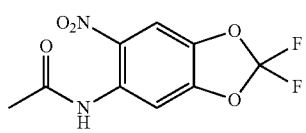 [SMILES: CC(=O)Nc1cc2c(cc1[N+](=O)[O-])OC(F)(F)O2]

N-(2,2-difluorobenzo[d][1,3]dioxol-5-yl)acetamide (11.39 g, 52.938 mmol) was dissolved in glacial acetic acid (50.4 ml). To the resulting mixture was added dropwise a mixture of fuming nitric acid (6.1 ml, 3.35 eq.) in glacial acetic acid (20.2 ml, 0.28 eq.). After addition, the reaction mixture was stirred for 22 h at room temperature. The reaction mixture was stirred at 60° C. overnight.

Subsequently, the reaction mixture was poured into a of ice and water mixture. The resulting precipitate was filtered off by suction filtration. The crude product was then purified by column chromatography on a silica gel flash column (eluent DCM:MeOH 95:5). The product was isolated and concentrated in vacuo to obtain a yellow solid (6.7 g, 49% yield, 100% purity).

$^1$H NMR (DMSO-$d_6$+CCl$_4$): 2.09 (3H, s, CH$_3$), 7.76 (1H, s, CH-arom.), 8.15 (1H, s, CH-arom.), 10.33 (1H, s, NH).

1.3 Synthesis of 2,2-difluoro-6-nitrobenzo[d][1,3]dioxol-5-amine

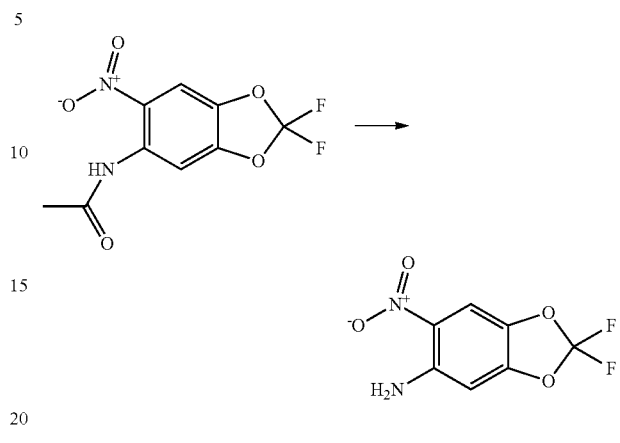

N-(2,2-difluoro-6-nitrobenzo[d][1,3]dioxol-5-yl)acetamide (6.76 g, 25.985 mmol) was dissolved in methanol (676 ml). The reaction mixture was cooled to 0° C. Then sodium methylate (ca. 25% in methanol) (30.3 ml, 5 eq.) was added and the resulting mixture was stirred for 20 min at 0° C. and subsequently for 25 min at 5° C. The reaction was then interrupted by adding glacial acetic acid (37.2 ml, 25 eq.).

The solvent was removed under reduced pressure, whereupon a liquid-oily residue formed. The last traces of solvent, together with the remaining glacial acetic acid, were removed by a two-fold co-evaporation with toluene. Upon addition of toluene, a white solid precipitated, which was filtered off by suction filtration. The filtrate was concentrated in vacuo and dried under reduced pressure. The crude product was purified by column chromatography on a silica gel flash column (eluent DCM:MeOH 95:5). The first spot as observed by thin layer chromatography under the same eluent conditions was isolated and the fractions containing the product were collected, concentrated in vacuo and dried to obtain an orange powder.

$^1$H NMR (DMSO-d6; CCl$_4$): 6.95 (1H, s, CH-arom.), 7.79 (2H, s, NH$_2$), 7.95 (1H, s, CH-arom.).

1.4 Synthesis of 2,2-difluorobenzo[d][1,3]dioxole-5,6-diamine

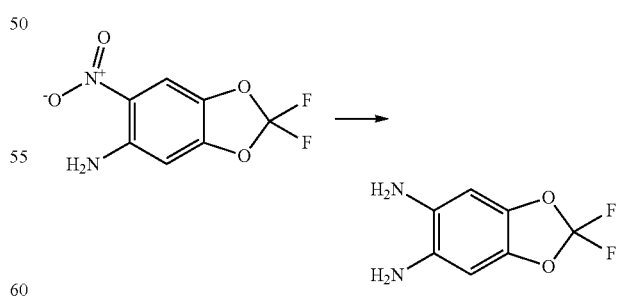

2,2-difluoro-6-nitrobenzo[d][1,3]dioxol-5-amine (770 mg, 3.53 mmol) was dissolved in dry methanol (100 ml) under an argon atmosphere and hydrogenated using Raney Nickel as catalyst for 1 h at room temperature.

The reaction mixture was filtered over CELLITE® and washed with methanol. The solvent was evaporated and concentrated in vacuo. A purple solid precipitated and was dried under reduced pressure. The crude greyish product (530 mg, 53% yield) was purified by column chromatography on a silica gel flash column (eluent DCM:MeOH 95:5). The selected fractions were combined and concentrated in vacuo. The crude product was precipitated as a hydrochloride using a 1.25 M hydrogen chloride solution in ethanol and an excess of ethyl acetate. The resulting suspension was stirred overnight. Subsequently, the solid was filtered off. Afterwards the obtained 2,2-difluorobenzo[d][1,3]dioxole-5,6-diamine hydrochloride was dissolved in water and extracted with ethylacetate. The aqueous layer was alkalized to pH 8-10 and extracted with ethyl acetate. The organic layer was then dried over magnesium sulfate, concentrated in vacuo and dried to obtain a brown solid (98% purity).

$^1$H NMR (DMSO-d6+CCl$_4$): 4.52 (4H, s, 2×NH$_2$), 6.52 (2H, s, CH-arom.).

1.5 Synthesis of 2,2-difluoro-5H-[1,3]dioxolo[4',5': 4,5]benzo[1,2-d]imidazol-6-amine hydrobromide (II)

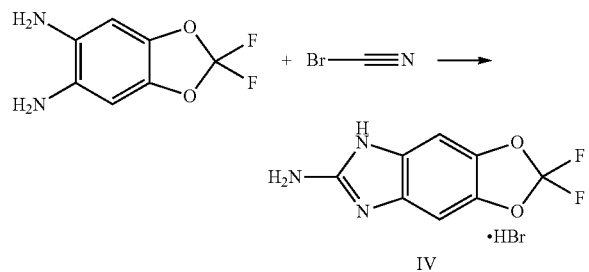

To a solution of 5,6-Diamino-2,2-difluoro-1,3-benzodioxole (4.91 g, 0.0261 mol) in dry methanol (98 ml) was added cyanogen bromide (3.23 g, 1.3 eq.). The reaction mixture was stirred overnight at room temperature.

The reaction mixture was subsequently concentrated in vacuo. The residue was then washed with dichloromethane and the precipitate was filtered off and dried to obtain a brown solid (6.72 g, 88% yield, 98% purity).

$^1$H NMR (DMSO-d6+CCl$_4$): 7.47 (2H, s, 2×CH-arom.), 8.46 (2H, s, NH$_2$), 12.58 (1H, s, NH).

2. Synthesis of Final Compounds (I)

2.1 General Procedure 1

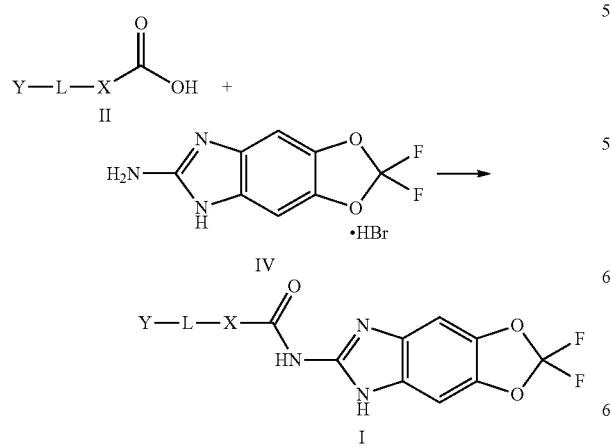

To a solution of II (1-2 eq.) in dry DMF, dioxane or dichloromethane, particularly dry DMF (dimethylformamide) (3-10 ml) were added IV (1 mmol). HBTU (2-(1H-Benzotriazole-1-yl)-1,1,3,3-Tetramethyluronium hexafluorophosphate) (1-1.4 eq.), DIPEA (N,N-Diisopropylethylamine) (1-5 eq.) or triethylamine (5 eq.), particularly DIPEA, and optionally DMAP (4-Dimethylaminopyridine) (0.1 eq.) were also added to the reaction mixture. The reaction temperature was usually in the range of from rt to 85° C., particularly rt. The reaction was usually allowed to process overnight (which as used herein specifies a duration of approximately between 12 and 24 h, depending on the reaction velocity).

After completion of the reactions, the reaction solution was subjected to one or more after-treatments including:

A) Extraction with organic solvents: The residue obtained from the reaction was dissolved in an organic solvent (such as ethyl acetate or dichloromethane) and was washed at least once with an aqueous 5% NaHCO$_3$, aqueous 5% citric acid and water. The organic layer was dried over magnesium sulfate and concentrated in vacuo.

B) Chromatography: The crude product obtained from the reaction was purified by column chromatography on a silica gel flash column, by preparative TLC (thin layer chromatography) or preparative HPLC (high pressure liquid chromatography) with a defined eluent proportion. After completion of the reaction, the crude product was purified by silica gel flash column chromatography (CHCl$_3$/EtOH=80:1+1 drop of HOAc).

C) Recrystallization: The crude product was crystallized from ethanol (with activated carbon).

D) Precipitation: After completion of the reaction, the reaction mixture was diluted with water, hexane or an aqueous Na$_2$CO$_3$-solution and/or was poured into ice water and the formed precipitate was filtered off.

E) Washing: The obtained solid (e.g. obtained by filtration) was washed with water, aqueous HCl or Na$_2$CO$_3$-solution and/or organic solvents.

F) Suspending, followed by filtration: The crude product was suspended in Et$_2$O (diethylether), filtered off and dried.

G) Neutralization and recovery: After completion of the reaction, the solvent was evaporated in vacuo, water was added and the precipitate was formed. An aqueous 3% ammonia solution, or alternatively a sodium hydrogen carbonate solution was added to the suspension till pH=8. After 30 min of stirring the precipitate was filtered off or the dissolved product was extracted.

2.2 Synthesis of N-(2,2-difluoro-5H-[1,3]dioxolo[4', 5':4,5]benzo[1,2-d]imidazol-6-yl)-2-(2-(trifluoromethoxy)benzamido)thiazole-4-carboxamide (1)

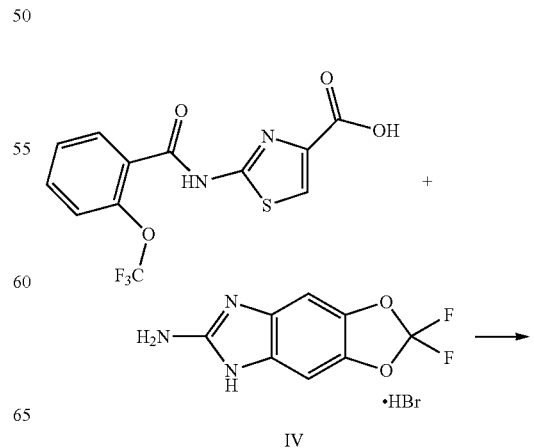

39

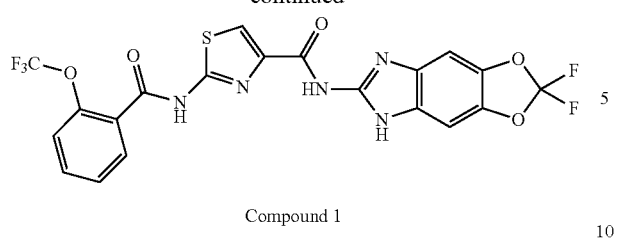

Compound 1

2,2-difluoro-5H-[1,3]dioxolo[4',5':4,5]benzo[1,2-d]imidazol-6-amine (3.28 mmol) and 2-(2-(trifluoromethoxy)benzamido)thiazole-4-carboxylic acid (3.28 mmol) were dissolved in dry dimethylformamide, 2-(1H-Benzotriazole-1-yl)-1,1,3,3-Tetramethyluronium hexafluorophosphate (HBTU) (3.28 mmol) and N,N-Diisopropylethylamine (DIPEA) (6.55 mmol) were added and the reaction mixture was stirred for 16 h at 85° C. The reaction mixture was then concentrated in vacuo. The residue was dissolved in EtOAc and was washed twice with an aqueous 5% sodium hydrogen carbonate solution, aqueous 5% citric acid solution and water. The organic layer was dried over magnesium sulfate and was concentrated in vacuo. The product was purified by silica gel flash chromatography with petrol ether/ethyl acetate. $^1$H NMR (DMSO+$d_6$; CCl$_4$): 7.48 (2H, s, CH-arom.), 7.54-7.59 (2H, m, CH-arom.), 7.70-7.76 (1H, m, CH-arom.), 7.80-7.83 (1H, dd, CH-arom.), 8.35 (1H, s, CH-thiazol), 11.14 (1H, s, NH), 12.49 (1H, s, NH), 13.12 (1H, s, NH).

2.3 General Procedure 2

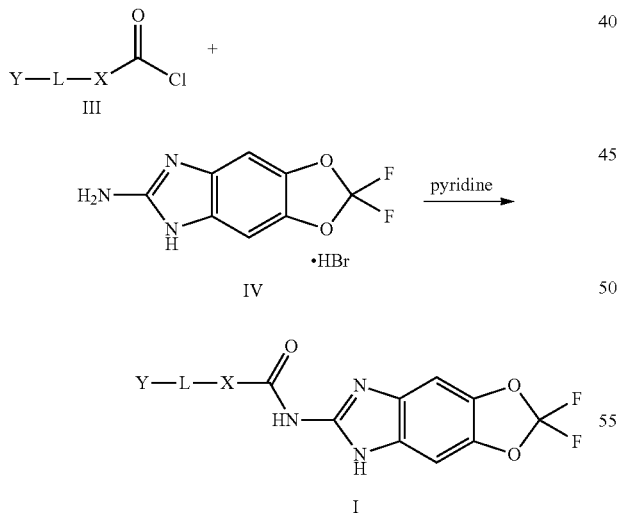

II (1-1.5 eq.) was added to the suspension of IV (1 eq.) in dry pyridine (1-3 ml). The resulting mixture was stirred at rt overnight.

After completion of the reaction, the reaction solution, where necessary, was subjected to after-treatments such as the ones defined above.

40

2.4 Synthesis of N-(2,2-difluoro-5H-[1,3]dioxolo[4',5':4,5]benzo[1,2-d]imidazol-6-yl)benzamide (49)

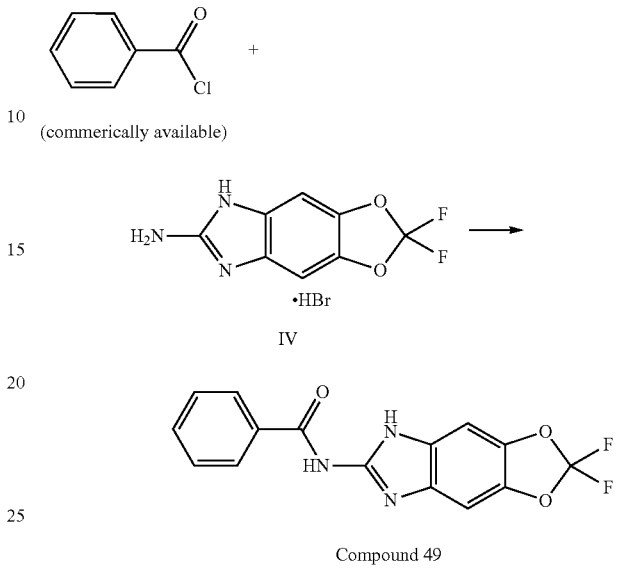

Compound 49

Benzoylchloride (0.179 g, 1.5 eq.) was added to the suspension of IV (0.25 g, 0.85 mmol) in dry pyridine (3 ml). The resulting mixture was stirred at rt overnight. The reaction mixture was diluted with water (20 ml) and the formed precipitate was filtered off, washed with water and recrystallized from ethanol to obtain a pure product (0.1 g, 37% yield). $^1$H NMR (400 MHz, DMSO-$d_6$+CCl$_4$): 7.32 (2H, s, CH-arom.), 7.44-7.54 (2H, m, CH-arom.), 7.54-7.64 (1H, m, CH-arom.), 8.13 (2H, d, CH-arom.), 12.29 (2H, s, NH).

2.5 General Procedure 3

I (1-1.5 eq.) was refluxed in SOCl$_2$ (3-5 ml) for 2 h. An excess of SOCl$_2$ was evaporated in vacuo and pyridine (3 ml) was added to the resulting residue. The mixture was then stirred for 10 min., IV (1 mmol) was added and the resulting mixture was stirred overnight at rt. After completion of the reaction, the reaction solution was subjected, where necessary, to after-treatments such as the ones defined above.

2.6 Synthesis of N-(2,2-difluoro-5H-[1,3]dioxolo[4',5':4,5]benzo[1,2-d]imidazol-6-yl)-4-methyl-1,2,3-thiadiazole-5-carboxamide (42)

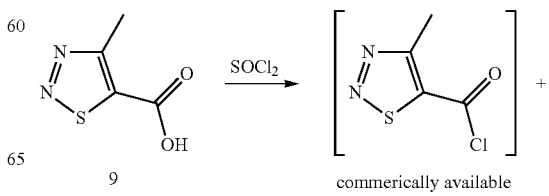

41

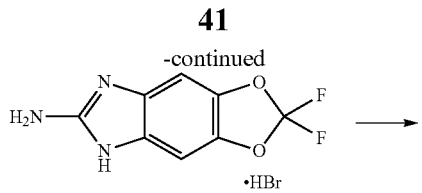

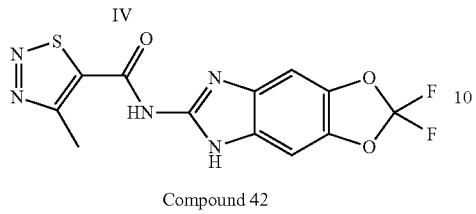

Compound 42

4-Methyl-1,2,3-thiadiazole-5-carboxylic acid (0.105 g, 1.43 eq.) was refluxed in SOCl$_2$ (4 ml) for 2 h. Excess SOCl$_2$ was evaporated in vacuo and pyridine (3 ml) was added to the resulting residue. The obtained mixture was stirred for 10 min, 2,2-difluoro-5H-[1,3]dioxolo[4',5':4,5]-benzo[1,2-d]imidazol-6-amine hydrobromide (0.15 g, 0.51 mmol) was added and stirring was continued overnight. Water (25 ml) was then added and the resulting suspension was stirred for 1 h. The obtained precipitate was filtered off, washed with water, dried and recrystallized from ethanol (with activated carbon) to obtain a pure solid (90 mg, 52% yield). $^1$H NMR (400 MHz, DMSO+CCl$_4$): 2.96 (3H, s, CH$_3$), 7.33 (2H, s, CH-benzimidazole), 12.78 (2H, s, NH).

2.7 General Procedure 4

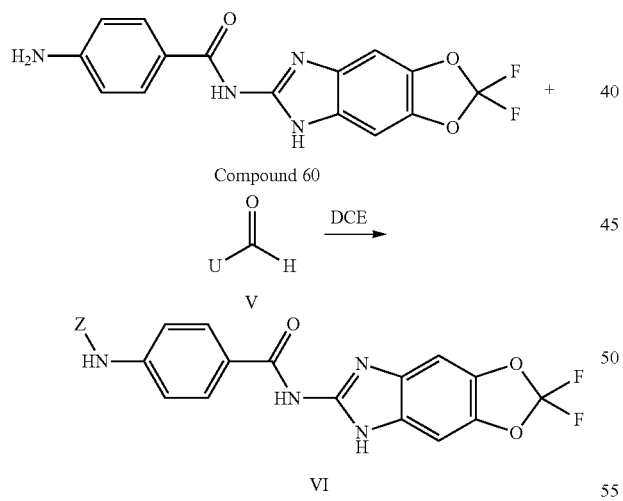

Z can be alkyl, dialkyl or arylalkyl as defined above; U can be alkyl, aryl or hydrogen as defined above V (1-1.5 eq.) was added to a suspension of compound 65 (1 mmol) in DCE (1,2-dichloroethene) (15 ml) and the mixture was stirred for 1 h. Then sodiumtriacetoxyborohydride (2 eq.), and acetic acid (0.5-2 ml) were added and the reaction mixture was stirred for 2 days. After completion of the reaction, the reaction solution was subjected, where necessary, to after-treatments such as the ones defined above

42

2.8 Synthesis of N-(2,2-difluoro-5H-[1,3]dioxolo[4',5':4,5]benzo[1,2-d]imidazol-6-yl)-4-(ethylamino)benzamide (77)

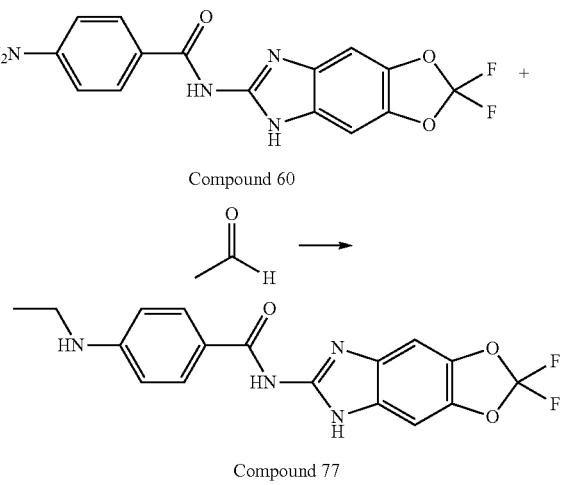

Compound 77

Acetaldehyde (0.013 ml, 1.1 eq.) was added to a suspension of compound 65 (0.07 g, 0.21 mmol) in DCE (15 ml) and the mixture was stirred for 1 h. Then sodiumtriacetoxyborohydride (0.089 g, 2 eq.) and acetic acid (0.3 ml) were added and the reaction mixture was stirred for 2 days. The mixture was then neutralized with an aqueous 10% sodium hydrogen carbonate solution and extracted with dichloromethane. The combined organic extracts were dried over MgSO$_4$, filtered and concentrated in vacuo. The residue was purified by silica gel flash column chromatography (CHCl$_3$/EtOH=80:1+1 drop of HOAc) to obtain the pure product (20.3 mg, 39% yield). $^1$H NMR (400 MHz, DMSO-d$_6$): 1.24 (3H, t, CH$_3$), 3.16 (2H, q, CH$_2$), 6.29 (1H, s, NH), 6.57 (2H, d, CH-arom.), 7.32 (2H, s, CH-benzimidazole), 7.93 (2H, d, CH-arom.), 11.48 (1H, s, NH), 12.40 (1H, s, NH)

3. Alternative Procedures for the Synthesis of Final Compounds 3.1 Synthesis of N-(2,2-difluoro-5H-[1,3]dioxolo[4',5':4,5]benzo[1,2-d]imidazol-6-yl)-5-(2,3-dihydrobenzofuran-5-yl)thiophene-3-carboxamide (38)

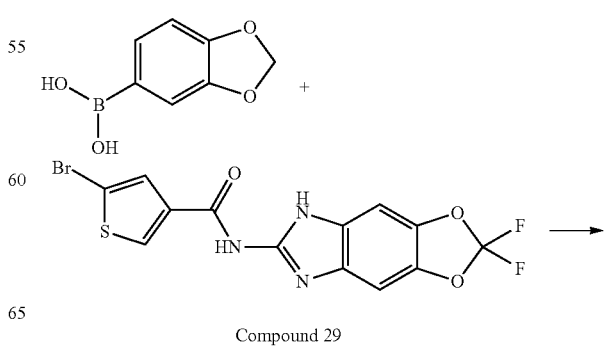

Compound 29

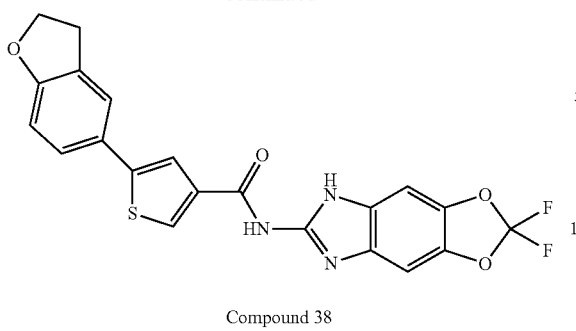

Compound 38

Compound 29 (0.1 g, 0.2486 mmol) and (2,3-dihydrobenzofuran-5-yl)boronic acid (0.612 g, 1.5 eq) were suspended in DME (1,2-dimethoxyethane). Tetrakis(triphenylphosphine)-palladium(0) (0.03 g, 0.2 eq) and an aqueous 2M $Na_2CO_3$ solution (0.5 ml, 4 eq.) were added. The reaction mixture was stirred 20 h at 100° C., subsequently dissolved in ethyl acetate and washed twice with water. The organic layer was concentrated in vacuo, the residue dissolved in methanol and purified by preparative HPLC to obtain the pure product (4 mg, 4% yield).

3.2 Synthesis of N-(2,2-difluoro-5H-[1,3]dioxolo[4',5':4,5]benzo[1,2-d]imidazol-6-yl)cyclohexanecarboxamide (80)

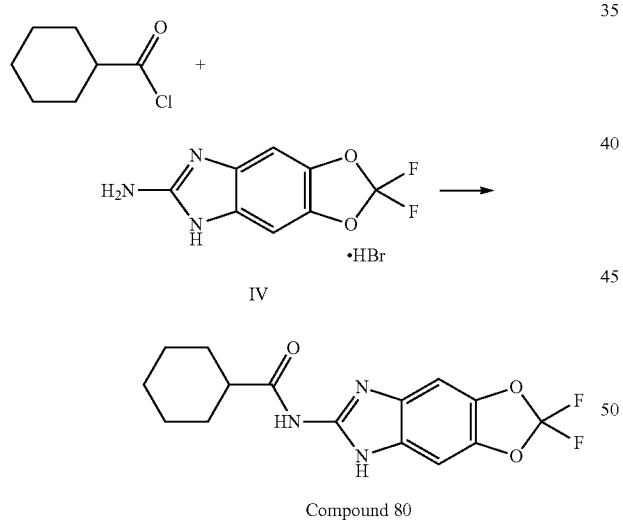

Compound 80

IV (0.06 g, 0.2 mmol) was refluxed in chloroform with cyclohexanecarbonyl chloride (32 µl, 1.1 eq.) in the presence of DIPEA (0.1 ml, 0.57 eq.) during 2 days. Subsequently, the solvent was evaporated and the residue was purified by silica gel flash column chromatography (eluent: ethyl acetate) to obtain the pure product (0.04 g, 61% yield). $^1$H-NMR (400 MHz, DMSO-d6): 1.26-1.35 (5H, m, CH2), 1.38-1.42 (1H, m, CH2), 1.51-1.86 (4H, m, CH2), 3.07-3.45 (1H, m, CH), 7.18 (1H, s, CH-arom.), 7.31 (1H, s, Ch-arom.), 11.36 (1H, s, NH), 12.11 (1H, s, NH).

3.3 Synthesis of 4-amino-N-(2,2-difluoro-5H-[1,3]dioxolo[4',5':4,5]benzo[1,2-d]imidazol-6-yl)benzamide (60)

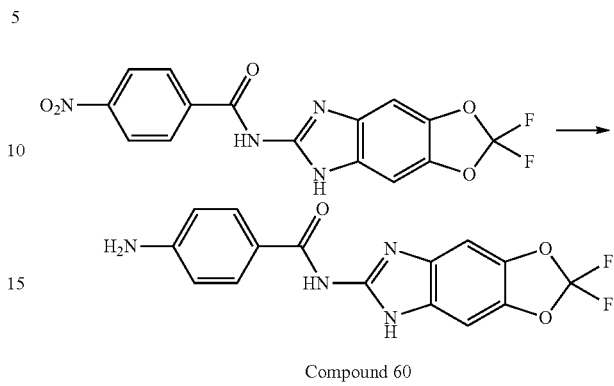

Compound 60

N-(2,2-difluoro-5H-[1,3]dioxolo[4',5':4,5]benzo[1,2-d]imidazol-6-yl)-4-nitrobenzamide (0.32 g, 0.88 mmol) was suspended in ethanol (20 ml), hydrazine hydrate (0.3 ml) and Pd/C (0.16 g), were added to the suspension and the mixture was refluxed during 1.5 h. The catalyst was then filtered off; the solution was evaporated in vacuum till dryness. The residue was washed with water to obtain the pure product (0.23 g, 79% yield). NMR $^1$H (400 MHz, DMSO-$d_6$): 5.68 (2H, s, CH-arom.), 6.68 (2H, d, CH-arom.), 7.24 (2H, s, $NH_2$), 7.86 (2H, d, CH-arom.), 11.37 (1H, s, NH), 12.31 (1H, s, NH).

4. Synthesis of Intermediates

4.1 Synthesis of ethyl 2-(2-(trifluoromethoxy)benzamido)thiazole-4-carboxylate

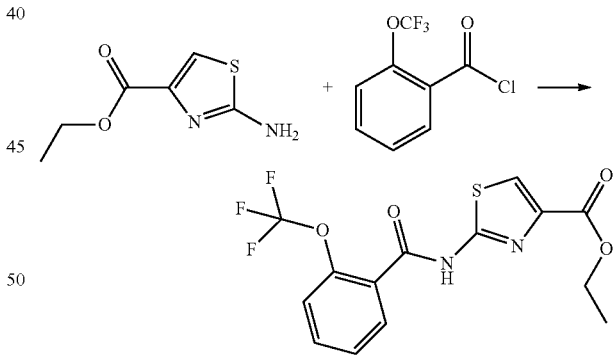

To a solution of Ethyl 2-aminothiazole-4-carboxylate (12 g, 70 mmol, 1 eq.) in dry THF (300 ml) was added DIPEA (250 ml, 209 mmol, 3 eq.). A solution of 2-(Trifluoromethoxy)-benzoyl chloride (19 g, 84 mmol, 1.2 eq.) in THF (50 ml) was then added dropwise at 0° C. The reaction mixture was stirred for 24 h at rt. Water (50 ml) was then added and THF was removed under reduced pressure. The obtained residue was extracted with DCM (dichloromethane). The organic layer was dried over $MgSO_4$, filtered and concentrated under reduced pressure. The residue was purified by flash column chromatography on silica gel (PE/EtOAc 80:20). The product was obtained as a white solid (12 g, 33 mmol, 48% yield). $^1$H NMR (DMSO-$d_6$): 1.28-0.133

(3H, t, CH₃), 4.26-4.33 (2H, q, CH₂), 7.51-7.57 (2H, m, CH-arom.), 7.68-7.74 (1H, m, CH-arom.), 7.78-7.81 (1H, dd, CH-arom.), 8.14 (1H, s, CH-thiazole), 13.11 (1H, s, NH).

4.2 Synthesis of 2-(2-(trifluoromethoxy)benzamido)thiazole-4-carboxylic acid

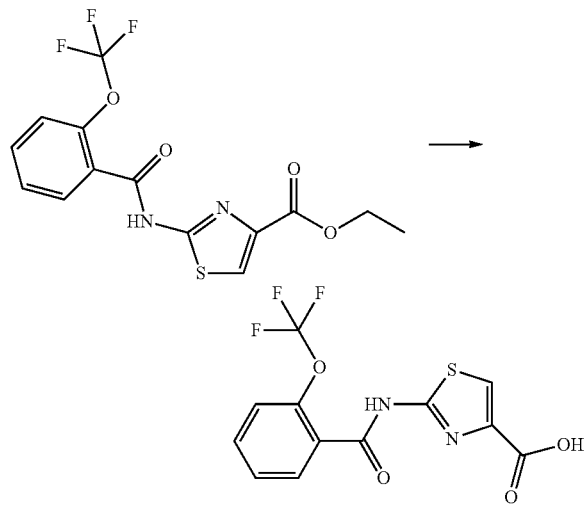

Ethyl 2-(2-(trifluoromethoxy)benzamido)thiazole-4-carboxylate (10 g, 28 mmol, 1 eq.) was dissolved in THF (20 ml) and an aqueous 2M NaOH solution (110 ml) was added at rt. The reaction mixture was stirred for 24 h at rt. THF was then removed under reduced pressure. The residual aqueous phase was acidified to pH=1-2 using 15% aqueous HCl. The precipitate was collected by filtration, washed with water and dried. The product was obtained as a white solid (10.4 g, 31 mmol, yield >90%). ¹H NMR (DMSO-d₆): 7.51-7.57 (2H, m, CH-arom.), 7.68-7.74 (1H, m, CH-arom.), 7.78-7.81 (1H, dd, CH-arom.), 8.06 (1H, s, CH-thiazole), 13.01 (1H, s, NH).

4.3 Synthesis of ethyl 2-((4-methyl-6-(trifluoromethyl)pyrimidin-2-yl)amino)thiazole-4-carboxylate

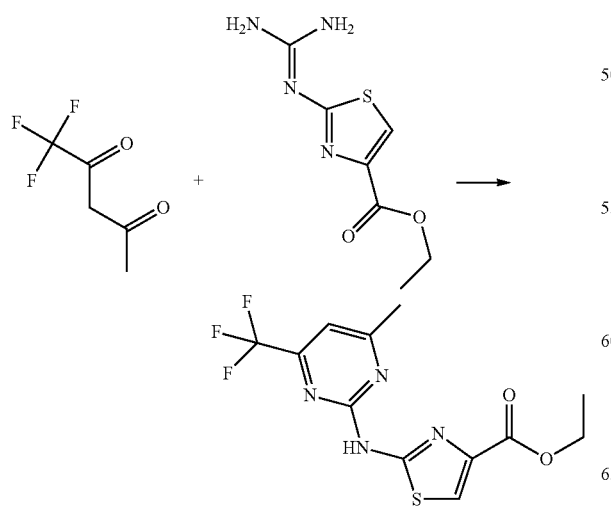

Ethyl 2-(diaminomethyleneamino)thiazole-4-carboxylate (2 g, 9.3 mmol, 1 eq.) was dissolved in EtOH (200 ml) and 1,1,1-trifluoropentane-2,4-dione (1.2 ml, 9.3 mmol, 1 eq.) was added. The reaction mixture was stirred under reflux for 3.5 h. EtOH was then partly removed under reduced pressure until a precipitate was formed. The precipitate was collected by filtration, washed with EtOH and dried. The product was obtained as a light yellow solid (2.2 g, 6.6 mmol, 71% yield). ¹H NMR (DMSO-d₆): 1.28-1.33 (3H, t, CH₃), 2.58 (3H, s, CH₃), 4.25-4.32 (2H, q, CH₂), 7.45 (1H, s, CH-pyrimidine), 8.04 (1H, s, CH-thiazole), 12.39 (1H, s, NH).

4.4 Synthesis of 2-((4-methyl-6-(trifluoromethyl)pyrimidin-2-yl)amino)thiazole-4-carboxylic acid

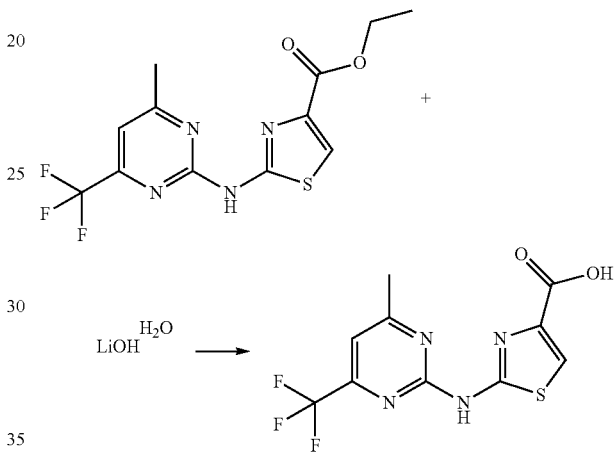

Ethyl 2-(4-methyl-6-(trifluoromethyl)pyrimidin-2-ylamino)thiazole-4-carboxylate (2.18 g, 6.56 mmol, 1 eq.) and LiOH (550 mg, 13.1 mmol, 2 eq.) were dissolved in a mixture of MeOH and water (52 ml: 18 ml). The reaction mixture was stirred at room temperature for 2 h. The reaction mixture was then acidified to pH=2 using an aqueous 10% HCl solution. MeOH was then removed under reduced pressure. The precipitate formed was collected by filtration to afford the product as a light yellow solid (2 g, 6.5 mmol, 99% yield). ¹H NMR (DMSO-d6): 2.64 (3H, s, CH₃), 7.50 (1H, s, CH-pyrimidine), 8.03 (1H, s, CH-thiazole), 12.39 (1H, s, NH).

4.5 Synthesis of ethyl 2-((2,6-dimethoxypyrimidin-4-yl)amino)thiazole-5-carboxylate

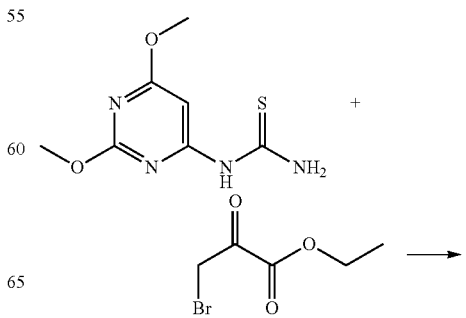

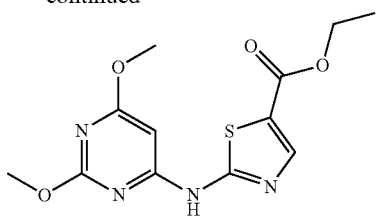

1-(2,6-dimethoxypyrimidin-4-yl)thiourea (6.133 g, 28.626 mmol) was suspended in dry DMF. The bromo pyruvate (6.699 g, 34.351 mmol) was dissolved in dry DMF and added dropwise to the mixture. The suspension cleared off and was stirred for 2 h at rt. The mixture was concentrated in vacuo to obtain the product as a yellowish solid (12.9 g, yield: >100%). LC/MS [M+H]$^+$: 310.96

4.6 Synthesis of 2-((2,6-dimethoxypyrimidin-4-yl)amino)thiazole-5-carboxylic acid

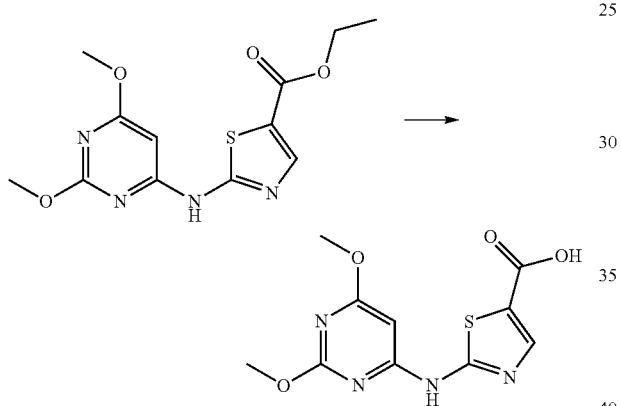

ethyl 2-((2,6-dimethoxypyrimidin-4-yl)amino)thiazole-5-carboxylate (9.0 g, 29 mmol) was suspended in EtOH (100 ml) and 2N NaOH (50 ml) was added and the mixture was stirred for 4 h at rt. A precipitate formed. Further 2N NaOH (40 ml) was added and the reaction mixture was stirred for 16 h at rt. The mixture was concentrated in vacuo. Upon addition of HCl (2 N) a precipitate was formed, which was filtered off and washed with water. The precipitate was dried in vacuo to obtain 11.58 g (89% yield) of the pure product. LC/MS [M+H]$^+$: 284.36

4.7 Synthesis of ethyl 5-(2-(trifluoromethoxy)benzamido)-1,2,4-thiadiazole-3-carboxylate

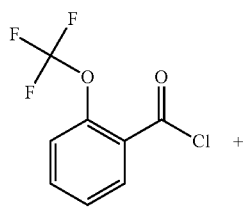

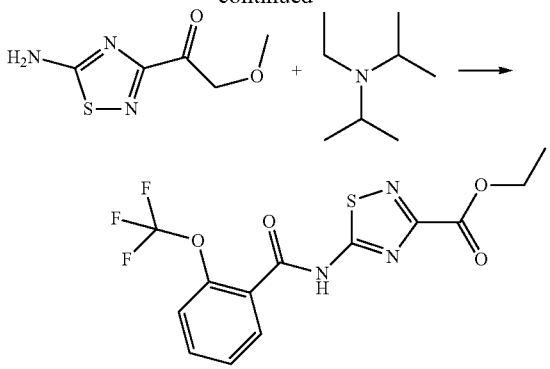

2-(Trifluoromethoxy)benzoyl chloride (1.1 g, 6.5 mmol, 1 eq.) was dissolved in THF (130 ml) and 2-(trifluoromethoxy)benzoyl chloride (1.5 g, 6.5 mmol, 1 eq.) and DIPEA (1.1 ml, 6.5 mmol, 1 eq.) were added. The reaction mixture was stirred at room temperature for 18 h. Subsequently, all volatiles were removed under reduced pressure. The obtained residue was triturated with ice water. The precipitate formed was collected by filtration and dried. The crude product was purified by flash column chromatography on silica gel (DCM/MeOH 95:5). The product was obtained as a light yellow solid (1.05 g, 2.9 mmol, 45% yield) and was used as such further. LC/MS [M+H]$^+$: 361.86; $^1$H NMR (DMSO-d$_6$): 1.31-1.36 (3H, t, CH$_3$), 4.34-4.41 (2H, q, CH$_2$), 7.56-7.58 (2H, m, CH-aromat), 7.75-7.81 (1H, m, CH-aromat), 7.88-7.92 (1H, dd, CH-aromat), 13.97 (1H, s, NH).

4.8 Synthesis of 5-(2-(trifluoromethoxy)benzamido)-1,2,4-thiadiazole-3-carboxylic acid Ethyl 5-(2-(trifluoromethoxy)benzamido)-1,2,4-thiadiazole-3-carboxylate (1 g, 2.9 mmol, 1 eq.) and LiOH (244 mg, 5.8 mmol, 2 eq.) were dissolved in a mixture of EtOH and H$_2$O (3:1) (40 ml) and the reaction mixture was stirred at room temperature for 2 h. The mixture was then acidified to pH=5 using an aqueous 10% HCl solution. The reaction mixture was then concentrated in vacuo. After cooling with an ice-bath, a precipitate formed, which was filtered off, washed with water and dried in vacuo. The product was obtained as a white solid (638 mg, 1.9 mmol, 66% yield). LC/MS [M+H]$^+$: 333.87

4.9 Synthesis of ethyl 2-(2,3-dihydrobenzofuran-5-yl)oxazole-4-carboxylate

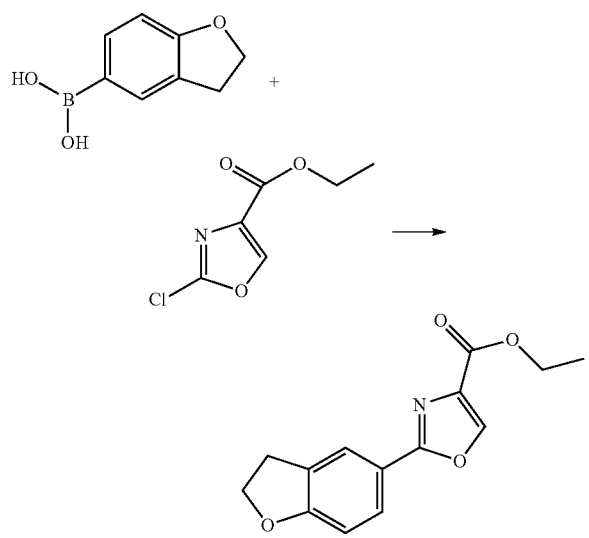

2-Chloro-oxazole-4-carboxylic acid ethyl ester (1.5 g, 8.5 mmol, 1 eq.) and 2,3-Dihydro-1-benzofuran-5-ylboronic acid (2.1 g, 12.8 mmol, 1.5 eq.) were suspended in DME (170 ml). Tetrakis(triphenylphosphine)palladium(0) (987 mg, 0.85 mmol, 0.1 eq.) and an aqueous 2M sodium carbonate solution (17.1 ml, 34.2 mmol, 4 eq.) were added. The reaction mixture was stirred at 90° C. for 6 h. DME was then removed under reduced pressure. The obtained residue was dissolved in EtOAc and was washed three times with water. The organic layer was dried over MgSO$_4$, filtered and concentrated in vacuo. The obtained crude product was purified by flash column chromatography on silica gel (PE/EtOAc 9:1 to 8:2). The fractions containing the product were collected and concentrated in vacuo. The product was obtained as a yellow oil (472 mg, Purity: ca. 50%). LC/MS [M+H]$^+$: 259.10

4.10 Synthesis of 2-(2,3-dihydrobenzofuran-5-yl)oxazole-4-carboxylic acid

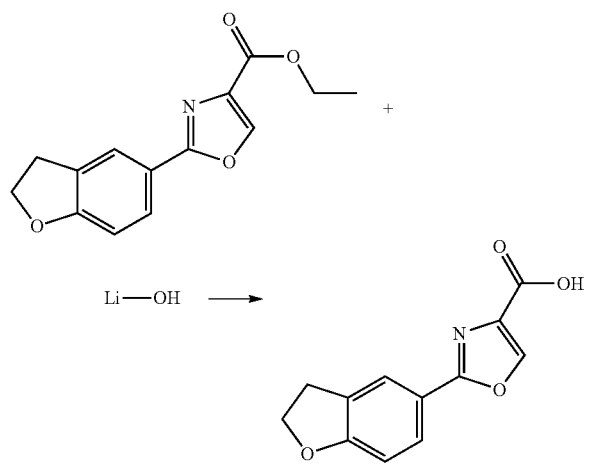

To a solution of Ethyl 2-(2,3-dihydrobenzofuran-5-yl)oxazole-4-carboxylate (472 mg, 1.8 mmol, 1 eq.) in a mixture of THF and H$_2$O (2:1; 15 ml) was added LiOH (402 mg, 9.6 mmol, 5 eq.) at rt. The reaction mixture was stirred at rt for 18 h. The reaction mixture was then concentrated in vacuo and partitioned between water (50 ml) and Et$_2$O (50 ml). The aqueous layer was acidified to pH=2-3 with an aqueous 1 M HCl solution. The resulting aqueous layer was extracted twice with EtOAc. The organic layer obtained from the extraction with EtOAc was dried over MgSO$_4$, filtered and concentrated in vacuo. The product was obtained as a brown crystalline solid (168 mg, 0.7 mmol, 40% yield). LC/MS [M+H]$^+$: 231.87

4.11 Synthesis of ethyl 2-(3-(2-(trifluoromethoxy)phenyl)ureido)thiazole-4-carboxylate

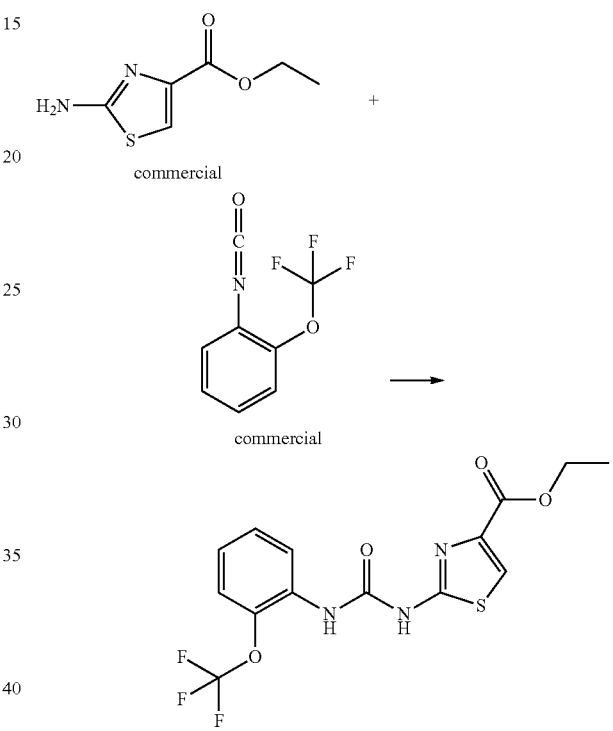

To a solution of ethyl 2-aminothiazole-4-carboxylate (1 g, 5.8 mmol, 1 eq.) in dry DCM (20 ml) was added a mixture of 1-isocyanato-2-(trifluoromethoxy)benzene (1.2 g, 5.8 mmol, 1 eq.) in dry DCM (10 ml). The reaction mixture was stirred at room temperature for 3 h. The precipitate formed was collected by filtration, washed with DCM and dried. The product was obtained as a white solid (1.9 g, 5 mmol, 86% yield). LC/MS [M+H]$^+$: 376.12

4.12 Synthesis of 2-(3-(2-(trifluoromethoxy)phenyl)ureido)thiazole-4-carboxylic acid

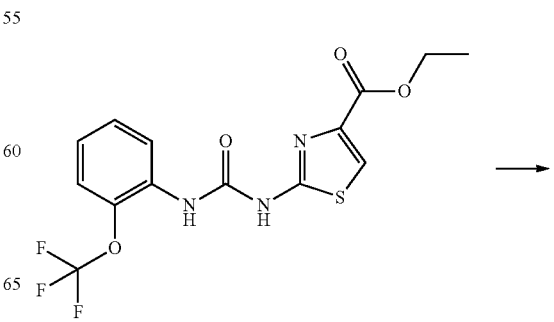

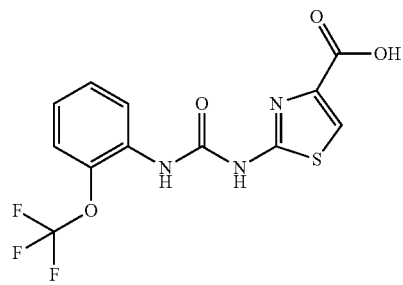

To a solution of ethyl 2-(3-(2-(trifluoromethoxy)phenyl)ureido)thiazole-4-carboxylate (1.5 g, 4.11 mmol, 1 eq.) in dry dioxane (10 ml) was added dropwise an aqueous 2M NaOH solution (2.3 ml, 4.5 mmol, 1.1 eq.) at 0° C. The reaction mixture was stirred at rt for 8 h. After addition of an aqueous 2M HCl solution (2.3 ml) a solid precipitated. The solid was collected by filtration, washed with water and dried. The product was obtained as a white solid (1.4 g, 3.9 mmol, 95% yield). LC/MS [M+H]$^+$: 348.06

4.13 Synthesis of methyl 3-(2-(trifluoromethoxy)benzamido)-1H-1,2,4-triazole-5-carboxylate

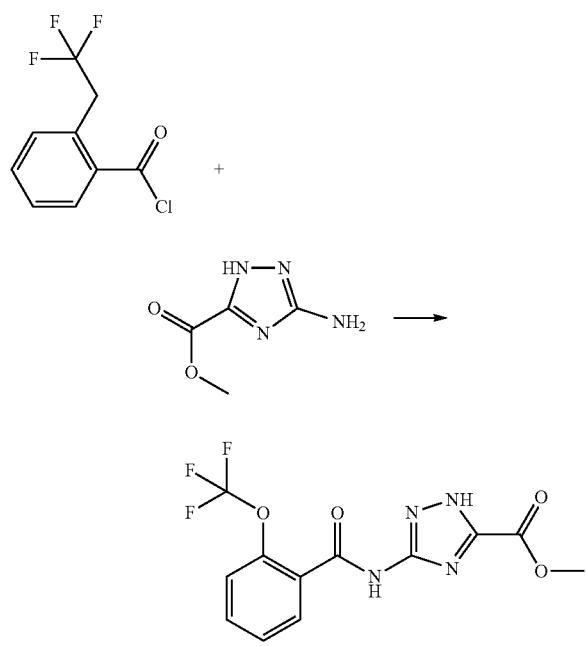

2-(trifluoromethoxy)benzoyl chloride (0.26 ml, 1.2 eq.) was added dropwise to a suspension of methyl 3-amino-1H-1,2,4-triazole-5-carboxylate (0.22 g, 1.4 mmol) in pyridine (3 ml). The reaction mixture was stirred at rt overnight. Then the mixture was diluted with water (20 ml) and stirred for 30 min. A colorless oil was formed. The Water/pyridine solution was decanted and the residual oil was treated with hexane to obtain 0.167 g of a colorless precipitate, which was used in the subsequent synthesis steps without further characterization.

4.14 Synthesis of 3-(2-(trifluoromethoxy)benzamido)-1H-1,2,4-triazole-5-carboxylic acid

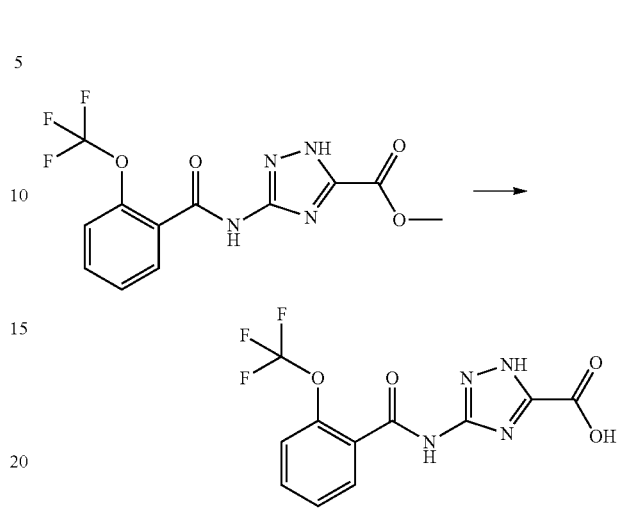

To a solution of methyl 3-(2-(trifluoromethoxy)benzamido)-1H-1,2,4-triazole-5-carboxylate (0.16 g) in the mixture of ethanol, water and potassium hydroxide (15 ml/15 ml/0.15 g) was refluxed for 15 min. Ethanol was subsequently removed. The resulting solution was diluted with water and neutralized with HCl until pH=3. The colorless precipitate was filtered off and washed with water to obtain 0.117 g of the pure product. NMR $^1$H (400 MHz, DMSO-d$_6$): 7.41 (1H, d, CH-arom.), 7.49 (1H, t, CH-arom.), 7.65 (1H, t, CH-arom.), 7.73 (1H, d, CH-arom.), 12.29 (1H.s, NH), 12.98 (1H, s, OH), 14.03 (1H, s, NH).

4.15 Synthesis of ethyl 5-acetamido-1H-1,2,4-triazole-3-carboxylate

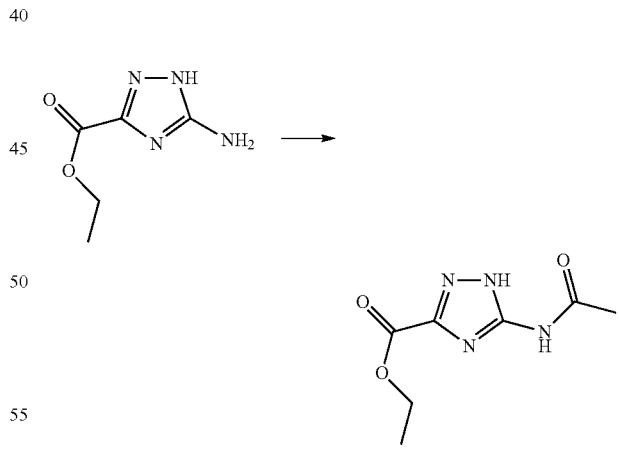

A suspension of ethyl 5-amino-1H-1,2,4-triazole-3-carboxylate in acetic anhydride was refluxed for 30 min. Excess acetic anhydride was evaporated. Water was added to the residue and the mixture was stirred overnight. The colourless product was filtered off, washed with water and dried to obtain 0.134 g (53% yield) of the product. $^1$H-NMR (40 MHz, DMSO-d$_6$): 1.35 (3H. t. OCH$_2$CH$_3$), 2.12 (3H, s, COCH$_3$), 4.3 (2H, q, OCH$_2$CH$_3$), 11.71 (1H, s, NHCO), 13.74 (1H, s, NH-triazole).

4.16 Synthesis of 5-acetamido-1H-1,2,4-triazole-3-carboxylic acid

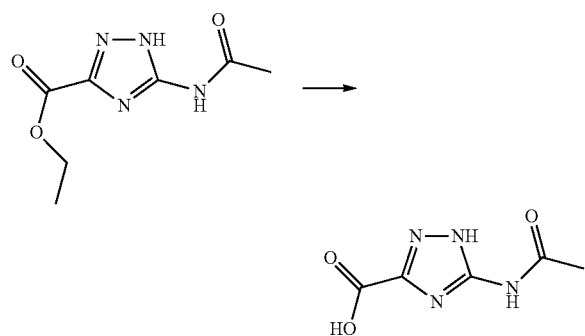

A solution of ethyl 5-acetamido-1H-1,2,4-triazole-3-carboxylate (0.13 g, 0.66 mmol) in NaOH/H$_2$O (0.079 g/5 ml) was stirred for 6 h. The solution was then acidified with conc. HCl to pH=2 and the colorless precipitate was filtered off and dried to give the pure product (0.076 g, 69% yield). $^1$H-NMR (40 MHz, DMSO-d$_6$): 2.12 (3H, s, COCH$_3$), 11.65 (1H, s, NHCO), 13.67 (1H, s, NH-triazole).

4.17 Synthesis of (6-Amino-2,2-difluoro-5H-[1,3]dioxolo[4',5':4,5]benzo[1,2-d]imidazol-5-yl)(1-methyl-1H-pyrrol-2-yl)methanone

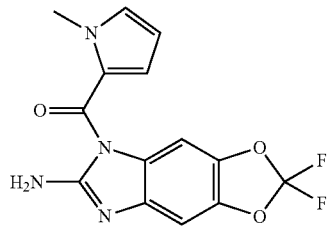 [SMILES: Cn1cccc1C(=O)n1c(N)nc2cc3c(cc21)OC(F)(F)O3]

The compound was synthesized by the aforementioned general synthesis protocols 1, D and C as described above.

Other carboxylic acid derivatives were synthesized analogously to the aforementioned synthesis protocols, which are to be understood as exemplary synthesis protocols.

5. Alternative Procedures for the Synthesis of Final Compounds

5.1 Synthesis of 4-Amino-N-(2,2-difluoro-5H-[1,3]dioxolo[4',5':4,5]benzo[1,2-d]imidazol-6-yl)-1H-pyrrole-2-carboxamide (15B)

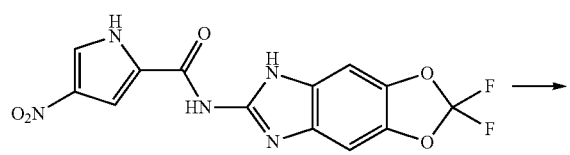

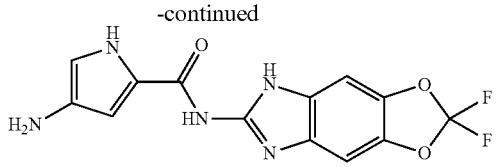

N-(2,2-difluoro-5H-[1,3]dioxolo[4',5':4,5]benzo[1,2-d]imidazol-6-yl)-4-nitro-1H-pyrrole-2-carboxamide (XX) (110.0 mg, 0.313 mmol) was dissolved in 10 ml methanol and palladium on carbon (10%/C, 53.33 mg, 0.501 mmol) was added. The reaction flask was then purged with hydrogen and the reaction mixture was stirred for 2 h under an hydrogen atmosphere. The reaction mixture was filtered over celite and the filtrate was concentrated in vacuo. The crude solid was washed with water and dried. The product was obtained as a brown solid (28 mg, 0.09 mmol, 28% yield).

5.2 Synthesis of 3-((2,2-Difluoro-5H-[1,3]dioxolo[4',5':4,5]benzo[1,2-d]imidazol-6-yl)carbamoyl)benzoic acid (18B)

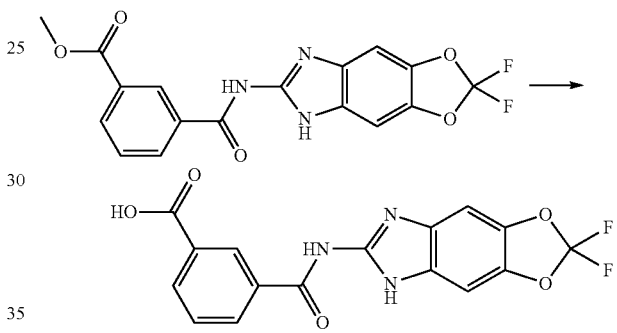

To a solution of ethyl 2-(2,3-dihydrobenzofuran-5-yl)oxazole-4-carboxylate (32 mg, 0.085 mmol) in 6 ml THF/H$_2$O (1:1), Lithiumhydroxid monohydrate (56% LiOH, 25 mg, 0.597 mmol) was added at room temperature The reaction mixture was stirred overnight at room temperature. The reaction mixture was concentrated in vacuo and the aqueous layer was acidified to pH 2-3 with an aqueous 1 mol/l hydrochlorid acid solution. The resulting solid was filtered off and dried. The product was obtained as a bright brown solid (14 mg, 0.04 mmol, 46% yield).

5.3 Synthesis of N-(2,2-Difluoro-5H-[1,3]dioxolo[4',5':4,5]benzo[1,2-d]imidazol-6-yl)-1-methyl-1H-pyrrole-2-carboxamide (20B)

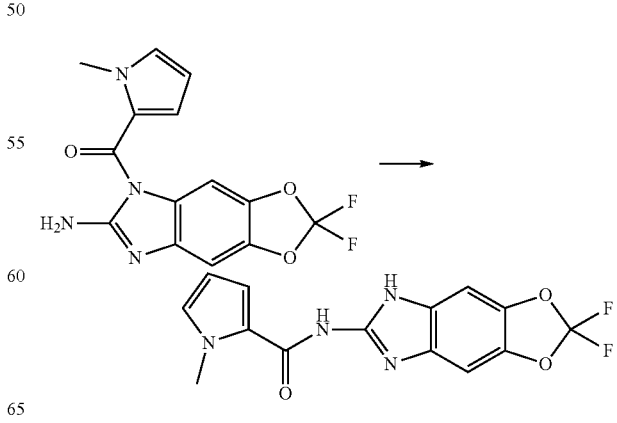

A suspension of (6-amino-2,2-difluoro-5H-[1,3]dioxolo[4',5':4,5]benzo[1,2-d]imidazol-5-yl)(1-methyl-1H-pyrrol- 2-yl)methanone (37.82 mg, 0.118 mmol) in 3 ml xylene and 1 ml DMF was refluxed for 4 h. The reaction mixture was lyophilized. The crude product was purified by preparative TLC (DCM:MeOH 9:1) (PLC silica gel 60 $F_{254}$, 1 mm). The highest spot was isolated and purified by a second preparative TLC with the same conditions as described above. The product was obtained as a beige solid (6 mg, 0.02 mmol, 16% yield).

6. Analysis of Synthesis Products

Analytical LC/ESI-MS parameters: Waters 2700 Autosampler. 1× Waters 1525 Multisolvent Delivery System 5 µL sample loop. Column, Phenomenex Onyx™ Monolythic C18 50.2 mm, with stainless steel 2 µm prefilter. Eluent A, $H_2O$+0.1% HCOOH; eluent B, MeCN. Gradient, 5% B to 100% B within 3.80 min, then isocratic for 0.20 min, then back to 5% B within 0.07 min, then isocratic for 0.23 min; flow, 0.6 mL/min and 1.2 mL/min. Waters Micromass ZQ single quadrupole mass spectrometer with electrospray source. MS method, MS4_15 minPM-80-800-35V; positive/negative ion mode scanning, m/z 80-800 or 80-900 in 1 s; capillary voltage, 3.50 kV; cone voltage, 35 V; multiplier voltage, 650 V; probe and desolvation gas temperature, 120° C. and 300° C., respectively. Waters 2487 Dual λ Absorbance Detector set to 254 nm. Software: Waters Masslynx V 4.0.

7. Exemplary Compounds of the Present Invention

TABLE 1

Exemplary compounds.

| No. | Structure | CK1 delta Assay | CK1 epsiplon Assay | HH Assay | Wnt Assay | [M + H]+ | General procedure/aftertreatment |
|---|---|---|---|---|---|---|---|
| 1 | 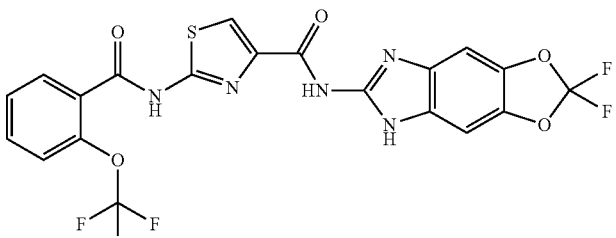 N-(2,2-difluoro-5H-[1,3]dioxolo[4',5':4,5]benzo[1,2-d]imidazol-6-yl)-2-(2-(trifluoromethoxy)benzamido)thiazole-4-carboxamide | +++ | +++ | + | +++ | 527.85 | 1 A, B |
| 2 | 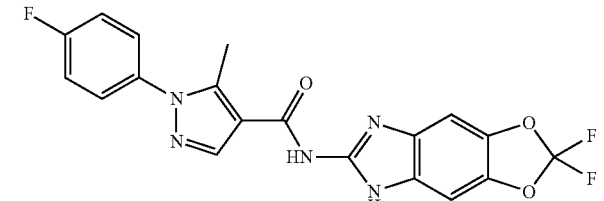 N-(2,2-difluoro-5H-[1,3]dioxolo[4',5':4,5]benzo[1,2-d]imidazol-6-yl)-1-(4-fluorophenyl)-5-methyl-1H-pyrazole-4-carboxamide | +++ | ++ | + |  | 415.89 | 1 A, B |
| 3 | 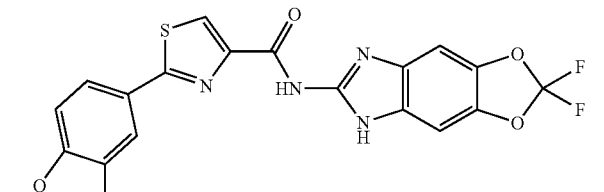 N-(2,2-difluoro-5H-[1,3]dioxolo[4',5':4,5]benzo[1,2-d]imidazol-6-yl)-2-(2,3-dihydrobenzofuran-5-yl)thiazole-4-carboxamide | +++ | ++ | +++ |  | 442.88 | 1 A, F |
| 4 | 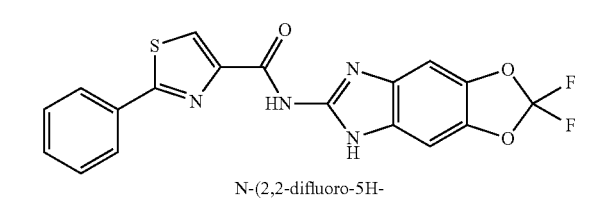 N-(2,2-difluoro-5H-[1,3]dioxolo[4',5':4,5]benzo[1,2-d]imidazol-6-yl)-2-phenylthiazole-4-carboxamide | ++ | ++ |  |  | 401.05 | 1 E |

TABLE 1-continued

Exemplary compounds.

| No. | Structure | CK1 delta Assay | CK1 epsilon Assay | HH Assay | Wnt Assay | [M + H]+ | General procedure/after-treatment |
|---|---|---|---|---|---|---|---|
| 5 | N-(2,2-difluoro-5H-[1,3]dioxolo[4',5':4,5]benzo[1,2-d]imidazol-6-yl)-2-(4-(trifluoromethyl)phenyl)thiazole-4-carboxamide | + | + | | | 469.00 | 1 A, F |
| 6 | 2-(2,3-dichlorophenyl)-N-(2,2-difluoro-5H-[1,3]dioxolo[4',5':4,5]benzo[1,2-d]imidazol-6-yl)thiazole-4-carboxamide | + | + | | | 468.76 | 1 A, F |
| 7 | 3-amino-N-(2,2-difluoro-5H-[1,3]dioxolo[4',5':4,5]benzo[1,2-d]imidazol-6-yl)pyrazine-2-carboxamide | + | + | + | | 334.74 | 1 A, F |
| 8 | 2-(4-chlorobenzamido)-N-(2,2-difluoro-5H-[1,3]dioxolo[4',5':4,5]benzo[1,2-d]imidazol-6-yl)thiazole-4-carboxamide | ++ | ++ | | | 477.89 | 1 A |
| 9 | 2-cinnamamido-N-(2,2-difluoro-5H-[1,3]dioxolo[4',5':4,5]benzo[1,2-d]imidazol-6-yl)oxazole-4-carboxamide | + | + | | | 454.02 | 1 A, F |
| 10 | N-(2,2-difluoro-5H-[1,3]dioxolo[4',5':4,5]benzo[1,2-d]imidazol-6-yl)-2-(furan-2-carboxamido)oxazole-4-carboxamide | ++ | + | | | 417.88 | 1 F |

TABLE 1-continued

Exemplary compounds.

| No. | Structure | CK1 delta Assay | CK1 epsiplon Assay | HH Assay | Wnt Assay | [M + H]+ | General procedure/ after-treatment |
|---|---|---|---|---|---|---|---|
| 11 | N-(2,2-difluoro-5H-[1,3]dioxolo[4',5':4,5]benzo[1,2-d]imidazol-6-yl)-2-(furan-2-carboxamido)thiazole-4-carboxamide | +++ | +++ | | | 434.03 | 1 A, F |
| 12 | N-(2,2-difluoro-5H-[1,3]dioxolo[4',5':4,5]benzo[1,2-d]imidazol-6-yl)-2-(2-methoxybenzamido)oxazole-4-carboxamide | ++ | + | | | 457.94 | 1 A, F |
| 14 | 1-(3,4-dichlorophenyl)-N-(2,2-difluoro-5H-[1,3]dioxolo[4',5':4,5]benzo[1,2-d]imidazol-6-yl)-3,5-dimethyl-1H-pyrazole-4-carboxamide | + | + | | | 479.80 | 1 A, B |
| 15 | N-(2,2-difluoro-5H-[1,3]dioxolo[4',5':4,5]benzo[1,2-d]imidazol-6-yl)-3,5-dimethyl-1-phenyl-1H-pyrazole-4-carboxamide | + | + | | | 411.8 | 1 A, F |
| 16 | N-(2,2-difluoro-5H-[1,3]dioxolo[4',5':4,5]benzo[1,2-d]imidazol-6-yl)-1-phenyl-3-(trifluoromethyl)-1H-pyrazole-4-carboxamide | ++ | ++ | | | 451.88 | 1 A, B |

TABLE 1-continued

Exemplary compounds.

| No. | Structure | CK1 delta Assay | CK1 epsilon Assay | HH Assay | Wnt Assay | [M + H]+ | General procedure/after-treatment |
|---|---|---|---|---|---|---|---|
| 17 | N-(2,2-difluoro-5H-[1,3]dioxolo[4',5':4,5]benzo[1,2-d]imidazol-6-yl)-5-(2-(trifluoromethoxy)benzamido)-1,2,4-thiadiazole-3-carboxamide | +++ | +++ | | | 528.91 | 1 A, B |
| 18 | N-(2,2-difluoro-5H-[1,3]dioxolo[4',5':4,5]benzo[1,2-d]imidazol-6-yl)isonicotinamide | +++ | ++ | | | 320.11 | 1 A, B |
| 19 | N-(2,2-difluoro-5H-[1,3]dioxolo[4',5':4,5]benzo[1,2-d]imidazol-6-yl)-2-(2,5-dimethoxyphenylsulfonamido)thiazole-4-carboxamide | +++ | +++ | | | 539.8 | 1 A, B |
| 20 | N-(2,2-difluoro-5H-[1,3]dioxolo[4',5':4,5]benzo[1,2-d]imidazol-6-yl)thiophene-3-carboxamide | +++ | ++ | | | 323.95 | 2 D, E |
| 21 | N-(2,2-difluoro-5H-[1,3]dioxolo[4',5':4,5]benzo[1,2-d]imidazol-6-yl)-2-(isonicotinamido)thiazole-4-carboxamide | +++ | +++ | | | 444.83 | 1 D, A, B |
| 22 | 3-amino-6-bromo-N-(2,2-difluoro-5H-[1,3]dioxolo[4',5':4,5]benzo[1,2-d]imidazol-6-yl)pyrazine-2-carboxamide | ++ | + | | | 414.73 | 1 D, B |

TABLE 1-continued

Exemplary compounds.

| No. | Structure | CK1 delta Assay | CK1 epsilon Assay | HH Assay | Wnt Assay | [M + H]+ | General procedure/ after-treatment |
|---|---|---|---|---|---|---|---|
| 23 | N-(2,2-difluoro-5H-[1,3]dioxolo[4',5':4,5]benzo[1,2-d]imidazol-6-yl)-2-((4-(trifluoromethoxy)phenyl)amino)thiazole-4-carboxamide | + | + | | | 499.86 | 1 D, B |
| 24 | N-(2,2-difluoro-5H-[1,3]dioxolo[4',5':4,5]benzo[1,2-d]imidazol-6-yl)-2-morpholinooxazole-4-carboxamide | ++ | ++ | | | 393.70 | 1 A, D |
| 25 | N-(2,2-difluoro-5H-[1,3]dioxolo[4',5':4,5]benzo[1,2-d]imidazol-6-yl)-2-((4-methyl-6-(trifluoromethyl)pyrimidin-2-yl)amino)thiazole-4-carboxamide | + | + | | | 499.84 | 1 F |
| 26 | N-(2,2-difluoro-5H-[1,3]dioxolo[4',5':4,5]benzo[1,2-d]imidazol-6-yl)-2-(3-(2-(trifluoromethoxy)phenyl)ureido)thiazole-4-carboxamide | +++ | +++ | | | 542.97 | 1 A, B |
| 27 | N-(2,2-difluoro-5H-[1,3]dioxolo[4',5':4,5]benzo[1,2-d]imidazol-6-yl)pyrazine-2-carboxamide | + | + | + | | 319.71 | 1 A |
| 28 | N-(2,2-difluoro-5H-[1,3]dioxolo[4',5':4,5]benzo[1,2-d]imidazol-6-yl)-2,5-dimethylthiophene-3-carboxamide | ++ | ++ | | | 351.81 | 1 A, B |

TABLE 1-continued

Exemplary compounds.

| No. | Structure | CK1 delta Assay | CK1 epsilon Assay | HH Assay | Wnt Assay | [M + H]+ | General procedure/ after-treatment |
|---|---|---|---|---|---|---|---|
| 29 | 5-bromo-N-(2,2-difluoro-5H-[1,3]dioxolo[4',5':4,5]benzo[1,2-d]imidazol-6-yl)thiophene-3-carboxamide | +++ | +++ | | | 403.64 | 1 A, E |
| 30 | N-(2,2-difluoro-5H-[1,3]dioxolo[4',5':4,5]benzo[1,2-d]imidazol-6-yl)-5-nitrothiophene-3-carboxamide | +++ | +++ | | | 368.74 | 1 A, B |
| 31 | N-(2,2-difluoro-5H-[1,3]dioxolo[4'5':4,5]benzo[1,2-d]imidazol-6-yl)benzo[b]thiophene-3-carboxamide | +++ | ++ | | | 373.90 | 1 A, F |
| 32 | N-(2,2-difluoro-5H-[1,3]dioxolo[4',5':4,5]benzo[1,2-d]imidazol-6-yl)furan-3-carboxamide | ++ | +++ | | | 307.95 | 1 D, B |
| 33 | N-(2,2-difluoro-5H-[1,3]dioxolo[4',5':4,5]benzo[1,2-d]imidazol-6-yl)-2-methylfuran-3-carboxamide | +++ | ++ | | | 321.85 | 1 A, B |
| 34 | N-(2,2-difluoro-5H-[1,3]dioxolo[4',5':4,5]benzo[1,2-d]imidazol-6-yl)-2,5-dimethylfuran-3-carboxamide | + | + | | | 335.86 | 1 A, B |
| 35 | N-(2,2-difluoro-5H-[1,3]dioxolo[4',5':4,5]benzo[1,2-d]imidazol-6-yl)oxazole-4-carboxamide | ++ | + | | | 308.90 | 1 A, B |

TABLE 1-continued

Exemplary compounds.

| No. | Structure | CK1 delta Assay | CK1 epsilon Assay | HH Assay | Wnt Assay | [M + H]+ | General procedure/ after-treatment |
|---|---|---|---|---|---|---|---|
| 36 | N-(2,2-difluoro-5H-[1,3]dioxolo[4',5':4,5]benzo[1,2-d]imidazol-6-yl)-1-(3-fluorophenyl)-5-(trifluoromethyl)-1H-1,2,3-triazole-4-carboxamide | ++ | + | | | 470.78 | 1 A, F |
| 37 | N-(2,2-difluoro-5H-[1,3]dioxolo[4',5':4,5]benzo[1,2-d]imidazol-6-yl)-2-morpholinothiazole-4-carboxamide | +++ | ++ | | | 410.40 | 1 A, E |
| 38 | N-(2,2-difluoro-5H-[1,3]dioxolo[4',5':4,5]benzo[1,2-d]imidazol-6-yl)-5-(2,3-dihydrobenzofuran-5-yl)thiophene-3-carboxamide | +++ | ++ | | | 441.77 | see description of alternative procedures |
| 39 | 2-(benzo[d][1,3]dioxol-5-yl)-N-(2,2-difluoro-5H-[1,3]dioxolo[4',5':4,5]benzo[1,2-d]imidazol-6-yl)thiazole-4-carboxamide | + | ++ | | | 444.80 | 1 A, E |
| 40 | N-(2,2-difluoro-5H-[1,3]dioxolo[4',5':4,5]benzo[1,2-d]imidazol-6-yl)-2-(2,3-dihydrobenzofuran-5-yl)oxazole-4-carboxamide | + | + | | | 426.84 | 1 A, F |

TABLE 1-continued

Exemplary compounds.

| No. | Structure | CK1 delta Assay | CK1 epsilon Assay | HH Assay | Wnt Assay | [M + H]+ | General procedure/ after-treatment |
|---|---|---|---|---|---|---|---|
| 41 | 3-chloro-N-(2,2-difluoro-5H-[1,3]dioxolo[4',5':4,5]benzo[1,2-d]imidazol-6-yl)benzamide | +++ | +++ | | | 351.8 | 2 D, E, C |
| 42 | N-(2,2-difluoro-5H-[1,3]dioxolo[4',5':4,5]benzo[1,2-d]imidazol-6-yl)-4-methyl-1,2,3-thiadiazole-5-carboxamide | + | + | | | 339.81 | 3 D, E, C |
| 43 | 2,4-dichloro-N-(2,2-difluoro-5H-[1,3]dioxolo[4',5':4,5]benzo[1,2-d]imidazol-6-yl)benzamide | ++ | ++ | | | 385.7 | 2 D, E, C |
| 44 | N-(2,2-difluoro-5H-[1,3]dioxolo[4',5':4,5]benzo[1,2-d]imidazol-6-yl)thiazole-4-carboxamide | ++ | ++ | | | 324.8 | 3 D, E, C |
| 45 | N-(2,2-difluoro-5H-[1,3]dioxolo[4',5':4,5]benzo[1,2-d]imidazol-6-yl)thiophene-2-carboxamide | ++ | ++ | | | 323.8 | 2 D, E, C |
| 46 | N-(2,2-difluoro-5H-[1,3]dioxolo[4',5':4,5]benzo[1,2-d]imidazol-6-yl)-4-methoxybenzamide | ++ | ++ | | | 347.8 | 2 D, E, C |

TABLE 1-continued

Exemplary compounds.

| No. | Structure | CK1 delta Assay | CK1 epsilon Assay | HH Assay | Wnt Assay | [M + H]+ | General procedure/ after-treatment |
|---|---|---|---|---|---|---|---|
| 47 | N-(2,2-difluoro-5H-[1,3]dioxolo[4',5':4,5]benzo[1,2-d]imidazol-6-yl)-2-(trifluoromethoxy)benzamide | ++ | + | | | 401.7 | 2 D, E, C |
| 48 | N-(2,2-difluoro-5H-[1,3]dioxolo[4',5':4,5]benzo[1,2-d]imidazol-6-yl)-2-(2-(trifluoromethoxy)benzamido)oxazole-5-carboxamide | +++ | ++ | | | 511.7 | 1 D.E, B, C |
| 49 | N-(2,2-difluoro-5H-[1,3]dioxolo[4',5':4,5]benzo[1,2-d]imidazol-6-yl)benzamide | +++ | +++ | | | 317.9 | 2 D, E, C |
| 50 | N-(2,2-difluoro-5H-[1,3]dioxolo[4',5':4,5]benzo[1,2-d]imidazol-6-yl)-5-methyl-3-phenylisoxazole-4-carboxamide | + | | | | 398.8 | 3 D, G, B |
| 51 | 3-(2,4-dichlorobenzamido)-N-(2,2-difluoro-5H-[1,3]dioxolo[4',5':4,5]benzo[1,2-d]imidazol-6-yl)-1H-1,2,4-triazole-5-carboxamide | +++ | ++ | | | 496.02 | 1 D, E, C |

TABLE 1-continued

Exemplary compounds.

| No. | Structure | CK1 delta Assay | CK1 epsilon Assay | HH Assay | Wnt Assay | [M + H]+ | General procedure/ after-treatment |
|---|---|---|---|---|---|---|---|
| 52 | N-(2,2-difluoro-5H-[1,3]dioxolo[4',5':4,5]benzo[1,2-d]imidazol-6-yl)-3-(2-(trifluoromethoxy)benzamido)-1H-1,2,4-triazole-5-carboxamide | +++ | ++ | | | 512.31 | 1 D, E, c |
| 54 | N-(2,2-difluoro-5H-[1,3]dioxolo[4',5':4,5]benzo[1,2-d]imidazol-6-yl)-2,6-difluorobenzamide | ++ | + | | | 353.8 | 2 D, E, C |
| 55 | 2-bromo-N-(2,2-difluoro-5H-[1,3]dioxolo[4',5':4,5]benzo[1,2-d]imidazol-6-yl)thiazole-4-carboxamide | ++ | ++ | | | 402.40 | 1 |
| 56 | N-(2,2-difluoro-5H-[1,3]dioxolo[4',5':4,5]benzo[1,2-d]imidazol-6-yl)-3-methoxybenzamide | +++ | +++ | +++ | +++ | 347.8 | 2 D |
| 57 | 5-(3-chlorobenzamido)-N-(2,2-difluoro-5H-[1,3]dioxolo[4',5':4,5]benzo[1,2-d]imidazol-6-yl)-1,2,4-thiadiazole-3-carboxamide | +++ | +++ | | | 478.7 | 1 D, E |
| 58 | N-(2,2-difluoro-5H-[1,3]dioxolo[4',5':4,5]benzo[1,2-d]imidazol-6-yl)-4-nitrobenzamide | ++ | | | | 363.21 | 1 D, E, C |

TABLE 1-continued

Exemplary compounds.

| No. | Structure | CK1 delta Assay | CK1 epsilon Assay | HH Assay | Wnt Assay | [M + H]+ | General procedure/after-treatment |
|---|---|---|---|---|---|---|---|
| 59 | N-(2,2-difluoro-5H-[1,3]dioxolo[4',5':4,5]benzo[1,2-d]imidazol-6-yl)quinoline-2-carboxamide | + | | | | 369.24 | 1 D, E, C |
| 60 | 4-amino-N-(2,2-difluoro-5H-[1,3]dioxolo[4',5':4,5]benzo[1,2-d]imidazol-6-yl)benzamide | +++ | | | | 332.9 | see description of alternative procedures |
| 61 | N-(2,2-difluoro-5H-[1,3]dioxolo[4',5':4,5]benzo[1,2-d]imidazol-6-yl)-3-(4-nitrobenzamido)-1H-1,2,4-triazole-5-carboxamide | + | + | | | 487.14 | 1 D, E |
| 62 | N-(2,2-difluoro-5H-[1,3]dioxolo[4',5':4,5]benzo[1,2-d]imidazol-6-yl)-4-sulfamoylbenzamide | +++ | | | | 396.61 | 1 D, F, B |
| 63 | N-(2,2-difluoro-5H-[1,3]dioxolo[4',5':4,5]benzo[1,2-d]imidazol-6-yl)-5-nitrothiophene-2-carboxamide | ++ | | | | 368.73 | 1 A, B |
| 64 | 3-chloro-N-(2,2-difluoro-5H-[1,3]dioxolo[4',5':4,5]benzo[1,2-d]imidazol-6-yl)thiophene-2-carboxamide | + | | | | 357.72 | 1 A, B |
| 65 | N-(2,2-difluoro-5H-[1,3]dioxolo[4',5':4,5]benzo[1,2-d]imidazol-6-yl)-3-nitrobenzamide | +++ | | | | 362.78 | 1 A, E |

TABLE 1-continued

Exemplary compounds.

| No. | Structure | CK1 delta Assay | CK1 epsilon Assay | HH Assay | Wnt Assay | [M + H]+ | General procedure/ after- treatment |
|---|---|---|---|---|---|---|---|
| 66 | N-(2,2-difluoro-5H-[1,3]dioxolo[4',5':4,5]benzo[1,2-d]imidazol-6-yl)-3-(trifluoromethyl)benzamide | +++ | | | | 386.45 | 2 D, B, F |
| 67 | N-(2,2-difluoro-5H-[1,3]dioxolo[4',5':4,5]benzo[1,2-d]imidazol-6-yl)picolinamide | + | | | | 318.43 | 2 D |
| 68 | N-(2,2-difluoro-5H-[1,3]dioxolo[4',5':4,5]benzo[1,2-d]imidazol-6-yl)-2-methylbenzamide | ++ | + | | | 331.85 | 1 D, B |
| 69 | N-(2,2-difluoro-5H-[1,3]dioxolo[4',5':4,5]benzo[1,2-d]imidazol-6-yl)-2-(4-methoxybenzamido)thiazole-4-carboxamide | +++ | ++ | | | 473.76 | 1 D, B |
| 70 | N-(2,2-difluoro-5H-[1,3]dioxolo[4',5':4,5]benzo[1,2-d]imidazol-6-yl)-3-fluorobenzamide | +++ | | | | 336.22 | 2 D, C |
| 71 | N-(2,2-difluoro-5H-[1,3]dioxolo[4',5':4,5]benzo[1,2-d]imidazol-6-yl)oxazole-5-carboxamide | ++ | | | | 308.93 | 1 D, E |

TABLE 1-continued

Exemplary compounds.

| No. | Structure | CK1 delta Assay | CK1 epsilon Assay | HH Assay | Wnt Assay | [M + H]+ | General procedure/ after-treatment |
|---|---|---|---|---|---|---|---|
| 72 | N-(2,2-difluoro-5H-[1,3]dioxolo[4',5':4,5]benzo[1,2-d]imidazol-6-yl)isoxazole-5-carboxamide | ++ | | | | 308.82 | 1 D, B |
| 73 | N-(2,2-difluoro-5H-[1,3]dioxolo[4',5':4,5]benzo[1,2-d]imidazol-6-yl)-1H-pyrazole-3-carboxamide | + | | | | 307.82 | 1 D, C |
| 74 | 4-(diethylamino)-N-(2,2-difluoro-5H-[1,3]dioxolo[4',5':4,5]benzo[1,2-d]imidazol-6-yl)benzamide | ++ | | | | 388.9 | 4 G, C |
| 75 | N-(2,2-difluoro-5H-[1,3]dioxolo[4',5':4,5]benzo[1,2-d]imidazol-6-yl)-4-(dimethylamino)benzamide | +++ | | | | 360.9 | 4 G, C |
| 76 | 4-(benzylamino)-N-(2,2-difluoro-5H-[1,3]dioxolo[4',5':4,5]benzo[1,2-d]imidazol-6-yl)benzamide | +++ | | | | 422.8 | 4 G, C |
| 77 | N-(2,2-difluoro-5H-[1,3]dioxolo[4',5':4,5]benzo[1,2-d]imidazol-6-yl)-4-(ethylamino)benzamide | +++ | | | | 360.9 | 4 G, C |
| 78 | N-(2,2-difluoro-5H-[1,3]dioxolo[4',5':4,5]benzo[1,2-d]imidazol-6-yl)nicotinamide | +++ | | | | 318.8 | 1 D, E |

TABLE 1-continued

Exemplary compounds.

| No. | Structure | CK1 delta Assay | CK1 epsiplon Assay | HH Assay | Wnt Assay | [M + H]+ | General procedure/ after-treatment |
|---|---|---|---|---|---|---|---|
| 79 | 2-amino-N-(2,2-difluoro-5H-[1,3]dioxolo[4',5':4,5]benzo[1,2-d]imidazol-6-yl)thiophene-3-carboxamide | ++ | ++ | | | 338.81 | see description of alternative procedures |
| 80 | N-(2,2-difluoro-5H-[1,3]dioxolo[4',5':4,5]benzo[1,2-d]imidazol-6-yl)cyclohexanecarboxamide | +++ | | | | 323.9 | see description of alternative procedures |
| 81 | N-(2,2-difluoro-5H-[1,3]dioxolo[4',5':4,5]benzo[1,2-d]imidazol-6-yl)-2-(thiophen-3-yl)thiazole-4-carboxamide | +++ | | | | 406.7 | 1 E |
| 82 | N-(2,2-difluoro-5H-[1,3]dioxolo[4',5':4,5]benzo[1,2-d]imidazol-6-yl)-2-(2,3-dihydrobenzo[b][1,4]dioxin-6-yl)thiazole-4-carboxamide | +++ | | | | 459.2 | 1 D, E, B |
| 83 | N-(2,2-difluoro-5H-[1,3]dioxolo[4',5':4,5]benzo[1,2-d]imidazol-6-yl)-5-sulfamoylthiophene-3-carboxamide | +++ | +++ | | | 402.77 | 1 D, B |
| 84 | N-(2,2-difluoro-5H-[1,3]dioxolo[4',5':4,5]benzo[1,2-d]imidazol-6-yl)-1H-1,2,4-triazole-3-carboxamide | + | + | | | 308.89 | 1 A, E |

TABLE 1-continued

Exemplary compounds.

| No. | Structure | CK1 delta Assay | CK1 epsilon Assay | HH Assay | Wnt Assay | [M + H]+ | General procedure/ after-treatment |
|---|---|---|---|---|---|---|---|
| 85 | N-(2,2-difluoro-5H-[1,3]dioxolo[4',5':4,5]benzo[1,2-d]imidazol-6-yl)-5-(methylsulfonyl)thiophene-2-carboxamide | ++ | ++ | | | 401.76 | 1 D, B |
| 86 | 5-chloro-N-(2,2-difluoro-5H-[1,3]dioxolo[4',5':4,5]benzo[1,2-d]imidazol-6-yl)-2-hydroxybenzamide | + | + | | | 367.74 | 1 A, B |
| 87 | 3-amino-N-(2,2-difluoro-5H-[1,3]dioxolo[4',5':4,5]benzo[1,2-d]imidazol-6-yl)benzamide | +++ | ++ | | | 332.88 | 1 A, D |
| 88 | N-(2,2-difluoro-5H-[1,3]dioxolo[4',5':4,5]benzo[1,2-d]imidazol-6-yl)-4-nitro-1H-pyrrole-2-carboxamide | +++ | +++ | | | 351.78 | 1 D, B |
| 89 | N-(2,2-difluoro-5H-[1,3]dioxolo[4',5':4,5]benzo[1,2-d]imidazol-6-yl)-5-(4-methylbenzamido)-1,2,4-thiadiazole-3-carboxamide | ++ | ++ | | | 458.8 | 1 D, E |
| 90 | N-(2,2-difluoro-5H-[1,3]dioxolo[4',5':4,5]benzo[1,2-d]imidazol-6-yl)-5-(4-methoxybenzamido)-1,2,4-thiadiazole-3-carboxamide | + | + | | | 474.7 | 1 D, E |

TABLE 1-continued

Exemplary compounds.

| No. | Structure | CK1 delta Assay | CK1 epsilon Assay | HH Assay | Wnt Assay | [M + H]+ | General procedure/ after-treatment |
|---|---|---|---|---|---|---|---|
| 91 | 5-(4-chlorobenzamido)-N-(2,2-difluoro-5H-[1,3]dioxolo[4',5':4,5]benzo[1,2-d]imidazol-6-yl)-1,2,4-thiadiazole-3-carboxamide | +++ | +++ | | | 478.7 | 1 D, E |
| 92 | N-(2,2-difluoro-5H-[1,3]dioxolo[4',5':4,5]benzo[1,2-d]imidazol-6-yl)-5-(4-fluorobenzamido)-1,2,4-thiadiazole-3-carboxamide | +++ | +++ | | | 462.8 | 1 D, E |
| 93 | 4-cyano-N-(2,2-difluoro-5H-[1,3]dioxolo[4',5':4,5]benzo[1,2-d]imidazol-6-yl)-2-fluorobenzamide | + | | | | 360.8 | 1 D, G, E |
| 94 | N¹-(2,2-difluoro-5H-[1,3]dioxolo[4',5':4,5]benzo[1,2-d]imidazol-6-yl)-2-fluoroterephthalamide | +++ | | | | 378.8 | 1 D, G, E |
| 95 | 3-acetamido-N-(2,2-difluoro-5H-[1,3]dioxolo[4',5':4,5]benzo[1,2-d]imidazol-6-yl)-1H-1,2,4-triazole-5-carboxamide | + | + | | | 365.8 | 1 E |
| 96 | N-(2,2-difluoro-5H-[1,3]dioxolo[4',5':4,5]benzo[1,2-d]imidazol-6-yl)-1H-1,2,4-triazole-5-carboxamide | + | + | | | 308.9 | 1 E |

TABLE 1-continued

Exemplary compounds.

| No. | Structure | CK1 delta Assay | CK1 epsilon Assay | HH Assay | Wnt Assay | [M + H]+ | General procedure/ after-treatment |
|---|---|---|---|---|---|---|---|
| 97 | N-(2,2-difluoro-5H-[1,3]dioxolo[4'5':4,5]benzo[1,2-d]imidazol-6-yl)-2-(1-(thieno[3,2-d]pyrimidin-4-yl)piperidin-4-yl)thiazole-4-carboxamide | ++ | ++ | | | 541.92 | 1 A, F |
| 98 | N-(2,2-difluoro-5H-[1,3]dioxolo[4'5':4,5]benzo[1,2-d]imidazol-6-yl)-2-(3-(2-morpholinoethyl)-2-oxo-2,3-dihydro-1H-benzo[d]imidazol-1-yl)thiazole-4-carboxamide | ++ | + | | | 570.27 | 1 A, B |
| 99 | N-(2,2-difluoro-5H-[1,3]dioxolo[4',5':4,5]benzo[1,2-d]imidazol-6-yl)-2-((2,6-dimethoxypyrimidin-4-yl)amino)thiazole-5-carboxamide | + | + | | | 477.84 | 1 A, B |
| 100 | N-(2,2-difluoro-5H-[1,3]dioxolo[4',5':4,5]benzo[1,2-d]imidazol-6-yl)-3-sulfamoylbenzamide | +++ | | | | 397.13 | 1 A, B, F |
| 101 | N-(2,2-difluoro-5H-[1,3]dioxolo[4',5':4,5]benzo[1,2-d]imidazol-6-yl)-4-sulfamoyl-1H-pyrrole-2-carboxamide | +++ | | | | 385.75 | 1 A, B |

TABLE 1-continued

Exemplary compounds.

| No. | Structure | CK1 delta Assay | CK1 epsilon Assay | HH Assay | Wnt Assay | [M + H]+ | General procedure/ after-treatment |
|---|---|---|---|---|---|---|---|
| 102 | N-(2,2-difluoro-5H-[1,3]dioxolo[4',5':4,5]benzo[1,2-d]imidazol-6-yl)-3-(dimethylamino)benzamide | +++ | +++ | ++ | | 360.91 | 1 D, B |
| 103 | N-(2,2-difluoro-5H-[1,3]dioxolo[4',5':4,5]benzo[1,2-d]imidazol-6-yl)-1H-imidazole-4-carboxamide | ++ | | | | 307.87 | 1 A, B |
| 104 | 4-acetyl-N-(2,2-difluoro-5H-[1,3]dioxolo[4',5':4,5]benzo[1,2-d]imidazol-6-yl)-1H-pyrrole-2-carboxamide | +++ | +++ | | | 348.87 | 1 D, B |
| 105 | methyl 3-((2,2-difluoro-5H-[1,3]dioxolo[4',5':4,5]benzo[1,2-d]imidazol-6-yl)carbamoyl)benzoate | +++ | +++ | | | 375.73 | 1 D, B |
| 106 | 4-chloro-N-(2,2-difluoro-5H-[1,3]dioxolo[4',5':4,5]benzo[1,2-d]imidazol-6-yl)benzamide | + | | | | 351.78 | 1 D, E |
| 107 | N-(2,2-difluoro-5H-[1,3]dioxolo[4',5':4,5]benzo[1,2-d]imidazol-6-yl)-4-methylbenzamide | + | | | | 331.84 | 2 A, B |

TABLE 1-continued

Exemplary compounds.

| No. | Structure | CK1 delta Assay | CK1 epsilon Assay | HH Assay | Wnt Assay | [M + H]+ | General procedure/ after-treatment |
|---|---|---|---|---|---|---|---|
| 108 | N-(2,2-difluoro-5H-[1,3]dioxolo[4',5':4,5]benzo[1,2-d]imidazol-6-yl)-3-(methylsulfonamido)benzamide | +++ | | | | 410.74 | 1 D, B |
| 109 | 3,4-dichloro-N-(2,2-difluoro-5H-[1,3]dioxolo[4',5':4,5]benzo[1,2-d]imidazol-6-yl)benzamide | ++ | | | | 385.72 | 2 A, B |
| 110 | 6-amino-N-(2,2-difluoro-5H-[1,3]dioxolo[4',5':4,5]benzo[1,2-d]imidazol-6-yl)nicotinamide | ++ | | | | 333.85 | 1 A, B |
| 111 | N1-(2,2-difluoro-5H-[1,3]dioxolo[4',5':4,5]benzo[1,2-d]imidazol-6-yl)terephthalamide | +++ | +++ | | | 360.85 | 1 A, F |
| 112 | N-(2,2-difluoro-5H-[1,3]dioxolo[4',5':4,5]benzo[1,2-d]imidazol-6-yl)-6-sulfamoylnicotinamide | +++ | | | | 397.77 | 1 A, F |
| 113 | N-(2,2-difluoro-5H-[1,3]dioxolo[4',5':4,5]benzo[1,2-d]imidazol-6-yl)-3-hydroxybenzamide | +++ | | | | 333.85 | 1 A, B |

TABLE 1-continued

Exemplary compounds.

| No. | Structure | CK1 delta Assay | CK1 epsilon Assay | HH Assay | Wnt Assay | [M + H]+ | General procedure/ after-treatment |
|---|---|---|---|---|---|---|---|
| 114 | 3-acetyl-N-(2,2-difluoro-5H-[1,3]dioxolo[4',5':4,5]benzo[1,2-d]imidazol-6-yl)benzamide | +++ | | | | 359.82 | 1 D, F |
| 115 | 4-(tert-butyl)-N-(2,2-difluoro-5H-[1,3]dioxolo[4',5':4,5]benzo[1,2-d]imidazol-6-yl)benzamide | ++ | | | | 373.84 | 1 D, F |
| 116 | 3-cyano-N-(2,2-difluoro-5H-[1,3]dioxolo[4',5':4,5]benzo[1,2-d]imidazol-6-yl)benzamide | +++ | | | | 342.85 | 1 D, E |
| 117 | N-(2,2-difluoro-5H-[1,3]dioxolo[4',5':4,5]benzo[1,2-d]imidazol-6-yl)-4-(morpholinosulfonyl)benzamide | +++ | +++ | | | 467.03 | 1 D, E |
| 118 | N-(2,2-difluoro-5H-[1,3]dioxolo[4',5':4,5]benzo[1,2-d]imidazol-6-yl)-3-(1H-tetrazol-5-yl)benzamide | +++ | +++ | | | 385.79 | 1 D, A, E |
| 119 | N-(2,2-difluoro-5H-[1,3]dioxolo[4',5':4,5]benzo[1,2-d]imidazol-6-yl)-4-fluorobenzamide | ++ | | | | 335.86 | 1 D, F |

TABLE 1-continued

Exemplary compounds.

| No. | Structure | CK1 delta Assay | CK1 epsiplon Assay | HH Assay | Wnt Assay | [M + H]+ | General procedure/ after-treatment |
|---|---|---|---|---|---|---|---|
| 120 | N-(2,2-difluoro-5H-[1,3]dioxolo[4',5':4,5]benzo[1,2-d]imidazol-6-yl)-3-(trifluoromethoxy)benzamide | ++ | | | | 401.73 | 2 A, B |
| 121 | N-(2,2-difluoro-5H-[1,3]dioxolo[4',5':4,5]benzo[1,2-d]imidazol-6-yl)-3-(difluoromethoxy)benzamide | +++ | | | | 384.98 | 1 D, B |
| 122 | N-(2,2-difluoro-5H-[1,3]dioxolo[4',5':4,5]benzo[1,2-d]imidazol-6-yl)-3-(pyrrolidin-1-yl)benzamide | +++ | | +++ | | 386.89 | 1 D, B |
| 123 | N-(2,2-difluoro-5H-[1,3]dioxolo[4',5':4,5]benzo[1,2-d]imidazol-6-yl)-5-methoxynicotinamide | +++ | +++ | | | 348.76 | 1 D, E |
| 124 | N-(2,2-difluoro-5H-[1,3]dioxolo[4',5':4,5]benzo[1,2-d]imidazol-6-yl)-2-methoxyisonicotinamide | +++ | +++ | | | 348.85 | 1 D, E |
| 125 | N-(2,2-difluoro-5H-[1,3]dioxolo[4',5':4,5]benzo[1,2-d]imidazol-6-yl)-2-(dimethylamino)isonicotinamide | +++ | | | + | 361.89 | 1 D |

TABLE 1-continued

Exemplary compounds.

| No. | Structure | CK1 delta Assay | CK1 epsiplon Assay | HH Assay | Wnt Assay | [M + H]+ | General procedure/ after- treatment |
|---|---|---|---|---|---|---|---|
| 126 | 4-amino-N-(2,2-difluoro-5H-[1,3]dioxolo[4',5':4,5]benzo[1,2-d]imidazol-6-yl)-3-(trifluoromethyl)benzamide | +++ | | | | 400.79 | 1 A, B |
| 127 | 4-amino-N-(2,2-difluoro-5H-[1,3]dioxolo[4',5':4,5]benzo[1,2-d]imidazol-6-yl)-3-fluorobenzamide | ++ | | | | 350.78 | 1 A, B |
| 128 | N-(2,2-difluoro-5H-[1,3]dioxolo[4',5':4,5]benzo[1,2-d]imidazol-6-yl)-3-(piperidin-1-yl)benzamide | +++ | | | | 400.81 | 1 D, E |
| 129 | 3-(4-chlorobenzamido)-N-(2,2-difluoro-5H-[1,3]dioxolo[4',5':4,5]benzo[1,2-d]imidazol-6-yl)-1H-1,2,4-triazole-5-carboxamide | ++ | + | | | 462.74 | 1 D, E |
| 130 | N-(2,2-difluoro-5H-[1,3]dioxolo[4',5':4,5]benzo[1,2-d]imidazol-6-yl)-3-(3,5-dimethyl-1H-pyrazol-1-yl)benzamide | +++ | +++ | +++ | | 412.36 | 1 D, B |

TABLE 1-continued

Exemplary compounds.

| No. | Structure | CK1 delta Assay | CK1 epsilon Assay | HH Assay | Wnt Assay | [M + H]+ | General procedure/ after- treatment |
|---|---|---|---|---|---|---|---|
| 131 | N-(2,2-difluoro-5H-[1,3]dioxolo[4',5':4,5]benzo[1,2-d]imidazol-6-yl)-3-(5-isopropyl-1,2,4-oxadiazol-3-yl)benzamide | +++ | | | | 428.35 | 1 D, B |
| 132 | 3-(5-(tert-butyl)-1,2,4-oxadiazol-3-yl)-N-(2,2-difluoro-5H-[1,3]dioxolo[4',5':4,5]benzo[1,2-d]imidazol-6-yl)benzamide | +++ | | | | 442.39 | 1 D, B |
| 133 | (S)-N-(2,2-difluoro-5H-[1,3]dioxolo[4',5':4,5]benzo[1,2-d]imidazol-6-yl)-2-(6-methoxynaphthalen-2-yl)propanamide | +++ | +++ | | | 426.12 | 2 D, C |
| 134 | N-(2,2-difluoro-5H-[1,3]dioxolo[4',5':4,5]benzo[1,2-d]imidazol-6-yl)-2-(4-methyl-1,2,3-thiadiazol-5-yl)thiazole-4-carboxamide | +++ | +++ | | | 423.01 | 1 E |
| 135 | N-(2,2-difluoro-5H-[1,3]dioxolo[4',5':4,5]benzo[1,2-d]imidazol-6-yl)-[2,4'-bithiazole]-4-carboxamide | +++ | +++ | | | 408.00 | 1 D, E, C |

TABLE 1-continued

Exemplary compounds.

| No. | Structure | CK1 delta Assay | CK1 epsiplon Assay | HH Assay | Wnt Assay | [M + H]+ | General procedure/ after-treatment |
|---|---|---|---|---|---|---|---|
| 136 | N-(2,2-difluoro-5H-[1,3]dioxolo[4',5':4,5]benzo[1,2-d]imidazol-6-yl)-2-(thiophen-2-yl)oxazole-4-carboxamide | +++ | ++ | | | 391.02 | 1 D, E, C |
| 137 | N-(2,2-difluoro-5H-[1,3]dioxolo[4',5':4,5]benzo[1,2-d]imidazol-6-yl)-3-(5-methyl-1,2,4-oxadiazol-3-yl)benzamide | +++ | +++ | ++ | +++ | 400.1 | 1 D, E, C |
| 138 | N-(2,2-difluoro-5H-[1,3]dioxolo[4',5':4,5]benzo[1,2-d]imidazol-6-yl)-5-(thiophen-2-yl)isoxazole-3-carboxamide | +++ | +++ | ++ | | 391.02 | 1 D, E, C |
| 139 | ethyl 1-(3-((2,2-difluoro-5H-[1,3]dioxolo[4',5':4,5]benzo[1,2-d]imidazol-6-yl)carbamoyl)phenyl)-2,5-dimethyl-1H-pyrrole-3-carboxylate | +++ | | | | 483.14 | 1 D, E, B |
| 140 | N-(2,2-difluoro-5H-[1,3]dioxolo[4',5':4,5]benzo[1,2-d]imidazol-6-yl)-3-(1H-imidazol-2-yl)benzamide | +++ | +++ | ++ | +++ | 384.10 | 1 D, E, C |

TABLE 1-continued

Exemplary compounds.

| No. | Structure | CK1 delta Assay | CK1 epsilon Assay | HH Assay | Wnt Assay | [M + H]+ | General procedure/ after-treatment |
|---|---|---|---|---|---|---|---|
| 141 | N-(2,2-difluoro-5H-[1,3]dioxolo[4',5':4,5]benzo[1,2-d]imidazol-6-yl)-2-(5-methylisoxazol-3-yl)thiazole-4-carboxamide | +++ | +++ | | | 406.03 | 1 D, E, C |
| 142 | N-(2,2-difluoro-5H-[1,3]dioxolo[4',5':4,5]benzo[1,2-d]imidazol-6-yl)-4-(1H-pyrazol-1-yl)benzamide | +++ | + | | | 384.1 | 1 D, E, C |
| 143 | N-(2,2-difluoro-5H-[1,3]dioxolo[4',5':4,5]benzo[1,2-d]imidazol-6-yl)-5-(furan-2-yl)isoxazole-3-carboxamide | ++ | ++ | | | 375.05 | 1 D, E, C |
| 144 | N-(2,2-difluoro-5H-[1,3]dioxolo[4',5':4,5]benzo[1,2-d]imidazol-6-yl)-5-(1,3-dimethyl-1H-pyrazol-4-yl)isoxazole-3-carboxamide | +++ | + | | | 403.09 | 1 D, E, C |
| 145 | N-(2,2-difluoro-5H-[1,3]dioxolo[4',5':4,5]benzo[1,2-d]imidazol-6-yl)-5-methylisoxazole-3-carboxamide | + | | | | 323.06 | 1 D, E, C |

TABLE 1-continued

Exemplary compounds.

| No. | Structure | CK1 delta Assay | CK1 epsilon Assay | HH Assay | Wnt Assay | [M + H]+ | General procedure/ aftertreatment |
|---|---|---|---|---|---|---|---|
| 146 | N-(2,2-difluoro-5H-[1,3]dioxolo[4',5':4,5]benzo[1,2-d]imidazol-6-yl)-1,5-dimethyl-1H-pyrazole-3-carboxamide | + | | | | 336.09 | 1 D, E, B |
| 147 | 3-(5-cyclopropyl-1,2,4-oxadiazol-3-yl)-N-(2,2-difluoro-5H-[1,3]dioxolo[4',5':4,5]benzo[1,2-d]imidazol-6-yl)benzamide | +++ | +++ | ++ | | 426.10 | 1 D, C |
| 148 | N-(2,2-difluoro-5H-[1,3]dioxolo[4',5':4,5]benzo[1,2-d]imidazol-6-yl)-3-(5-methyl-1H-tetrazol-1-yl)benzamide | +++ | +++ | | +++ | 400.09 | 1 D, C |
| 149 | N-(2,2-difluoro-5H-[1,3]dioxolo[4',5':4,5]benzo[1,2-d]imidazol-6-yl)-3-(1H-tetrazol-1-yl)benzamide | +++ | +++ | + | ++ | 386.08 | 1 D, C |

The symbols in the columns "CK1 delta Assay" and "CK1 epsilon Assay" have the following meanings: +++: $IC_{50}$ < 200 nM, ++: $IC_{50}$ 200-1000 nM, +: $IC_{50}$ > 1 μM, each determined according to the kinase assays as described herein below. The symbols in the column "HH Assay" have the following meanings: +++: $IC_{50}$ ≤ 500 nM, ++: $IC_{50}$ > 500-1000 nM, +: $IC_{50}$ 1-15 μM, each determined according to the Hedgehog reporter assay as described herein below. The symbols in the column "Wnt Assay" have the following meanings: +++: $IC_{50}$ < 5 μM, ++: $IC_{50}$ 5-20 μM, each determined according to the Wnt reporter assay as described herein below. The indications in the column "General procedure/aftertreatment" refers to the protocols as described above.

8. Further Exemplary Compounds of the Present Invention

TABLE 2

*Further Exemplary compounds. The symbols in the columns have the same meaning as in above Table 1.*

| No. | Structure | CK1 delta Assay | CK1 epsilon Assay | HH Assay | WNT Assay | [M+ H]+ | General procedure/ aftertreatment |
|---|---|---|---|---|---|---|---|
| 1B | 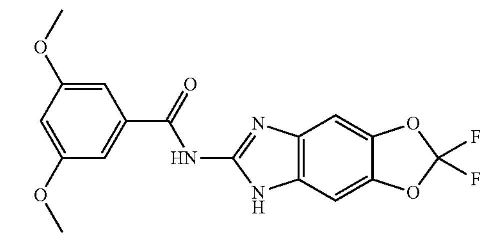 | +++ | +++ | | +++ | 378.0 | 1<br>D, E |
| 2B | 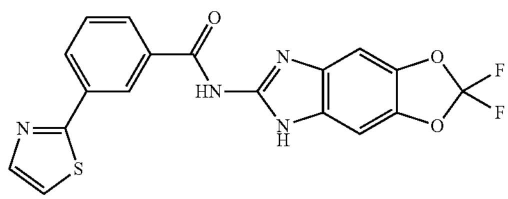 | +++ | | | +++ | 401.0 | 1<br>D, E |
| 3B | 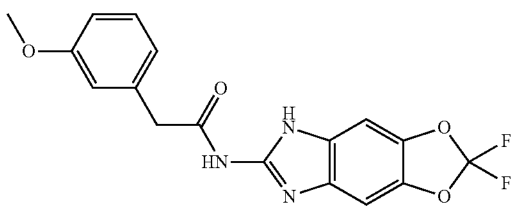 | +++ | +++ | ++ | | 362.0 | 1<br>D, E |
| 4B | 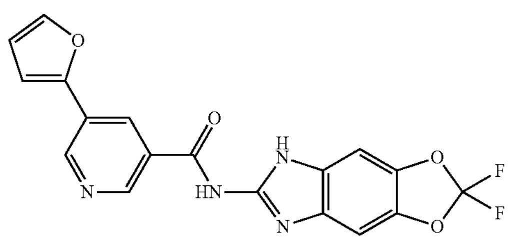 | +++ | | | | 385.1 | 1<br>D, E |
| 5B | 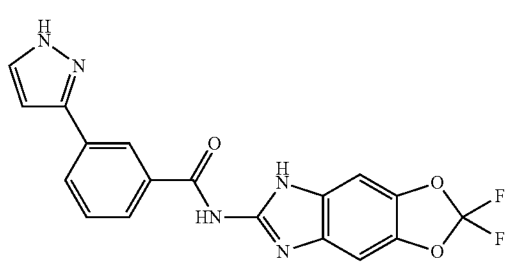 | +++ | | | + | 384.0 | 1<br>D, E, B, F |
| 6B | 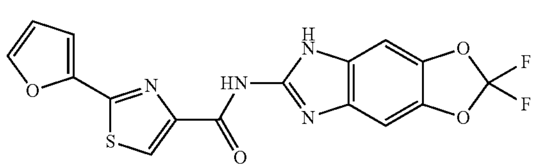 | +++ | +++ | ++ | | 391.02 | 1<br>E |

TABLE 2-continued

Further Exemplary compounds. The symbols in the columns have the same meaning as in above Table 1.

| No. | Structure | CK1 delta Assay | CK1 epsilon Assay | HH Assay | WNT Assay | [M+ H]+ | General procedure/ aftertreatment |
|---|---|---|---|---|---|---|---|
| 7B | 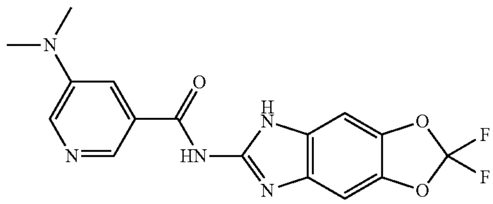 | +++ | + | | | 404.2 | 1<br>D, E |
| 8B | 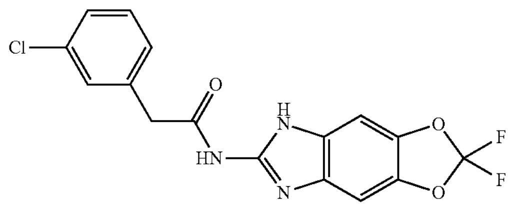 | +++ | +++ | | | 366.0 | 1<br>D, E, B |
| 9B | 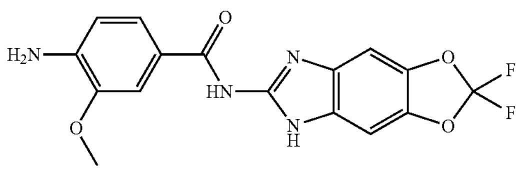 | +++ | | +++ | +++ | 363.0 | 3<br>A, B |
| 10B | 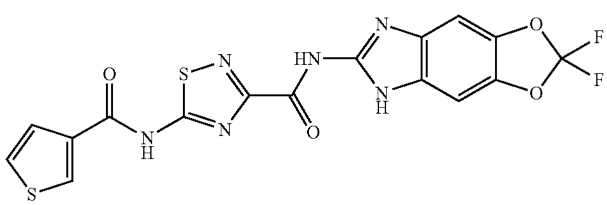 | +++ | | | | 451.00 | 1<br>D, E |
| 11B | 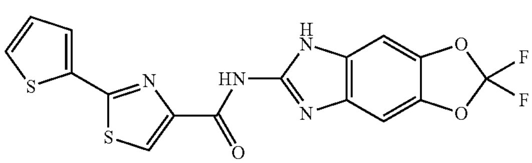 | +++ | + | | | 407.00 | 1<br>E |
| 12B | 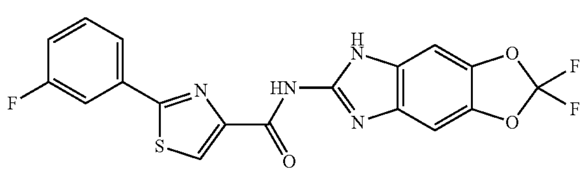 | +++ | | | | 419.03 | 1<br>E |
| 13B | 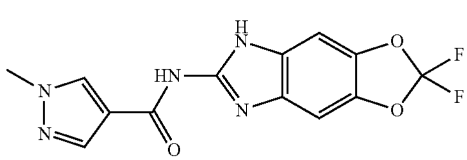 | +++ | | | | 322.07 | 1<br>D, E |

TABLE 2-continued

Further Exemplary compounds. The symbols in the columns have the same meaning as in above Table 1.

| No. | Structure | CK1 delta Assay | CK1 epsilon Assay | HH Assay | WNT Assay | [M+ H]+ | General procedure/ aftertreatment |
|---|---|---|---|---|---|---|---|
| 14B | 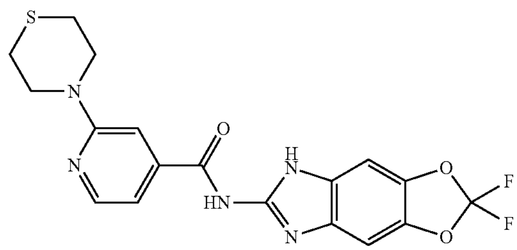 | +++ | | | | 420.1 | 1<br>D, E, B |
| 15B | 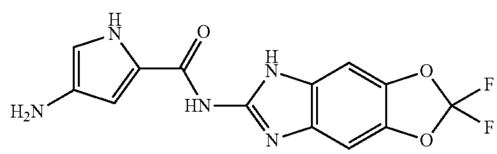 | +++ | ++ | | | 321.9 | see Example 5.1 |
| 16B | 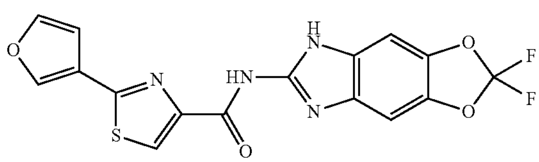 | +++ | | + | | 390.8 | 1<br>E, B |
| 17B | 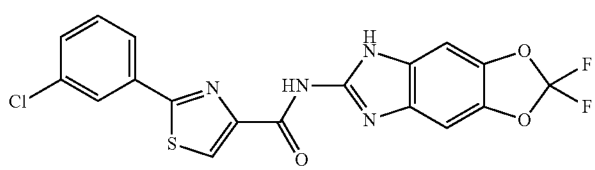 | +++ | ++ | | | 435.01 | 1<br>E, B |
| 18B | 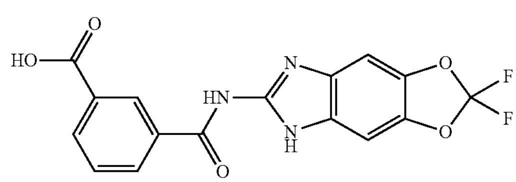 | ++ | ++ | | | 361.9 | see Example 5.3 |
| 19B | 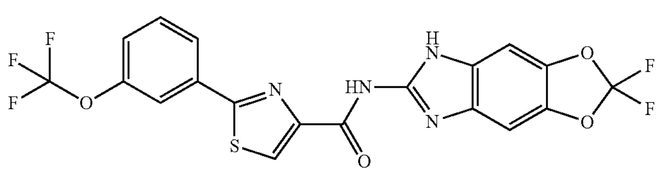 | ++ | | | | 485.03 | 1<br>E |
| 20B | 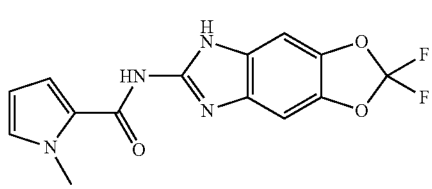 | ++ | + | | | 321.0 | see Example 5.3 |
| 21B | 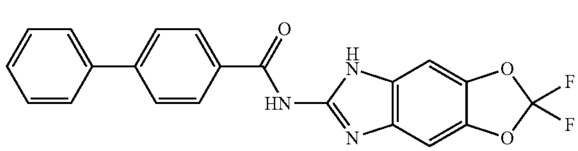 | ++ | | | | 394.0 | 1<br>D, E |

TABLE 2-continued

Further Exemplary compounds. The symbols in the columns have the same meaning as in above Table 1.

| No. | Structure | CK1 delta Assay | CK1 epsilon Assay | HH Assay | WNT Assay | [M+ H]+ | General procedure/ aftertreatment |
|---|---|---|---|---|---|---|---|
| 22B | 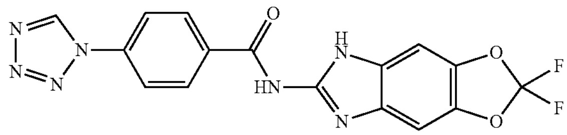 | +++ | | | | 386.07 | 1 D, C |
| 23B | 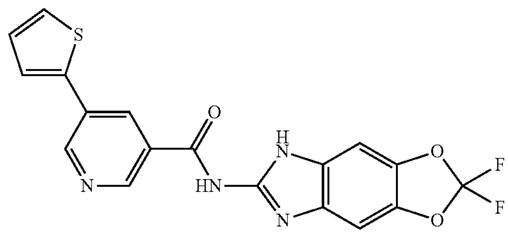 | +++ | | | | 401.0 | 1 D, E |
| 24B | 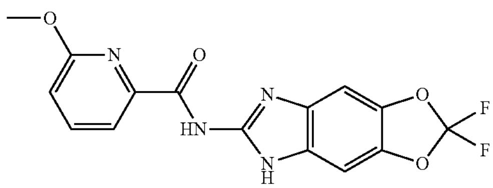 | ++ | | | | 349.0 | 1 D, E or F |
| 25B | 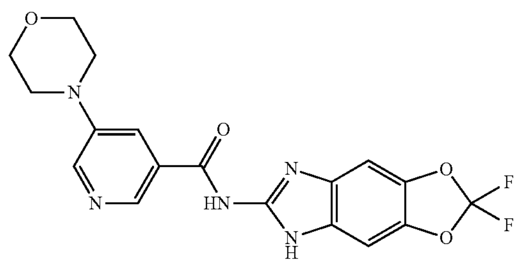 | +++ | | | | 404.0 | 1 D, E, F |
| 26B | 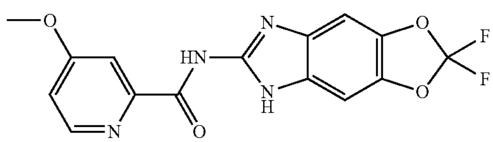 | + | | | | 349.0 | 1 D, E, F |

9. NMR Data for Exemplary Compounds of the Present Invention

4: NMR $^1$H (400 MHz, CDCl$_3$): 7.12 (1H, s, CH-benzimidazole), 7.24 (1H, s, CH-benzimidazole), 7.47 (3H, m, CH-arom.), 7.90 (2H, m, CH-arom.), 8.29 (1H, s, CH-thiazole), 10.62 (1H, s, NH), 11.23 (1H, s, NH)

17: $^1$H NMR (400 MHz, DMSO-d6+CCl$_4$): 7.50 (2H, s, CH-benzimidaz.), 7.57-7.63 (2H, m CH-arom.), 7.74-7.80 (1H, m, CH-arom.), 7.91-7.94 (1H, dd, CH-arom.), 12.36 (2H, s, NH).

44: $^1$H NMR (400 MHz, DMSO-d$_6$+CCl$_4$): 7.33 (2H, s, CH-benzimidazole), 8.64 (1H, d, CH-thiazole), 9.20 (1H, d, CH-thiazole), 11.08 (1H, s, NH), 12.40 (1H, s, NH).

50: $^1$H NMR (400 MHz, DMSO-d$_6$): 2.67 (3H, s, CH$_3$), 7.31 (2H, s, CH-benzimidazole), 7.39-7.54 (3H, m, CH-arom.), 7.61-7.74 (2H, m, CH-arom.), 12.26 (2H, s, NH).

51: $^1$H NMR (400 MHz, DMSO-d$_6$): 7.39 (2H, s, CH-arom.), 7.49 (1H, d, CH-arom.), 7.61 (1H, s, CH-arom.), 7.67 (1H, d, CH-arom.), 11.21 (1H, s, NH), 12.48 (2H, s, NH), 14.65 (1H, s, NH).

52: $^1$H NMR (400 MHz, DMSO-d$_6$): 7.39 (2H, s, CH-arom.), 7.42 (1H, d, CH-arom.), 7.51 (1H, t, CH-arom.), 7.67 (1H, t, CH-arom.), 7.77 (1H, d, CH-arom.), 11.15 (1H, s, NH), 12.43 (2H, s, NH), 14.64 (1H, s, NH).

53: $^1$H NMR (400 MHz, DMSO-d$_6$): 7.39 (2H, s, CH-arom.), 7.54 (1H, t, CH-arom.), 7.63 (1H, d, CH-arom.), 8.07 (1H, d, CH-arom.), 8.15 (1H, s, CH-arom.), 11.30 (1H, s, NH), 12.48 (2H, s, 2×NH), 14.51 (1H, s, NH).

54: $^1$H NMR (400 MHz, DMSO-d$_6$): 7.13 (2H, t, CH-arom.), 7.33 (2H, s, CH-arom.), 7.52-7.59 (1H, m, CH-arom.), 12.40 (2H, s, NH).

55: $^1$H NMR (400 MHz, DMSO-d$_6$+CCl$_4$): 7.32 (2H, s, CH-benzimidazole), 8.61 (1H, s, CH-thiazole), 11.0-12.5 (2H, s, 2×NH).

56: $^1$H NMR (400 MHz, DMSO-d$_6$): 3.89 (3H, s, CH$_3$), 7.13 (2H, d, CH-arom.), 7.34 (2H, s, CH-arom.), 7.41 (1H, t, CH-arom.), 7.71 (2H, s, CH-arom.), 12.13 (1H, s, NH), 12.37 (1H, s NH).

58: $^1$H NMR (400 MHz, DMSO-d$_6$): 7.35 (2H, s, CH-arom.), 8.32 (2H, d, CH-arom.), 8.37 (2H, d, CH-arom.), 12.51 (2H, s, 2×NH).

59: $^1$H NMR (400 MHz, DMSO-d$_6$): 7.39 (2H, s, CH-arom.), 7.74 (1H, t, CH-arom.), 7.89 (1H, t, CH-arom.), 8.08 (1H, d, CH-arom.), 8.27 (1H, d, CH-arom.), 8.32 (1H, d, CH-arom.), 8.61 (2H, d, CH-arom.), 11.32 (1H, s, NH), 12.53 (1H, s, NH).

61: $^1$H NMR (400 MHz, DMSO-d$_6$): 7.42 (2H, s, CH-arom.), 8.34 (2H, d, CH-arom.), 8.39 (2H, d, CH-arom.), 11.41 (1H, s, NH), 12.51 (2H, s, NH), 14.28 (1H, s, NH).

74: $^1$H NMR (400 MHz, CDCl$_3$): 1.16 (6H, t, 2*CH$_3$), 3.39 (4H, q, 2×CH$_2$), 6.44 (1H, s, CH-arom.), 6.57 (2H, d, CH-arom.), 7.07 (1H, s, CH-arom.), 7.92 (2H, d, CH-arom.), 11.78 (1H, s, NH), 12.72 (1H, s, NH).

75: $^1$H NMR (400 MHz, CDCl$_3$): 3.03 (6H, s, 2×CH$_3$), 6.50 (1H, s, CH-arom.), 6.60 (2H, d, CH-arom.), 7.09 (1H, s, CH-arom.), 7.91 (2H, d, CH-arom.), 11.71 (1H, s, NH), 12.32 (1H, s, NH)

76: $^1$H NMR (400 MHz, DMSO-d$_6$): 4.36 (2H, d, CH$_2$), 6.59 (2H, d, CH-arom.), 6.94 (1H, t, CH-arom.), 7.19-7.35 (6H, m, CH-arom.), 7.89 (2H, d, CH-arom.), 11.40 (1H, s, NH), 12.31 (1H, s, NH).

78: $^1$H NMR (400 MHz, DMSO-d$_6$): 7.33 (2H, s, CH-arom.), 7.47-7.51 (1H, m, CH-arom.), 8.45 (1H, dt, CH-arom.), 8.72 (1H, d, CH-arom.), 9.23 (1H, d, CH-arom.), 12.40 (1H, s, NH).

81: $^1$H NMR (400 MHz, DMSO-d$_6$+CCl$_4$): 7.32 (2H, s, CH-benzimidazole), 7.62 (1H, m, CH-thien.), 7.75 (1H, m, CH-thien.), 8.27 (1H, m, CH-thien.), 8.49 (1H, s, CH-thiazole), 11.29 (1H, s, NH), 12.42 (1H, s, NH).

89: $^1$H NMR (400 MHz, DMSO-d$_6$): 2.44 (3H, s, CH$_3$), 7.39 (2H, dd, CH-arom), 7.42 (2H, s, CH-arom.), 8.10 (2H, dd, CH-arom.), 11.56-11.92 (1H, s, NH), 12.32-12.64 (1H, s, NH), 13.70-14.94 (1H, s, NH).

90: $^1$H NMR (400 MHz, DMSO-d$_6$): 3.89 (3H, s, CH3), 7.06 (2H. dd, CH-arom.), 7.36 (2H, s, CH-arom.), 8.20 (2H, dd, CH-arom.), 11.21-12.90 (2H, s, NH), 13.37-13.94 (1H, s, NH).

91: $^1$H NMR (400 MHz, DMSO-d$_6$): 7.36 (2H, s, CH-benzimidazole), 7.58 (2H, dd, CH-arom.), 8.22 (2H, dd, CH-arom.), 11.40-12.95 (3H, s, NH).

92: $^1$H NMR (400 MHz, DMSO-d$_6$): 7.32 (2H, d, CH-arom.), 7.36 (2H, s, CH-arom.), 8.30 (2H, dd, CH-arom.), 11.22-12.80 (2H, s, NH), 13.17-14.49 (1H, s, NH).

95: $^1$H NMR (400 MHz, DMSO-d$_6$): 2.16 (3H, s, CH$_3$), 7.42 (2H, s, CH-arom.), 11.23 (1H, s, NH), 11.79 (1H, s, NH), 12.49 (1H, s, NH), 14.05 (1H, s, NH).

96: $^1$H NMR (400 MHz, DMSO-d$_6$): 7.41 (2H, s, CH-arom.), 8.64 (1H, s, CH-triazole), 12.80-13.20 (3H, s, 3×NH).

10. Determination of the Inhibitory Capacity; Casein Kinase Assays

The substrate CK1tide (peptide HAAIGDDDDAYSITS-NH$_2$) was prepared in a concentration of 20 µM in the freshly prepared Base Reaction Buffer (20 mM Hepes (pH 7.5), 10 mM MgCl$_2$, 1 mM EGTA, 0.02% Brij35, 0.02 mg/ml BSA, 0.1 mM Na$_3$VO$_4$, 2 mM DTT, 1% DMSO). The recombinant protein Casein kinase 1 delta (CSKN1D) was added to the substrate solution in a concentration of 5 nM and gently mixed. Dilution series in of compounds of the present invention in DMSO were added to the reaction mixture, followed after 20 min by addition of a mixture of ATP and $^{33}$P-ATP (specific activity 0.01 µCi/µl final) to a final concentration of 10 µM. Reactions were carried out at 25° C. for 120 min, followed by spotting the reactions onto P81 ion exchange filter paper. Unbound phosphate was removed by washing of the filters in 0.75% phosphoric acid. After subtraction of the background, which was derived from control reactions containing inactive enzyme, kinase activity data were expressed as percent remaining kinase activity in the test samples compared to vehicle (DMSO) reactions. IC$_{50}$ values and curve fits were obtained using the program Prism® (Graph Pad Software).

The above assay was also used to determine the inhibitory capacity of the compounds of the present invention on Casein Kinase 1 epsilon, wherein instead of CSKN1D, recombinant protein Casein kinase 1 epsilon (CSKN1E) was added to the substrate solution in a concentration of 30 nM and gently mixed.

The above tables 1 and 2 provide an overview of the results of the compounds in the CK1 delta and epsilon kinase Assays.

11. Determination of Proliferation Inhibition on a Panel of Cancer Cell Lines; Proliferation Assay For the determination of the inhibitory capacity of compounds of the present invention (in the following: "test compound(s)") on cell growth, cancer cells were seeded into microtitre plates, treated with different concentrations of test compound or left untreated, and after 72 h the protein content was determined as an equivalent for the cell number.

Test compounds were dissolved in 100% DMSO and predilutions in cell culture medium were prepared with a final concentration of 0.1% DMSO in medium. The cell culture medium for dilution of the test compounds, consecutive culturing of cell lines and usage during the assay was a cell line specific medium as recommended by the cell line supplier and identical for all three applications mentioned above. After a 24-hour pre-growth period of the seeded cancer cells, the test compound containing media or medium containing 0.1% DMSO as control was added to the cells. The cells were allowed to grow at 37° C. for 72 hours. In addition, all experiments contained a few plates with cells that were processed for measurement immediately after the 24 hours recovery period. These plates contained information about the cell number that existed before treatment, at time zero, and served to calculate the cytotoxicity and/or growth inhibitory effects.

After treatment, cells were precipitated by addition of 10% TCA (trichloracetic acid). Prior to fixation, the media was aspirated. After an hour of incubation at 4° C. the plates were washed twice with 400 µl of deionized water. Cells were then stained with 100 µl of a 0.08% wt/v SRB (sulforhodamine). The plates were allowed to sit for at least 30 min and washed six times with 1% acetic acid to remove unbound staining agent. The plates were left to dry at room temperature and bound SRB was solubilized with 100 µl of 10 mM Tris base. Measurement of optical density was performed at 560 nm on a Victor 2 plate reader (Perkin Elmer, Germany).

One common way to express the effect of an anticancer agent is to measure cell viability and survival in the presence of the test agent as % Treated/Control×100. The relationship between the viability and dose is called a dose response curve. Those dose response curves were determined by using algorithms developed by Oncolead GmbH & Co. KG, Munich, Germany, that can be compared to commercial applications, e.g. XLfit™ (ID Business Solutions Ltd., Guildford, UK) algorithm "205". The potency of a given test compound to inhibit cell growth was specified as the IC$_{50}$ value (drug concentration needed for 50% inhibition of cell growth).

The IC$_{50}$ of the compound of Example 56, determined as described above, with the following cell lines was in all cases 1 µM or lower: 22RV1 (prostate), 5637 (bladder), 786O (kidney), A204 (muscle), A2780 (ovary), A375 (skin), A431 (skin), A549 (lung), A673 (muscle), ACHN (kidney), ASPC1 (pancreas), BT20 (breast), BXPC3 (pancreas), C33A (cervix), CAKI1 (kidney), CALU6 (lung), CASKI (cervix), CLS439 (bladder), COLO205 (colon), DLD1 (colon), DU145 (prostate), EFO21 (ovary), EJ28 (bladder), HCT116 (colon), HCT15 (colon), HEK293 (kidney), HELA (cervix), HEPG2 (liver), HS729 (muscle), HS578T (breast), HT1080 (connective tissue), HT29 (colon), IMR90 (lung), IGROV1 (ovary), J82 (bladder), JAR (placenta), JEG3 (placenta), JIMT1 (breast), LOVO (colon), MCF7 (breast), MDAMB435 (skin), MDAMB436 (breast), MDAMB468 (breast), MG63 (bone), MHHES1 (bone), MIAPACA2 (pancreas), MT3 (breast), NCIH292 (lung), NCIH358M (lung), NCIH460 (lung), NCIH82 (lung), OVCAR3 (ovary), OVCAR4 (ovary), PANC1 (pancreas), PANC1005 (pancreas), PC3 (prostate), PLCPRF5 (liver), RD (muscle), RDES (bone), SAOS2 (bone), SF268 (brain), SF295 (brain), SKBR3 (breast), SKHEP1 (liver), SKLMS1 (uterus), SKMEL28 (skin), SKMEL5 (skin), SKNAS (brain), SKNSH (brain), SNB75 (brain), SW620 (colon), T24 (bladder), TE671 (muscle), U2OS (bone), U87MG (brain). UMUC3 (bladder), SKOV3 (ovary), in the following cases 100 nM or lower: A2780 (ovary), A375 (skin), A673 (muscle), BXPC3 (pancreas), CALU6 (lung), EJ28 (bladder), HCT116 (colon), HCT15 (colon), JAR (placenta), LOVO (colon), MCF7 (breast), MDAMB435 (skin), MG63 (bone), MHHES1 (bone), NCIH358M (lung), PC3 (prostate), SF295 (brain), SKMEL5 (skin), SKNAS (brain).

12. Inhibition of Anchorage Independent Growth, Soft Agar Colony Formation

To analyze anchorage-independent growth, cells were seeded in 12-well plates in 0.4% select Agar® on top of 0.5% bottom select Agar® (Invitrogen) according to standard protocols. 8000 PANC1 cells were seeded in 400 µl select agar and the compound according to the present invention or DMSO as control was added in a final volume of 400 µl growth medium to the top agar. Cultures were grown for 21 days at 37° C. in a humidified atmosphere of 5% CO$_2$. Fresh growth medium was added against drying-out twice per week. Colony growth in soft agar cultures was quantified using Colony Counter software (Microtech Nition).

Depending on the addition of Culture plates exhibit growth of cancer cell colonies, wherein some colonies develop into macrocolonies having a diameter which is approximately ≥4 times larger than the median diameter over all cancer cell colonies (in said well). The inhibition of both overall colony formation (including macrocolony formation) and macrocolony formation alone by compounds of the present invention was determined, results are shown in FIG. 1. Macrocolonies of this cell line are rare but highly clonogenic, tumor-initiating cells with high activity of the Hedgehog signaling pathway. Inhibition of those macrocolonies in vitro can be interpreted to relate to cancer stem cell inhibition in tumor bearing patients (Eberl et al., EMBO Mol Med, 2011, 4, 218-233).

Growth medium Stock solutions (sterilized, stored at 4° C.): 2×DMEM, GIBCO powder: 26.76 g DMEM powder (GIBCO, with 4.5 g/l Glucose), 7.4 g NaHCO3, 220 mg Sodium Pyruvate (Sigma, 11.0 mg/ml solution); dissolve in water, adjust pH with 2M Hepes to 7.2; final volume 1 liter.

2×DMEM, PAA powder: 27 g DMEM powder (PAA Art. No. G0006,3010, with 4.5 g/l Glucose, with Sodium Pyruvate), 7.4 g NaHCO3; dissolve in water, adjust pH to 6.8-7.5 with 1N HCl; final volume 1 liter.

Before usage, add 50 ml FBS and 5 ml PenStrep (100× stock) to 200 ml aliquot; store this 2× medium for maximum 6-8 weeks at 4° C.

2× stock solutions of 1% (bottom) and 0.8% (top) Select Agar: 1 g or 0.8 g, respectively, Select Agar (Invitrogen, Art. No. 30391-023) in 100 ml water (=1% or 0.8% final, respectively). Store at 4° C. until needed.

Bottom Agar (=0.5% agar final concentration): Melt "1% Select Agar"-stock in microwave; cool down to 42° C. in a water bath; warm 2×DMEM to 37° C.; mix Select Agar and 2×DMEM solution 1:1 (avoid bubbles); plate 800 µl Agar/DMEM mix in each well; allow to cool and harden completely (room temperature) can be stored at 4° C. for up to 2 weeks prior to use.

Top Agar (=0.4% agar final concentration, containing cells); Melt "0.8% Select Agar"-stock in microwave; cool down to 40° C. in a water bath; warm 2×DMEM to 37° C.; let bottom agar plates warm to room temperature (or warm in 37° C. incubator); mix Select Agar and 2×DMEM solution 1:1 (avoid bubbles); aliquot Agar/DMEM mix in 15 ml tubes and store at 40° C.; Trypsinize cells and determine cell count; add 8000 cells per well to Agar/DMEM mix; again mix by gently inverting tube and plate out; allow to cool and harden top agar in laminar flow (~30 min; room temperature); pipette 400 µl medium (containing optional chemical substances) onto top agar to prevent drying-out; Replace supernatant as appropriate (e.g. 2× per week).

13. Wnt Reporter Assay

The Wnt reporter assay was performed in stably transfected human HEK293 cells. Wnt signaling was induced by administration of Wnt3a protein and read out by β-Lactamase mediated cleavage of CCF4-AM and subsequent fluorescent detection.

CellSensor LEF/TCF-bla FreeStyle 293F cells (invitrogen #K1677) contain a beta-lactamase reporter gene under control of the β-catenin/LEF/TCF binding elements stably integrated into FreeStyle 293F cells. This cell line can be used to detect antagonists of the Wnt/β-catenin signaling pathway when stimulated by mouse Wnt3a or LiCl. The detection of beta-lactamase is possible with LiveBLAzer FRET-B/G Loading Kit (invitrogen #K1095) with CCF4-AM as substrate.

Culture Medium: DMEM Medium+10% dialyzed FBS (PAN 2102-P290310), +1% NEAA (PAA M11-003), +1% P/S (Penicillin/Streptomycin, PAA P11-010)+25 mM HEPES (PAA S11-001), +5 µg/ml Blasticidin (PAA P05-017).

Assay Medium: Opti-MEM (Gibco 11058-021)+0.5% dialyzed FBS (PAN 2102-P290310), +1% NEAA (PAA M11-003), +1% P/S (PAA P11-010), +10 mM HEPES (PAA S11-001), +1 mM Na-Pyruvate (PAA S11-003).

Cells (CellSensor LEF/TCF-bla FreeStyle 293F, invitrogen K1677) were split with Culture Medium to reach a confluence at the beginning of the assay of 80-90%.

At start of the assay, cells were harvested from culture and resuspend in assay medium at density of 0.66*10^6 cells/ml. Subsequently, 60 µl cell suspension were pipetted in each well of a Poly-D-Lysine 96 well Plate (BD #354640, vertical rows are marked 1 through 12, horizontal lanes are marked A through H),

|   | 1 | 2 | 3 | 4 | 5 | 6 | 7 | 8 | 9 | 10 | 11 | 12 |
|---|---|---|---|---|---|---|---|---|---|----|----|----|
| A | \multicolumn{12}{c}{120 µl Medium} |
| B | 60 µl cells + 60 µl medium | 60 µl cells | 60 µl cells | 60 µl cells | 60 µl cells | 60 µl cells | 60 µl cells | 60 µl cells | 60 µl cells | 60 µl cells | 60 µl cells | 60 µl medium |
| C | | | | | | | | | | | | |
| D | | | | | | | | | | | | |
| E | | | | | | | | | | | | |
| F | 60 µl cells + 60 µl medium | 60 µl cells | 60 µl cells | 60 µl cells | 60 µl cells | 60 µl cells | 60 µl cells | 60 µl cells | 60 µl cells | 60 µl cells | 60 µl cells | 60 µl cells |
| G | | | | | | | | | | | | |
| H | 120 µl Medium | | | | | | | | | | | |

Plates were subsequently incubated at 37° C. for at least 2 h.

To stimulate with Wnt3a, overnight prestimulation of Wnt signalling pathway with LiCl is necessary. Subsequently, an 8M aqueous LiCl solution was diluted 1:200 in assay medium, and 30 µl of said diluted LiCl solution was plated into the appropriate wells (see below pipetting scheme). Plates were then incubated at 37° C. over night.

Subsequently, compounds and controls were prepared as follows: mWnt3a (R&D 1324-WN, dissolved in PBS+0.1% BSA to 40 µg/ml) was diluted 1:100 in assay medium (=400 ng/ml). Compounds (Cpd) were diluted to a concentration of 10 mM in DMSO to prepare dilution series in assay medium (final concentrations 30 µM, 10 µM, 3 µM, 1 µM, 0.3 µM, 0.1 µM, 0.03 µM and 0.01 µM), which were pipetted into the appropriate wells (see below pipetting scheme). For each dilution of each compound, 3 replicates were tested. Final DMSO concentration was 0.3%.

LiCl and mWnt3a stimulated cells were used as High control (HC), unstimulated cells were used as low control, a blank was prepared from cell free medium plus mWnt3a, and a functional control was prepared with a known Wnt inhibitor (e.g. PKF118-310), final concentrations were as above.

Pipetting Scheme:

the dark (it is possible to incubate over night). Subsequently, plates were measured in the BMG FluorStar® plate reader at an emission wavelengths of 460 and 520 nm and with an excitation wavelength of 405 nm.

To determine potential cytotoxicity of the compounds, plates were centrifuge and the supernatant was discarded by dumping the plates. Subsequently, 100 µl Opti-MEM and 50 µl ViaLight (Lonza #LT07-321) Lysis Buffer were added to each well, followed by incubation for 10 min at room temperature (25° C.). Subsequently, 100 µl ViaLight reagent were added to each well, followed by incubation for 2 min at room temperature (25° C.) in the dark. Optionally, 200 µl of the obtained suspension were transferred to a white 96 well plate. The luminescence was measured with a Tecan Ultra plate reader.

13. Hedgehog Reporter Assay

In order to investigate the potency of test compounds to inhibit the Hedgehog signaling pathway, a Gli-Reporter assay was performed.

The "Gli Reporter—NIH3T3 Cell Line" contains the firefly luciferase gene under the control of Gli responsive elements stably integrated into murine NIH3T3 cells (cells purchased from Amsbio). The luciferase expression corre-

|   | 1 | 2 | 3 | 4 | 5 | 6 | 7 | 8 | 9 | 10 | 11 | 12 |
|---|---|---|---|---|---|---|---|---|---|----|----|----|
| A | \multicolumn{6}{c}{120 µl medium} | \multicolumn{6}{c}{120 µl medium} |
| B | 60 µl cells + 60 µl medium | 60 µl cells + 30 µl medium + 30 µl HC | 60 µl cells + 30 µl medium + 30 µl Comp. | 60 µl cells + 30 µl medium + 30 µl Comp. | 60 µl cells + 30 µl medium + 30 µl Comp. | 60 µl cells + 30 µl medium + 30 µl Comp. | 60 µl cells + 30 µl medium + 30 µl Comp. | 60 µl cells + 30 µl medium + 30 µl Comp. | 60 µl cells + 30 µl medium + 30 µl Comp. | 60 µl cells + 30 µl medium + 30 µl Comp. | 60 µl cells + 30 µl medium + 30 µl HC | 60 µl cells + 30 µl medium + 30 µl blank |
| C | | | | | | | | | | | | |
| D | | | | | | | | | | | | |
| E | | | | | | | | | | | | |
| F | 60 µl cells + 60 µl medium | 60 µl cells + 30 µl medium + 30 µl LC | 60 µl cells + 30 µl medium + 30 µl Comp. | 60 µl cells + 30 µl medium + 30 µl Comp. | 60 µl cells + 30 µl medium + 30 µl Comp. | 60 µl cells + 30 µl medium + 30 µl Comp. | 60 µl cells + 30 µl medium + 30 µl Comp. | 60 µl cells + 30 µl medium + 30 µl Comp. | 60 µl cells + 30 µl medium + 30 µl Comp. | 60 µl cells + 30 µl medium + 30 µl Comp. | 60 µl cells + 30 µl medium + 30 µl PKF118-310 | 60 µl cells + 30 µl medium + 30 µl LC |
| G | | | | | | | | | | | | |
| H | \multicolumn{6}{c}{120 µl medium} | \multicolumn{6}{c}{120 µl medium} |

Subsequently, the well was incubated for 5 h at 37° C.

At t=23 hours, FRET reagent mix (Loading Kit with CCF4-AM, Life Technologies #K1096) was prepared; per plate: 138 µl Solution B, 13.8 µl FRET-reagent, and 2300 µl Solution C. 24 µl FRET reagent mix were plated to each well, subsequently plates were incubated for at least 2 h in lates with activation of the hedgehog signaling pathway. This cell line is validated for its response to stimulation with murine Sonic Hedgehog and to treatment with inhibitors of the hedgehog signaling pathway. A multiplexed viability assay was used to discriminate inhibition on the pathway activity from cell toxicity.

Growth Medium: DMEM, 10% Calf Serum, 1% Penicillin/Streptomycin 500 μg/ml Geneticin (G418 Stock 50 mg/ml).

Assay Medium: Opti-MEM® Reduced Serum Medium, 0.5% Calf Serum, 1% non-essential amino acids, 1 mM Na-pyruvate, 10 mM HEPES, 1% Penicillin/Streptomycin.

25,000 cells per well were seeded into a white 96 well plate in 1000 growth medium and incubated over night at 37° C. and 5% $CO_2$. After removing the supernatant the test compounds and controls (known GLI inhibitor, e.g. GANT-61) were added in different concentrations in a final volume of 45 μl and incubated for 1 h at 37° C. and 5% $CO_2$. For the stimulation of the Hedgehog pathway 5 μl of 10 μg/ml concentrated murine sonic hedgehog (SHH) was added to the cells. A final concentration of 1 μg/ml mSHH and 0.1% DMSO was reached per well. After incubation for 24 h at 37° C. the cells were investigated for viability and reporter activity.

Viability: For the determination of the viability of the treated cells the CellTiter-Fluor Kit from Promega was used. Essentially, only proteases of viable cells are able to cleave the cell-permeant substrate Gly-Phe-AFCoumarin (GF-AFC). By this cleavage the fluorescent AFC is set free and can be detected in a fluorescence reader. For this assay 10 μl of GF-AFC substrate (CellTiter-Fluor, Promega #G6082) was diluted in 2 ml assay buffer from the CellTiter-Fluor Kit and 10 μl of this dilution was added per well to the cells and incubated for 30 min at 37° C. The fluorescence was measured with excitation at 380-400 nm and emission at 505 nm.

Reporter activity: The firefly luciferase reporter activity was detected with the ONE-Glo™ Luciferase Assay System from Promega. For this assay 50 μl ONE-Glo luciferase reagent (Promega #E6120, contains cell lysis buffer and luciferin) was added to each well and incubated at room temperature for 5 min. Luminescence was detected in a plate reader and served as a degree for reporter activity.

The invention claimed is:
1. A compound of formula (I),

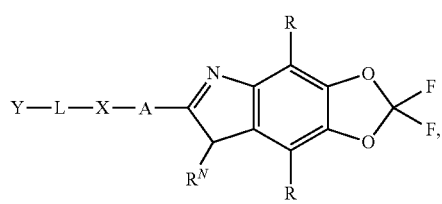

wherein
R is in each case independently H, halogen, $C_{1-4}$-alkyl, $C_{1-4}$-haloalkyl, $C_{1-4}$-haloalkoxy, $C_{1-4}$-alkoxy, —S—R'", —SO—R'", —N(R''')$_2$, —NH(R'''), —NHCO(R'''), —CONH$_2$, —CONH(R'''), —CO(R'''), —COH, —COO(R'''), —COOH, —SO$_2$NH$_2$, —SO$_2$NH(R'''), —SO$_2$(R'''), or —NH—SO$_2$(R'''),
wherein, in the cases where R is $C_{1-4}$-alkyl, $C_{1-4}$-haloalkyl, $C_{1-4}$-haloalkoxy, or $C_{1-4}$-alkoxy, R is unsubstituted or substituted with one or more substituents R'', wherein in each case independently R'' is H, halogen, or OH;
R''' is independently H, $C_{1-2}$-alkyl or $C_{1-2}$-haloalkyl;
$R^N$ is independently H, $C_{1-4}$-alkyl, $C_{1-4}$-haloalkyl, —NH$_2$, —NH(R'''), —CONH$_2$, —CONH(R'''), —CO (R'''), —COH, —COO(R'''), —SO$_2$NH$_2$, —SO$_2$NH (R'''), —SO$_2$(R'''), or —NH—SO$_2$(R'''), wherein R''' is as defined above;
A is independently *—N($R^a$)CO—, *—CON($R^a$)—, *—SO$_2$N($R^a$)—, or *—N($R^a$)—SO$_2$—,
wherein $R^a$ is H or $C_{1-4}$-alkyl,
and wherein * specifies the point of attachment to X;
X is independently aryl, cycloalkyl, aralkyl, heterocyclyl, or heteroaryl, wherein X is unsubstituted or substituted with one or more substituents $R^X$, wherein in each case independently $R^X$ is halogen, $C_{1-6}$-alkyl, $C_{1-6}$-haloalkyl, $C_{1-6}$-haloalkoxy, OH, $C_{1-6}$-alkoxy, aryl, heteroaryl, cycloalkyl, heterocyclyl, —S—$C_{1-6}$-alkyl, —S—$C_{1-6}$-haloalkyl, nitro, —NH$_2$, —N($C_{1-6}$-alkyl)$_2$, —NH($C_{1-6}$-alkyl), —NHCO($C_{1-6}$-alkyl), —CONH$_2$, —CONH($C_{1-6}$-alkyl), —CO($C_{1-6}$-alkyl), —COH, —COO($C_{1-6}$-alkyl), —COOH, —SO$_2$NH$_2$, —SO$_2$NH ($C_{1-6}$-alkyl), —SO$_2$($C_{1-6}$-alkyl), —NH—SO$_2$($C_{1-6}$-alkyl), $C_{3-6}$-cycloalkyl, or —CN;
L is independently a bond or a linker group, wherein said linker group is *—NHCO—, *—CONH—, *—NH—, *—N($C_{1-4}$-alkyl)-, *—C=N($C_{1-4}$-alkyl)-, *—NH—$C_{1-4}$-alkyl-, *—$C_{1-4}$-alkyl-NH—, *—NHCONH—, *—CO—, *—SO$_2$—, $C_{1-4}$-alkyl, *—$C_{1-2}$-alkyl-O—$C_{1-2}$-alkyl-, *—NHCO—CH=CH—, *—CH=CH—CONH—, *—SO$_2$NH—, *—NHSO$_2$—, or pyridinyl, and wherein * specifies the point of attachment to X; and
Y is H, alkyl, aryl, aralkyl, cycloalkyl, heterocyclyl, or heteroaryl, wherein Y is unsubstituted or substituted with one or more substituents $R^Y$, wherein in each case independently $R^Y$ is halogen, $C_{1-6}$-alkyl, $C_{1-6}$-haloalkyl, $C_{1-6}$-haloalkoxy, OH, $C_{1-6}$-alkoxy, aryl, heteroaryl, cycloalkyl, heterocyclyl, —S—$C_{1-6}$-alkyl, —S—$C_{1-6}$-haloalkyl, nitro, —NH$_2$, —N($C_{1-6}$-alkyl)$_2$, —NH($C_{1-6}$-alkyl), —NHCO($C_{1-6}$-alkyl), —CONH$_2$, —CONH($C_{1-6}$-alkyl), —CO($C_{1-6}$-alkyl), —COH, —COO($C_{1-6}$-alkyl), —COOH, —SO$_2$NH$_2$, —SO$_2$NH ($C_{1-6}$-alkyl), —SO$_2$($C_{1-6}$-alkyl), —NH—SO$_2$($C_{1-6}$-alkyl), $C_{1-6}$-alkyl-heterocyclyl, cycloalkyl, or —CN;
or physiologically acceptable solvate or salt thereof;
or physiologically acceptable prodrug of said compound wherein at least one of the following groups is derivatized as follows: a carboxylic acid group is derivatized into an ester, a hydroxyl group is derivatized into an ester, a carboxylic acid is derivatized into an amide, an amine is derivatized into an amide, or a hydroxyl group is derivatized into a phosphate ester.

2. A compound according to claim 1, which is a compound of formula (Ia) or a physiologically acceptable prodrug, solvate or salt thereof,

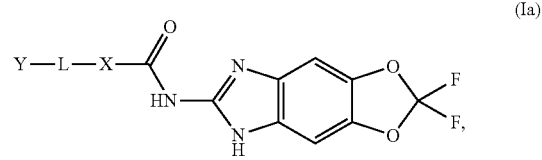

wherein
X is independently aryl, cycloalkyl, aralkyl, heterocyclyl, or heteroaryl, wherein X is unsubstituted or substituted with one or more substituents $R^X$, wherein in each case independently $R^X$ is halogen, $C_{1-6}$-alkyl, $C_{1-6}$-haloalkyl, $C_{1-6}$-haloalkoxy, OH, $C_{1-6}$-alkoxy, aryl, heteroaryl, cycloalkyl, heterocyclyl, —S—C$_{1-6}$-alkyl, —S—C$_{1-6}$-haloalkyl, nitro, —NH$_2$, —N(C$_{1-6}$-alkyl)$_2$, —NH(C$_{1-6}$-alkyl), —NHCO(C$_{1-6}$-alkyl), —CONH$_2$, —CONH(C$_{1-6}$-alkyl), —CO(C$_{1-6}$-alkyl), —COH, —COO(C$_{1-6}$-alkyl), —COOH, —SO$_2$NH$_2$, —SO$_2$NH(C$_{1-6}$-alkyl), —SO$_2$(C$_{1-6}$-alkyl), —NH—SO$_2$(C$_{1-6}$-alkyl), C$_{3-6}$-cycloalkyl, or —CN;

L is independently a bond or a linker group, wherein said linker group is *—NHCO—, *—CONH—, *—NH—, *—N(C$_{1-4}$-alkyl)-, *—C═N(C$_{1-4}$-alkyl)-, *—NH—C$_{1-4}$-alkyl, *—C$_{1-4}$-alkyl-NH—, *—NHCONH—, *—CO—, *—SO$_2$—, C$_{1-4}$-alkyl, *—C$_{1-2}$-alkyl-O—C$_{1-2}$-alkyl-, *—NHCO—CH═CH—, *—CH═CH—CONH—, *—SO$_2$NH—, *—NHSO$_2$—, or pyridinyl, and wherein * specifies the point of attachment to X; and Y is independently H, alkyl, aryl, aralkyl, cycloalkyl, heterocyclyl, or heteroaryl, wherein said group Y is unsubstituted or substituted with one or more substituents R$^Y$, wherein in each case independently R$^Y$ is halogen, C$_{1-6}$-alkyl, C$_{1-6}$-haloalkyl, C$_{1-6}$-haloalkoxy, OH, C$_{1-6}$-alkoxy, aryl, heteroaryl, cycloalkyl, heterocyclyl, —S—C$_{1-6}$-alkyl, —S—C$_{1-6}$-haloalkyl, nitro, —NH$_2$, —N(C$_{1-6}$-alkyl)$_2$, —NH(C$_{1-6}$-alkyl), —NHCO(C$_{1-6}$-alkyl), —CONH$_2$, —CONH(C$_{1-6}$-alkyl), —CO(C$_{1-6}$-alkyl), —COH, —COO(C$_{1-6}$-alkyl), —COOH, —SO$_2$NH$_2$, —SO$_2$NH(C$_{1-6}$-alkyl), —SO$_2$(C$_{1-6}$-alkyl), —NH—SO$_2$(C$_{1-6}$-alkyl), C$_{1-6}$-alkyl-heterocyclyl, cycloalkyl, or —CN.

3. The compound according to claim 1, or a physiologically acceptable prodrug, solvate or salt thereof, wherein X is independently aryl, aralkyl, cycloalkyl, heterocyclyl, or heteroaryl, wherein X is unsubstituted or substituted with one or more substituents R$^X$, wherein in each case independently R$^X$ is F, Cl, Br, I, C$_{1-6}$-alkyl, C$_{1-6}$-haloalkyl, C$_{1-6}$-haloalkoxy, OH, C$_{1-6}$-alkoxy, nitro, —NH$_2$, —N(C$_{1-6}$-alkyl)$_2$, —NH(C$_{1-6}$-alkyl), —NHCO(C$_{1-6}$-alkyl), —CONH$_2$, —CONH(C$_{1-6}$-alkyl), —SO$_2$NH$_2$, —SO$_2$NH(C$_{1-6}$-alkyl), —SO$_2$(C$_{1-6}$-alkyl), C$_{3-6}$-cycloalkyl, —NH—SO$_2$(C$_{1-6}$-alkyl), —COOH, —COO—C$_{1-6}$-alkyl, or —CN;

L is independently a bond or a linker group, wherein said linker group is *—NHCO—, *—NH—, *—NHCH$_2$—, *—NHCONH—, *—NHCO—CH═CH—, *—NHSO$_2$—, *—SO$_2$—, or pyridinyl, and wherein * specifies the point of attachment to X; and Y is independently H, aryl, cycloalkyl, heterocyclyl, or heteroaryl, wherein Y is unsubstituted or substituted with one or more substituents R$^Y$, wherein in each case independently R$^Y$ is F, Cl, Br, C$_{1-6}$-alkyl, C$_{1-6}$-haloalkyl, C$_{1-6}$-haloalkoxy, C$_{1-6}$-alkoxy, C$_{1-6}$-alkyl-morpholinyl, or nitro.

4. The compound according to claim 1, or a physiologically acceptable prodrug, solvate or salt thereof, wherein X is independently 1,2,3-thiadiazolyl, 1,2,4-thiadiazolyl, 1H-1,2,3-triazolyl, 1H-1,2,4-triazolyl, 1H-pyrazolyl, 1H-pyrrolyl, phenyl, benzo[b]thiophenyl, cyclohexyl, furyl, isoxazolyl, oxazolyl, imidazolyl, 1H-pyrazolyl, pyrazinyl, pyridyl, quinolinyl, 1-(naphthalen-2-yl) ethyl, thiazolyl, benzyl, or thiophenyl, wherein X is unsubstituted or substituted with one or more substituents R$^X$, wherein in each case independently R$^X$ is selected F, Cl, Br, methyl, tert-butyl, trifluoromethyl, trifluoromethoxy, difluoromethoxy, OH, acetyl, methylcarbamoyl, methoxy, nitro, —NH$_2$, —N(ethyl)$_2$, —N(methyl)$_2$, —NH(ethyl), —NHCOCH$_3$, —CONH$_2$, —SO$_2$NH$_2$, —SO$_2$(methyl), —NH—SO$_2$(methyl), —COOH, or —CN;

L is independently a bond or a linker group, wherein said linker group is *—NHCO—, *—NH—, *—NHCH$_2$—, *—NHCONH—, *—NHCO—CH═CH—, *-pyridinyl-, —SO$_2$—, or *—NHSO$_2$—, and wherein * specifies the point of attachment to X; and Y is independently H, phenyl, furyl, thiophenyl, pyridyl, pyrimidyl, 2,3-dihydrobenzo[b][1,4]dioxinyl, 2,3-dihydrobenzofuranyl, benzo[d][1,3]dioxolyl, thieno[3,2-d]pyrimidinyl, 2-oxo-2,3-dihydrobenzoimidazolyl, pyrrolidinyl, tetrazolyl, piperidinyl, pyrazolyl, 1,2,4-oxadiazolyl, 1,2,3-thiadiazolyl, pyrrolyl, imidazolyl, isoxazolyl, thiazolyl, thiomorpholinyl, or morpholinyl, wherein Y is unsubstituted or with one or two substituents R$^Y$, wherein in each case independently R$^Y$ is F, Cl, methyl, isopropyl, tert-butyl, trifluoromethyl, trifluoromethoxy, methoxy, methylcarbamoyl, cyclopropyl, 2-morpholinoethyl, or nitro.

5. The compound according to claim 1, or a physiologically acceptable prodrug, solvate or salt thereof, wherein X is independently selected from

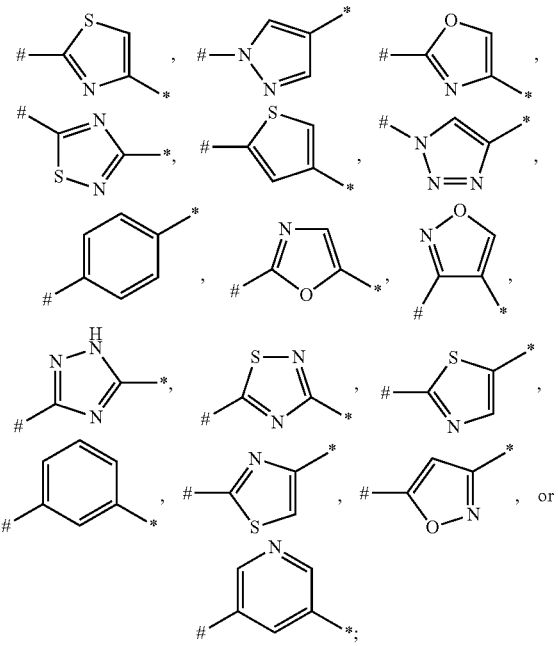

wherein * specifies the point of attachment to the central moiety, # specifies the point of attachment to L and wherein X is unsubstituted or substituted with one or more substituents R$^X$;

L is independently a bond or a linker group, wherein said linker group is *—NHCO—, *—NH—, *—NHCH$_2$—, *—NHCONH—, *—NHCO—CH═CH—, *-pyridinyl-, —SO$_2$—, or *—NHSO$_2$—, and wherein * specifies the point of attachment to X;

Y is independently H or selected from

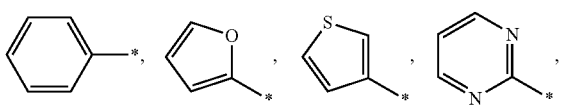

125
-continued

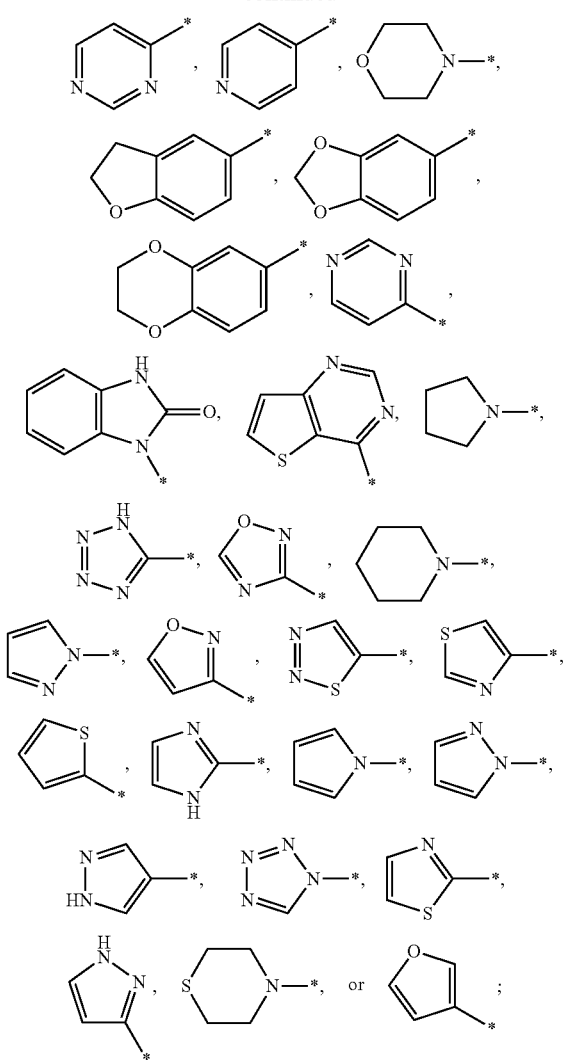

wherein * specifies the point of attachment to L and wherein Y is unsubstituted or substituted with one or more substituents $R^Y$;

or wherein X is selected from

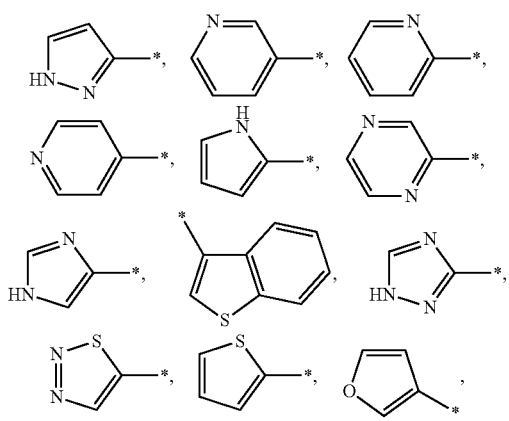

126
-continued

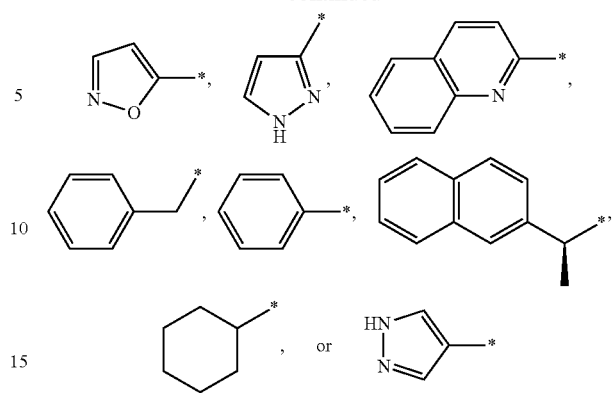

wherein * specifies the point of attachment to the central moiety, wherein L is a bond, Y is H, and wherein X is unsubstituted or substituted with one or more substituents $R^X$;

wherein each $R^Y$ is independently F, Cl, methyl, isopropyl, tert-butyl, trifluoromethyl, trifluoromethoxy, methoxy, methylcarbamoyl, cyclopropyl, 2-morpholinoethyl, or nitro; and wherein each $R^X$ is independently F, Cl, Br, methyl, tert-butyl, trifluoromethyl, trifluoromethoxy, difluoromethoxy, OH, acetyl, methylcarbamoyl, methoxy, nitro, —$NH_2$, —N(ethyl)$_2$, —N(methyl)$_2$, —NH(ethyl), —$NHCOCH_3$, —$CONH_2$, —$SO_2NH_2$, —$SO_2$(methyl), —NH—$SO_2$(methyl), —COOH, or —CN.

6. The compound according to claim 1, wherein said compound is selected from the following compounds:

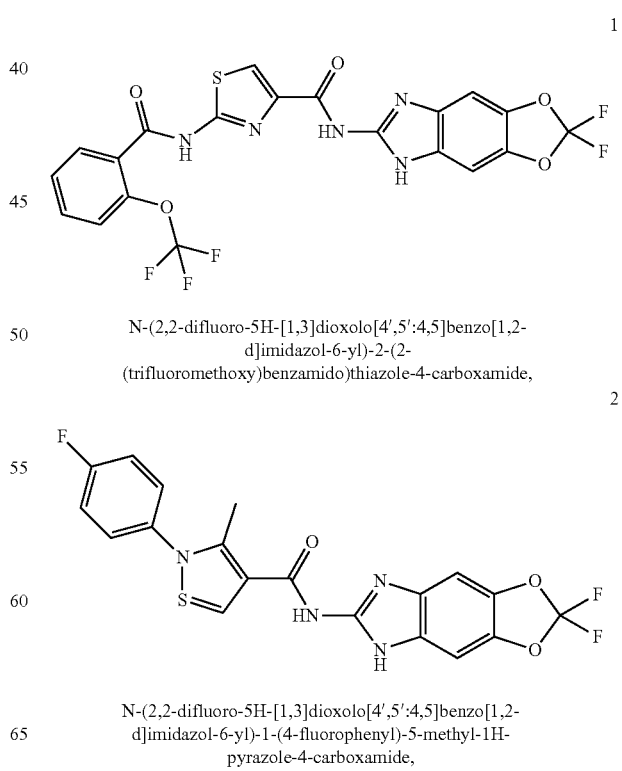

N-(2,2-difluoro-5H-[1,3]dioxolo[4',5':4,5]benzo[1,2-d]imidazol-6-yl)-2-(2-(trifluoromethoxy)benzamido)thiazole-4-carboxamide, N-(2,2-difluoro-5H-[1,3]dioxolo[4',5':4,5]benzo[1,2-d]imidazol-6-yl)-1-(4-fluorophenyl)-5-methyl-1H-pyrazole-4-carboxamide, -continued

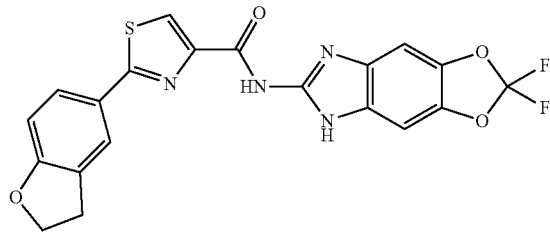

N-(2,2-difluoro-5H-[1,3]dioxolo[4',5':4,5]benzo[1,2-d]imidazol-6-yl)-2-(2,3-dihydrobenzofuran-5-yl)thiazole-4-carboxamide,

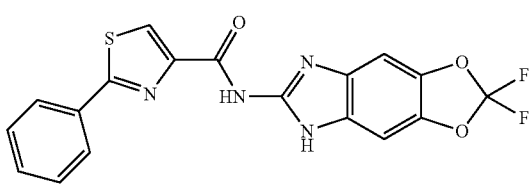

N-(2,2-difluoro-5H-[1,3]dioxolo[4',5':4,5]benzo[1,2-d]imidazol-6-yl)-2-phenylthiazole-4-carboxamide,

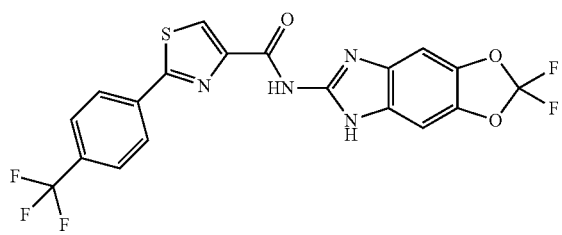

N-(2,2-difluoro-5H-[1,3]dioxolo[4',5':4,5]benzo[1,2-d]imidazol-6-yl)-2-(4-(trifluoromethyl)phenyl)thiazole-4-carboxamide,

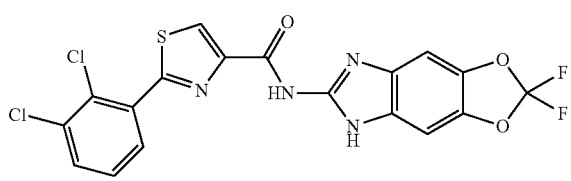

N-(2,3-dichlorophenyl-N-(2,2-difluoro-5H-[1,3]dioxolo[4',5':4,5]benzo[1,2-d]imidazol-6-yl)thiazole-4-carboxamide,

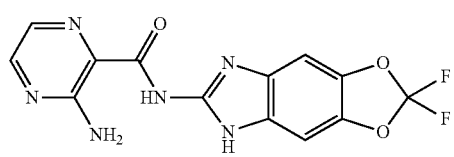 [SMILES: Nc1nccnc1C(=O)Nc1nc2cc3c(cc2[nH]1)OC(F)(F)O3]

3-amino-N-(2,2-difluoro-5H-[1,3]dioxolo[4',5':4,5]benzo[1,2-d]imidazol-6-yl)pyrazine-2-carboxamide, -continued

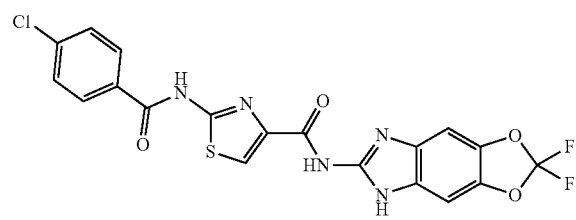

2-(4-chlorobenzamido)-N-(2,2-difluoro-5H-[1,3]dioxolo[4',5':4,5]benzo[1,2-d]imidazol-6-yl)thiazole-4-carboxamide,

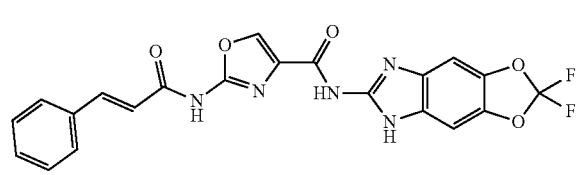

2-cinnamamido)-N-(2,2-difluoro-5H-[1,3]dioxolo[4',5':4,5]benzo[1,2-d]imidazol-6-yl)oxazole-4-carboxamide,

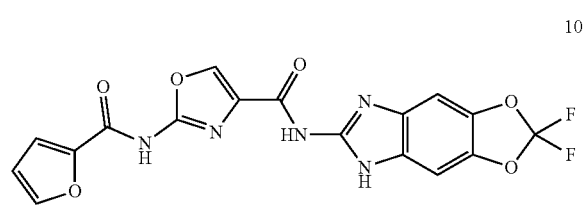

N-(2,2-difluoro-5H-[1,3]dioxolo[4',5':4,5]benzo[1,2-d]imidazol-6-yl)-2-(furan-2-carboxamido)oxazole-4-carboxamide,

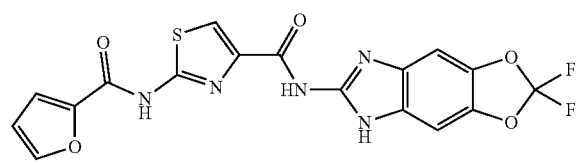

N-(2,2-difluoro-5H-[1,3]dioxolo[4',5':4,5]benzo[1,2-d]imidazol-6-yl)-2-(furan-2-carboxamido)thiazole-4-carboxamide,

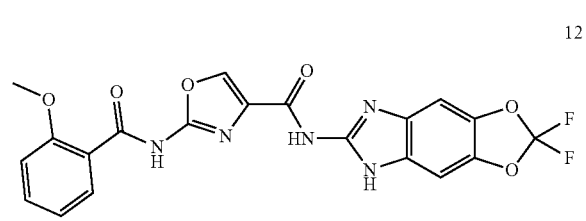

N-(2,2-difluoro-5H-[1,3]dioxolo[4',5':4,5]benzo[1,2-d]imidazol-6-yl)-2-(2-methoxybenzamido)-4-carboxamide,

13

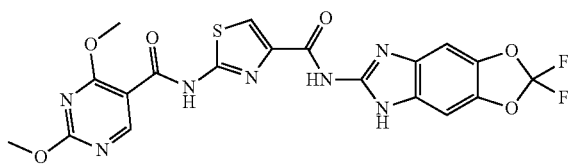

N-(2,2-difluoro-5H-[1,3]dioxolo[4',5':4,5]benzo[1,2-d]imidazol-6-yl)-2-(2-methoxybenzamido)-4-carboxamide,

14

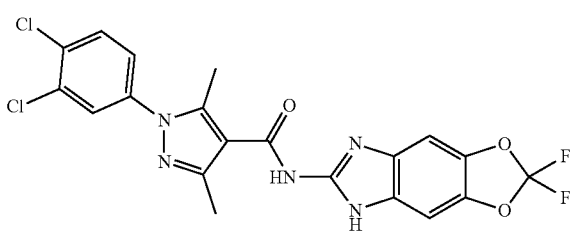

1-(3,4-dichlorophenyl)-N-(2,2-difluoro-5H-[1,3]dioxolo[4',5':4,5]benzo[1,2-d]imidazol-6-yl)-3,5-dimethyl-1H-pyrazole-4-carboxamide,

15

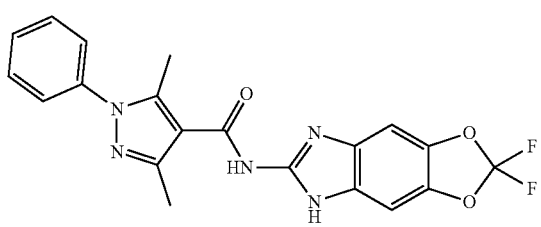

N-(2,2-difluoro-5H-[1,3]dioxolo[4',5':4,5]benzo[1,2-d]imidazol-6-yl)-3,5-dimethyl-1-phenyl-1H-pyrazole-4-carboxamide,

16

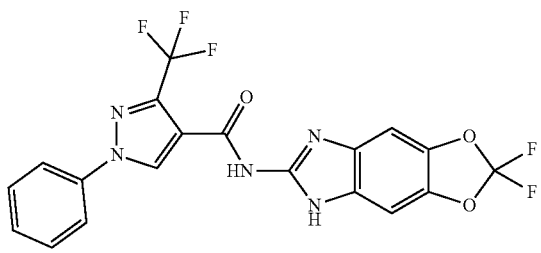

N-(2,2-difluoro-5H-[1,3]dioxolo[4',5':4,5]benzo[1,2-d]imidazol-6-yl)-1-phenyl-3-(trifluoromethyl)-1H-pyrazole-4-carboxamide,

17

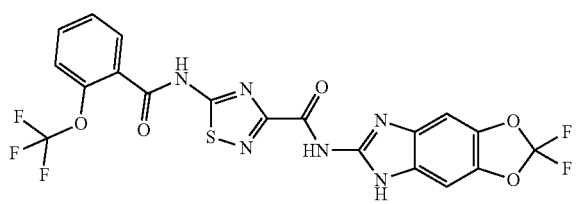

N-(2,2-difluoro-5H-[1,3]dioxolo[4',5':4,5]benzo[1,2-d]imidazol-6-yl)-5-(2-(trifluoromethoxy)benzamido)-1,2,4-thiadiazole-3-carboxamide,

18

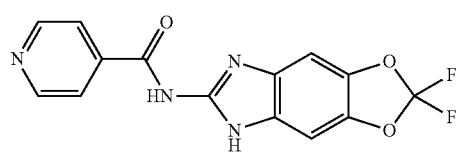 [SMILES: O=C(Nc1nc2cc3c(cc2[nH]1)OC(F)(F)O3)c1ccncc1]

N-(2,2-difluoro-5H-[1,3]dioxolo[4',5':4,5]benzo[1,2-d]imidazol-6-yl)isonicotinamide,

19

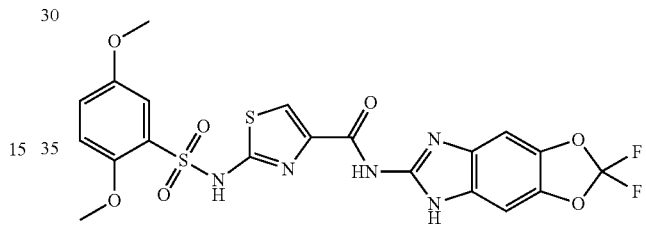

N-(2,2-difluoro-5H-[1,3]dioxolo[4',5':4,5]benzo[1,2-d]imidazol-6-yl)-2-(2,5-dimethoxyphenylsulfonamido)thiazole-4-carboxamide,

20

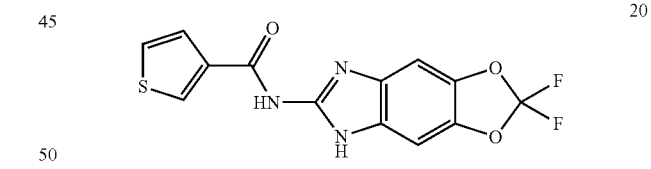

N-(2,2-difluoro-5H-[1,3]dioxolo[4',5':4,5]benzo[1,2-d]imidazol-6-yl)thiophene-3-carboxamide,

21

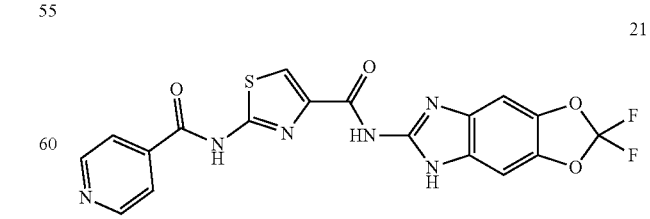

N-(2,2-difluoro-5H-[1,3]dioxolo[4',5':4,5]benzo[1,2-d]imidazol-6-yl)-2-(isonicotinamido)thiazole-4-carboxamide, -continued

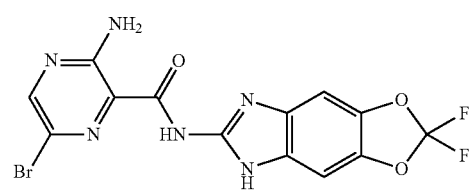 [SMILES: Nc1ncc(Br)nc1C(=O)Nc1nc2cc3c(cc2[nH]1)OC(F)(F)O3]

3-amino-6-bromo-N-(2,2-difluoro-5H-
[1,3]dioxolo[4',5':4,5]benzo[1,2-d]imidazol-6-
yl)pyrazine-2-carboxamide,

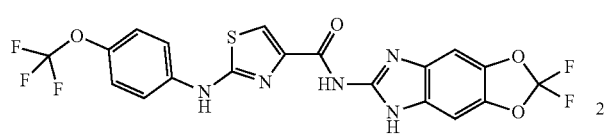

N-(2,2-difluoro-5H-[1,3]dioxolo[4',5':4,5]benzo[1,2-
d]imidazol-6-yl)-2-((4-
(trifluoromethoxy)phenyl)amino)thiazole-4-carboxamide,

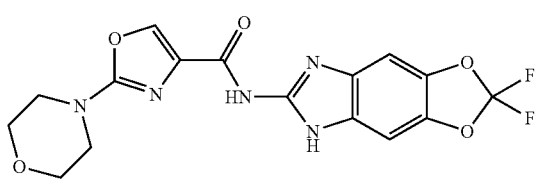

N-(2,2-difluoro-5H-[1,3]dioxolo[4',5':4,5]benzo[1,2-
d]imidazol-6-yl)-2-morpholinooxazole-4-carboxamide,

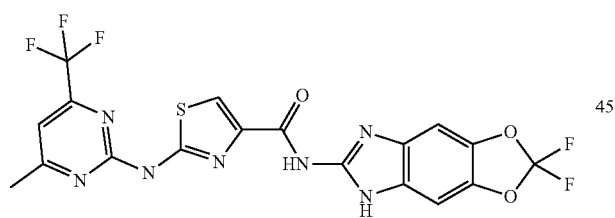

N-(2,2-difluoro-5H-[1,3]dioxolo[4',5':4,5]benzo[1,2-
d]imidazol-6-yl)-2-((4-methyl-6-(trifluoromethyl)pyrimidin-
2-yl)amino)thiazole-4-carboxamide,

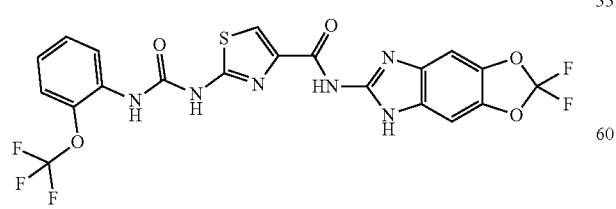

N-(2,2-difluoro-5H-[1,3]dioxolo[4',5':4,5]benzo[1,2-
d]imidazol-6-yl)-2-(3-(2-
(trifluoromethyl)phenyl)ureido)thiazole-4-carboxamide,

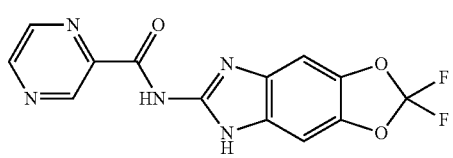

N-(2,2-difluoro-5H-[1,3]dioxolo[4',5':4,5]benzo[1,2-
d]imidazol-6-yl)pyrazine-2-carboxamide,

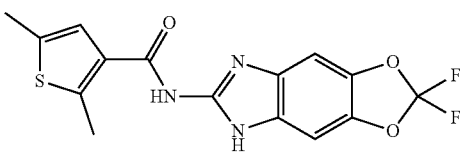

N-(2,2-difluoro-5H-[1,3]dioxolo[4',5':4,5]benzo[1,2-
d]imidazol-6-yl)-2,5-dimethylthiophene-3-
carboxamide,

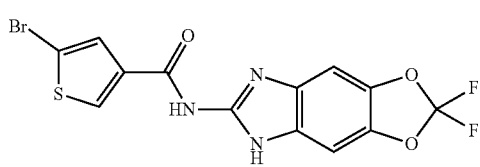

5-bromo-N-(2,2-difluoro-5H-
[1,3]dioxolo[4',5':4,5]benzo[1,2-d]imidazol-6-
yl)thiophene-3-carboxamide,

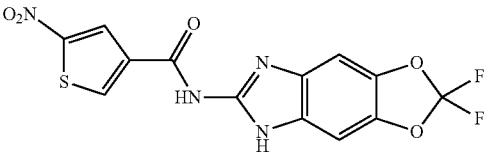

N-(2,2-difluoro-5H-[1,3]dioxolo[4',5':4,5]benzo[1,2-
d]imidazol-6-yl)-5-nitrothiophene-3-carboxamide,

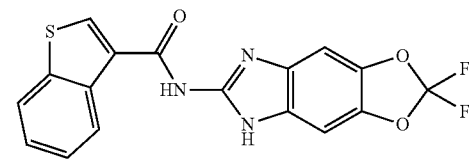 [SMILES: O=C(Nc1nc2cc3c(cc2[nH]1)OC(F)(F)O3)c1csc2ccccc12]

N-(2,2-difluoro-5H-[1,3]dioxolo[4',5':4,5]benzo[1,2-
d]imidazol-6-yl)benzo[b]thiophene-3-carboxamide,

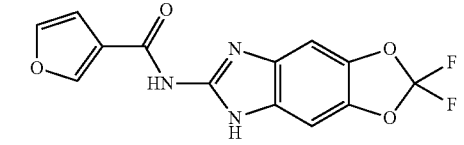

N-(2,2-difluoro-5H-[1,3]dioxolo[4',5':4,5]benzo[1,2-
d]imidazol-6-yl)furan-3-carboxamide,

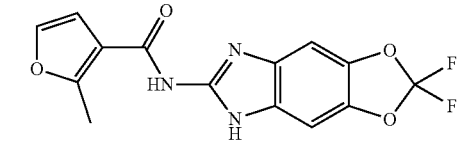 [SMILES: Cc1occc1C(=O)Nc1nc2cc3c(cc2[nH]1)OC(F)(F)O3]

N-(2,2-difluoro-5H-[1,3]dioxolo[4',5':4,5]benzo[1,2-
d]imidazol-6-yl)-2-methylfuran-3-carboxamide,

34

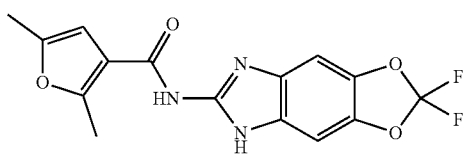

N-(2,2-difluoro-5H-[1,3]dioxolo[4′,5′:4,5]benzo[1,2-d]imidazol-6-yl)-2,5-dimethylfuran-3-carboxamide,

35

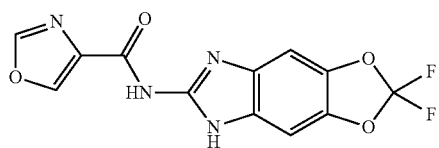 [SMILES: O=C(Nc1nc2cc3c(cc2[nH]1)OC(F)(F)O3)c1cocn1]

N-(2,2-difluoro-5H-[1,3]dioxolo[4′,5′:4,5]benzo[1,2-d]imidazol-6-yl)oxazole-4-carboxamide,

36

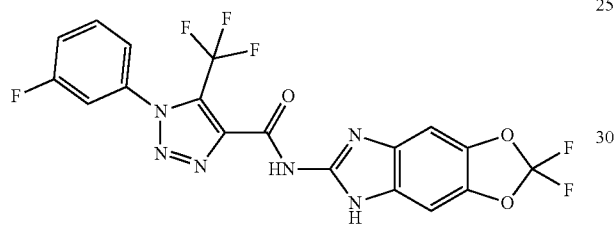

N-(2,2-difluoro-5H-[1,3]dioxolo[4′,5′:4,5]benzo[1,2-d]imidazol-6-yl)-1-(3-fluorophenyl)-5-(trifluoromethyl)-1H-1,2,3-triazole-4-carboxamide,

37

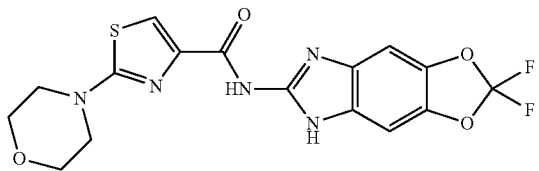

N-(2,2-difluoro-5H-[1,3]dioxolo[4′,5′:4,5]benzo[1,2-d]imidazol-6-yl)-2-morpholinothiazole-4-carboxamide,

38

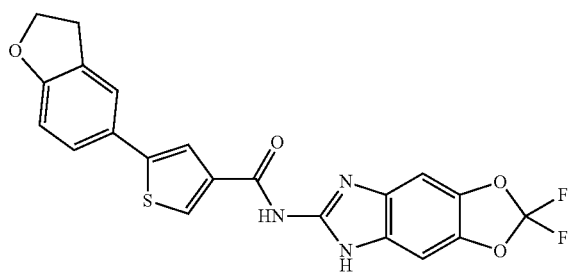

N-(2,2-difluoro-5H-[1,3]dioxolo[4′,5′:4,5]benzo[1,2-d]imidazol-6-yl)-5-(2,3-dihydrobenzofuran-5-yl)thiophene-3-carboxamide,

39

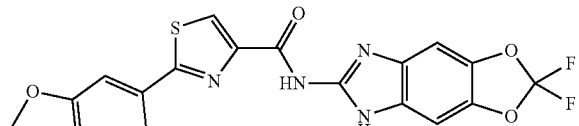

N-(2,2-difluoro-5H-[1,3]dioxolo[4′,5′:4,5]benzo[1,2-d]imidazol-6-yl)-5-(2,3-dihydrobenzofuran-5-yl)thiophene-3-carboxamide,

40

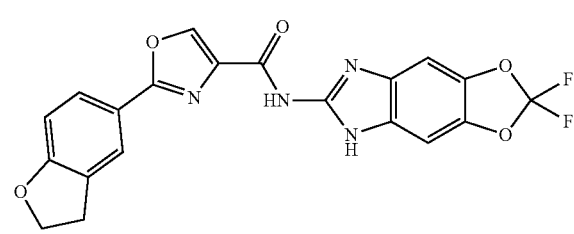

N-(2,2-difluoro-5H-[1,3]dioxolo[4′,5′:4,5]benzo[1,2-d]imidazol-6-yl)-2-(2,3-dihydrobenzofuran-5-yl)oxazole-4-carboxamide,

41

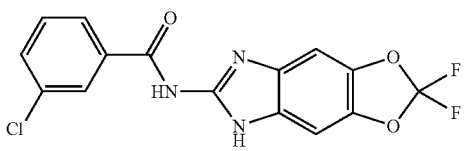 [SMILES: O=C(Nc1nc2cc3c(cc2[nH]1)OC(F)(F)O3)c1cccc(Cl)c1]

3-chloro-N-(2,2-difluoro-5H-[1,3]dioxolo[4′,5′:4,5]benzo[1,2-d]imidazol-6-yl)benzamide,

42

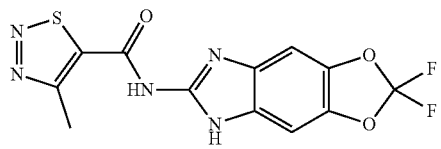 [SMILES: Cc1nnsc1C(=O)Nc1nc2cc3c(cc2[nH]1)OC(F)(F)O3]

N-(2,2-difluoro-5H-[1,3]dioxolo[4′,5′:4,5]benzo[1,2-d]imidazol-6-yl)-4-methyl-1,2,3-thiadiazole-5-carboxamide,

43

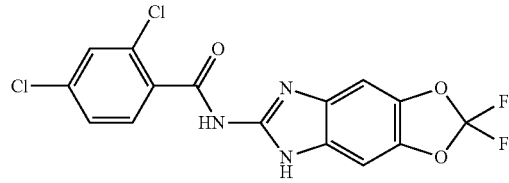 [SMILES: O=C(Nc1nc2cc3c(cc2[nH]1)OC(F)(F)O3)c1ccc(Cl)cc1Cl]

2,4-dichloro-N-(2,2-difluoro-5H-[1,3]dioxolo[4′,5′:4,5]benzo[1,2-d]imidazol-6-yl)benzamide,

44

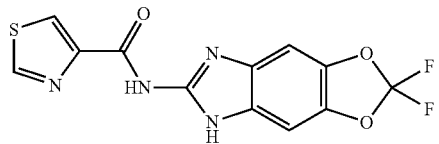 [SMILES: O=C(Nc1nc2cc3c(cc2[nH]1)OC(F)(F)O3)c1cscn1]

N-(2,2-difluoro-5H-[1,3]dioxolo[4′,5′:4,5]benzo[1,2-d]imidazol-6-yl)thiazole-4-carboxamide,

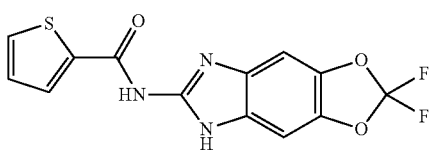 [SMILES: O=C(Nc1nc2cc3c(cc2[nH]1)OC(F)(F)O3)c1cccs1]

N-(2,2-difluoro-5H-[1,3]dioxolo[4',5':4,5]benzo[1,2-d]imidazol-6-yl)thiophene-2-carboxamide,

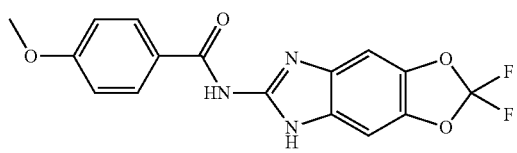 [SMILES: COc1ccc(C(=O)Nc2nc3cc4c(cc3[nH]2)OC(F)(F)O4)cc1]

N-(2,2-difluoro-5H-[1,3]dioxolo[4',5':4,5]benzo[1,2-d]imidazol-6-yl)-4-methoxybenzamide,

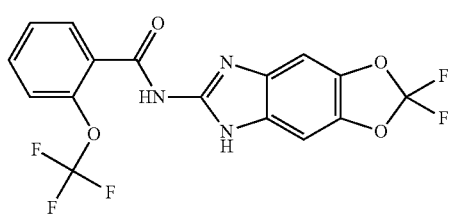 [SMILES: O=C(Nc1nc2cc3c(cc2[nH]1)OC(F)(F)O3)c1ccccc1OC(F)(F)F]

N-(2,2-difluoro-5H-[1,3]dioxolo[4',5':4,5]benzo[1,2-d]imidazol-6-yl)-2-(trifluoromethoxy)benzamide,

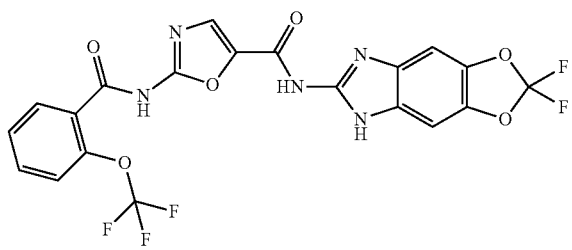

N-(2,2-difluoro-5H-[1,3]dioxolo[4',5':4,5]benzo[1,2-d]imidazol-6-yl)-2-(2-(trifluoromethoxy)benzamido)oxazole-5-carboxamide,

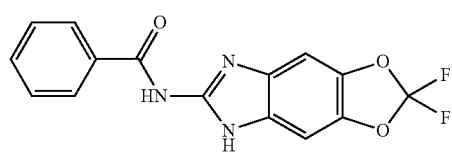 [SMILES: O=C(Nc1nc2cc3c(cc2[nH]1)OC(F)(F)O3)c1ccccc1]

N-(2,2-difluoro-5H-[1,3]dioxolo[4',5':4,5]benzo[1,2-d]imidazol-6-yl)benzamide,

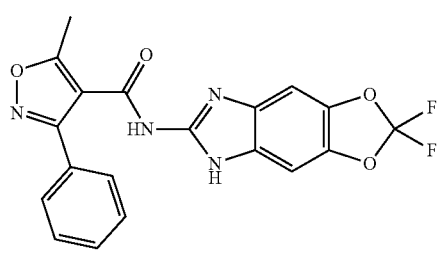 [SMILES: Cc1onc(-c2ccccc2)c1C(=O)Nc1nc2cc3c(cc2[nH]1)OC(F)(F)O3]

N-(2,2-difluoro-5H-[1,3]dioxolo[4',5':4,5]benzo[1,2-d]imidazol-6-yl)-5-methyl-3-phenylisoxazole-4-carboxamide,

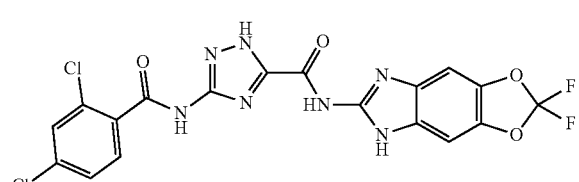

3-(2,4-dichlorobenzamido)-N-(2,2-difluoro-5H-[1,3]dioxolo[4',5':4,5]benzo[1,2-d]imidazol-6-yl)-1H-1,2,4-triazole-5-carboxamide,

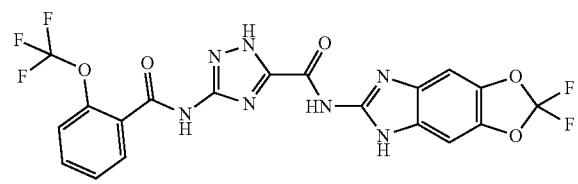

N-(2,2-difluoro-5H-[1,3]dioxolo[4',5':4,5]benzo[1,2-d]imidazol-6-yl)-3-(2-(trifluoromethoxy)benzamido)-1H-1,2,4-triazole-5-carboxamide,

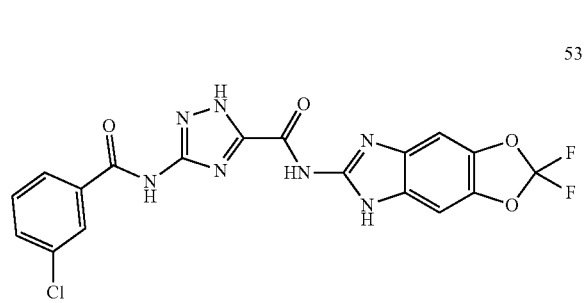

3-(3-chlorobenzamido)-N-(2,2-difluoro-5H-[1,3]dioxolo[4',5':4,5]benzo[1,2-d]imidazol-6-yl)-1H-1,2,4-triazole-5-carboxamide,

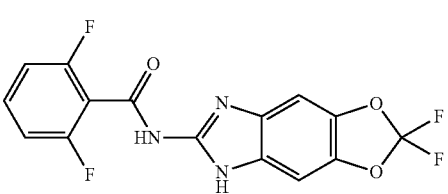 [SMILES: O=C(Nc1nc2cc3c(cc2[nH]1)OC(F)(F)O3)c1c(F)cccc1F]

N-(2,2-difluoro-5H-[1,3]dioxolo[4',5':4,5]benzo[1,2-d]imidazol-6-yl)-2,6-difluorobenzamide,

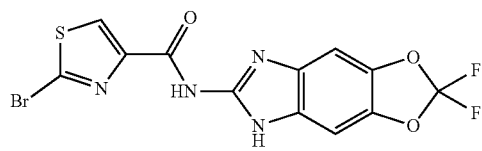

2-bromo-N-(2,2-difluoro-5H-
[1,3]dioxolo[4',5':4,5]benzo[1,2-d]imidazol-6-
yl)thiazole-4-carboxamide,

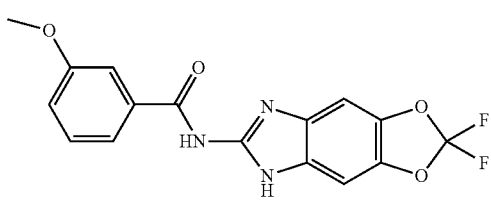

N-(2,2-difluoro-5H-[1,3]dioxolo[4',5':4,5]benzo[1,2-
d]imidazol-6-yl)-3-methoxybenzamide,

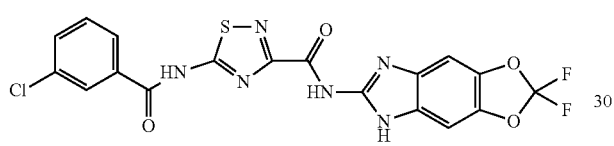

5-(3-chlorobenzamido)-N-(2,2-difluoro-5H-
[1,3]dioxolo[4',5':4,5]benzo[1,2-d]imidazol-6-yl)-
1,2,4-thiadiazole-3-carboxamide,

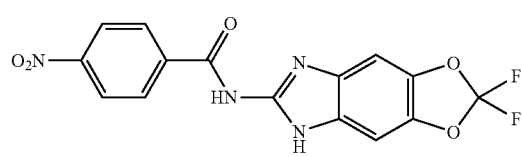

N-(2,2-difluoro-5H-[1,3]dioxolo[4',5':4,5]benzo[1,2-
d]imidazol-6-yl)-4-nitrobenzamide,

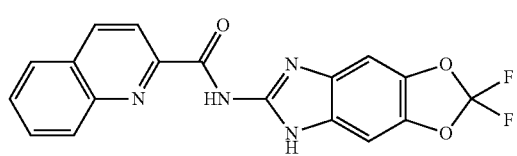

N-(2,2-difluoro-5H-[1,3]dioxolo[4',5':4,5]benzo[1,2-
d]imidazol-6-yl)quinoline-2-carboxamide,

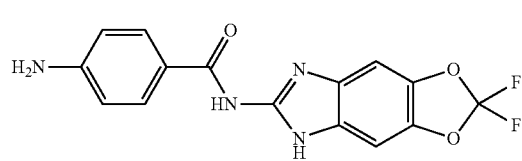 [SMILES: O=C(Nc1nc2cc3c(cc2[nH]1)OC(F)(F)O3)c1ccc([N+](=O)[O-])cc1]

4 amino-N-(2,2-difluoro-5H-[1,3]dioxolo[4',5':4,5]benzo[1,2-
d]imidazol-6-yl)benzamide,

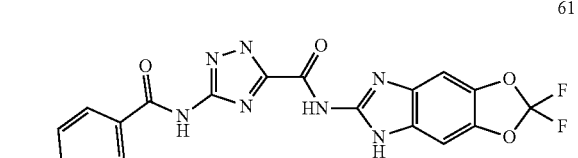

N-(2,2-difluoro-5H-[1,3]dioxolo[4',5':4,5]benzo[1,2-
d]imidazol-6-yl)-4-sulfamoylbenzamide,

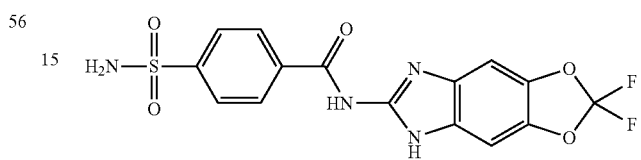

N-(2,2-difluoro-5H-[1,3]dioxolo[4',5':4,5]benzo[1,2-
d]imidazol-6-yl)-4-sulfamoylbenzamide,

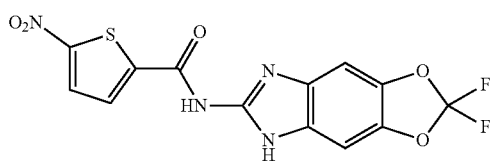

N-(2,2-difluoro-5H-[1,3]dioxolo[4',5':4,5]benzo[1,2-
d]imidazol-6-yl)-5-nitrothiophene-2-carboxamide,

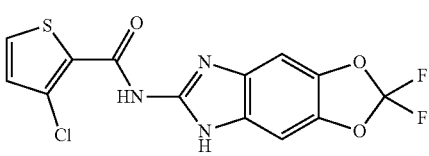 [SMILES: O=C(Nc1nc2cc3c(cc2[nH]1)OC(F)(F)O3)c1sccc1Cl]

3-chloro-N-(2,2-difluoro-5H-[1,3]dioxolo[4',5':4,5]benzo[1,2-
d]imidazol-6-yl)thiophene-2-carboxamide,

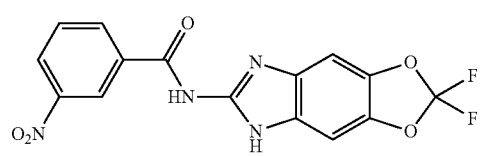 [SMILES: O=C(Nc1nc2cc3c(cc2[nH]1)OC(F)(F)O3)c1cccc([N+](=O)[O-])c1]

N-(2,2-difluoro-5H-[1,3]dioxolo[4',5':4,5]benzo[1,2-
d]imidazol-6-yl)-3-nitrobenzamide,

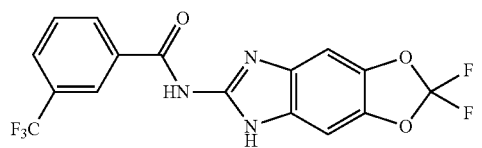

N-(2,2-difluoro-5H-[1,3]dioxolo[4',5':4,5]benzo[1,2-
d]imidazol-6-yl)-3-(trifluoromethyl)benzamide,

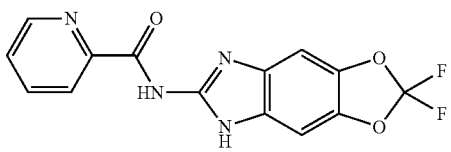 [SMILES: O=C(Nc1nc2cc3c(cc2[nH]1)OC(F)(F)O3)c1ccccn1]

N-(2,2-difluoro-5H-[1,3]dioxolo[4',5':4,5]benzo[1,2-
d]imidazol-6-yl)picolinamide,

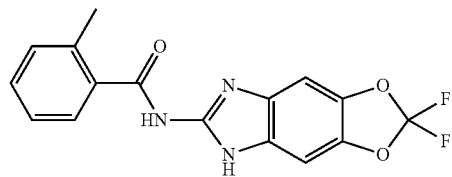 [SMILES: Cc1ccccc1C(=O)Nc1nc2cc3c(cc2[nH]1)OC(F)(F)O3]

N-(2,2-difluoro-5H-[1,3]dioxolo[4',5':4,5]benzo[1,2-d]imidazol-6-yl)-2-methylbenzamide,

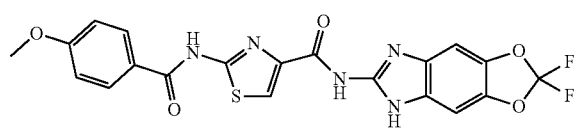

N-(2,2-difluoro-5H-[1,3]dioxolo[4',5':4,5]benzo[1,2-d]imidazol-6-yl)-2-(4-methoxybenzamido)thiazole-4-carboxamide,

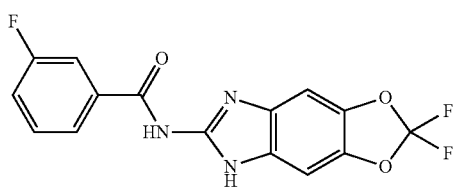 [SMILES: O=C(Nc1nc2cc3c(cc2[nH]1)OC(F)(F)O3)c1cccc(F)c1]

N-(2,2-difluoro-5H-[1,3]dioxolo[4',5':4,5]benzo[1,2-d]imidazol-6-yl)-3-fluorobenzamide,

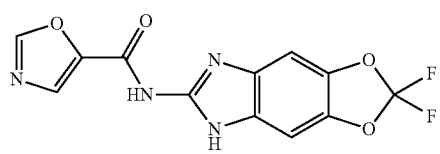 [SMILES: O=C(Nc1nc2cc3c(cc2[nH]1)OC(F)(F)O3)c1cnco1]

N-(2,2-difluoro-5H-[1,3]dioxolo[4',5':4,5]benzo[1,2-d]imidazol-6-yl)oxazole-5-carboxamide,

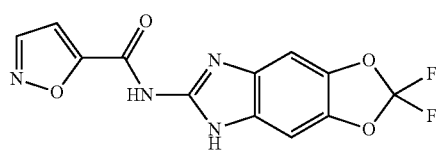 [SMILES: O=C(Nc1nc2cc3c(cc2[nH]1)OC(F)(F)O3)c1ccno1]

N-(2,2-difluoro-5H-[1,3]dioxolo[4',5':4,5]benzo[1,2-d]imidazol-6-yl)isoxazole-5-carboxamide,

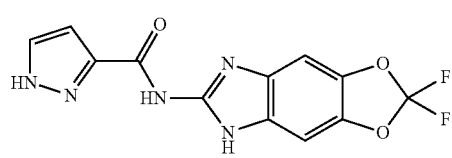 [SMILES: O=C(Nc1nc2cc3c(cc2[nH]1)OC(F)(F)O3)c1cc[nH]n1]

N-(2,2-difluoro-5H-[1,3]dioxolo[4',5':4,5]benzo[1,2-d]imidazol-6-yl)-1H-pyrazole-3-carboxamide,

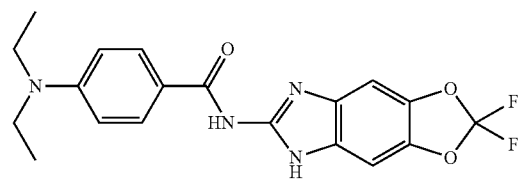 [SMILES: CCN(CC)c1ccc(C(=O)Nc2nc3cc4c(cc3[nH]2)OC(F)(F)O4)cc1]

4-(diethylamino)-N-(2,2-difluoro-5H-[1,3]dioxolo[4',5':4,5]benzo[1,2-d]imidazol-6-yl)benzamide,

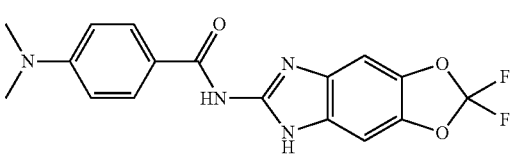 [SMILES: CN(C)c1ccc(C(=O)Nc2nc3cc4c(cc3[nH]2)OC(F)(F)O4)cc1]

N-(2,2-difluoro-5H-[1,3]dioxolo[4',5':4,5]benzo[1,2-d]imidazol-6-yl)-4-(dimethylamino)benzamide,

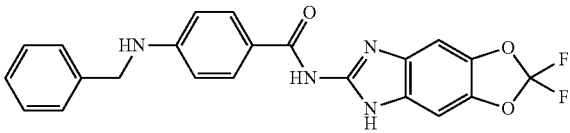

4-(benzylamino)-N-(2,2-difluoro-5H-[1,3]dioxolo[4',5':4,5]benzo[1,2-d]imidazol-6-yl)benzamide,

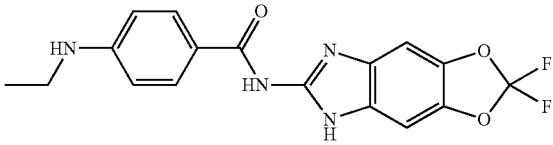 [SMILES: CCNc1ccc(C(=O)Nc2nc3cc4c(cc3[nH]2)OC(F)(F)O4)cc1]

N-(2,2-difluoro-5H-[1,3]dioxolo[4',5':4,5]benzo[1,2-d]imidazol-6-yl)-(ethylamino)benzamide,

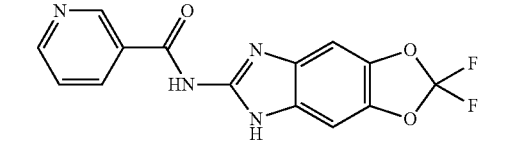

N-(2,2-difluoro-5H-[1,3]dioxolo[4',5':4,5]benzo[1,2-d]imidazol-6-yl)nicotinamide,

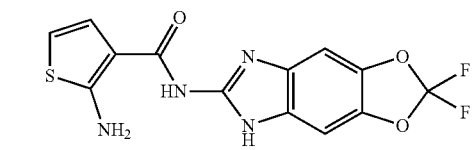 [SMILES: Nc1sccc1C(=O)Nc1nc2cc3c(cc2[nH]1)OC(F)(F)O3]

2-amino-N-(2,2-difluoro-5H-[1,3]dioxolo[4',5':4,5]benzo[1,2-d]imidazol-6-yl)thiophene-3-carboxamide, -continued

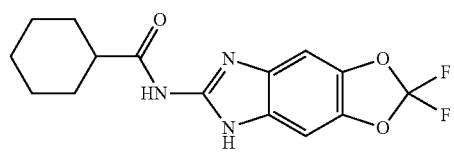 [SMILES: O=C(Nc1nc2cc3c(cc2[nH]1)OC(F)(F)O3)C1CCCCC1]

N-(2,2-difluoro-5H-[1,3]dioxolo[4′,5′:4,5]benzo[1,2-d]imidazol-6-yl)cyclohexanecarboxamide,

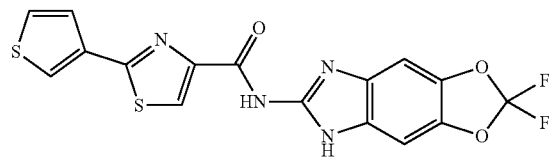 [SMILES: O=C(Nc1nc2cc3c(cc2[nH]1)OC(F)(F)O3)c1csc(-c2ccsc2)n1]

N-(2,2-difluoro-5H-[1,3]dioxolo[4′,5′:4,5]benzo[1,2-d]imidazol-6-yl)-2-(thiophen-3-yl)thiazole-4-carboxamide,

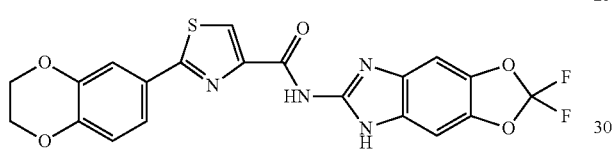

N-(2,2-difluoro-5H-[1,3]dioxolo[4′,5′:4,5]benzo[1,2-d]imidazol-6-yl)-2-(2,3-dihydrobenzo[b][1,4]dioxin-6-yl)thiazole-4-carboxamide

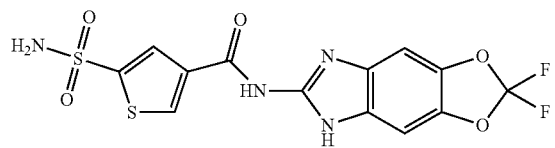

N-(2,2-difluoro-5H-[1,3]dioxolo[4′,5′:4,5]benzo[1,2-d]imidazol-6-yl)-5-sulfamoylthiophene-3-carboxamide,

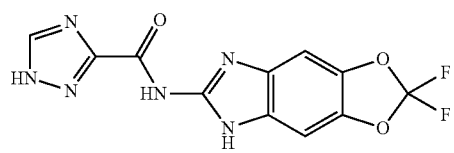

N-(2,2-difluoro-5H-[1,3]dioxolo[4′,5′:4,5]benzo[1,2-d]imidazol-6-yl)-1H-1,2,4-triazole-3-carboxamide,

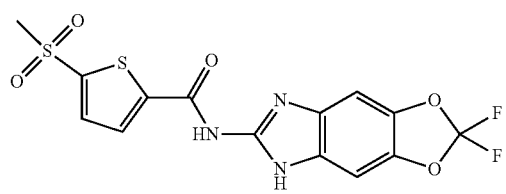

N-(2,2-difluoro-5H-[1,3]dioxolo[4′,5′:4,5]benzo[1,2-d]imidazol-6-yl)-5-(methylsulfonyl)thiophene-2-carboxamide, -continued

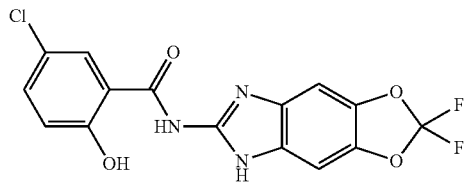 [SMILES: O=C(Nc1nc2cc3c(cc2[nH]1)OC(F)(F)O3)c1cc(Cl)ccc1O]

5-chloro-N-(2,2-difluoro-5H-[1,3]dioxolo[4′,5′:4,5]benzo[1,2-d]imidazol-6-yl)-2-hydroxybenzamide,

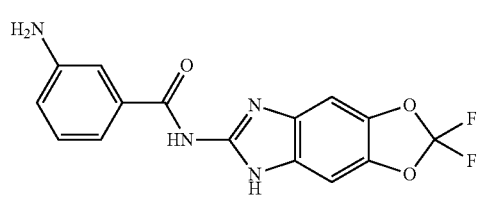 [SMILES: Nc1cccc(C(=O)Nc2nc3cc4c(cc3[nH]2)OC(F)(F)O4)c1]

3-amino-N-(2,2-difluoro-5H-[1,3]dioxolo[4′,5′:4,5]benzo[1,2-d]imidazol-6-yl)benzamide,

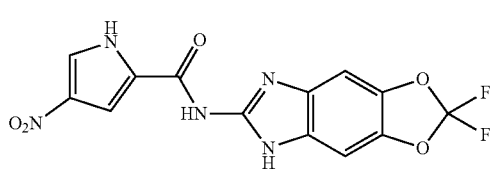 [SMILES: O=C(Nc1nc2cc3c(cc2[nH]1)OC(F)(F)O3)c1cc([N+](=O)[O-])c[nH]1]

N-(2,2-difluoro-5H-[1,3]dioxolo[4′,5′:4,5]benzo[1,2-d]imidazol-6-yl)-4-nitro-1H-pyrrole-2-carboxamide,

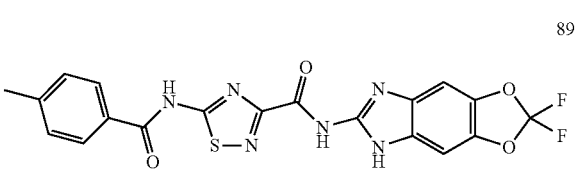

N-(2,2-difluoro-5H-[1,3]dioxolo[4′,5′:4,5]benzo[1,2-d]imidazol-6-yl)-5-(4-methylbenzamido)-1,2,4-thiadiazole-3-carboxamide,

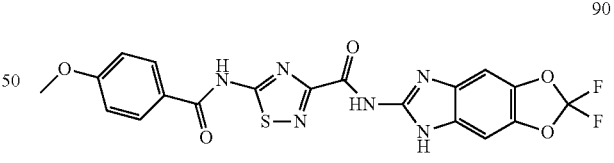

N-(2,2-difluoro-5H-[1,3]dioxolo[4′,5′:4,5]benzo[1,2-d]imidazol-6-yl)-5-(4-methylbenzamido)-1,2,4-thiadiazole-3-carboxamide,

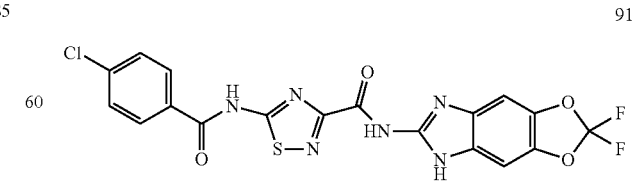

5-(4-chlorobenzamido)-N-(2,2-difluoro-5H-[1,3]dioxolo[4′,5′:4,5]benzo[1,2-d]imidazol-6-yl)-1,2,4-thiadiazole-3-carboxamide, -continued

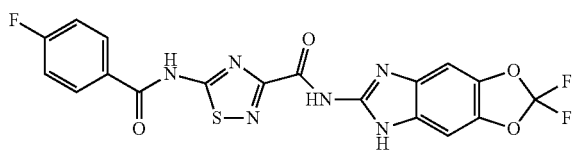

N-(2,2-difluoro-5H-[1,3]dioxolo[4',5':4,5]benzo[1,2-d]imidazol-6-yl)-5-(4-fluorobenzamido)-1,2,4-thiadiazole-3-carboxamide,

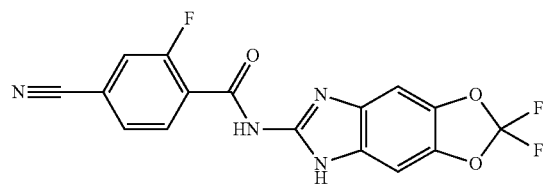 [SMILES: N#Cc1ccc(C(=O)Nc2nc3cc4c(cc3[nH]2)OC(F)(F)O4)c(F)c1]

4-cyano-N-(2,2-difluoro-5H-[1,3]dioxolo[4',5':4,5]benzo[1,2-d]imidazol-6-yl)-2-fluorobenzamide,

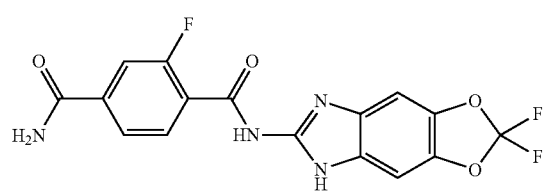 [SMILES: NC(=O)c1ccc(C(=O)Nc2nc3cc4c(cc3[nH]2)OC(F)(F)O4)c(F)c1]

$N^1$-(2,2-difluoro-5H-[1,3]dioxolo[4',5':4,5]benzo[1,2-d]imidazol-6-yl)-2-fluoroterephthalamide,

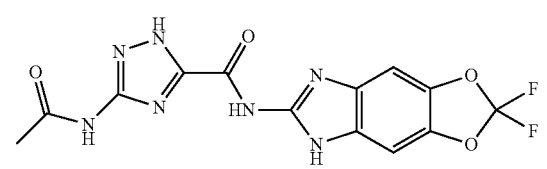

3-acetamido-N-(2,2-difluoro-5H-[1,3]dioxolo[4',5':4,5]benzo[1,2-d]imidazol-6-yl)-1H-1,2,4-triazole-5-carboxamide,

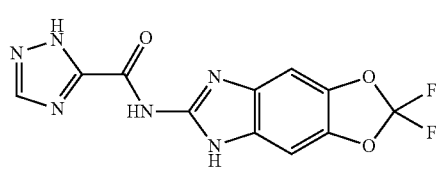 [SMILES: O=C(Nc1nc2cc3c(cc2[nH]1)OC(F)(F)O3)c1ncn[nH]1]

N-(2,2-difluoro-5H-[1,3]dioxolo[4',5':4,5]benzo[1,2-d]imidazol-6-yl)-1H-1,2,4-triazole-5-carboxamide,

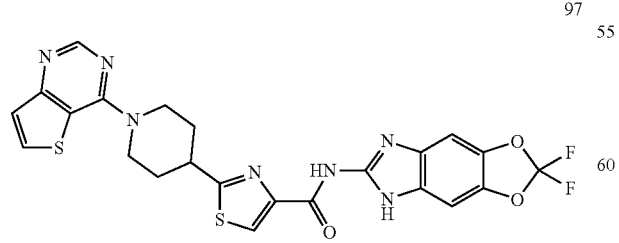

N-(2,2-difluoro-5H-[1,3]dioxolo[4',5':4,5]benzo[1,2-d]imidazol-6-yl)-2-(1-(thieno[3,2-d]pyrimidin-4-yl)piperidin-4-yl)thiazole-4-carboxamide,

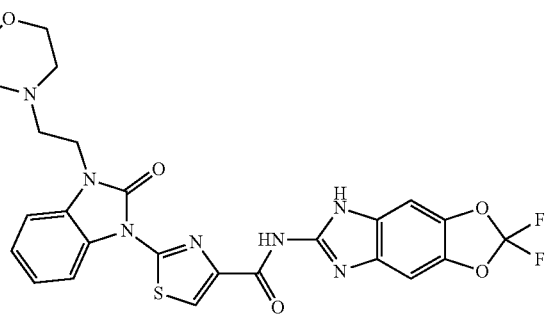

N-(2,2-difluoro-5H-[1,3]dioxolo[4',5':4,5]benzo[1,2-d]imidazol-6-yl)-2-(3-(2-morpholinoethyl)-2-oxo-2,3-dihydro-1H-benzo[d]imidazol-1-yl)thiazole-4-carboxamide,

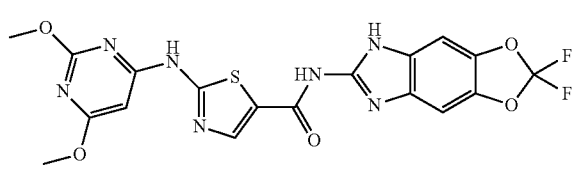

N-(2,2-difluoro-5H-[1,3]dioxolo[4',5':4,5]benzo[1,2-d]imidazol-6-yl)-2-((2,6-dimethoxypyrimidin-4-yl)amino)thiazole-5-carboxamide,

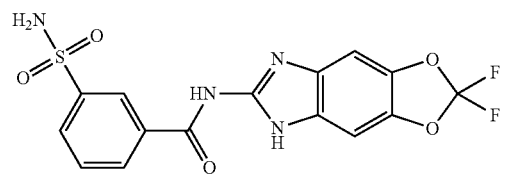 [SMILES: NS(=O)(=O)c1cccc(C(=O)Nc2nc3cc4c(cc3[nH]2)OC(F)(F)O4)c1]

N-(2,2-difluoro-5H-[1,3]dioxolo[4',5':4,5]benzo[1,2-d]imidazol-6-yl)-3-sulfamoylbenzamide,

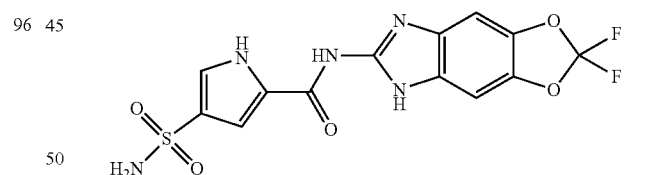

N-(2,2-difluoro-5H-[1,3]dioxolo[4',5':4,5]benzo[1,2-d]imidazol-6-yl)-4-sulfamoyl-1H-pyrrole-2-carboxamide,

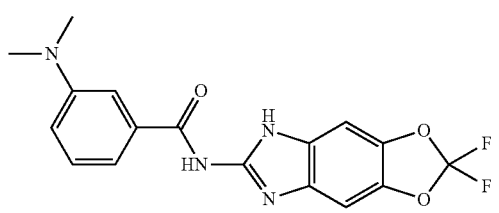

N-(2,2-difluoro-5H-[1,3]dioxolo[4',5':4,5]benzo[1,2-d]imidazol-6-yl)-3-(dimethylamino)benzamide,

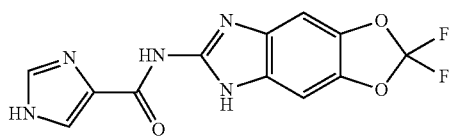 [SMILES: O=C(Nc1nc2cc3c(cc2[nH]1)OC(F)(F)O3)c1c[nH]cn1]

N-(2,2-difluoro-5H-
[1,3]dioxolo[4',5':4,5]benzo[1,2-d]imidazol-6-yl)-
1H-imidazole-4-carboxamide,

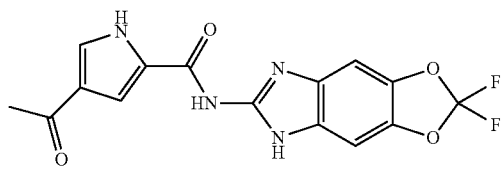

4-acetyl-N-(2,2-difluoro-5H-
[1,3]dioxolo[4',5':4,5]benzo[1,2-d]imidazol-6-yl)-
1H-pyrrole-2-carboxamide,

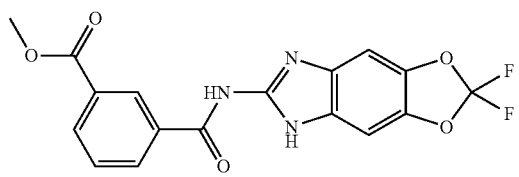 [SMILES: COC(=O)c1cccc(C(=O)Nc2nc3cc4c(cc3[nH]2)OC(F)(F)O4)c1]

methyl 3-((2,2-difluoro-5H-
[1,3]dioxolo[4',5':4,5]benzo[1,2-d]benzo[1,2-
d]imidazol-6-yl)carbamoyl)benzoate,

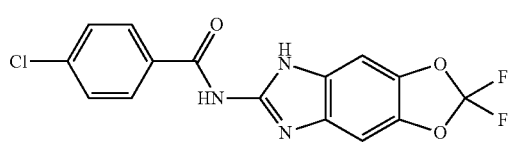 [SMILES: O=C(Nc1nc2cc3c(cc2[nH]1)OC(F)(F)O3)c1ccc(Cl)cc1]

4-chloro-N-(2,2-difluoro-5H-
[1,3]dioxolo[4',5':4,5]benzo[1,2-d]imidazol-
6-yl)benzamide,

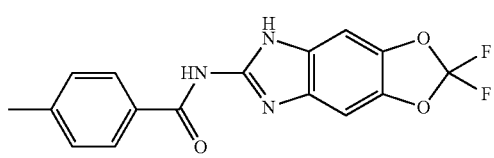 [SMILES: Cc1ccc(C(=O)Nc2nc3cc4c(cc3[nH]2)OC(F)(F)O4)cc1]

methyl 3-((2,2-difluoro-5H-
[1,3]dioxolo[4',5':4,5]benzo[1,2-d]benzo[1,2-
d]imidazol-6-yl)carbamoyl)benzoate,

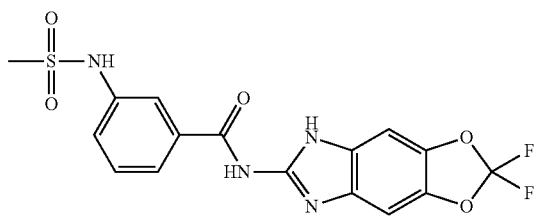 [SMILES: CS(=O)(=O)Nc1cccc(C(=O)Nc2nc3cc4c(cc3[nH]2)OC(F)(F)O4)c1]

N-(2,2-difluoro-5H-
[1,3]dioxolo[4',5':4,5]benzo[1,2-d]imidazol-6-yl)-3-
(methylsulfonamido)benzamide,

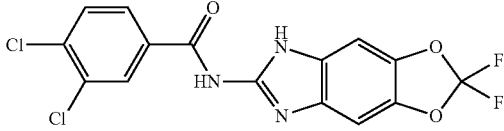 [SMILES: O=C(Nc1nc2cc3c(cc2[nH]1)OC(F)(F)O3)c1ccc(Cl)c(Cl)c1]

3,4-dichloro-N-(2,2-difluoro-5H-
[1,3]dioxolo[4',5':4,5]benzo[1,2-d]imidazol-
6-yl)benzamide,

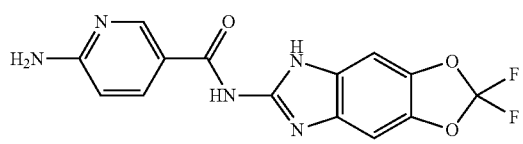 [SMILES: Nc1ccc(C(=O)Nc2nc3cc4c(cc3[nH]2)OC(F)(F)O4)cn1]

6-amino-N-(2,2-difluoro-5H-
[1,3]dioxolo[4',5':4,5]benzo[1,2-d]imidazol-6-
yl)nicotinamide,

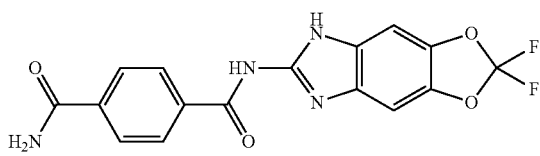 [SMILES: NC(=O)c1ccc(C(=O)Nc2nc3cc4c(cc3[nH]2)OC(F)(F)O4)cc1]

N¹-(2,2-difluoro-5H-
[1,3]dioxolo[4',5':4,5]benzo[1,2-d]benzo[1,2-
d]imidazol-6-yl)terephthalamide,

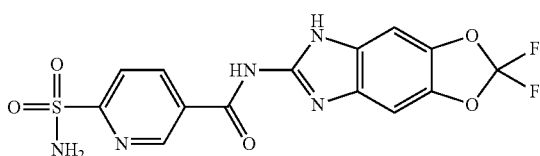

N-(2,2-difluoro-5H-
[1,3]dioxolo[4',5':4,5]benzo[1,2-d]imidazol-6-yl)-
6-sulfamoylnicotinamide,

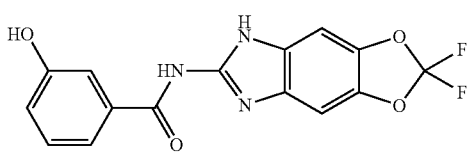 [SMILES: O=C(Nc1nc2cc3c(cc2[nH]1)OC(F)(F)O3)c1cccc(O)c1]

N-(2,2-difluoro-5H-
[1,3]dioxolo[4',5':4,5]benzo[1,2-d]-3-
hydroxybenzamide,

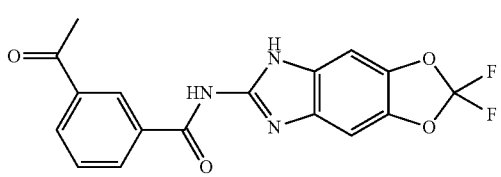 [SMILES: CC(=O)c1cccc(C(=O)Nc2nc3cc4c(cc3[nH]2)OC(F)(F)O4)c1]

3-acetyl-N-(2,2-difluoro-5H-
[1,3]dioxolo[4',5':4,5]benzo[1,2-d]imidazol-6-
yl)benzamide,

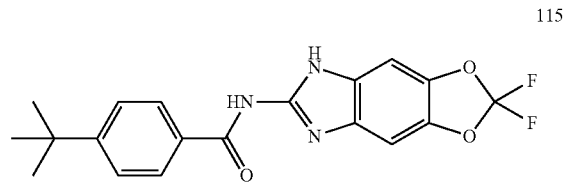

4-(tert-butyl)-N-(2,2-difluoro-5H-
[1,3]dioxolo[4′,5′:4,5]benzo[1,2-d]imidazol-6-
yl)benzamide,

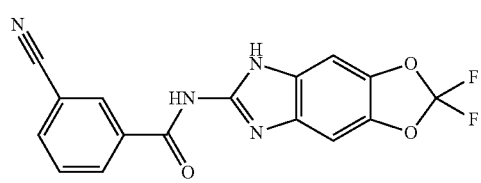

3-cyano-N-(2,2-difluoro-5H-
[1,3]dioxolo[4′,5′:4,5]benzo[1,2-d]imidazol-6-
yl)benzamide,

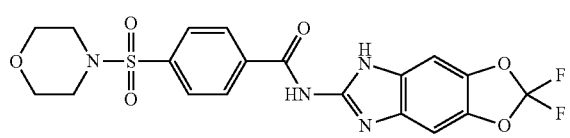 [SMILES: O=C(Nc1nc2cc3c(cc2[nH]1)OC(F)(F)O3)c1ccc(S(=O)(=O)N2CCOCC2)cc1]

N-(2,2-difluoro-5H-
[1,3]dioxolo[4′,5′:4,5]benzo[1,2-
d]imidazol-6-yl)-4-(morpholinosulfonyl)benzamide,

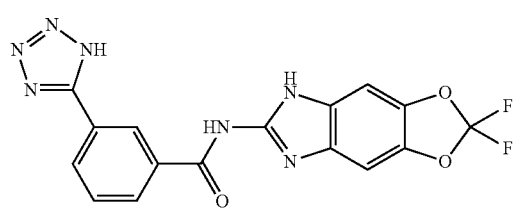 [SMILES: O=C(Nc1nc2cc3c(cc2[nH]1)OC(F)(F)O3)c1cccc(-c2nnn[nH]2)c1]

N-(2,2-difluoro-5H-
[1,3]dioxolo[4′,5′:4,5]benzo[1,2-d]imidazol-6-yl)-3-
(trifluoromethoxy)benzamide,

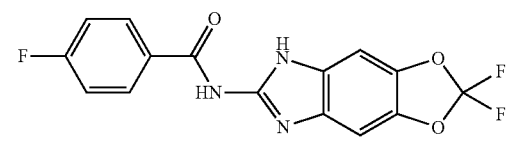 [SMILES: O=C(Nc1nc2cc3c(cc2[nH]1)OC(F)(F)O3)c1ccc(F)cc1]

N-(2,2-difluoro-5H-
[1,3]dioxolo[4′,5′:4,5]benzo[1,2-
d]imidazol-6-yl)-4-fluorobenzamide,

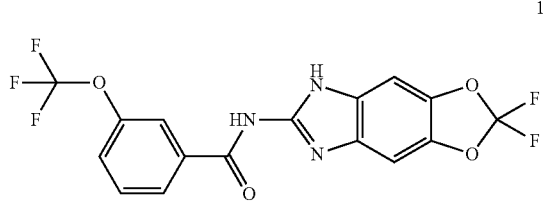

N-(2,2-difluoro-5H-
[1,3]dioxolo[4′,5′:4,5]benzo[1,2-
d]imidazol-6-yl)-3-(trifluoromethoxy)benzamide,

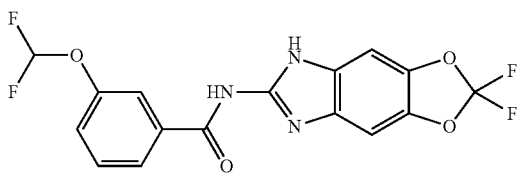 [SMILES: O=C(Nc1nc2cc3c(cc2[nH]1)OC(F)(F)O3)c1cccc(OC(F)F)c1]

N-(2,2-difluoro-5H-
[1,3]dioxolo[4′,5′:4,5]benzo[1,2-d]imidazol-6-
yl)-3-(difluoromethoxy)benzamide,

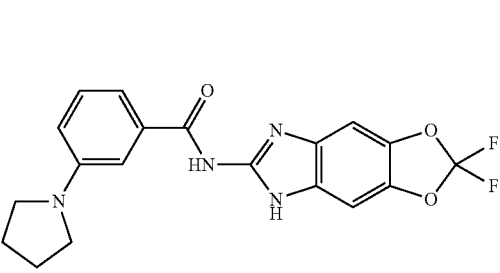

N-(2,2-difluoro-5H-
[1,3]dioxolo[4′,5′:4,5]benzo[1,2-
d]imidazol-6-yl)-3-(pyrrolidin-1-yl)benzamide,

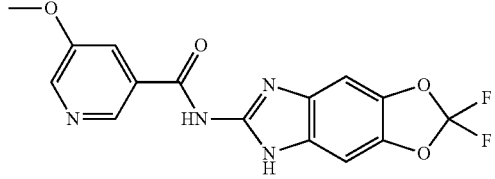 [SMILES: COc1cncc(C(=O)Nc2nc3cc4c(cc3[nH]2)OC(F)(F)O4)c1]

N-(2,2-difluoro-5H-[1,3]dioxolo[4′,5′:4,5]benzo[1,2-
d]imidazol-6-yl)-5-methoxynicotinamide,

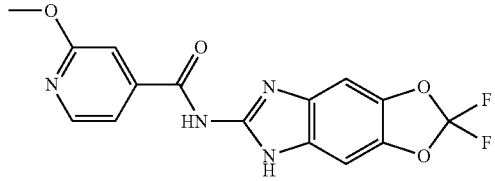

N-(2,2-difluoro-5H-[1,3]dioxolo[4′,5′:4,5]benzo[1,2-
d]imidazol-6-yl)-2-methoxyiosnicotinamide,

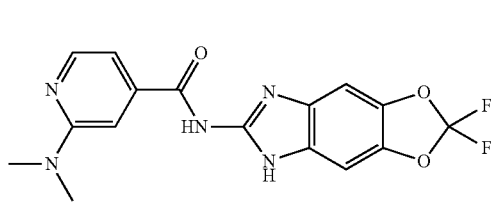

N-(2,2-difluoro-5H-[1,3]dioxolo[4′,5′:4,5]benzo[1,2-
d]imidazol-6-yl)-2-
(dimethylamino)isonicotinamide, -continued

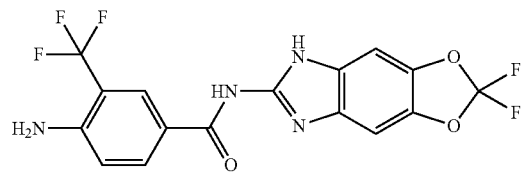 [SMILES: Nc1ccc(C(=O)Nc2nc3cc4c(cc3[nH]2)OC(F)(F)O4)cc1C(F)(F)F]

4-amino-N-(2,2-difluoro-5H-[1,3]dioxolo[4',5':4,5]benzo[1,2-d]imidazol-6-yl)-3-(trifluoromethyl)benzamide,

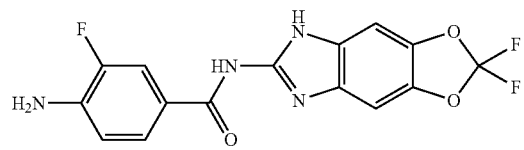 [SMILES: Nc1ccc(C(=O)Nc2nc3cc4c(cc3[nH]2)OC(F)(F)O4)cc1F]

4-amino-N-(2,2-difluoro-5H-[1,3]dioxolo[4',5':4,5]benzo[1,2-d]imidazol-6-yl)-3-fluorobenzamide,

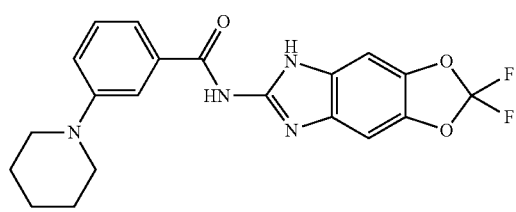

N-(2,2-difluoro-5H-[1,3]dioxolo[4',5':4,5]benzo[1,2-d]imidazol-6-yl)-3-(piperidin-1-yl)benzamide,

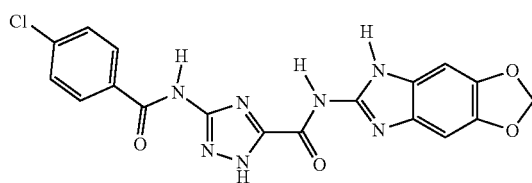

3-(4-chlorobenzamido)-N-(2,2-difluoro-5H-[1,3]dioxolo[4',5':4,5]benzo[1,2-d]imidazol-6-yl)-1H-1,2,4-triazole-5-carboxamide,

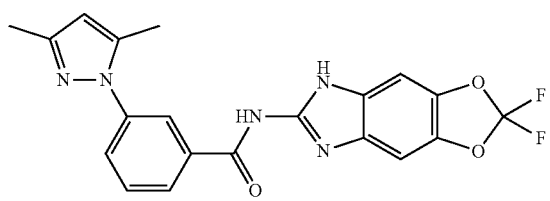 [SMILES: Cc1cc(C)n(-c2cccc(C(=O)Nc3nc4cc5c(cc4[nH]3)OC(F)(F)O5)c2)n1]

N-(2,2-difluoro-5H-[1,3]dioxolo[4',5':4,5]benzo[1,2-d]imidazol-6-yl)-3-(3,5-dimethyl-1H-pyrazol-1-yl)benzamide,

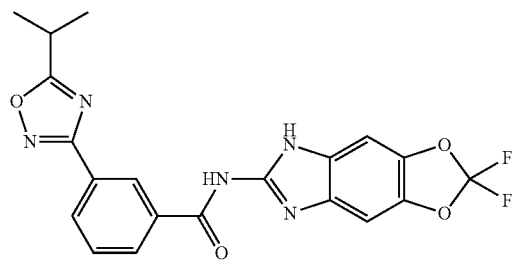 [SMILES: CC(C)c1nc(-c2cccc(C(=O)Nc3nc4cc5c(cc4[nH]3)OC(F)(F)O5)c2)no1]

N-(2,2-difluoro-5H-[1,3]dioxolo[4',5':4,5]benzo[1,2-d]imidazol-6-yl)-3-(5-isopropyl-1,2,4-oxadiazol-3-yl)benzamide,

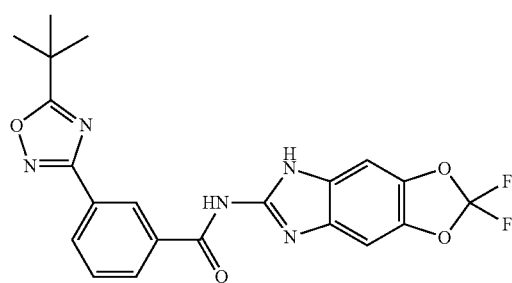 [SMILES: CC(C)(C)c1nc(-c2cccc(C(=O)Nc3nc4cc5c(cc4[nH]3)OC(F)(F)O5)c2)no1]

3-(5-(tert-butyl)-1,2,4-oxadiazol-3-yl)-N-(2,2-difluoro-5H-[1,3]dioxolo[4',5':4,5]benzo[1,2-d]imidazol-6-yl)benzamide,

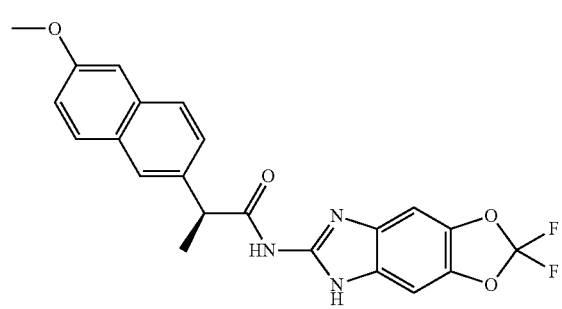 [SMILES: COc1ccc2cc([C@H](C)C(=O)Nc3nc4cc5c(cc4[nH]3)OC(F)(F)O5)ccc2c1]

(S)-N-(2,2-difluoro-5H-[1,3]dioxolo[4',5':4,5]benzo[1,2-d]imidazol-6-yl)-2-(6-methoxynaphthalen-2-yl)propanamide,

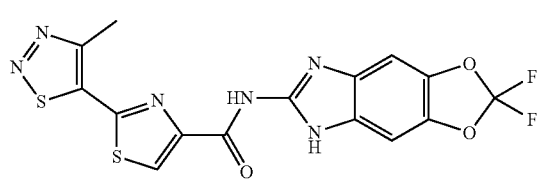

N-(2,2-difluoro-5H-[1,3]dioxolo[4',5':4,5]benzo[1,2-d]imidazol-6-yl)-2-(4-methyl-1,2,3-thiadiazol-5-yl)thiazole-4-carboxamide,

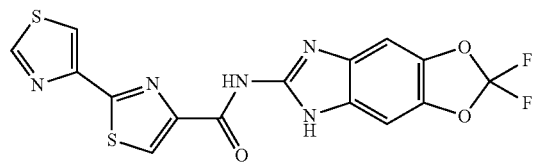

N-(2,2-difluoro-5H-[1,3]dioxolo[4',5':4,5]benzo[1,2-d]imidazol-6-yl)-[2,4'-bithiazole]-4-carboxamide,

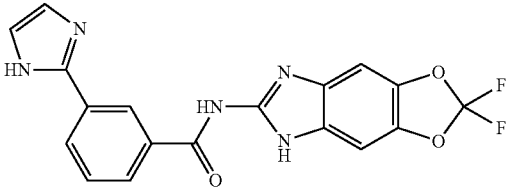

N-(2,2-difluoro-5H-[1,3]dioxolo[4',5':4,5]benzo[1,2-d]imidazol-6-yl)-3-(1H-imidazol-2-yl)benzamide,

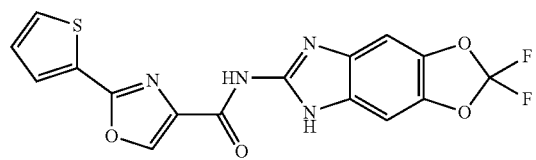

N-(2,2-difluoro-5H-[1,3]dioxolo[4',5':4,5]benzo[1,2-d]imidazol-6-yl)-2-(thiophen-2-yl)oxazole-4-carboxamide,

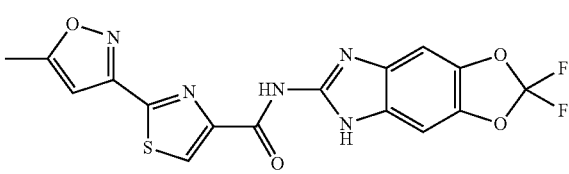

N-(2,2-difluoro-5H-[1,3]dioxolo[4',5':4,5]benzo[1,2-d]imidazol-6-yl)-2-(5-methylisoxazol-3-yl)thiazole-4-carboxamide,

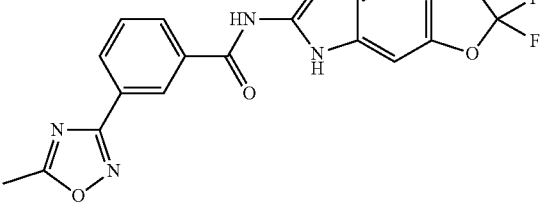

N-(2,2-difluoro-5H-[1,3]dioxolo[4',5':4,5]benzo[1,2-d]imidazol-6-yl)-3-(5-methyl-1,2,4-oxadiazol-3-yl)benzamide,

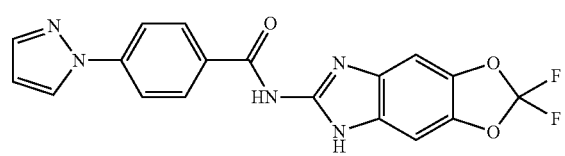 [SMILES: O=C(Nc1nc2cc3c(cc2[nH]1)OC(F)(F)O3)c1ccc(-n2cccn2)cc1]

N-(2,2-difluoro-5H-[1,3]dioxolo[4',5':4,5]benzo[1,2-d]imidazol-6-yl)-4-(1H-pyrazol-1-yl)benzamide,

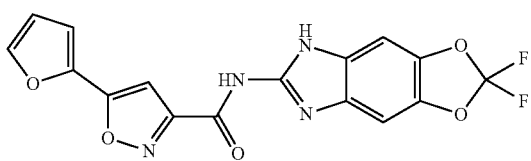

N-(2,2-difluoro-5H-[1,3]dioxolo[4',5':4,5]benzo[1,2-d]imidazol-6-yl)-5-(furan-2-yl)isoxazole-3-carboxamide,

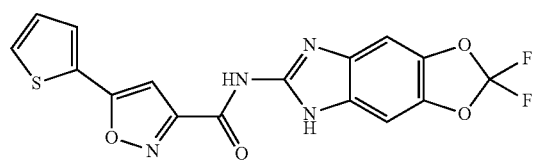

N-(2,2-difluoro-5H-[1,3]dioxolo[4',5':4,5]benzo[1,2-d]imidazol-6-yl)-5-(thiophen-2-yl)isoxazole-3-carboxamide,

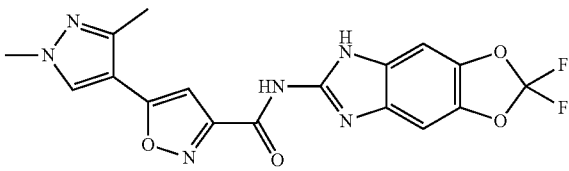

N-(2,2-difluoro-5H-[1,3]dioxolo[4',5':4,5]benzo[1,2-d]imidazol-6-yl)-5-(1,3-dimethyl-1H-pyrazol-4-yl)isoxazole-3-carboxamide,

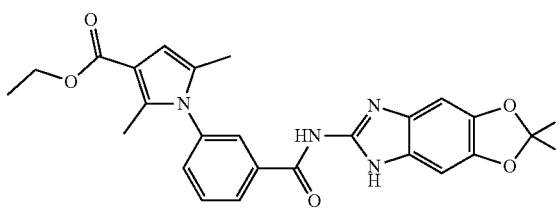

ethyl 1-(3-((2,2-difluoro-5H-[1,3]dioxolo[4',5':4,5]benzo[1,2-d]imidazol-6-yl)carbamoyl)phenyl)-2,5-dimethyl-1H-pyrrole-3-carboxylate,

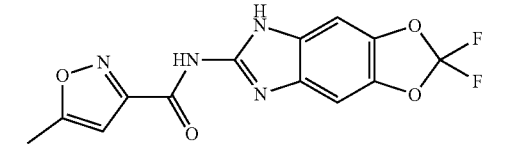

N-(2,2-difluoro-5H-[1,3]dioxolo[4',5':4,5]benzo[1,2-d]imidazol-6-yl)-5-methylisoxazole-3-carboxamide,

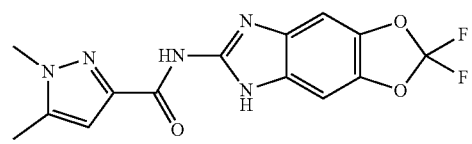

N-(2,2-difluoro-5H-[1,3]dioxolo[4′,5′:4,5]benzo[1,2-d]imidazol-6-yl)-1,5-dimethyl-1H-pyrazole-3-carboxamide,

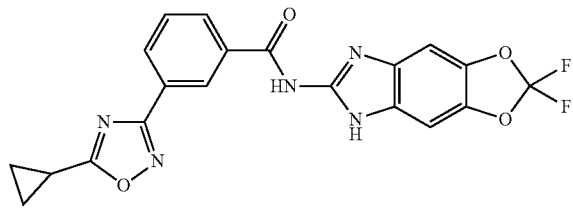

3-(5-cyclopropyl-1,2,4-oxadiazol-3-yl)-N-(2,2-difluoro-5H-[1,3]dioxolo[4′,5′:4,5]benzo[1,2-d]imidazol-6-yl)benzamide,

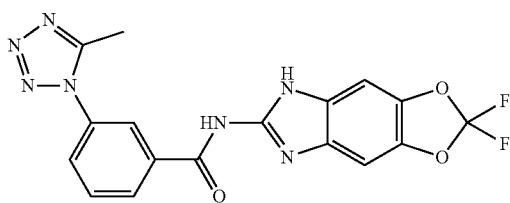

N-(2,2-difluoro-5H-[1,3]dioxolo[4′,5′:4,5]benzo[1,2-d]imidazol-6-yl)-3-(5-methyl-1H-tetrazol-1-yl)benzamide,

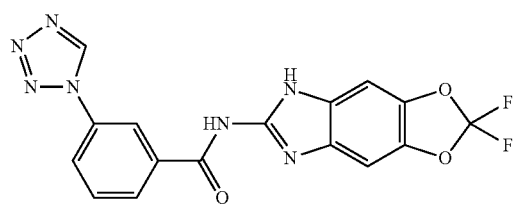

N-(2,2-difluoro-5H-[1,3]dioxolo[4′,5′:4,5]benzo[1,2-d]imidazol-6-yl)-3-(1H-tetrazol-1-yl)benzamide,

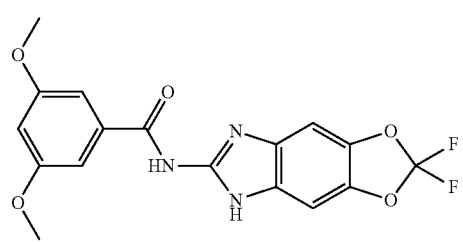 [SMILES: COc1cc(OC)cc(C(=O)Nc2nc3cc4c(cc3[nH]2)OC(F)(F)O4)c1]

N-(2,2-difluoro-5H-[1,3]dioxolo[4′,5′:4,5]benzo[1,2-d]imidazol-6-yl)-3,5-dimethoxybenzamide,

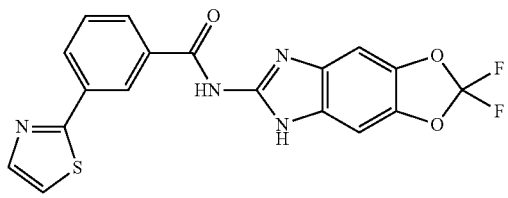

N-(2,2-difluoro-5H-[1,3]dioxolo[4′,5′:4,5]benzo[1,2-d]imidazol-6-yl)-3-(thiazol-2-yl)benzamide,

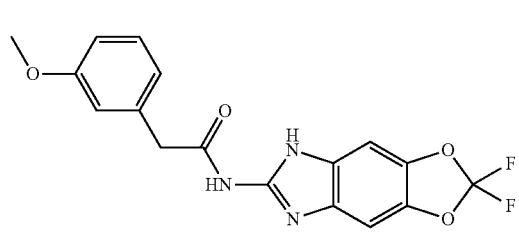 [SMILES: COc1cccc(CC(=O)Nc2nc3cc4c(cc3[nH]2)OC(F)(F)O4)c1]

N-(2,2-difluoro-5H-[1,3]dioxolo[4′,5′:4,5]benzo[1,2-d]imidazol-6-yl)-2-(3-methoxyphenyl)acetamide),

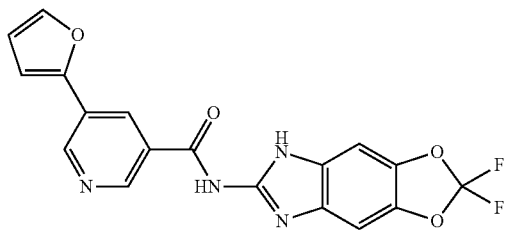

N-(2,2-difluoro-5H-[1,3]dioxolo[4′,5′:4,5]benzo[1,2-d]imidazol-6-yl)-5-(furan-2-yl)nicotinamide,

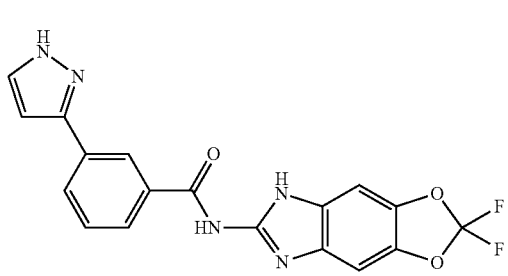 [SMILES: O=C(Nc1nc2cc3c(cc2[nH]1)OC(F)(F)O3)c1cccc(-c2cc[nH]n2)c1]

N-(2,2-difluoro-5H-[1,3]dioxolo[4′,5′:4,5]benzo[1,2-d]imidazol-6-yl)-3-(1H-pyrazol-3-yl)benzamide,

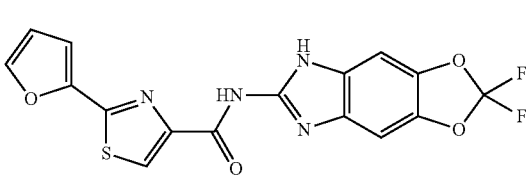

N-(2,2-difluoro-5H-[1,3]dioxolo[4′,5′:4,5]benzo[1,2-d]imidazol-6-yl)-2-(furan-2-yl)thiazole-4-carboxamide,

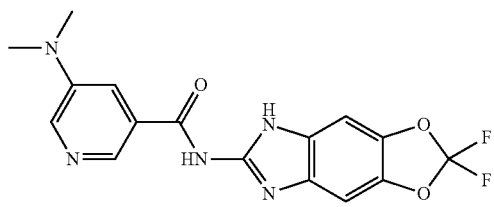 [SMILES: CN(C)c1cncc(C(=O)Nc2nc3cc4c(cc3[nH]2)OC(F)(F)O4)c1]

N-(2,2-difluoro-5H-[1,3]dioxolo[4′,5′:4,5]benzo[1,2-d]imidazol-6-yl)-5-(dimethylamino)nicotinamide,

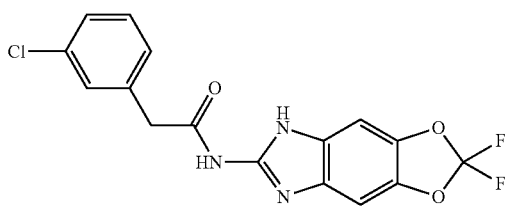

2-(3-chlorophenyl)-N-(2,2-difluoro-5H-[1,3]dioxolo[4′,5′:4,5]benzo[1,2-d]imidazol-6-yl)acetamide,

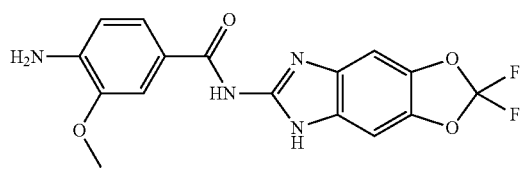 [SMILES: COc1cc(C(=O)Nc2nc3cc4c(cc3[nH]2)OC(F)(F)O4)ccc1N]

4-amino-N-(2,2-difluoro-5H-[1,3]dioxolo[4′,5′:4,5]benzo[1,2-d]imidazol-6-yl)-3-methoxybenzamide,

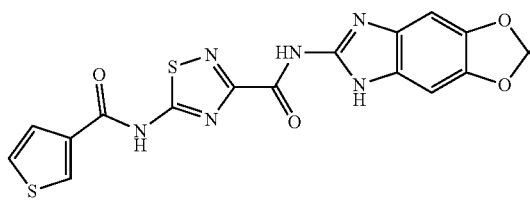

N-(2,2-difluoro-5H-[1,3]dioxolo[4′,5′:4,5]benzo[1,2-d]imidazol-6-yl)-5-(thiophene-3-carboxamido)-1,2,4-thiadiazole-3-carboxamide,

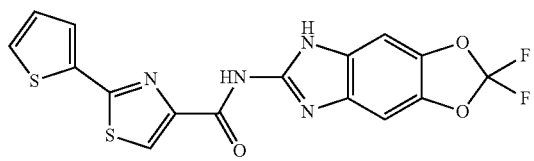

N-(2,2-difluoro-5H-[1,3]dioxolo[4′,5′:4,5]benzo[1,2-d]imidazol-6-yl)-2-(thiophen-2-yl)thiazole-4-carboxamide,

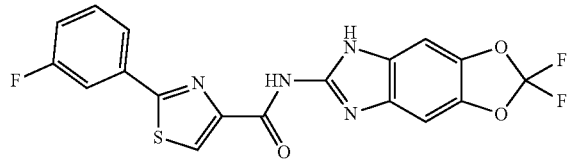

N-(2,2-difluoro-5H-[1,3]dioxolo[4′,5′:4,5]benzo[1,2-d]imidazol-6-yl)-2-(3-fluorophenyl)thiazole-4-carboxamide,

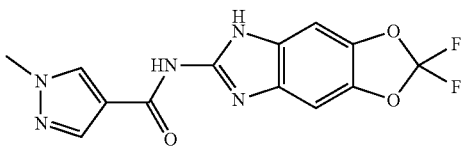

N-(2,2-difluoro-5H-[1,3]dioxolo[4′,5′:4,5]benzo[1,2-d]imidazol-6-yl)-1-methyl-1H-pyrazole-4-carboxamide,

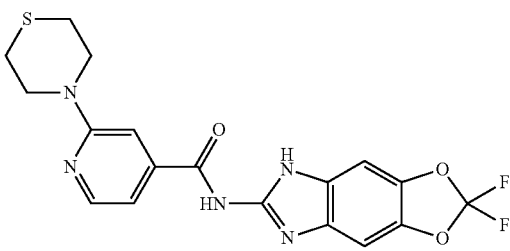

N-(2,2-difluoro-5H-[1,3]dioxolo[4′,5′:4,5]benzo[1,2-d]imidazol-6-yl)-2-thiomorpholinoisonicotinamide,

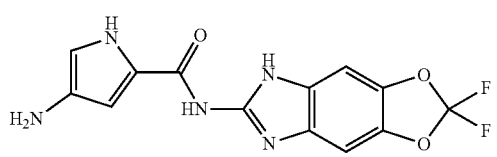

4-amino-N-(2,2-difluoro-5H-[1,3]dioxolo[4′,5′:4,5]benzo[1,2-d]imidazol-6-yl)-1H-pyrrole-2-carboxamide,

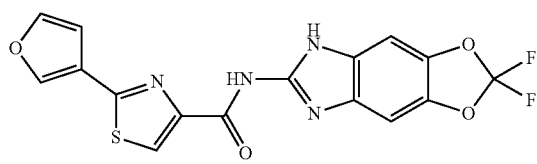

N-(2,2-difluoro-5H-[1,3]dioxolo[4′,5′:4,5]benzo[1,2-d]imidazol-6-yl)-2-(furan-3-yl)thiazole-4-carboxamide,

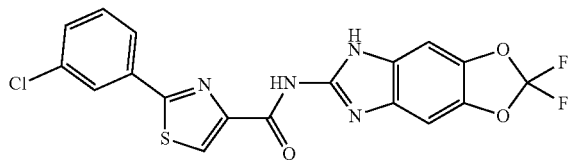

2-(3-chlorophenyl)-N-(2,2-difluoro-5H-[1,3]dioxolo[4′,5′:4,5]benzo[1,2-d]imidazol-6-yl)thiazole-4-carboxamide, -continued

18B

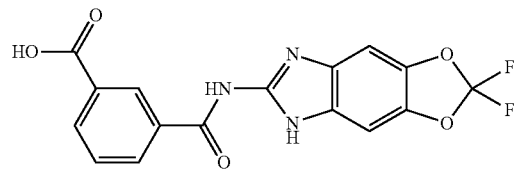 [SMILES: O=C(O)c1cccc(C(=O)Nc2nc3cc4c(cc3[nH]2)OC(F)(F)O4)c1]

3-((2,2-difluoro-5H-[1,3]dioxolo[4',5':4,5]benzo[1,2-d]imidazol-6-yl)carbamoyl)benzoic acid,

19B

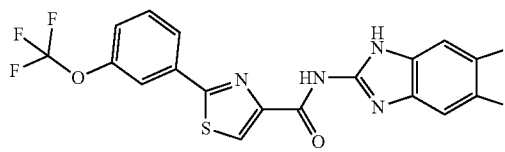

N-(2,2-difluoro-5H-[1,3]dioxolo[4',5':4,5]benzo[1,2-d]imidazol-6-yl)-2-(3-(trifluoromethoxy)phenyl)thiazole-4-carboxamide,

20B

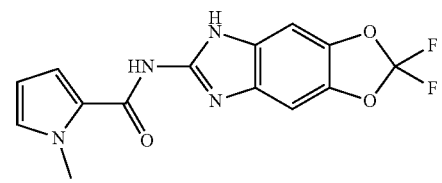

N-(2,2-difluoro-5H-[1,3]dioxolo[4',5':4,5]benzo[1,2-d]imidazol-6-yl)-1-methyl-1H-pyrrole-2-carboxamide,

21B

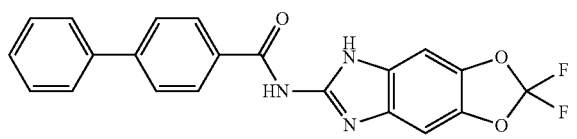 [SMILES: O=C(Nc1nc2cc3c(cc2[nH]1)OC(F)(F)O3)c1ccc(-c2ccccc2)cc1]

N-(2,2-difluoro-5H-[1,3]dioxolo[4',5':4,5]benzo[1,2-d]imidazol-6-yl)-[1,1'-biphenyl]-4-carboxamide,

22B

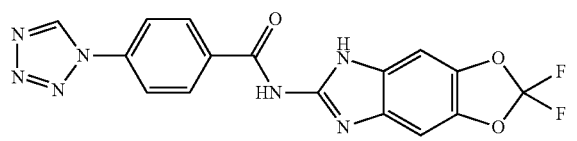

N-(2,2-difluoro-5H-[1,3]dioxolo[4',5':4,5]benzo[1,2-d]imidazol-6-yl)-4-(1H-tetrazol-1-yl)benzamide, -continued

23B

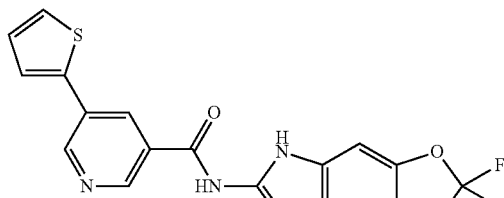

N-(2,2-difluoro-5H-[1,3]dioxolo[4',5':4,5]benzo[1,2-d]imidazol-6-yl)-5-(thiophen-2-yl)nicotinamide,

24B

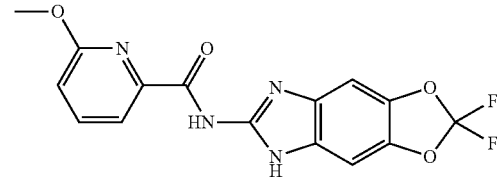 [SMILES: COc1cccc(C(=O)Nc2nc3cc4c(cc3[nH]2)OC(F)(F)O4)n1]

N-(2,2-difluoro-5H-[1,3]dioxolo[4',5':4,5]benzo[1,2-d]imidazol-6-yl)-6-methoxypicolinamide,

25B

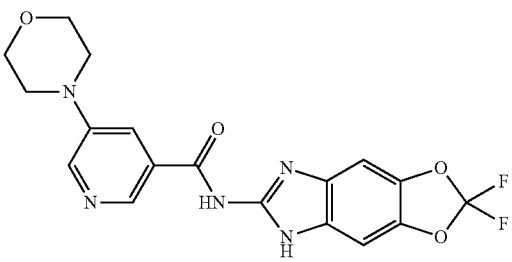 [SMILES: O=C(Nc1nc2cc3c(cc2[nH]1)OC(F)(F)O3)c1cncc(N2CCOCC2)c1]

N-(2,2-difluoro-5H-[1,3]dioxolo[4',5':4,5]benzo[1,2-d]imidazol-6-yl)-5-morpholinonicotinamide, or

26B

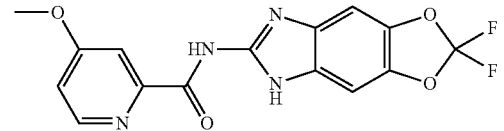 [SMILES: COc1ccnc(C(=O)Nc2nc3cc4c(cc3[nH]2)OC(F)(F)O4)c1]

N-(2,2-difluoro-5H-[1,3]dioxolo[4',5':4,5]benzo[1,2-d]imidazol-6-yl)-4-methoxypicolinamide, or a physiologically acceptable prodrug, solvate or salt thereof.

7. The compound according to claim 1, wherein said compound is selected from the following compounds:

| No. | Structure |
|---|---|
| 1 | <br>N-(2,2-difluoro-5H-[1,3]dioxolo[4',5':4,5]benzo[1,2-d]imidazol-6-yl)-2-(2-(trifluoromethoxy)benzamido)thiazole-4-carboxamide, |

-continued

| No. | Structure |
|---|---|
| 2 | N-(2,2-difluoro-5H-[1,3]dioxolo[4',5':4,5]benzo[1,2-d]imidazol-6-yl)-1-(4-fluorophenyl)-5-methyl-1H-pyrazole-4-carboxamide, |
| 3 | N-(2,2-difluoro-5H-[1,3]dioxolo[4',5':4,5]benzo[1,2-d]imidazol-6-yl)-2-(2,3-dihydrobenzofuran-5-yl)thiazole-4-carboxamide, |
| 11 | N-(2,2-difluoro-5H-[1,3]dioxolo[4',5':4,5]benzo[1,2-d]imidazol-6-yl)-2-(furan-2-carboxamido)thiazole-4-carboxamide, |
| 17 | N-(2,2-difluoro-5H-[1,3]dioxolo[4',5':4,5]benzo[1,2-d]imidazol-6-yl)-5-(2-(trifluoromethoxy)benzamido)-1,2,4-thiadiazole-3-carboxamide, |
| 18 | N-(2,2-difluoro-5H-[1,3]dioxolo[4',5':4,5]benzo[1,2-d]imidazol-6-yl)isonicotinamide, |
| 19 | N-(2,2-difluoro-5H-[1,3]dioxolo[4',5':4,5]benzo[1,2-d]imidazol-6-yl)-2-(2,5-dimethoxyphenylsulfonamido)thiazole-4-carboxamide, |

| No. | Structure |
|---|---|
| 20 | 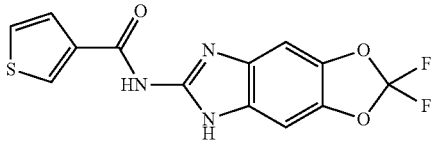 [SMILES: O=C(Nc1nc2cc3c(cc2[nH]1)OC(F)(F)O3)c1ccsc1]<br>N-(2,2-difluoro-5H-[1,3]dioxolo[4',5':4,5]benzo[1,2-d]imidazol-6-yl)thiophene-3-carboxamide, |
| 21 | 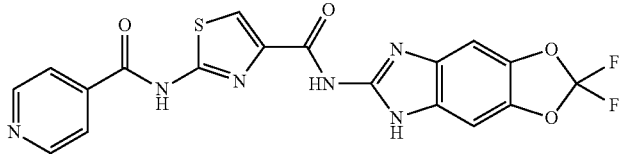 [SMILES: O=C(Nc1nc(C(=O)Nc2nc3cc4c(cc3[nH]2)OC(F)(F)O4)cs1)c1ccncc1]<br>N-(2,2-difluoro-5H-[1,3]dioxolo[4',5':4,5]benzo[1,2-d]imidazol-6-yl)-2-(isonicotinamido)thiazole-4-carboxamide, |
| 26 | 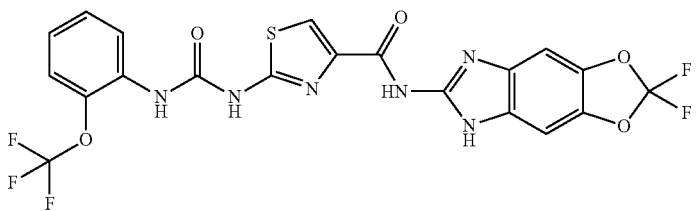 [SMILES: O=C(Nc1nc(C(=O)Nc2nc3cc4c(cc3[nH]2)OC(F)(F)O4)cs1)Nc1ccccc1OC(F)(F)F]<br>N-(2,2-difluoro-5H-[1,3]dioxolo[4',5':4,5]benzo[1,2-d]imidazol-6-yl)-2-(3-(2-(trifluoromethoxy)phenyl)ureido)thiazole-4-carboxamide, |
| 29 | 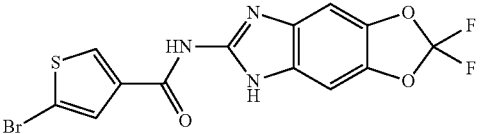 [SMILES: O=C(Nc1nc2cc3c(cc2[nH]1)OC(F)(F)O3)c1csc(Br)c1]<br>5-bromo-N-(2,2-difluoro-5H-[1,3]dioxolo[4',5':4,5]benzo[1,2-d]imidazol-6-yl)thiophene-3-carboxamide, |
| 30 | 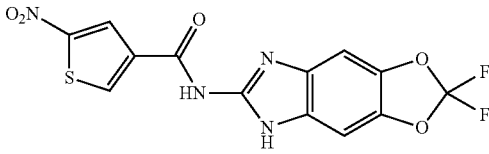 [SMILES: O=C(Nc1nc2cc3c(cc2[nH]1)OC(F)(F)O3)c1csc([N+](=O)[O-])c1]<br>N-(2,2-difluoro-5H-[1,3]dioxolo[4',5':4,5]benzo[1,2-d]imidazol-6-yl)-5-nitrothiophene-3-carboxamide, |
| 31 | 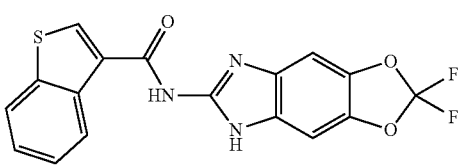 [SMILES: O=C(Nc1nc2cc3c(cc2[nH]1)OC(F)(F)O3)c1csc2ccccc12]<br>N-(2,2-difluoro-5H-[1,3]dioxolo[4',5':4,5]benzo[1,2-d]imidazol-6-yl)benzo[b]thiophene-3-carboxamide, |

| No. | Structure |
|---|---|
| 33 | 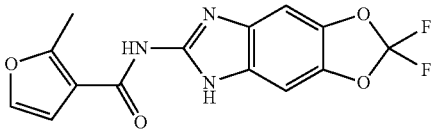 [SMILES: Cc1occc1C(=O)Nc1nc2cc3c(cc2[nH]1)OC(F)(F)O3]<br>N-(2,2-difluoro-5H-[1,3]dioxolo[4',5':4,5]benzo[1,2-d]imidazol-6-yl)-2-methylfuran-3-carboxamide, |
| 37 | 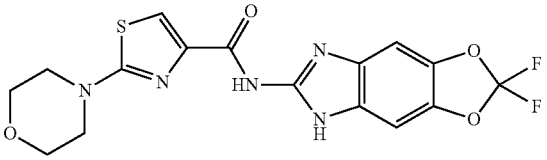 [SMILES: O=C(Nc1nc2cc3c(cc2[nH]1)OC(F)(F)O3)c1csc(N2CCOCC2)n1]<br>N-(2,2-difluoro-5H-[1,3]dioxolo[4',5':4,5]benzo[1,2-d]imidazol-6-yl)-2-morpholinothiazole-4-carboxamide, |
| 38 | 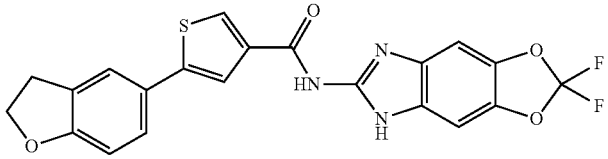 [SMILES: O=C(Nc1nc2cc3c(cc2[nH]1)OC(F)(F)O3)c1csc(-c2ccc3c(c2)CCO3)c1]<br>N-(2,2-difluoro-5H-[1,3]dioxolo[4',5':4,5]benzo[1,2-d]imidazol-6-yl)-5-(2,3-dihydrobenzofuran-5-yl)thiophene-3-carboxamide, |
| 41 | 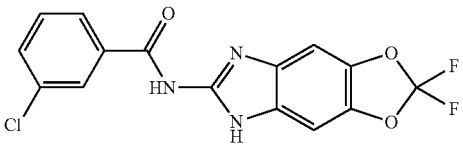 [SMILES: O=C(Nc1nc2cc3c(cc2[nH]1)OC(F)(F)O3)c1cccc(Cl)c1]<br>3-chloro-N-(2,2-difluoro-5H-[1,3]dioxolo[4',5':4,5]benzo[1,2-d]imidazol-6-yl)benzamide, |
| 48 | 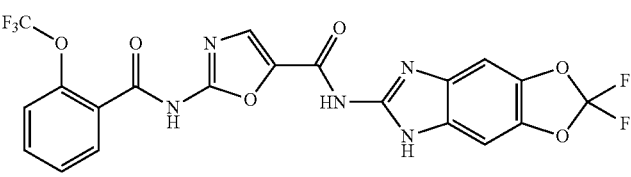 [SMILES: O=C(Nc1nc2cc3c(cc2[nH]1)OC(F)(F)O3)c1cnc(NC(=O)c2ccccc2OC(F)(F)F)o1]<br>N-(2,2-difluoro-5H-[1,3]dioxolo[4',5':4,5]benzo[1,2-d]imidazol-6-yl)-2-(2-(trifluoromethoxy)benzamido)oxazole-5-carboxamide, |
| 49 | 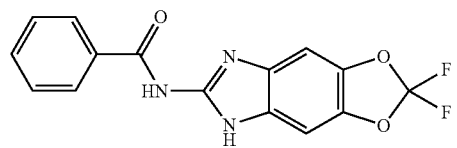 [SMILES: O=C(Nc1nc2cc3c(cc2[nH]1)OC(F)(F)O3)c1ccccc1]<br>N-(2,2-difluoro-5H-[1,3]dioxolo[4',5':4,5]benzo[1,2-d]imidazol-6-yl)benzamide, |

-continued

| No. | Structure |
|---|---|
| 51 | 3-(2,4-dichlorobenzamido)-N-(2,2-difluoro-5H-[1,3]dioxolo[4',5':4,5]benzo[1,2-d]imidazol-6-yl)-1H-1,2,4-triazole-5-carboxamide, |
| 52 | N-(2,2-difluoro-5H-[1,3]dioxolo[4',5':4,5]benzo[1,2-d]imidazol-6-yl)-3-(2-(trifluoromethoxy)benzamido)-1H-1,2,4-triazole-5-carboxamide, |
| 56 | N-(2,2-difluoro-5H-[1,3]dioxolo[4',5':4,5]benzo[1,2-d]imidazol-6-yl)-3-methoxybenzamide, |
| 57 | 5-(3-chlorobenzamido)-N-(2,2-difluoro-5H[1,3]dioxolo[4',5':4,5]benzo[1,2-d]imidazol-6-yl)-1,2,4-thiadiazole-3-carboxamide, |
| 60 | 4-amino-N-(2,2-difluoro-5H-[1,3]dioxolo[4',5':4,5]benzo[1,2-d]imidazol-6-yl)benzamide, |
| 62 | N-(2,2-difluoro-5H-[1,3]dioxolo[4',5':4,5]benzo[1,2-d]imidazol-6-yl)-4-sulfamoylbenzamide, |

| No. | Structure |
|---|---|
| 65 | 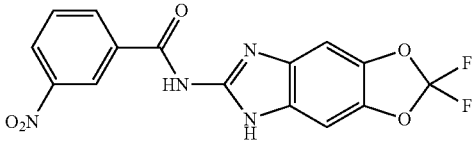 [SMILES: O=C(Nc1nc2cc3c(cc2[nH]1)OC(F)(F)O3)c1cccc([N+](=O)[O-])c1]
N-(2,2-difluoro-5H-[1,3]dioxolo[4',5':4,5]benzo[1,2-d]imidazol-6-yl)-3-nitrobenzamide, |
| 66 | 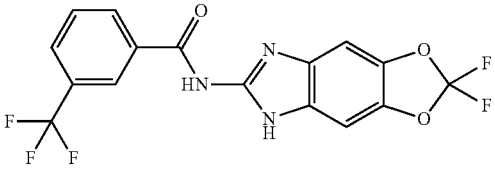 [SMILES: O=C(Nc1nc2cc3c(cc2[nH]1)OC(F)(F)O3)c1cccc(C(F)(F)F)c1]
N-(2,2-difluoro-5H-[1,3]dioxolo[4',5':4,5]benzo[1,2-d]imidazol-6-yl)-3-(trifluoromethyl)benzamide, |
| 69 | 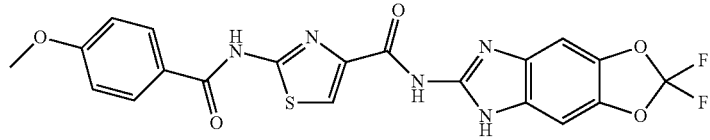 [SMILES: COc1ccc(C(=O)Nc2nc(C(=O)Nc3nc4cc5c(cc4[nH]3)OC(F)(F)O5)cs2)cc1]
N-(2,2-difluoro-5H-[1,3]dioxolo[4',5':4,5]benzo[1,2-d]imidazol-6-yl)-2-(4-methoxybenzamido)thiazole-4-carboxamide, |
| 70 | 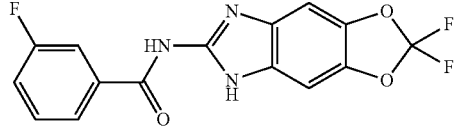 [SMILES: O=C(Nc1nc2cc3c(cc2[nH]1)OC(F)(F)O3)c1cccc(F)c1]
N-(2,2-difluoro-5H-[1,3]dioxolo[4',5':4,5]benzo[1,2-d]imidazol-6-yl)-3-fluorobenzamide, |
| 75 | 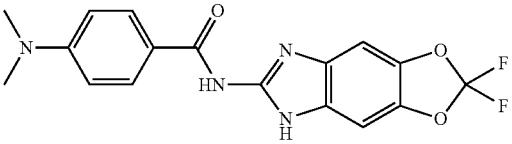 [SMILES: CN(C)c1ccc(C(=O)Nc2nc3cc4c(cc3[nH]2)OC(F)(F)O4)cc1]
N-(2,2-difluoro-5H-[1,3]dioxolo[4',5':4,5]benzo[1,2-d]imidazol-6-yl)-4-(dimethylamino)benzamide, |
| 76 | 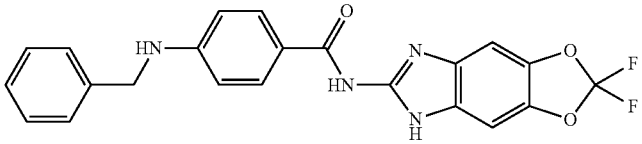 [SMILES: O=C(Nc1nc2cc3c(cc2[nH]1)OC(F)(F)O3)c1ccc(NCc2ccccc2)cc1]
4-(benzylamino)-N-(2,2-difluoro-5H-[1,3]dioxolo[4',5':4,5]benzo[1,2-d]imidazol-6-yl)benzamide, |
| 77 | 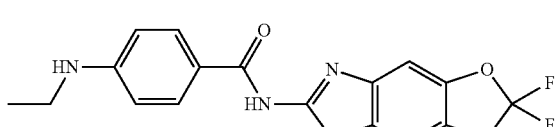
N-(2,2-difluoro-5H-[1,3]dioxolo[4',5':4,5]benzo[1,2-d]imidazol-6-yl)-4-(ethylamino)benzamide, |

| No. | Structure |
|-----|-----------|
| 78 | 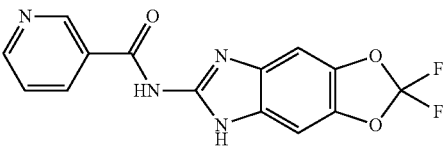 [SMILES: O=C(Nc1nc2cc3c(cc2[nH]1)OC(F)(F)O3)c1cccnc1]<br>N-(2,2-difluoro-5H-[1,3]dioxolo[4',5':4,5]benzo[1,2-d]imidazol-6-yl)nicotinamide, |
| 80 | 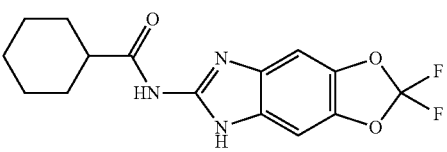 [SMILES: O=C(Nc1nc2cc3c(cc2[nH]1)OC(F)(F)O3)C1CCCCC1]<br>N-(2,2-difluoro-5H-[1,3]dioxolo[4',5':4,5]benzo[1,2-d]imidazol-6-yl)cyclohexanecarboxamide, |
| 81 | 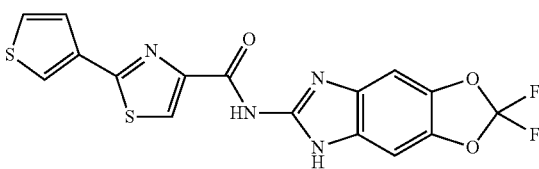 [SMILES: O=C(Nc1nc2cc3c(cc2[nH]1)OC(F)(F)O3)c1csc(-c2ccsc2)n1]<br>N-(2,2-difluoro-5H-[1,3]dioxolo[4',5':4,5]benzo[1,2-d]imidazol-6-yl)-2-(thiophen-3-yl)thiazole-4-carboxamide, |
| 82 | 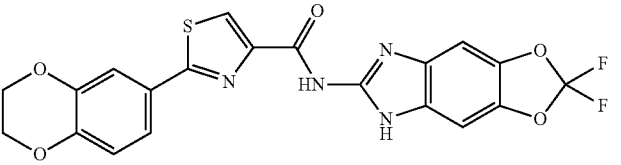 [SMILES: O=C(Nc1nc2cc3c(cc2[nH]1)OC(F)(F)O3)c1csc(-c2ccc3c(c2)OCCO3)n1]<br>N-(2,2-difluoro-5H-[1,3]dioxolo[4',5':4,5]benzo[1,2-d]imidazol-6-yl)-2-(2,3-dihydrobenzo[b][1,4]dioxin-6-yl)thiazole-4-carboxamide, |
| 83 | 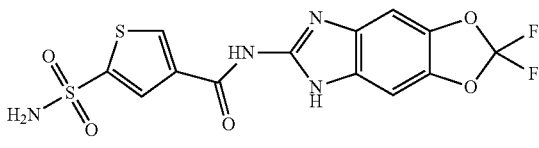 [SMILES: NS(=O)(=O)c1cc(C(=O)Nc2nc3cc4c(cc3[nH]2)OC(F)(F)O4)cs1]<br>N-(2,2-difluoro-5H-[1,3]dioxolo[4,'5':4,5]benzo[1,2-d]imidazol-6-yl)-5-sulfamoylthiophene-3-carboxamide, |
| 87 | 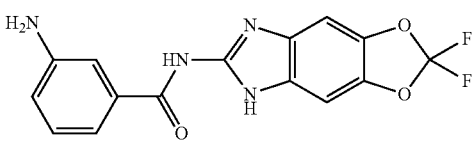 [SMILES: Nc1cccc(C(=O)Nc2nc3cc4c(cc3[nH]2)OC(F)(F)O4)c1]<br>3-amino-N-(2,2-difluoro-5H-[1,3]dioxolo[4',5':4,5]benzo[1,2-d]imidazol-6-yl)benzamide, |

| No. | Structure |
|---|---|
| 88 | N-(2,2-difluoro-5H-[1,3]dioxolo[4',5':4,5]benzo[1,2-d]imidazol-6-yl)-4-nitro-1H-pyrrole-2-carboxamide, |
| 91 | 5-(4-chlorobenzamido)-N-(2,2-difluoro-5H-[1,3]dioxolo[4',5':4,5]benzo[1,2-d]imidazol-6-yl)-1,2,4-thiadiazole-3-carboxamide, |
| 92 | N-(2,2-difluoro-5H-[1,3]dioxolo[4',5':4,5]benzo[1,2-d]imidazol-6-yl)-5-(4-fluorobenzamido)-1,2,4-thiadiazole-3-carboxamide, |
| 94 | $N^1$-(2,2-difluoro-5H[1,3]dioxolo[4',5':4,5]benzo[1,2-d]imidazol-6-yl)-2-fluoroterephthalamide, |
| 100 | N-(2,2-difluoro-5H-[1,3]dioxolo[4',5':4,5]benzo[1,2-d]imidazol-6-yl)-3-sulfamoylbenzamide, |
| 101 | N-(2,2-difluoro-5H-[1,3]dioxolo[4',5':4,5]benzo[1,2-d]imidazol-6-yl)-4-sulfamoyl-1H-pyrrole-2-carboxamide, |

-continued

| No. | Structure |
|---|---|
| 102 | 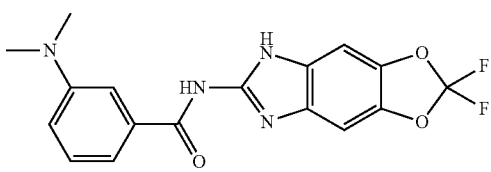<br>N-(2,2-difluoro-5H-[1,3]dioxolo<br>[4',5':4,5]benzo[1,2-d]imidazol-6-yl)-3-<br>(dimethylamino)benzamide, |
| 104 | 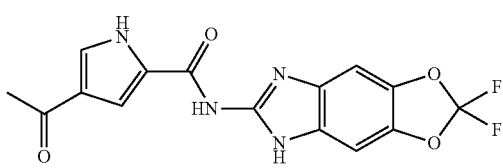 [SMILES: CC(=O)c1c[nH]c(C(=O)Nc2nc3cc4c(cc3[nH]2)OC(F)(F)O4)c1]<br>4-acetyl-N-(2,2-difluoro-5H-[1,3]dioxolo<br>[4',5':4,5]benzo[1,2-d]imidazol-6-yl)-<br>1H-pyrrole-2-carboxamide, |
| 105 | 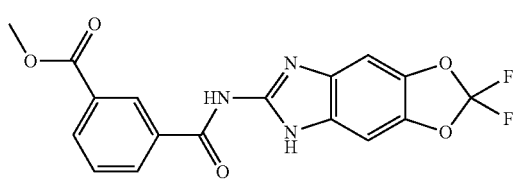 [SMILES: COC(=O)c1cccc(C(=O)Nc2nc3cc4c(cc3[nH]2)OC(F)(F)O4)c1]<br>methyl 3-((2,2-difluoro-5H-<br>[1,3]dioxolo[4',5':4,5]benzo[1,2-<br>d]imidazol-6-yl)carbamoyl)benzoate, |
| 108 | 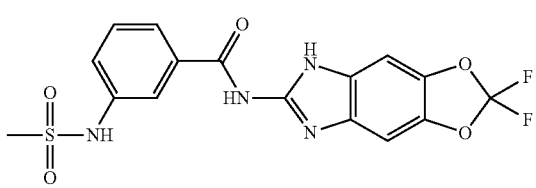 [SMILES: CS(=O)(=O)Nc1cccc(C(=O)Nc2nc3cc4c(cc3[nH]2)OC(F)(F)O4)c1]<br>N-(2,2-difluoro-5H-[1,3]dioxolo[4',5':4,5]<br>benzo[1,2-d]imidazol-6-yl)-3-<br>(methylsulfonamido)benzamide, |
| 111 | 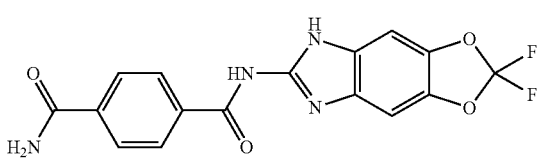<br>N$^1$-(2,2-difluoro-5H-[1,3]dioxolo[4',5':4,5]<br>benzo[1,2-d]imidazol-6-yl)terephthalamide, |
| 112 | 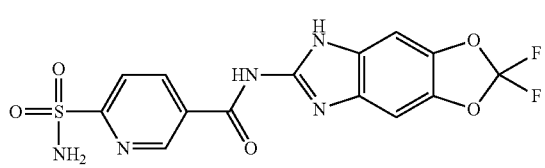 [SMILES: NS(=O)(=O)c1ccc(C(=O)Nc2nc3cc4c(cc3[nH]2)OC(F)(F)O4)cn1]<br>N-(2,2-difluoro-5H-<br>[1,3]dioxolo[4',5':4,5]benzo[1,2-d]imidazol-6-yl)-<br>6-sulfamoylnicotinamide, |

-continued

| No. | Structure |
|-----|-----------|
| 113 | 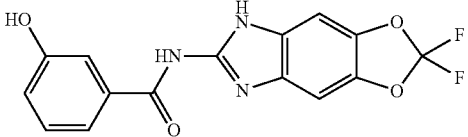 [SMILES: O=C(Nc1nc2cc3c(cc2[nH]1)OC(F)(F)O3)c1cccc(O)c1]<br>N-(2,2-difluoro-5H-[1,3]dioxolo[4',5':4,5]benzo[1,2-d]imidazol-6-yl)-3-hydroxybenzamide, |
| 114 | 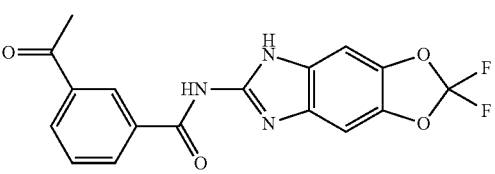<br>3-acetyl-N-(2,2-difluoro-5H-[1,3]dioxolo[4',5':4,5]benzo[1,2-d]imidazol-6-yl)benzamide, |
| 116 | 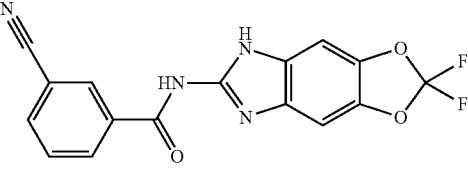 [SMILES: N#Cc1cccc(C(=O)Nc2nc3cc4c(cc3[nH]2)OC(F)(F)O4)c1]<br>3-cyano-N-(2,2-difluoro-5H-[1,3]dioxolo[4',5':4,5]benzo[1,2-d]imidazol-6-yl)benzamide, |
| 117 | 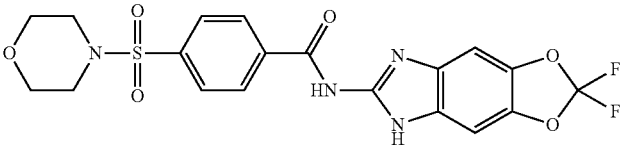 [SMILES: O=C(Nc1nc2cc3c(cc2[nH]1)OC(F)(F)O3)c1ccc(S(=O)(=O)N2CCOCC2)cc1]<br>N-(2,2-difluoro-5H-[1,3]dioxolo[4',5':4,5]benzo[1,2-d]imidazol-6-yl)-4-(morpholinosulfonyl)benzamide, |
| 118 | 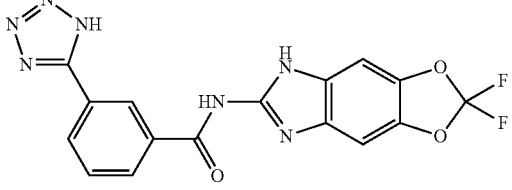<br>N-(2,2-difluoro-5H-[1,3]dioxolo[4',5':4,5]benzo[1,2-d]imidazol-6-yl)-3-(1H-tetrazol-5-yl)benzamide, |
| 121 | 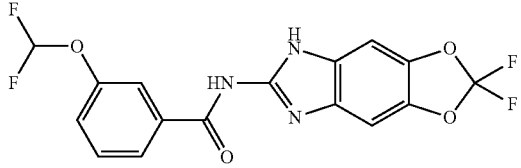 [SMILES: O=C(Nc1nc2cc3c(cc2[nH]1)OC(F)(F)O3)c1cccc(OC(F)F)c1]<br>N-(2,2-difluoro-5H-[1,3]dioxolo[4',5':4,5]benzo[1,2-d]imidazol-6-yl)-3-(difluoromethoxy)benzamide, |

-continued

| No. | Structure |
|---|---|
| 122 | N-(2,2-difluoro-5H-[1,3]dioxolo[4',5':4,5]benzo[1,2-d]imidazol-6-yl)-3-(pyrrolidin-1-yl)benzamide, |
| 123 | N-(2,2-difluoro-5H-[1,3]dioxolo[4',5':4,5]benzo[1,2-d]imidazol-6-yl)-5-methoxynicotinamide, |
| 124 | N-(2,2-difluoro-5H-[1,3]dioxolo[4',5':4,5]benzo[1,2-d]imidazol-6-yl)-2-methoxyisonicotinamide, |
| 125 | N-(2,2-difluoro-5H-[1,3]dioxolo[4',5':4,5]benzo[1,2-d]imidazol-6-yl)-2-(dimethylamino)isonicotinamide, |
| 126 | 4-amino-N-(2,2-difluoro-5H-[1,3]dioxolo[4',5':4,5]benzo[1,2-d]imidazol-6-yl)-3-(trifluoromethyl)benzamide, |
| 128 | N-(2,2-difluoro-5H-[1,3]dioxolo[4',5':4,5]benzo[1,2-d]imidazol-6-yl)-3-(piperidin-1-yl)benzamide, |

| No. | Structure |
|---|---|
| 130 | 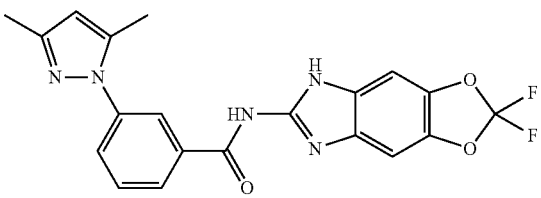 [SMILES: Cc1cc(C)n(-c2cccc(C(=O)Nc3nc4cc5c(cc4[nH]3)OC(F)(F)O5)c2)n1]<br>N-(2,2-difluoro-5H-[1,3]dioxolo[4',5':4,5]benzo[1,2-d]imidazol-6-yl)-3-(3,5-dimethyl-1H-pyrazol-1-yl)benzamide, |
| 131 | 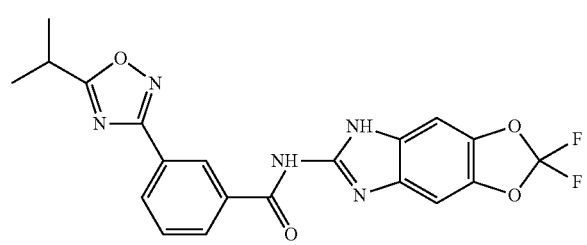 [SMILES: CC(C)c1nc(-c2cccc(C(=O)Nc3nc4cc5c(cc4[nH]3)OC(F)(F)O5)c2)no1]<br>N-(2,2-difluoro-5H-[1,3]dioxolo[4',5':4,5]benzo[1,2-d]imidazol-6-yl)-3-(5-isopropyl-1,2,4-oxadiazol-3-yl)benzamide, |
| 132 | 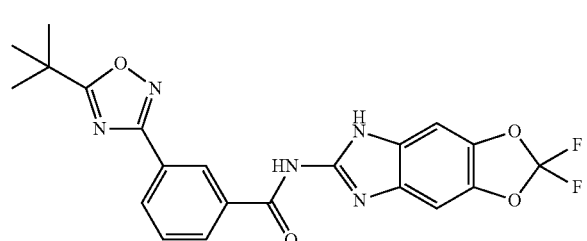<br>3-(5-(tert-butyl)-1,2,4-oxadiazol-3-yl)-N-(2,2-difluoro-5H-[1,3]dioxolo[4',5':4,5]benzo[1,2-d]imidazol-6-yl)benzamide, |
| 133 | 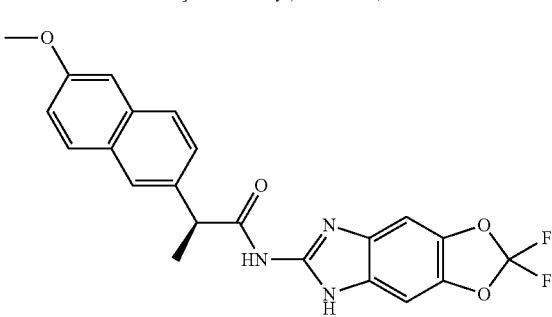<br>(S)-N-(2,2-difluoro-5H-[1,3]dioxolo[4',5':4,5]benzo[1,2-d]imidazol-6-yl)-2-(6-methoxynaphthalen-2-yl)propanamide, |
| 134 | 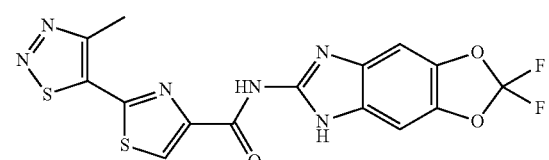<br>N-(2,2-difluoro-5H-[1,3]dioxolo[4',5':4,5]benzo[1,2-d]imidazol-6-yl)-2-(4-methyl-1,2,3-thiadiazol-5-yl)thiazole-4-carboxamide, |

-continued

| No. | Structure |
|---|---|
| 139 | 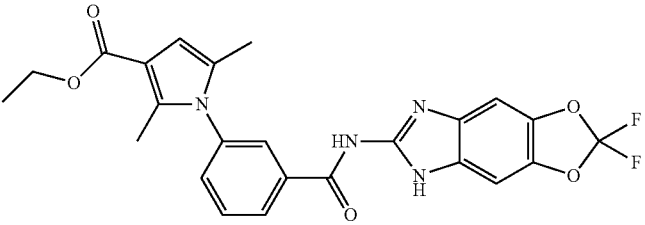 [SMILES: CCOC(=O)c1cc(C)n(-c2cccc(C(=O)Nc3nc4cc5c(cc4[nH]3)OC(F)(F)O5)c2)c1C]<br>ethyl 1-(3((2,2-difluoro-5H-[1,3]dioxolo[4',5':4,5]benzo[1,2-d]imidazol-6-yl)carbamoyl)phenyl)-2,5-dimethyl-1H-pyrrole-3-carboxylate, |
| 140 | 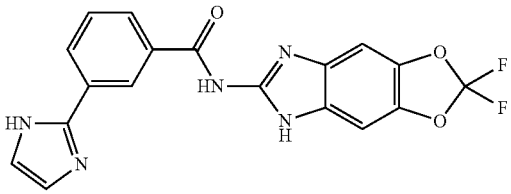 [SMILES: O=C(Nc1nc2cc3c(cc2[nH]1)OC(F)(F)O3)c1cccc(-c2ncc[nH]2)c1]<br>N-(2,2-difluoro-5H-[1,3]dioxolo[4',5':4,5]benzo[1,2-d]imidazol-6-yl)-3-(1H-imidazol-2-yl)benzamide, |
| 141 | 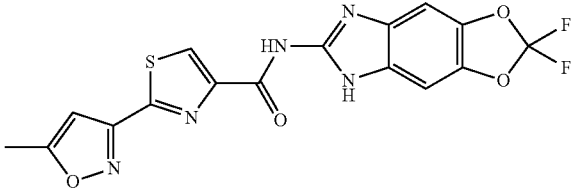 [SMILES: Cc1cc(-c2nc(C(=O)Nc3nc4cc5c(cc4[nH]3)OC(F)(F)O5)cs2)no1]<br>N-(2,2-difluoro-5H-[1,3]dioxolo[4',5':4,5]benzo[1,2-d]imidazol-6-yl)-2-(5-methylisoxazol-3-yl)thiazole-4-carboxamide, |
| 142 | 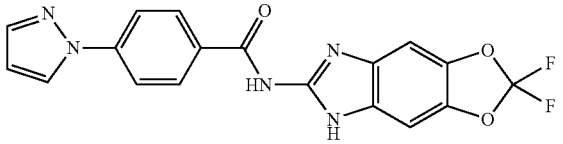 [SMILES: O=C(Nc1nc2cc3c(cc2[nH]1)OC(F)(F)O3)c1ccc(-n2cccn2)cc1]<br>N-(2,2-difluoro-5H-[1,3]dioxolo[4',5':4,5]benzo[1,2--d]imidazol-6-yl)-4-(1H-pyrazol-1-yl)benzamide, |
| 144 | 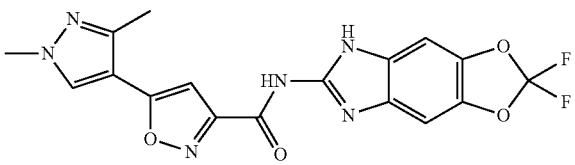 [SMILES: Cc1nn(C)cc1-c1cc(C(=O)Nc2nc3cc4c(cc3[nH]2)OC(F)(F)O4)no1]<br>N-(2,2-difluoro-5H-[1,3]dioxolo[4',5':4,5]benzo[1,2-d]imidazol-6-yl)-5-(1,3-dimethyl-1H-pyrazol-4-yl)isoxazole-3-carboxamide, |

| No. | Structure |
|-----|-----------|
| 147 | 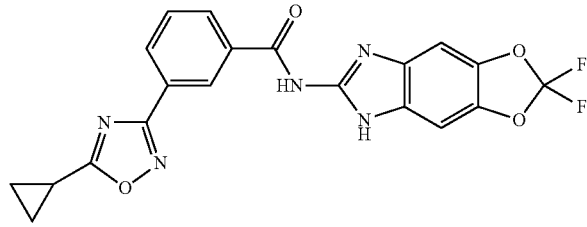 [SMILES: O=C(Nc1nc2cc3c(cc2[nH]1)OC(F)(F)O3)c1cccc(-c2noc(C3CC3)n2)c1]<br>3-(5-cyclopropyl-1,2,4-oxadiazol-3-yl)-N-(2,2-difluoro-5H-[1,3]dioxolo[4',5':4,5]benzo[1,2-d]imidazol-6-yl)benzamide, |
| 148 | 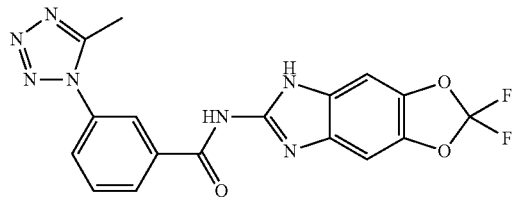 [SMILES: Cc1nnnn1-c1cccc(C(=O)Nc2nc3cc4c(cc3[nH]2)OC(F)(F)O4)c1]<br>N-(2,2-difluoro-5H-[1,3]dioxolo[4',5':4,5]benzo[1,2-d]imidazol-6-yl)-3-(5-methyl-1H-tetrazol-1-yl)benzamide, |
| 149 | 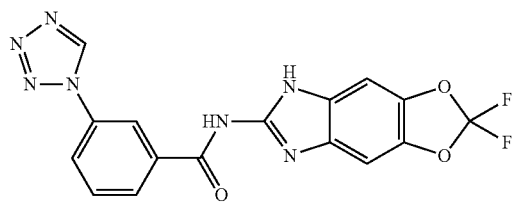 [SMILES: O=C(Nc1nc2cc3c(cc2[nH]1)OC(F)(F)O3)c1cccc(-n2cnnn2)c1]<br>N-(2,2-difluoro-5H-[1,3]dioxolo[4',5':4,5]benzo[1,2-d]imidazol-6-yl)-3-(1H-tetrazol-1-yl)benzamide, |
| 1B | 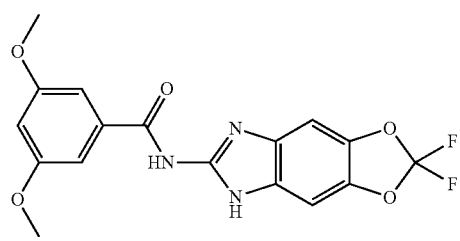<br>N-(2,2-difluoro-5H-[1,3]dioxolo[4',5':4,5]benzo[1,2-d]imidazol-6-yl)-3,5-dimethoxybenzamide, |
| 2B | 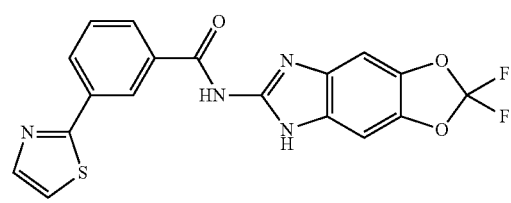 [SMILES: O=C(Nc1nc2cc3c(cc2[nH]1)OC(F)(F)O3)c1cccc(-c2nccs2)c1]<br>N-(2,2-difluoro-5H-[1,3]dioxolo[4',5':4,5]benzo[1,2-d]imidazol-6-yl)-3-(thiazol-2-yl)benzamide, |

| No. | Structure |
|---|---|
| 3B | 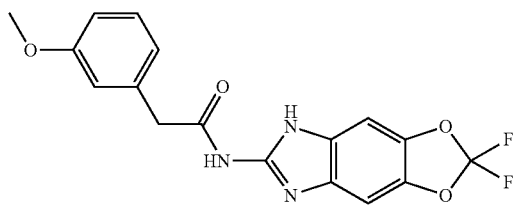 [SMILES: COc1cccc(CC(=O)Nc2nc3cc4c(cc3[nH]2)OC(F)(F)O4)c1] N-(2,2-difluoro-5H-[1,3]dioxolo[4',5':4,5]benzo[1,2-d]imidazol-6-yl)-2-(3-methoxyphenyl)acetamide, |
| 4B | 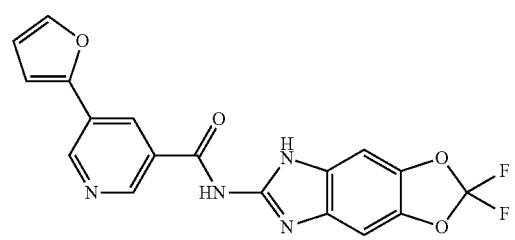 [SMILES: O=C(Nc1nc2cc3c(cc2[nH]1)OC(F)(F)O3)c1cncc(-c2ccco2)c1] N-(2,2-difluoro-5H-[1,3]dioxolo[4',5':4,5]benzo[1,2-d]imidazol-6-yl)-5-(furan-2-yl)nicotinamide, |
| 5B | 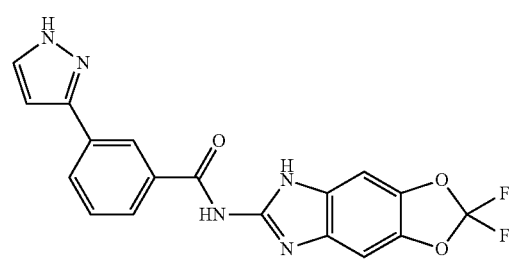 [SMILES: O=C(Nc1nc2cc3c(cc2[nH]1)OC(F)(F)O3)c1cccc(-c2cc[nH]n2)c1] N-(2,2-difluoro-5H-[1,3]dioxolo[4',5':4,5]benzo[1,2-d]imidazol-6-yl)-3-(1H-pyrazol-3-yl)benzamide, |
| 6B | 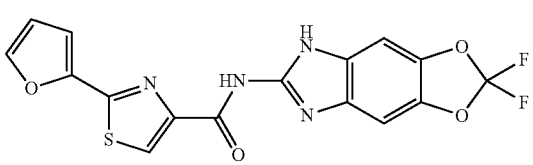 N-(2,2-difluoro-5H-[1,3]dioxolo[4',5':4,5]benzo[1,2-d]imidazol-6-yl)-2-(furan-2-yl)thiazole-4-carboxamide, |
| 7B | 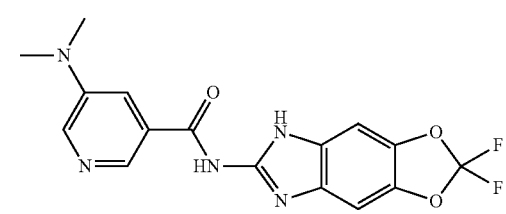 N-(2,2-difluoro-5H-[1,3]dioxolo[4',5':4,5]benzo[1,2-d]imidazol-6-yl)-5-(dimethylamino)nicotinamide, |

| No. | Structure |
|---|---|
| 8B | 2-(3-chlorophenyl)-N-(2,2-difluoro-5H-[1,3]dioxolo[4',5':4,5]benzo[1,2-d]imidazol-6-yl)acetamide, |
| 9B | 4-amino-N-(2,2-difluoro-5H-[1,3]dioxolo[4',5':4,5]benzo[1,2-d]imidazol-6-yl)-3-methoxybenzamide, |
| 10B | N-(2,2-difluoro-5H-[1,3]dioxolo[4',5':4,5]benzo[1,2-d]imidazol-6-yl)-5-(thiophene-3-carboxamido)-1,2,4-thiadiazole-3-carboxamide, |
| 11B | N-(2,2-difluoro-5H-[1,3]dioxolo[4',5':4,5]benzo[1,2-d]imidazol-6-yl)-2-(thiophen-2-yl)thiazole-4-carboxamide, |
| 12B | N-(2,2-difluoro-5H-[1,3]dioxolo[4',5':4,5]benzo[1,2-d]imidazol-6-yl)-2-(3-fluorophenyl)thiazole-4-carboxamide, |
| 13B | N-(2,2-difluoro-5H-[1,3]dioxolo[4',5':4,5]benzo[1,2-d]imidazol-6-yl)-1-methyl-1H-pyrazole-4-carboxamide, |

| No. | Structure |
|---|---|
| 14B | 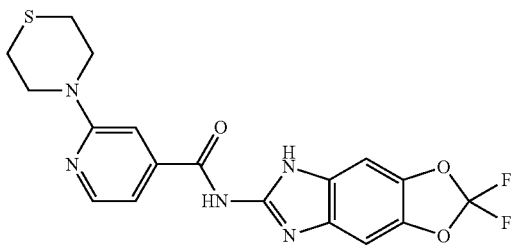 [SMILES: O=C(Nc1nc2cc3c(cc2[nH]1)OC(F)(F)O3)c1ccnc(N2CCSCC2)c1]<br>N-(2,2-difluoro-5H-<br>[1,3]dioxolo[4',5':4,5]benzo[1,2-d]imidazol-<br>6-yl)-2-thiomorpholinoisonicotinamide, |
| 15B | 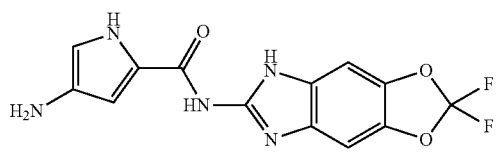 [SMILES: Nc1c[nH]c(C(=O)Nc2nc3cc4c(cc3[nH]2)OC(F)(F)O4)c1]<br>4-amino-N-(2,2-difluoro-5H-<br>[1,3]dioxolo[4',5':4,5]benzo[1.2-d]imidazol-<br>6-yl)-1H-pyrrole-2-carboxamide, |
| 16B | 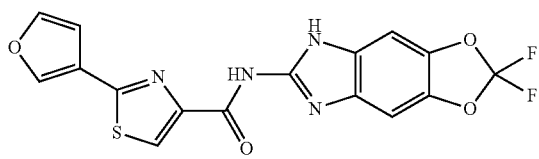 [SMILES: O=C(Nc1nc2cc3c(cc2[nH]1)OC(F)(F)O3)c1csc(-c2ccoc2)n1]<br>N-(2,2-difluoro-5H-<br>[1,3]dioxolo[4',5':4,5]benzo[1,2-d]imidazol-<br>6-yl)-2-(furan-3-yl)thiazole-4-carboxamide, |
| 17B | 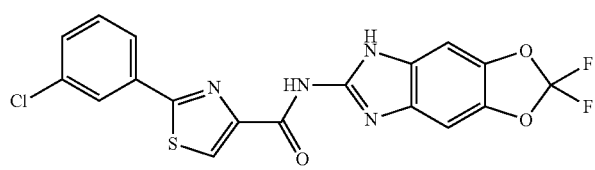 [SMILES: O=C(Nc1nc2cc3c(cc2[nH]1)OC(F)(F)O3)c1csc(-c2cccc(Cl)c2)n1]<br>2-(3-chlorophenyl)-N-(2,2-difluoro-5H-<br>[1,3]dioxolo[4',5':4,5]benzo[1,2-<br>d]imidazol-6-yl)thiazole-4-carboxamide, |
| 22B | 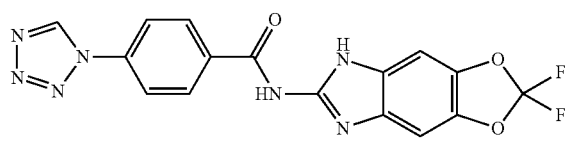<br>N-(2,2-difluoro-5H-<br>[1,3]dioxolo[4',5':4,5]benzo[1,2-d]imidazol-<br>6-yl)-4-(1H-tetrazol-1-yl)benzamide, |

| No. | Structure |
|---|---|
| 23B | 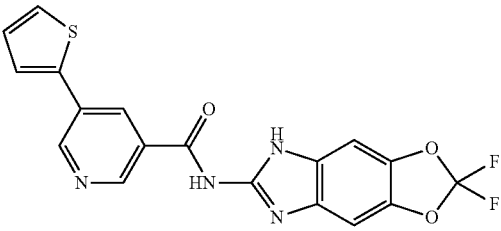<br>N-(2,2-difluoro-5H-[1,3]dioxolo[4',5':4,5]benzo[1,2-d]imidazol-6-yl)-5-(thiophen-2-yl)nicotinamide, or |
| 25B | 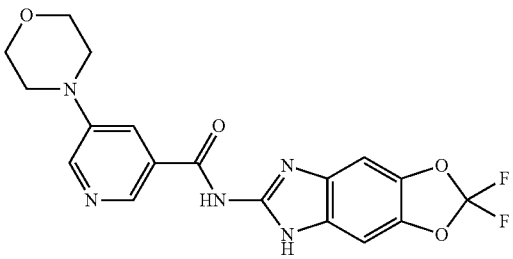 [SMILES: O=C(Nc1nc2cc3c(cc2[nH]1)OC(F)(F)O3)c1cncc(N2CCOCC2)c1]<br>N-(2,2-difluoro-5H-[1,3]dioxolo[4',5':4,5]benzo[1,2-d]imidazol-6-yl)-5-morpholinonicotinamide, | or a physiologically acceptable prodrug, solvate or salt thereof.

8. A pharmaceutical composition comprising a compound according to claim 1, or a physiologically acceptable prodrug, solvate or salt thereof, and one or more pharmaceutically acceptable excipients.

9. A method of treating an autoimmune inflammatory disorder, CNS disorder, a sleeping disorder in connection with the circadian clock mechanism, or a proliferative disease, comprising administering to a subject suffering from said disorder or disease an effective amount of a compound according to claim 1, or a physiologically acceptable prodrug, solvate or salt thereof.

10. A process for the preparation of a compound according to claim 1, wherein A is an —CONH— or —NHCO—, said process comprising coupling a compound of Formula IV with a compound of formula II;

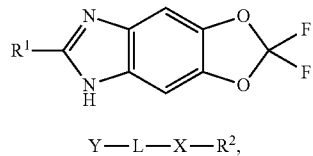

IV

Y—L—X—R², II wherein Y, L and X are as defined in claim 1, and wherein either R¹ is NH₂ and R² is COOH or COOCl, or wherein R² is NH₂ and R¹ is COOH or COOCl.

11. A compound according to claim 1, wherein Y is an unsubstituted phenyl group or a phenyl substituted by one or more substituents $R^Y$.

12. A compound according to claim 11, wherein Y is a phenyl group substituted with one or more substituents $R^Y$, wherein at least one of the substituents $R^Y$ is located in the meta position of the phenyl group, and wherein the ortho positions of the phenyl group are occupied by H, and wherein said ortho and meta positions are in relation to the point of attachment to L, or in the case where L is a bond, the point of attachment to X, respectively.

13. A compound according to claim 1, wherein $R^X$ is, in each occurrence independently, methyl, methylsulfonyl, fluorine, chlorine, bromine, trifluoromethyl, hydroxyl, amino, dimethylamino, ethylamino, diethylamino, benzylamino, nitro, methoxy, trifluoromethoxy, or cyano.

14. A compound according to claim 1, wherein L is a bond, or is *—NHCO—, *—NH SO₂—, *—SO₂—, *—CONH—, *—NH—, —NHCONH—, or *—SO₂NH—, wherein * specifies the point of attachment to X.

15. A compound according to claim 1, wherein L is *—NHCO—, *—NH, *—NHCONH—, or *—NHSO₂—, wherein * specifies the point of attachment to X.

16. A compound according to claim 1, wherein L is *—NHCO, wherein * specifies the point of attachment to X.

17. A compound according to claim 1, $R^Y$ is, in each occurrence independently, methyl, chlorine, fluorine, methoxy, trifluoromethoxy or nitro.

18. A compound according to claim 13, wherein $R^Y$ is, in each occurrence independently, methyl, chlorine, fluorine, methoxy, trifluoromethoxy or nitro.

19. A compound according to claim 6, wherein said compound is selected from compound nos. 1 to 149, physiologically acceptable solvates thereof, or physiologically acceptable salts thereof.

20. A compound according to claim 7, wherein said compound is selected from compound nos. 1, 2, 3, 11, 17, 18, 19, 20, 21, 26, 29, 30, 31, 33, 37, 38, 41, 48, 49, 51, 52, 56, 57, 60, 62, 65, 66, 69, 70, 75, 76, 77, 78, 80, 81, 82, 83, 87, 88, 91, 92, 94, 100, 101, 102, 104, 105, 108, 111, 112, 113, 114, 116, 117, 118, 121, 122, 123, 124, 125, 126, 128, 130, 131, 132, 133, 134, 135, 136, 137, 138, 139, 140, 141, 142, 144, 147, 148, or 149, physiologically acceptable solvates thereof, or physiologically acceptable salts thereof.

21. A compound according to claim 2, wherein
L is independently a bond or a linker group, wherein said linker group is *—NHCO—, *—CONH—, —NH—, *—N($C_{1-4}$-alkyl)-, *—NHCONH—, *—CO—, *—$SO_2$—, *—NHCO—CH=CH—, *—CH=CH—CONH—, *—$SO_2$NH—, *—NH$SO_2$—, or pyridinyl, and wherein * specifies the point of attachment to X;
$R^X$ is, in each occurrence independently, methyl, methylsulfonyl, fluorine, chlorine, bromine, trifluoromethyl, hydroxyl, amino, dimethylamino, ethylamino, diethylamino, benzylamino, nitro, methoxy, trifluoromethoxy, or cyano;
and
$R^Y$ is, in each occurrence independently, methyl, chlorine, fluorine, methoxy, trifluoromethoxy or nitro.

22. A method according to claim 9, wherein said method is for treating a cancer selected from hepatocarcinoma, adrenocortical carcinoma, AIDS-related lymphoma, anal cancer, basal cell carcinoma, bile duct cancer, bone cancer, brain stem glioma, cerebellar astrocytoma, cerebral astrocytoma, malignant glioma, ependymoma, medulloblastoma, supratentorial primitive neuroectodermal tumors, visual pathway and hypothalamic glioma, breast cancer, bronchial adenomas/carcinoids, Burkitt's lymphoma, gastrointestinal, central nervous system lymphoma, cervical cancer, chronic myeloproliferative disorders, colon cancer, colorectal cancer, cutaneous T-cell lymphoma, endometrial cancer, ependymoma, esophageal cancer, extracranial germ cell tumor, extragonadal germ cell tumor, ovarian germ cell tumor, eye cancer including intraocular melanoma and retinoblastoma, gallbladder cancer, gastrointestinal carcinoid tumor, gestational trophoblastic tumor, glioma, childhood brain stem glioma, head and neck cancer, hematologic cancer, adult and childhood (primary) hepatocellular cancer, hypopharyngeal cancer, islet cell or pancreatic cancer, renal cancer, laryngeal cancer, acute lymphoblastic leukemia, adult and childhood acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, Hodgkin's lymphoma, non-Hodgkin's lymphoma, primary central nervous system lymphoma, Waldenstrom's macroglobulinemia, merkel cell carcinoma, mesothelioma, metastatic squamous neck cancer with occult primary site, multiple endocrine neoplasia syndrome, multiple myeloma/plasma cell neoplasm, mycosis fungoides, myelodysplastic syndromes, myelodysplastic myeloproliferative diseases, multiple myeloma, chronic myeloproliferative disorders, nasal cavity and paranasal sinus cancer, nasopharyngeal cancer, neuroblastoma, oral cancer, oropharyngeal cancer, osteosarcoma/malignant fibrous histiocytoma of bone, ovarian cancer, ovarian epithelial cancer, ovarian low malignant potential tumor, pancreatic cancer, parathyroid cancer, penile cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter cancer, transitional cell cancer, rhabdomyosarcoma, salivary gland cancer, Ewing's sarcoma, Kaposi's sarcoma, soft tissue sarcoma, uterine sarcoma, sezary syndrome, skin cancer, including melanoma and non-melanoma skin cancer, small intestine cancer, squamous cell carcinoma, gastric cancer, supratentorial primitive neuroectodermal tumors, testicular cancer, thymoma, thymoma and thymic carcinoma, thyroid cancer, trophoblastic tumor, gestational, endometrial uterine cancer, uterine sarcoma, vaginal cancer, vulvar cancer, Waldenstrom's macroglobulinemia, or Wilms' tumor.

23. A method according to claim 9, wherein said method is for treating prostate cancer, bladder cancer, renal cancer, muscle cancer, ovarian cancer, skin cancer, lung, pancreatic cancer, breast cancer, cervical cancer, colon cancer, liver cancer, connective tissue cancer, placenta cancer, bone cancer, brain cancer, uterine cancer, cancer of the salivary glands, or testicular cancer.

24. A method according to claim 9, wherein said method is for treating inflammatory Bowel disease, multiple sclerosis, rheumatoid arthritis, autoimmune uveitis, Alzheimer's disease, Parkinson's disease, or sleeping disorders in connection with the circadian clock mechanism.

25. A method according to claim 9, wherein said method is for treating rheumatoid arthritis, Alzheimer's disease, or sleeping disorders in connection with the circadian clock mechanism.

26. A method according to claim 9, wherein said method is for treating a cancer, wherein in cells in said cancer the hedgehog signaling pathway is activated.

* * * * *

UNITED STATES PATENT AND TRADEMARK OFFICE
CERTIFICATE OF CORRECTION

PATENT NO. : 9,580,438 B2
APPLICATION NO. : 14/411795
DATED : February 28, 2017
INVENTOR(S) : Johann Leban et al.

Page 1 of 1

It is certified that error appears in the above-identified patent and that said Letters Patent is hereby corrected as shown below:

In the Claims

Column 121, Claim 1, Formula (I) presents as:

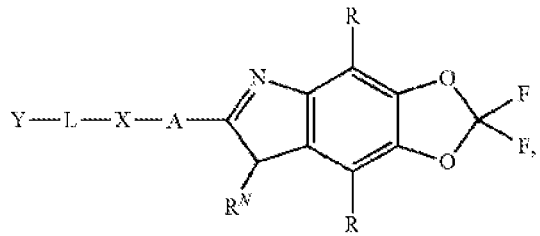

Should present as:

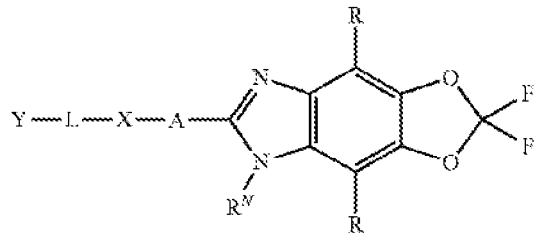

Signed and Sealed this
Fourth Day of July, 2017

Joseph Matal
*Performing the Functions and Duties of the
Under Secretary of Commerce for Intellectual Property and
Director of the United States Patent and Trademark Office*